United States Patent
Lee et al.

(10) Patent No.: US 9,771,373 B2
(45) Date of Patent: Sep. 26, 2017

(54) CONDENSED CYCLIC COMPOUND AND ORGANIC LIGHT-EMITTING DEVICE INCLUDING THE SAME

(71) Applicants: Samsung Electronics Co., Ltd., Suwon-si, Gyeonggi-do (KR); Samsung SDI Co., Ltd, Yongin-si, Gyeonggi-do (KR)

(72) Inventors: Sunyoung Lee, Seoul (KR); Soyeon Kim, Anyang-si (KR); Yoonhyun Kwak, Seoul (KR); Sangdong Kim, Hwaseong-si (KR); Sangyeob Lee, Hwaseong-si (KR)

(73) Assignees: SAMSUNG ELECTRONICS CO., LTD., Gyeonggi-Do (KR); SAMSUNG SDI CO., LTD., Gyeonggi-Do (KR)

( * ) Notice: Subject to any disclaimer, the term of this patent is extended or adjusted under 35 U.S.C. 154(b) by 185 days.

(21) Appl. No.: 14/599,724

(22) Filed: Jan. 19, 2015

(65) Prior Publication Data

US 2015/0333273 A1    Nov. 19, 2015

(30) Foreign Application Priority Data

May 15, 2014 (KR) .................. 10-2014-0058395

(51) Int. Cl.
| C07D 487/06 | (2006.01) |
| C07D 519/00 | (2006.01) |
| H01L 51/00 | (2006.01) |
| H01L 51/50 | (2006.01) |

(52) U.S. Cl.
CPC .......... *C07D 487/06* (2013.01); *C07D 519/00* (2013.01); *H01L 51/0067* (2013.01); *H01L 51/0072* (2013.01); *H01L 51/0085* (2013.01); *H01L 51/0087* (2013.01); *H01L 51/5012* (2013.01); *H01L 51/5016* (2013.01); *H01L 51/5024* (2013.01); *H01L 51/5072* (2013.01); *H01L 2251/5384* (2013.01)

(58) Field of Classification Search
None
See application file for complete search history.

(56) References Cited

U.S. PATENT DOCUMENTS

| 2010/0201301 A1 | 8/2010 | Lyden et al. |
| 2012/0292576 A1* | 11/2012 | Parham ............... C07D 209/86 252/500 |

FOREIGN PATENT DOCUMENTS

| DE | 102010005697 | 7/2011 |
| JP | 09298430 | 11/1997 |
| JP | 2004012492 | 1/2004 |
| JP | 2008043171 | 2/2008 |
| JP | 2008113506 | 5/2008 |
| JP | 2012191031 | 10/2012 |
| JP | 2012236786 | 12/2012 |
| JP | 2013048403 | 3/2013 |
| WO | 2011088877 | 7/2011 |

* cited by examiner

*Primary Examiner* — Gregory Clark
(74) *Attorney, Agent, or Firm* — Cantor Colburn LLP

(57) ABSTRACT

A condensed cyclic compound represented by one of Formulae 1A to 1C, wherein Formulae 1A to 1C are disclosed in the detailed description.

25 Claims, 1 Drawing Sheet

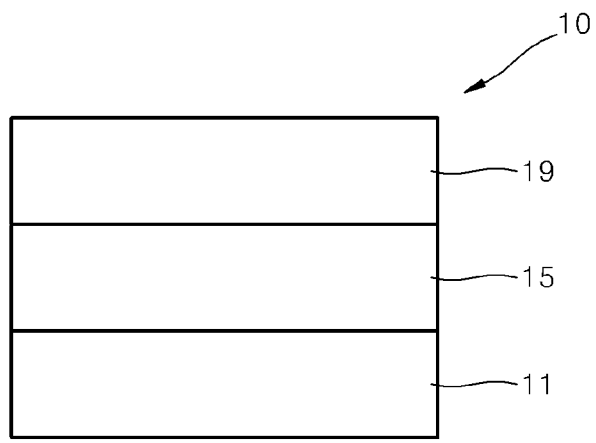

CONDENSED CYCLIC COMPOUND AND ORGANIC LIGHT-EMITTING DEVICE INCLUDING THE SAME

CROSS-REFERENCE TO RELATED APPLICATION

This application claims priority to Korean Patent Application No. 10-2014-0058395, filed on May 15, 2014, in the Korean Intellectual Property Office, and all the benefits accruing therefrom under 35 U.S.C. §119, the content of which is incorporated herein in its entirety by reference.

BACKGROUND

1. Field

One or more embodiments relate to condensed cyclic compounds and organic light-emitting devices including the same.

2. Description of the Related Art

Organic light-emitting devices (OLEDs) are self-emission devices that have wide viewing angles, high contrast ratios, and short response times. In addition, the OLEDs exhibit excellent brightness, driving voltage, and response speed characteristics, and produce full-color images.

A typical organic light-emitting device includes an anode, a cathode, and an organic layer that is disposed between the anode and the cathode and includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. Carriers, such as holes and electrons, are recombined in the emission layer to produce excitons. These excitons change from an excited state to a ground state, thereby generating light.

Various types of organic light emitting devices are known. However, there still remains a need in OLEDs having low driving voltage, high efficiency, high brightness, and long lifespan.

SUMMARY

Provided are novel condensed cyclic compounds and organic light-emitting devices including the same.

Additional aspects will be set forth in part in the description which follows and, in part, will be apparent from the description, or may be learned by practice of the presented embodiments.

According to an aspect, a condensed cyclic compound is represented by one of Formulae 1A to 1C:

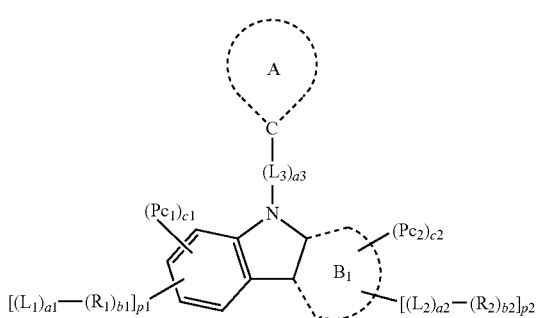

Formula 1A

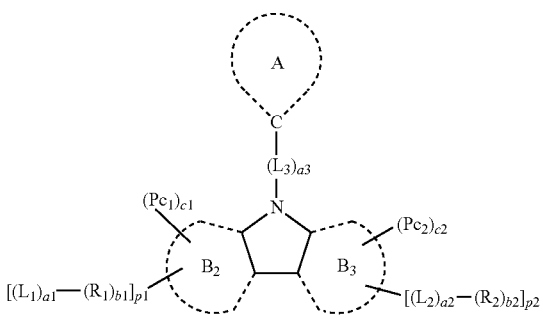

Formula 1B

Formula 1C

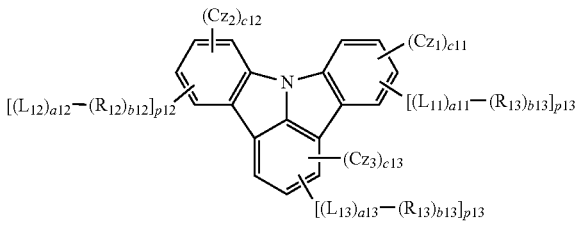

Formula 2A

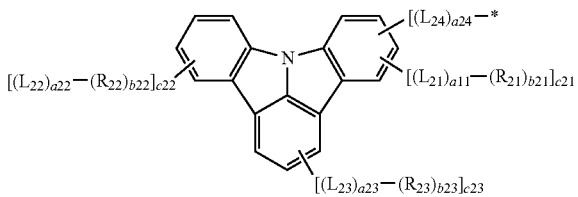

Formula 2B

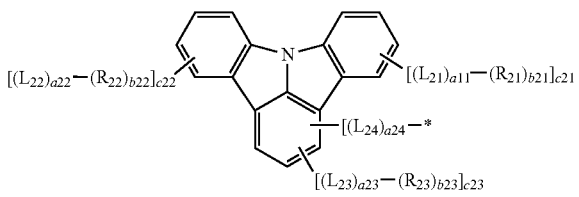

Formula 2C

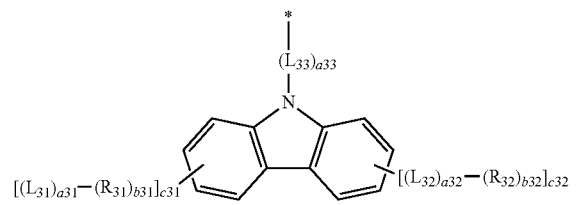

Formula 2D

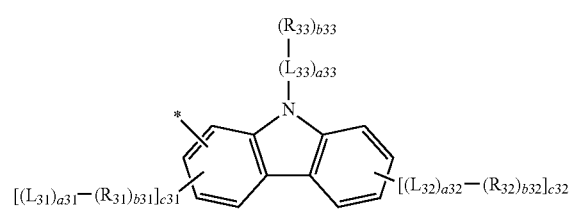

Formula 2E

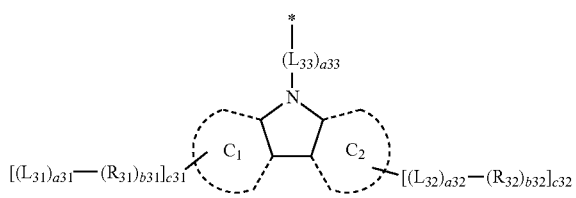

Formula 2F

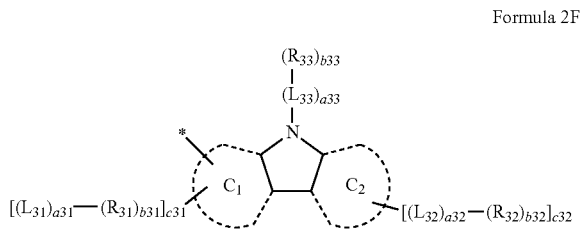

wherein in the formulae,

Ring A is a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, a group represented by Formula 2A, or a group represented by Formula 2B;

Ring $B_1$ is a $C_5$-$C_{20}$ carbocyclic group or a $C_2$-$C_{20}$ heterocyclic group that does not include a nitrogen atom as a ring-forming atom;

Ring $B_2$, Ring $B_3$, Ring $C_1$, and Ring $C_2$ are each independently a $C_5$-$C_{20}$ carbocyclic group, or a $C_2$-$C_{20}$ heterocyclic group, provided that at least one selected from Ring $B_2$ and Ring $B_3$ is a $C_2$-$C_{20}$ heterocyclic group including a nitrogen atom as a ring-forming atom, and at least one selected from Ring $C_1$ and Ring $C_2$ is a $C_2$-$C_{20}$ heterocyclic group including a nitrogen atom as a ring-forming atom;

$Pc_1$ and $Pc_2$ in Formula 1A and 1B are each independently a group represented by Formulae 2A or a group represented by Formula 2B;

$Cz_1$, $Cz_2$, and $Cz_3$ in Formula 1C are each independently a group represented by Formula 2C, a group represented by Formula 2D, a group represented by Formula 2E, or a group represented by Formula 2F;

c1, c2, c11, c12, c13, p1, p2, p11, p12, and p13 are each independently an integer selected from 0 to 3;

when c1 and c2 in Formula 1A and 1B both are 0, Ring A is a group represented by Formula 2A or a group represented by Formula 2B;

when Ring A in Formula 1A and 1B is neither a group represented by Formula 2A nor a group represented by Formula 2B;

$c1+c2 \neq 0$;

at least one selected from Ring A in Formula 1A, all $R_1$ in Formula 1A, and all $R_2$ in Formula 1A is a substituted or unsubstituted $C_2$-$C_{10}$ heterocycloalkyl group, a substituted or unsubstituted $C_2$-$C_{10}$ heterocycloalkenyl group, a substituted or unsubstituted $C_2$-$C_{60}$ heteroaryl group, or a substituted or unsubstituted monovalent non-aromatic condensed hetero-polycyclic group, each including at least one Moiety 1 as a ring-forming moiety;

the sum of c11, c12, and c13 in Formula 1C is not 0;

when each of $Cz_1$, $Cz_2$, and $Cz_3$ in Formula 1C is independently a group represented by Formula 2C or a group represented by Formula 2D, at least one selected from all $R_{11}$ in Formula 1C, all $R_{12}$ in Formula 1C, and all $R_{13}$ in Formula 1C is a substituted or unsubstituted $C_2$-$C_{10}$ heterocycloalkyl group, a substituted or unsubstituted $C_2$-$C_{10}$ heterocycloalkenyl group, a substituted or unsubstituted $C_2$-$C_{60}$ heteroaryl group, or a substituted or unsubstituted monovalent non-aromatic condensed hetero-polycyclic group, each including at least one Moiety 1 as a ring-forming moiety;

$L_1$ to $L_3$, $L_{11}$ to $L_{13}$, $L_{21}$ to $L_{24}$, and $L_{31}$ to $L_{33}$ are each independently selected from a substituted or unsubstituted $C_1$-$C_{60}$ alkylene group, a substituted or unsubstituted $C_2$-$C_{60}$ alkenylene group, a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, and a substituted or unsubstituted divalent non-aromatic condensed hetero-polycyclic group;

a1 to a3, a11 to a13, a21 to a24, and a31 to a33 are each independently an integer selected from 0 to 6;

$R_1$, $R_2$, $R_{11}$ to $R_{13}$, $R_{21}$ to $R_{23}$, and $R_{31}$ to $R_{33}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed hetero-polycyclic group, —N($Q_1$)($Q_2$), —Si($Q_3$)($Q_4$)($Q_5$), and —B($Q_6$)($Q_7$);

b1, b2, b11 to b13, b21 to b23, and b31 to b33 are each independently an integer selected from 0 to 4;

at least one of substituents of the substituted $C_1$-$C_{60}$ alkylene group, substituted $C_2$-$C_{60}$ alkenylene group, substituted $C_3$-$C_{10}$ cycloalkylene group, substituted $C_2$-$C_{10}$ heterocycloalkylene group, substituted $C_3$-$C_{10}$ cycloalkenylene group, substituted $C_2$-$C_{10}$ heterocycloalkenylene group, substituted $C_6$-$C_{60}$ arylene group, substituted $C_2$-$C_{60}$ heteroarylene group, substituted divalent non-aromatic condensed polycyclic group, substituted divalent non-aromatic condensed hetero-polycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_2$-$C_{60}$ heteroaryl group, a substituted monovalent non-aromatic condensed polycyclic group, and a substituted monovalent non-aromatic condensed hetero-polycyclic group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed hetero-polycyclic group, —$N(Q_{11})(Q_{12})$, —$Si(Q_{13})(Q_{14})(Q_{15})$, and —$B(Q_{16})(Q_{17})$;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed hetero-polycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, and —$B(Q_{26})(Q_{27})$; and —$N(Q_{31})(Q_{32})$, —$Si(Q_{33})(Q_{34})(Q_{35})$, and —$B(Q_{36})(Q_{37})$;

wherein $Q_1$ to $Q_7$, $Q_{11}$ to $Q_{17}$, $Q_{21}$ to $Q_{27}$, and $Q_{31}$ to $Q_{37}$ may be each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent non-aromatic condensed polycyclic group, and a monovalent non-aromatic hetero-condensed polycyclic group.

$$\!=\!N\!-\!* \qquad \text{Moiety 1}$$

in Moiety 1,  and * each indicates a binding site to a ring-forming atom included in a ring including Moiety 1.

According to another aspect, an organic light-emitting device includes:

a first electrode;

a second electrode; and an organic layer disposed between the first electrode and the second electrode, wherein the organic layer includes an emission layer, and further includes at least one condensed cyclic compound represented by Formula 1.

BRIEF DESCRIPTION OF THE DRAWINGS

These and/or other aspects will become apparent and more readily appreciated from the following description of the embodiments, taken in conjunction with FIG. 1 which is a schematic view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. The term "or" means "and/or." Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

A condensed cyclic compound according to an embodiment is represented by one of Formulae 1A to 1C:

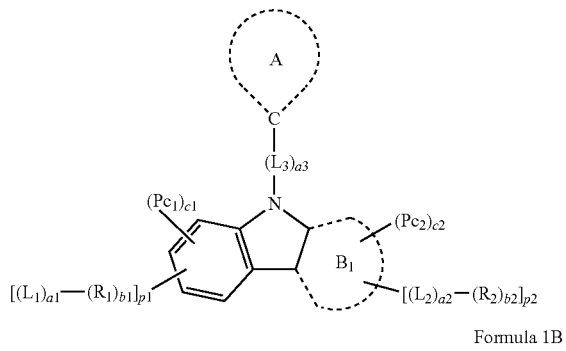

Formula 1A

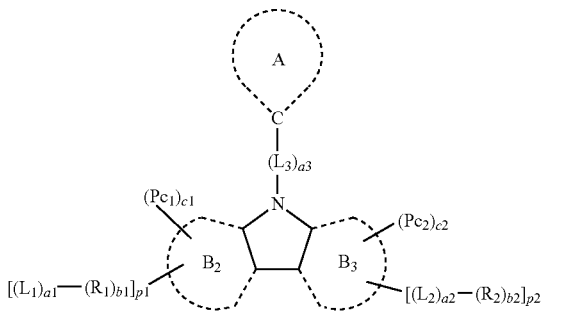

Formula 1B

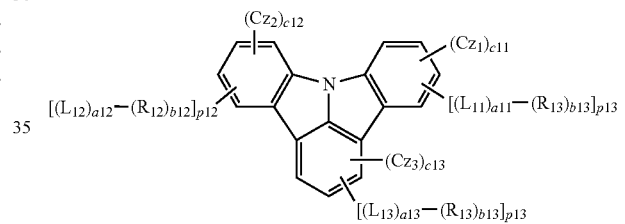

Formula 1C

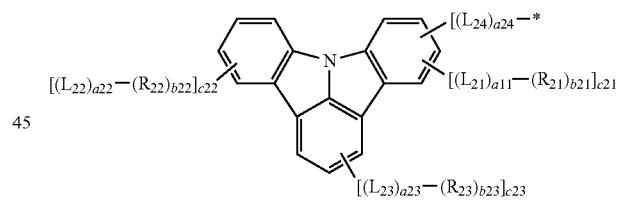

Formula 2A

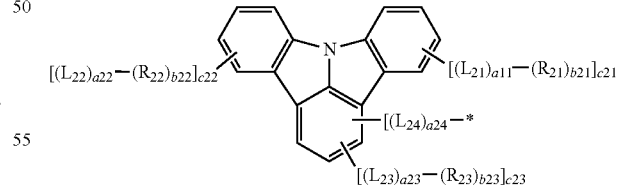

Formula 2B

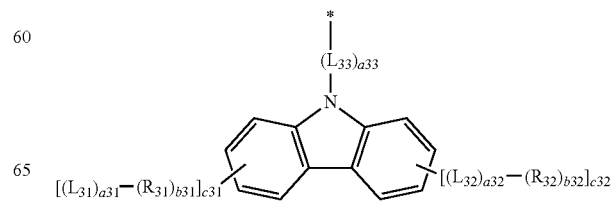

Formula 2C

-continued

Formula 2D

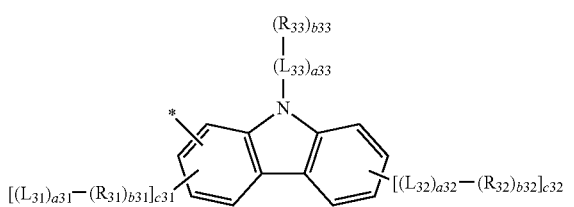

Formula 2E

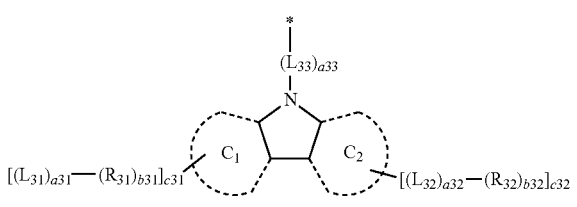

Formula 2F

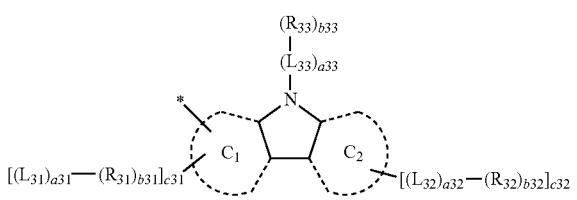

The relationships between the groups represented by Formulae 2A to 2F and the condensed cyclic compound represented by one of Formulae 1A to 1C will be described below in detail.

Ring A in Formula 1A may be a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, a group represented by Formula 2A, or a group represented by Formula 2B.

According to an embodiment, Ring A in Formula 1A may be selected from a phenyl group, a naphthyl group, a phenalenyl group, a phenanthrenyl group, an anthracenyl group, a triphenylenyl group, a pyrenyl group, a chrysenyl group, a pyrrolyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, phenanthridinyl, phenanthrolinyl, phenazinyl, a benzoimidazolyl group, an isobenzothiazolyl group, a benzooxazolyl group, an isobenzoxazolyl group, a triazolyl group, a tetrazolyl group, an oxadiazolyl group, a triazinyl group, an imidazopyridinyl group, an imidazopyrimidinyl group, a benzofuropyrazinyl group, a benzofuropyrimidinyl group, a benzofuropyridinyl group, a benzothienopyrazinyl group, a benzothienopyrimidinyl group, a benzothienopyridinyl group, a group represented by Formula 2A, and a group represented by Formula 2B; and a phenyl group, a naphthyl group, a phenalenyl group, a phenanthrenyl group, an anthracenyl group, a triphenylenyl group, a pyrenyl group, a chrysenyl group, a pyrrolyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, phenanthridinyl, phenanthrolinyl, phenazinyl, a benzoimidazolyl group, an isobenzothiazolyl group, a benzooxazolyl group, an isobenzoxazolyl group, a triazolyl group, a tetrazolyl group, an oxadiazolyl group, a triazinyl group, an imidazopyridinyl group, an imidazopyrimidinyl group, a benzofuropyrazinyl group, a benzofuropyrimidinyl group, a benzofuropyridinyl group, a benzothienopyrazinyl group, a benzothienopyrimidinyl group, and a benzothienopyridinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a phenyl group substituted with a $C_1$-$C_{20}$ alkyl group, a naphthyl group, a phenalenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, a naphthyridinyl group, a quinoxalinyl group, a quinazolinyl group, a biphenyl group, and —Si($Q_{33}$)($Q_{34}$)($Q_{35}$), wherein $Q_{33}$ to $Q_{35}$ may be each independently selected from a hydrogen, a $C_1$-$C_{20}$ alkyl group, a $C_1$-$C_{20}$ alkoxy group, a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group.

In some embodiments, Ring A in Formula 1A may be represented by one of Formulae 4-1 to 4-51, Formulae 6-1 to 6-5 below, a group represented Formula 2A, and a group represented by Formula 2B, but a formula representing Ring A is not limited thereto:

Formula 4-1

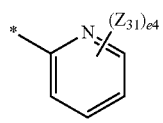

Formula 4-2

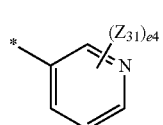

Formula 4-3

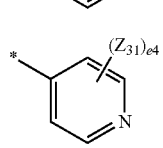

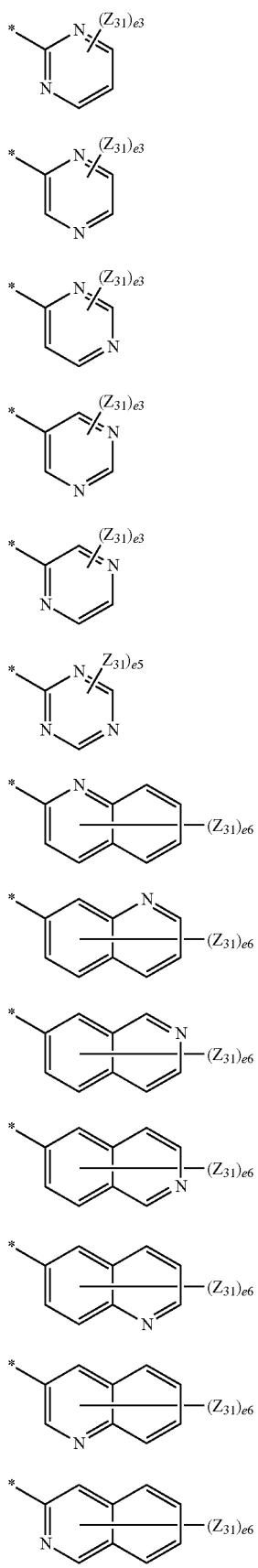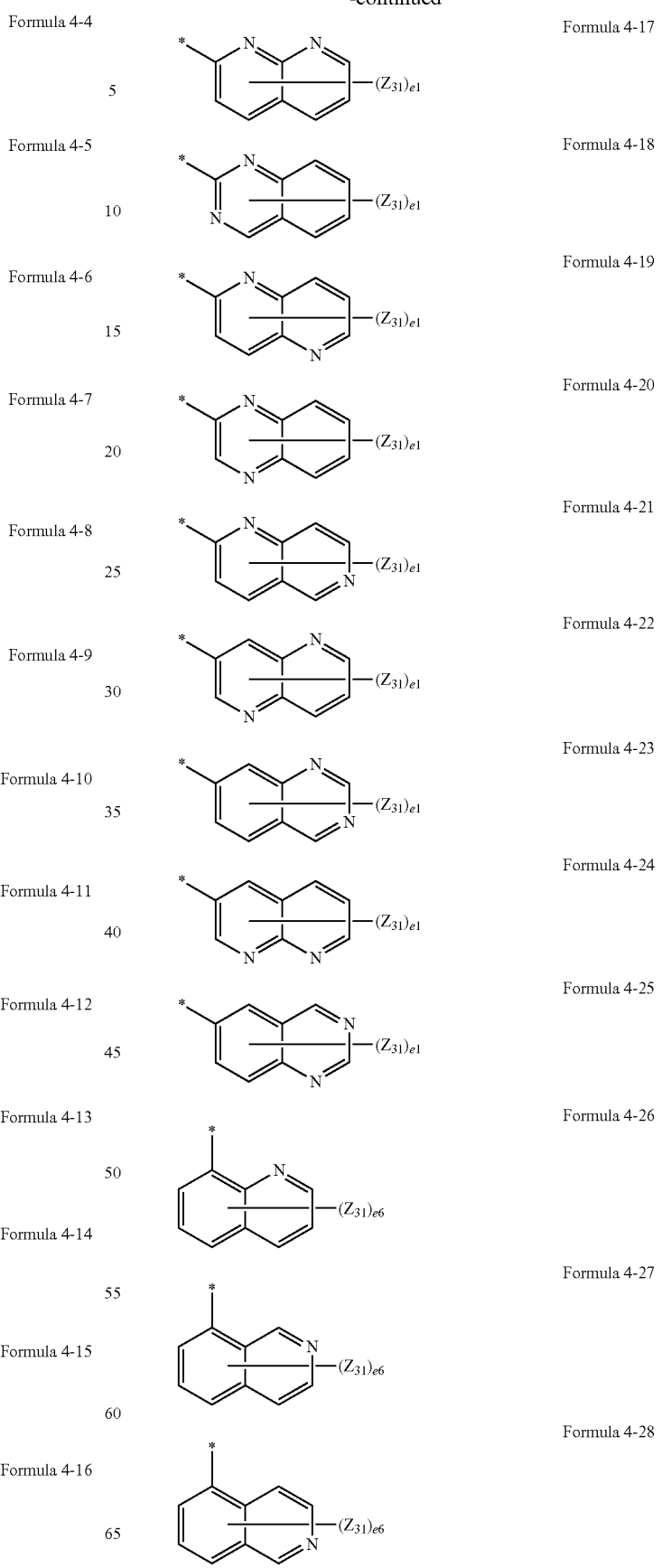

-continued
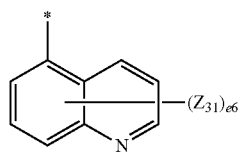
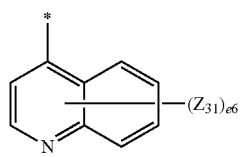
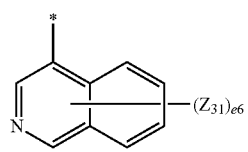

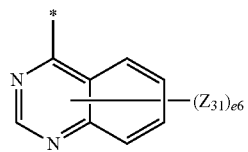

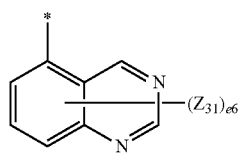

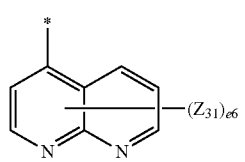
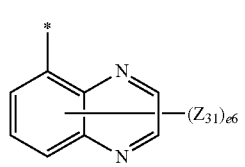
-continued
Formula 4-29
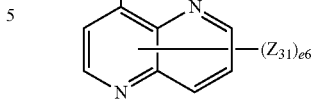
Formula 4-30
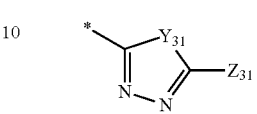
Formula 4-31
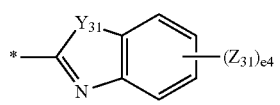
Formula 4-32
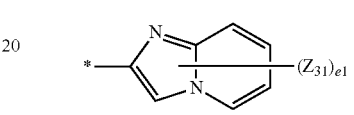
Formula 4-33
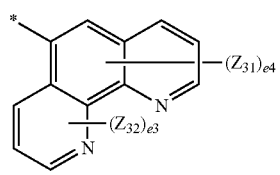
Formula 4-34
Formula 4-35
Formula 4-36
Formula 4-37
Formula 4-38
Formula 4-39
Formula 4-40
Formula 4-41
Formula 4-42
Formula 4-43
Formula 4-44
Formula 4-45
Formula 4-46
Formula 4-47
Formula 4-48
Formula 4-49

Formula 4-50

[chemical structure]

Formula 4-51

[chemical structure]

Formula 6-1

[chemical structure]

Formula 6-2

[chemical structure]

Formula 6-2

[chemical structure]

Formula 6-4

[chemical structure]

Formula 6-5

[chemical structure]

In Formulae 4-1 to 4-51 and 6-1 to 6-5, $Y_{31}$ is O, S, $C(Z_{33})(Z_{34})$, $N(Z_{35})$, or $Si(Z_{36})(Z_{37})$;

$Z_{31}$ to $Z_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group substituted with a $C_1$-$C_{20}$ alkyl group, a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, a quinoxalinyl group, a biphenyl group, and —$Si(Q_{33})(Q_{34})(Q_{35})$; wherein $Q_{33}$ to $Q_{35}$ are each independently selected from a hydrogen, a $C_1$-$C_{20}$ alkyl group, a $C_1$-$C_{20}$ alkoxy group, a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group;

e1 is an integer of 1 to 5;
e2 is an integer of 1 to 7;
e3 is an integer of 1 to 3;
e4 is an integer of 1 to 4;
e5 is an integer of 1 or 2;
e6 is an integer of 1 to 6; and
* indicates a binding site to a neighboring atom.

Ring $B_1$ in Formula 1A is a $C_5$-$C_{20}$ carbocyclic group or a $C_2$-$C_{20}$ heterocyclic group that does not includes a nitrogen atom as a ring-forming atom.

For example, Ring $B_1$ in Formula 1A may be a benzene, a naphthalene, an anthracene, a phenanthrene, a benzofuran, or a benzothiophene.

According to an embodiment, Ring $B_1$ in Formula 1A may be a benzene, a naphthalene, an anthracene, a phenanthrene, or a benzofuran.

Ring $B_2$, Ring $B_3$, Ring $C_1$, and Ring $C_2$ in Formulae 1B and 1C are each independently a $C_5$-$C_{20}$ carbocyclic group or a $C_2$-$C_{20}$ heterocyclic group, provided that at least one selected from Ring $B_2$ and Ring $B_3$ is a $C_2$-$C_{20}$ heterocyclic group including a nitrogen atom as a ring-forming atom, and at least one selected from Ring $C_1$ and Ring $C_2$ is a $C_2$-$C_{20}$ heterocyclic group including a nitrogen atom as a ring-forming atom.

In some embodiments, Ring $B_2$, Ring $B_3$, Ring $C_1$, and Ring $C_2$ may be each independently a benzene, a naphthalene, an anthracene, a phenanthrene, a benzofuran, a benzothiophene, a pyridine, a pyrimidine, a pyrazine, a benzofuropyrazine, a benzofuropyrimidine, benzofuropyridine, a benzothienopyrazine, a benzothienopyrimidine, or a benzothienopyridine;

at least one selected from Ring $B_2$ and Ring $B_3$ is a pyridine, a pyrimidine, a pyrazine, a benzofuropyrazine, a benzofuropyrimidine, a benzofuropyridine, a benzothienopyrazine, a benzothienopyrimidine, or a benzothienopyridine, and at least one selected from Ring $C_1$ and Ring $C_2$ is a pyridine, a pyrimidine, a pyrazine, a benzofuropyrazine, a benzofuropyrimidine, a benzofuropyridine, a benzothienopyrazine, a benzothienopyrimidine, or a benzothienopyridine.

In some embodiments, Ring $B_2$, Ring $B_3$, Ring $C_1$, and Ring $C_2$ may be each independently a benzene, a naphthalene, a pyridine, a pyrimidine, or a pyrazine;

at least one of Ring $B_2$ and Ring $B_3$ may be a pyridine, a pyrimidine, or a pyrazine; and at least one of Ring $C_1$ and Ring $C_2$ may be a pyridine, a pyrimidine, or a pyrazine.

$Pc_1$ and $Pc_2$ in Formula 1A and 1B are each independently a group represented by Formulae 2A or a group represented by Formula 2B.

Each of $Cz_1$, $Cz_2$, and $Cz_3$ in Formula 1C is independently a group represented by Formula 2C, a group represented by Formula 2D, a group represented by Formula 2E, or a group represented by Formula 2F.

c1, c2, c11, c12, c13, p1, p2, p11, p12, and p13 in Formulae 1A to 1C are each independently an integer selected from 0 to 3.

When each of c1 and c2 in Formulae 1A and 1B is 0, Ring A is a group represented by Formula 2A or a group represented by Formula 2B, and when Ring A in Formulae 1A and 1B is neither a group represented by Formula 2A nor a group represented by Formula 2B, c1+c2≠0.

That is, Formulae 1A and 1B necessarily include one selected from the group represented by Formula 2A and the group represented by Formula 2B.

At least one selected from Ring A in Formula 1A, all $R_1$ in Formula 1A, and all $R_2$ in Formula 1A is an electron transport moiety.

The electron transport moiety may be a substituted or unsubstituted $C_2$-$C_{10}$ heterocycloalkyl group, a substituted or unsubstituted $C_2$-$C_{10}$ heterocycloalkenyl group, a substituted or unsubstituted $C_2$-$C_{60}$ heteroaryl group, or a substituted or unsubstituted monovalent non-aromatic condensed hetero-polycyclic group, each including Moiety 1 below as a ring-forming moiety. Herein, a carbazole-based group that does not include Moiety 1 is not an electron transport moiety, due to the absence of Moiety 1.

$${=}N{-}* \qquad \text{Moiety 1}$$

in Moiety 1,  and * each indicates a binding site to a ring-forming atom in a ring including Moiety 1.

Examples of the electron transport moiety are groups represented by Formulae 4-1 to 4-51, but are not limited thereto.

The sum of c11, c12, and c13 in Formula 1C is not 0.

That is, Formula 1C necessarily includes at least one of groups represented by Formulae 2C to 2F.

When $Cz_1$, $Cz_2$, and $Cz_3$ in Formula 1C is a group represented by Formula 2C or a group represented by Formula 2D, at least one selected from $R_{11}$ in Formula 1C, $R_{12}$ in Formula 1C, and $R_{13}$ in Formula 1C is an electron transport moiety. Herein, the electron transport moiety has been described above and will not be repeated.

According to an embodiment, in Formulae 1A and 1B,
c1=0, c2=0, and Ring A is a group represented by Formula 2A or a group represented by Formula 2B;
c1=1 and c2=0; or
c1=1 and c2=1.

In some embodiments, in Formula 1C,
c11=1, c12=0, and c13=0;
c11=0, c12=0, and c13=1;
c11=1, c12=1, and c13=0; or
c11=1, c12=0, and c13=1.

$L_1$ to $L_3$, $L_{11}$ to $L_{13}$, $L_{21}$ to $L_{24}$, and $L_{31}$ to $L_{33}$ in Formulae 1A to 1C and 2A to 2F may be each independently selected from a substituted or unsubstituted $C_1$-$C_{60}$ alkylene group, a substituted or unsubstituted $C_2$-$C_{60}$ alkenylene group, a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, and a substituted or unsubstituted divalent non-aromatic condensed hetero-polycyclic group.

For example, $L_1$ to $L_3$, $L_{11}$ to $L_{13}$, $L_{21}$ to $L_{24}$ and $L_{31}$ to $L_{33}$ in Formulae 1A to 1C and 2A to 2F may be each independently selected from a phenylene group, a pentalenylene group, an indenylene group, a naphthylene group, an azulenylene group, a heptalenylene group, an indacenylene group, an acenaphthylene group, a fluorenylene group, a spiro-fluorenylene group, a phenalenylene group, a phenanthrenylene group, an anthracenylene group, a fluoranthrenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoxazolylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, an imidazopyrimidinylene group, and an imidazopyridinylene group; and a phenylene group, a pentalenylene group, an indenylene group, naphthylene group, an azulenylene group, a heptalenylene group, an indacenylene group, an acenaphthylene group, a fluorenylene group, a spiro-fluorenylene group, a phenalenylene group, a phenanthrenylene group, an anthracenylene group, a fluoranthrenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzooxazolylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group an imidazopyrimidinylene group, and an imidazopyridinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a $C_6$-$C_{20}$ aryl group, a $C_2$-$C_{20}$ heteroaryl group, a monovalent non-aromatic condensed polycyclic group, a monovalent non-aromatic condensed hetero-polycyclic group, and —Si($Q_{33}$)($Q_{34}$)($Q_{35}$);

wherein $Q_{33}$ to $Q_{35}$ are each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group a phthalazinyl group, a quinoxalinyl group, a cinnolinyl group, and a quinazolinyl group.

According to an embodiment, $L_1$ to $L_3$, $L_{11}$ to $L_{13}$, $L_{21}$ to $L_{24}$ and $L_{31}$ to $L_{33}$ in Formulae 1A to 1C and 2A to 2F may be each independently one selected from Formulae 2-1 to 2-37:

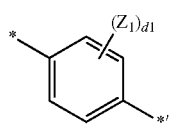

Formula 2-1

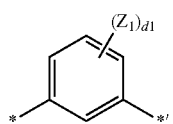

Formula 2-2

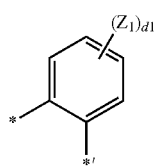

Formula 2-3

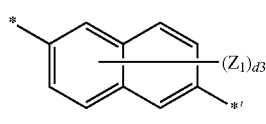

Formula 2-4

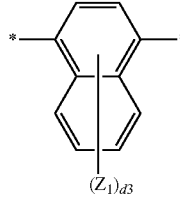

Formula 2-5

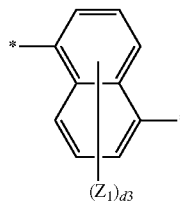

Formula 2-6

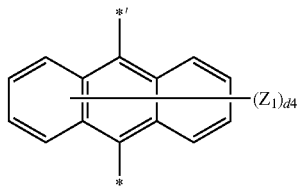

Formula 2-7

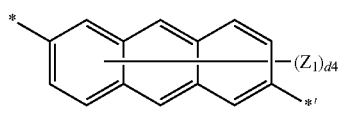

Formula 2-8

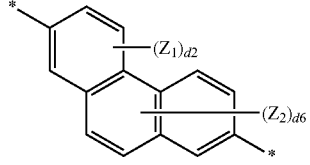

Formula 2-9

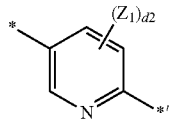

Formula 2-10

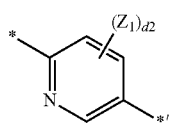

Formula 2-11

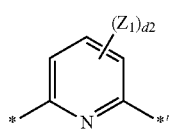

Formula 2-12

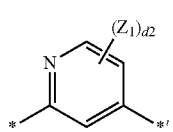

Formula 2-13

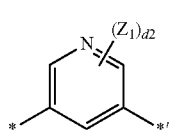

Formula 2-14

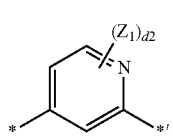

Formula 2-15

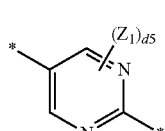

Formula 2-16

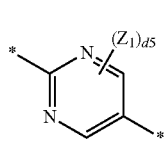

Formula 2-17

-continued

Formula 2-18

Formula 2-19

Formula 2-20

Formula 2-21

Formula 2-22

Formula 2-23

Formula 2-24

Formula 2-25

Formula 2-26

Formula 2-27

Formula 2-28

-continued

Formula 2-29

Formula 2-30

Formula 2-31

Formula 2-32

Formula 2-33

Formula 2-34

Formula 2-35

Formula 2-36

-continued

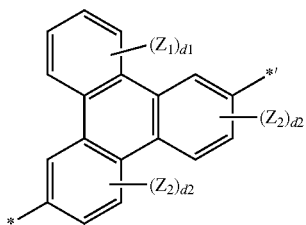

Formula 2-37 wherein in Formulae 2-1 to 2-37, $Y_1$ may be O, S, S(=O), S(=O)$_2$, C($Z_3$)($Z_4$), N($Z_5$), or Si($Z_6$)($Z_7$);

$Z_1$ to $Z_7$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, a quinoxalinyl group, a biphenyl group, and —Si($Q_{33}$)($Q_{34}$)($Q_{45}$), wherein $Q_{33}$ to $Q_{45}$ are each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group a phthalazinyl group, a quinoxalinyl group, a cinnolinyl group, and a quinazolinyl group;

d1 is an integer of 1 to 4;
d2 is an integer of 1 to 3;
d3 is an integer of 1 to 6;
d4 is an integer of 1 to 8;
d5 is an integer of 1 or 2;
d6 is an integer of 1 to 5; and
* indicates a binding site to a neighboring atom.

In some embodiments, $L_1$ to $L_3$, $L_{11}$ to $L_{13}$, $L_{21}$ to $L_{24}$ and $L_{31}$ to $L_{33}$ in Formulae 1A to 1C and 2A to 2F may be each independently selected from a phenylene group, a naphthylene group, a phenanthrenylene group, an anthracenylene group, a triphenylenylene group, and a carbazolylene group; and a phenylene group, a naphthylene group, a phenanthrenylene group, an anthracenylene group, a triphenylenylene group, and a carbazolylene group each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, a triphenylenyl group, a phenanthrenyl group, and a biphenyl group, but they are not limited thereto.

In some embodiments, $L_1$ to $L_3$, $L_{11}$ to $L_{13}$, $L_{21}$ to $L_{24}$ and $L_{31}$ to $L_{33}$ in Formulae 1A to 1C and 2A to 2F may be each independently one of Formulae 3-1 to 3-33, but are not limited thereto:

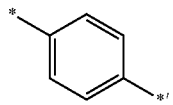

Formula 3-1

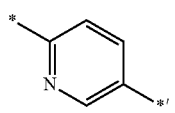

Formula 3-2

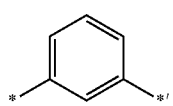

Formula 3-3

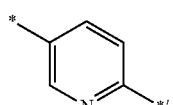

Formula 3-4

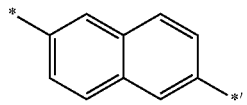

Formula 3-5

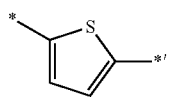

Formula 3-6

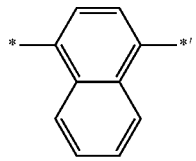

Formula 3-7

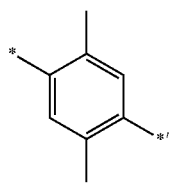

Formula 3-8

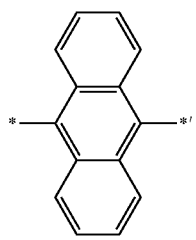

Formula 3-9

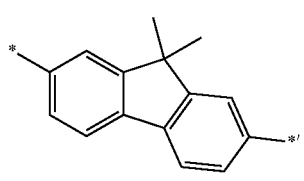

Formula 3-10

-continued
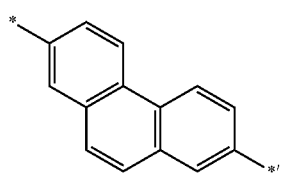
Formula 3-11
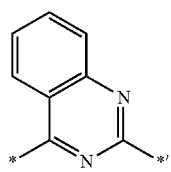
Formula 3-12
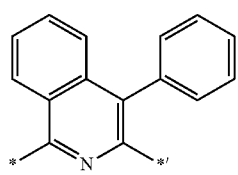
Formula 3-13
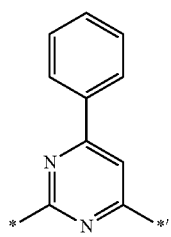
Formula 3-14
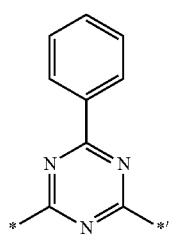
Formula 3-15
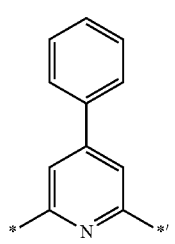
Formula 3-16
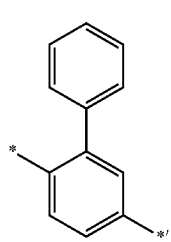
Formula 3-17
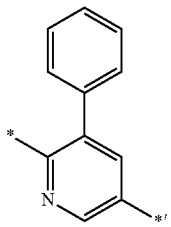
Formula 3-18
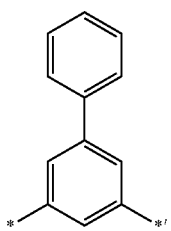
Formula 3-19
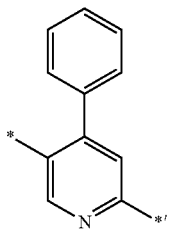
Formula 3-20
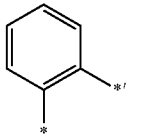
Formula 3-21
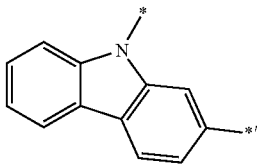
Formula 3-22
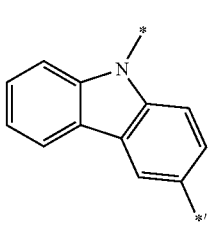
Formula 3-23
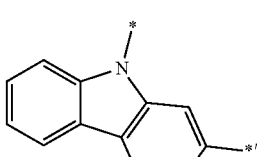
Formula 3-24
Formula 3-25

Formula 3-26
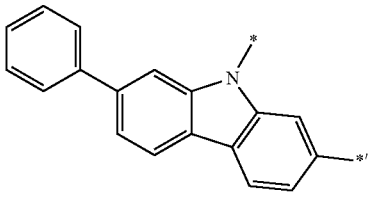

Formula 3-27
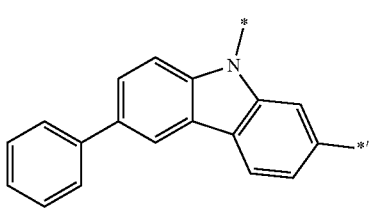

Formula 3-28
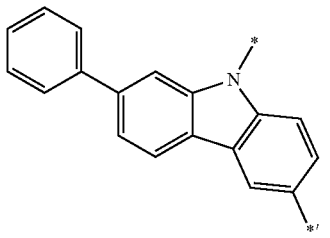

Formula 3-29
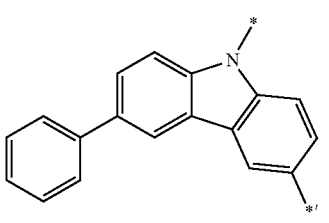

Formula 3-30
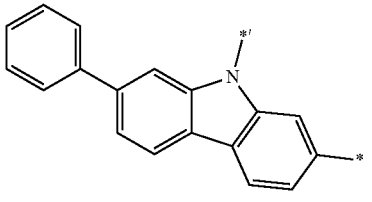

Formula 3-31
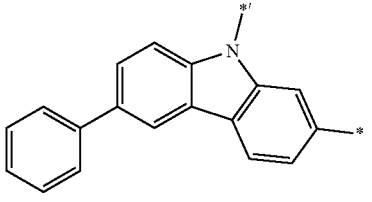

Formula 3-32
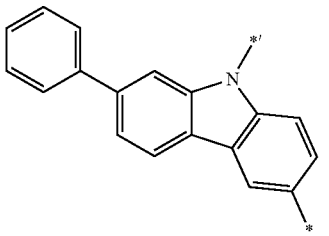

Formula 3-33
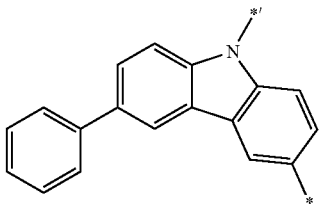

wherein * and *' in Formulae 3-1 to 3-33 each independently indicates a binding site to a neighboring atom.

a1 in Formulae 1A to 1C indicates the number of $L_1$, and may be 0, 1, 2, 3, 4 or 6, for example, 0, 1 or 2, or for example, 0 or 1. When a1 is 0, $L_1$ is a single bond. When a1 is 2 or more, groups $L_1$ may be identical or different. a2 to a3, a11 to a13, a21 to a24 and a31 to a33 may be understood by referring to the description presented in connection with a1 and structures of Formulae 1A to 1C and 2A to 2F.

According to an embodiment, a1 to a3, a11 to a13, a21 to a24 and a31 to a33 in Formula 1 may be each independently 0, 1, or 2, for example 0 or 1, but they are not limited thereto.

$R_1$, $R_2$, $R_{11}$ to $R_{13}$, $R_{21}$ to $R_{23}$, and $R_{31}$ to $R_{33}$ in Formulae 1A to 1C and 2A to 2F may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, a group represented by Formula 2A, a group represented by Formula 2B, —N($Q_1$)($Q_2$), —Si($Q_3$)($Q_4$)($Q_5$), and —B($Q_6$)($Q_7$).

For example, $R_1$, $R_2$, $R_{11}$ to $R_{13}$, $R_{21}$ to $R_{23}$, and $R_{31}$ to $R_{33}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, and a phosphoric acid or a salt thereof;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, phenanthridinyl, acridinyl, phenanthrolinyl, phenazinyl, a benzoimidazolyl group, a benzofuranyl group, a benzothiophenyl group, an isobenzothiazolyl group, a benzooxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a phenyl group substituted with a $C_1$-$C_{20}$ alkyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, a biphenyl group, and —Si($Q_{33}$)($Q_{34}$)($Q_{35}$); and —Si($Q_3$)($Q_4$)($Q_5$);

wherein $Q_3$ to $Q_5$ and $Q_{33}$ to $Q_{35}$ are each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group.

In some embodiments, $R_1$, $R_2$, $R_{11}$ to $R_{13}$, $R_{21}$ to $R_{23}$, and $R_{31}$ to $R_{33}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, and a phosphoric acid or a salt thereof;

one selected from Formulae 4-1 to 4-51, 5-1 to 5-6, and 6-1 to 6-5; and

—Si($Q_3$)($Q_4$)($Q_5$), wherein $Q_3$ to $Q_5$ may be each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group, but they are not limited thereto.

Formula 4-1

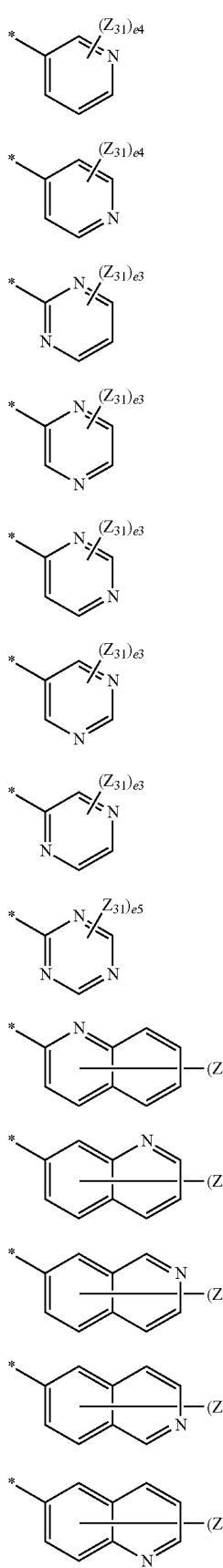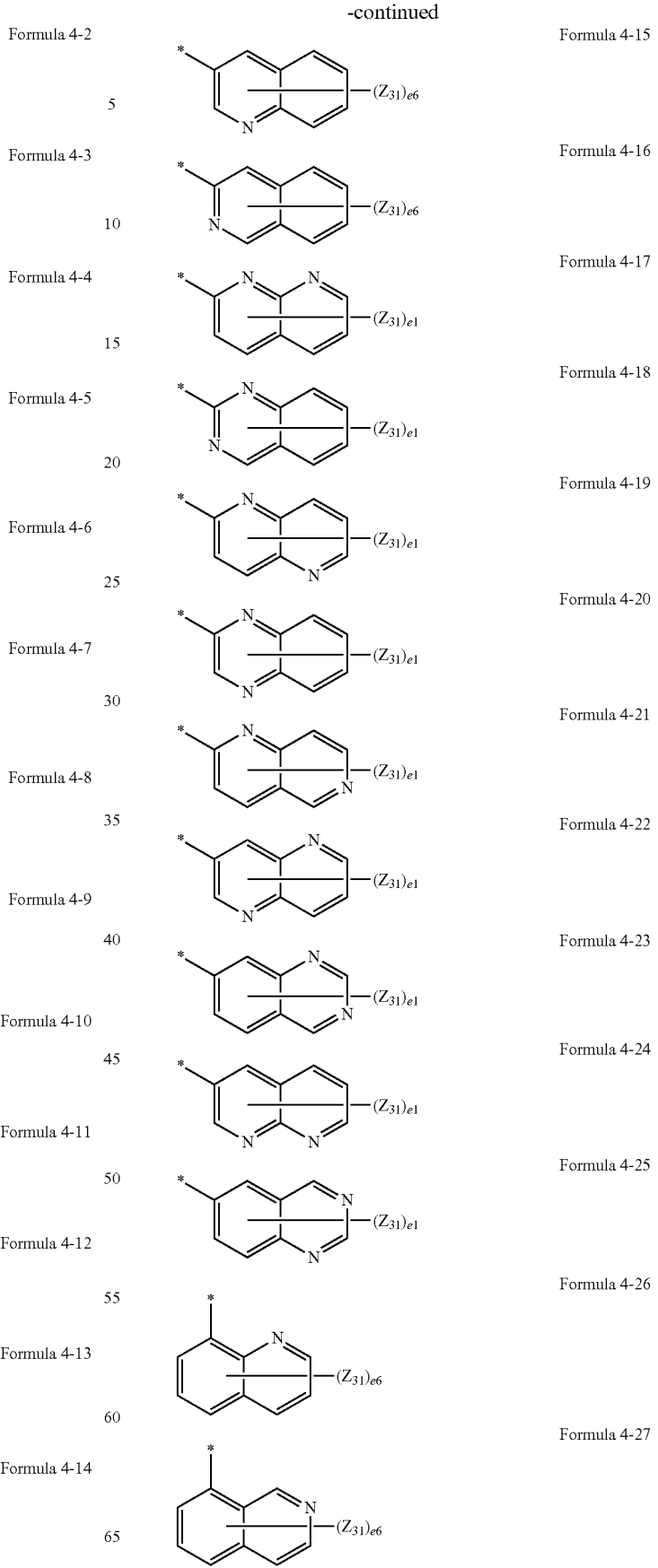

Formula 4-28
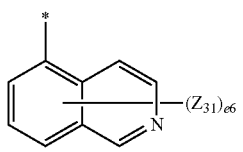
Formula 4-29
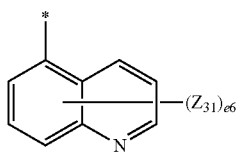
Formula 4-30
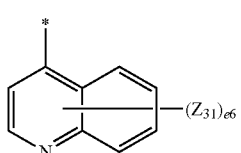
Formula 4-31
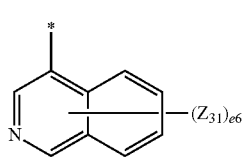
Formula 4-32
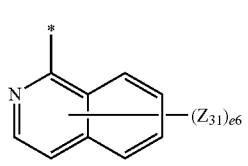
Formula 4-33
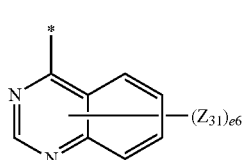
Formula 4-34
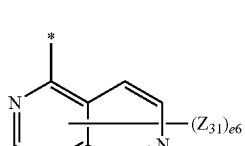
Formula 4-35
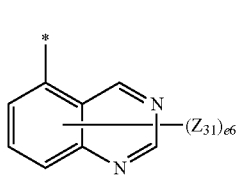
Formula 4-36
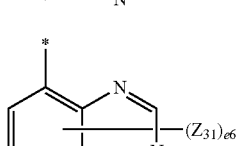
Formula 4-37
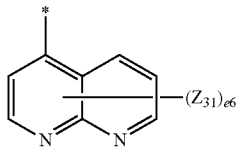
Formula 4-38
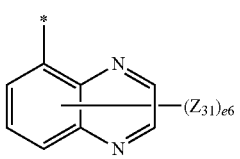
Formula 4-39
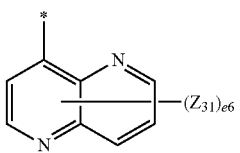
Formula 4-40
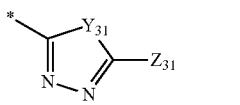
Formula 4-41
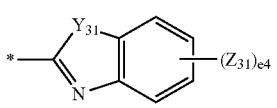
Formula 4-42
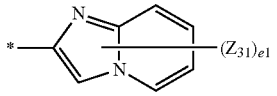
Formula 4-43
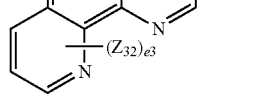
Formula 4-44
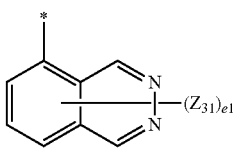
Formula 4-45
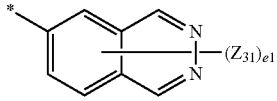
Formula 4-46
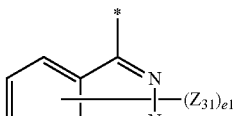
Formula 4-47
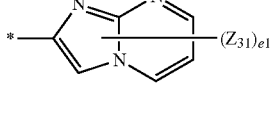
Formula 4-48
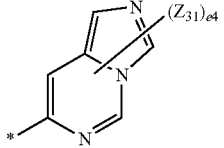

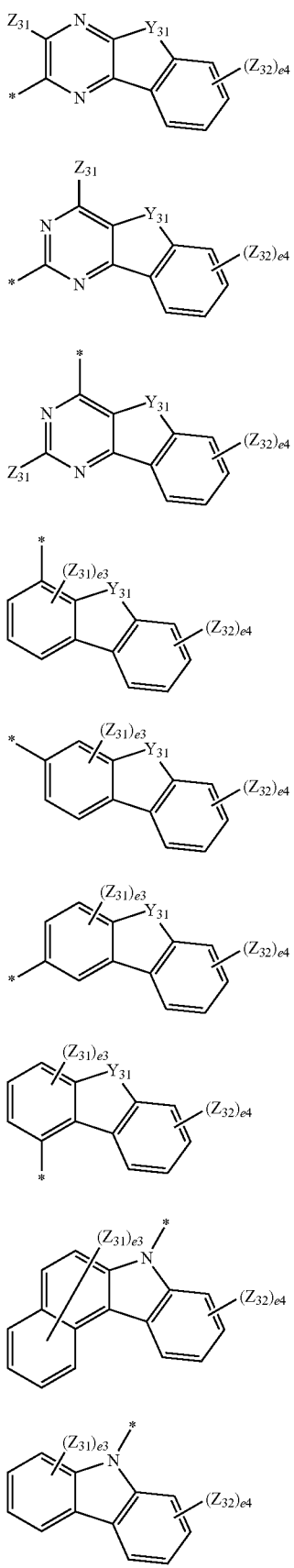

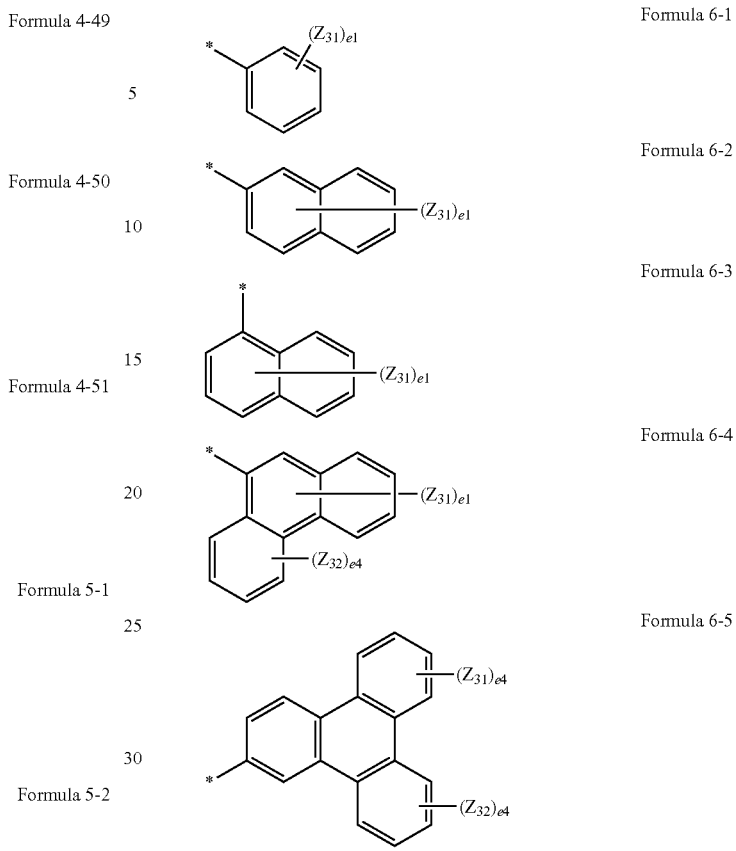

wherein in Formulae 4-1 to 4-51, 5-1 to 5-6, and 6-1 to 6-5, $Y_{31}$ is O, S, $C(Z_{33})(Z_{34})$, $N(Z_{35})$, or $Si(Z_{36})(Z_{37})$;

$Z_{31}$ to $Z_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group substituted with a $C_1$-$C_{20}$ alkyl group, a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, a quinoxalinyl group, a biphenyl group, and —$Si(Q_{33})(Q_{34})(Q_{35})$; wherein $Q_{33}$ to $Q_{35}$ are each independently selected from a hydrogen, a $C_1$-$C_{20}$ alkyl group, a $C_1$-$C_{20}$ alkoxy group, a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group;

e1 is an integer of 1 to 5;
e2 is an integer of 1 to 7;
e3 is an integer of 1 to 3;

e4 is an integer of 1 to 4;

e5 is an integer of 1 or 2;

e6 is an integer of 1 to 6; and

* indicates a binding site to a neighboring atom.

b1, b2, b11 to b13, b21 to b23, and b31 to b33 in the formulae above may be each independently an integer selected from 0 to 4. For example, b1, b2, b11 to b13, b21 to b23 and b31 to b33 may be each independently 0 or 1, but they are not limited thereto.

Formula 2A may be represented by one of Formulae 2A(1) to 2A(5) below, Formula 2B may be represented by one of Formulae 2B(1) and 2B(2) below, Formula 2D may be represented by one of Formulae 2D(1) to 2D(5) below, and Formula 2F may be represented by one of Formulae 2F(1) and 2F(2) below:

Formula 2A(1)

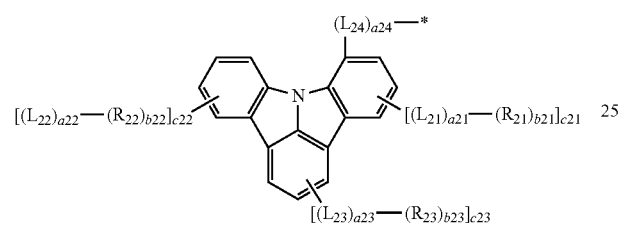

Formula 2A(2)

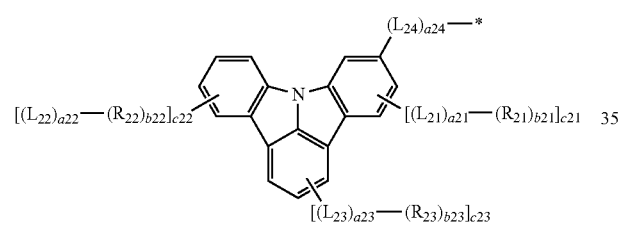

Formula 2A(3)

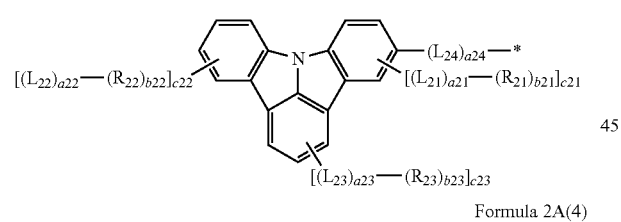

Formula 2A(4)

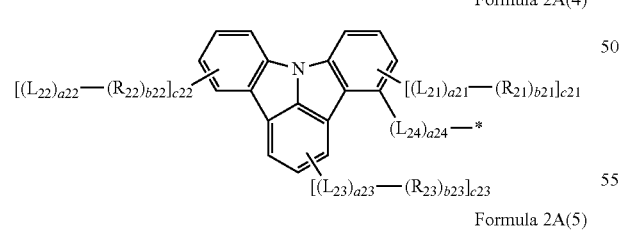

Formula 2A(5)

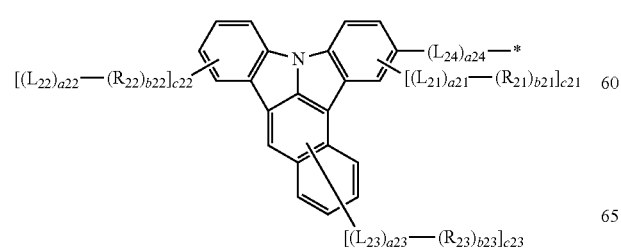

-continued

Formula 2B(1)

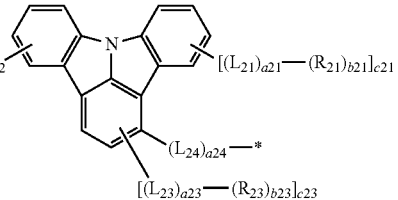

Formula 2B(2)

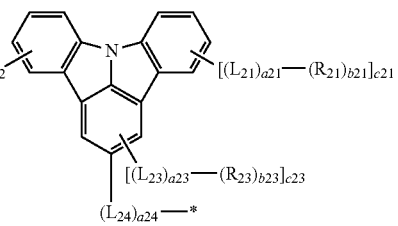

Formula 2E(1)

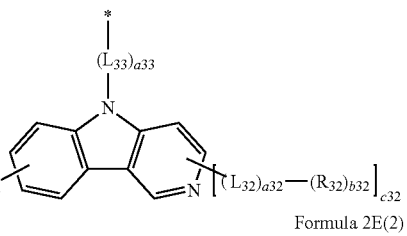

Formula 2E(2)

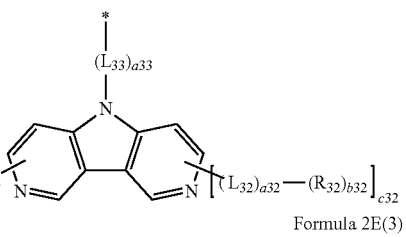

Formula 2E(3)

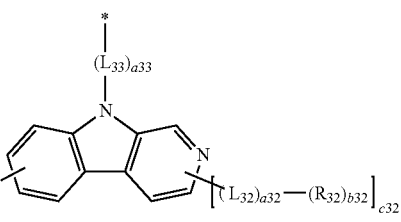

Formula 2E(4)

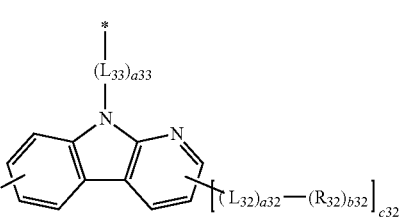

Formula 2E(5)

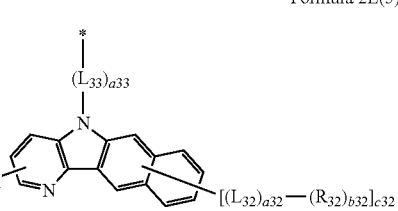

Formula 2F(1)

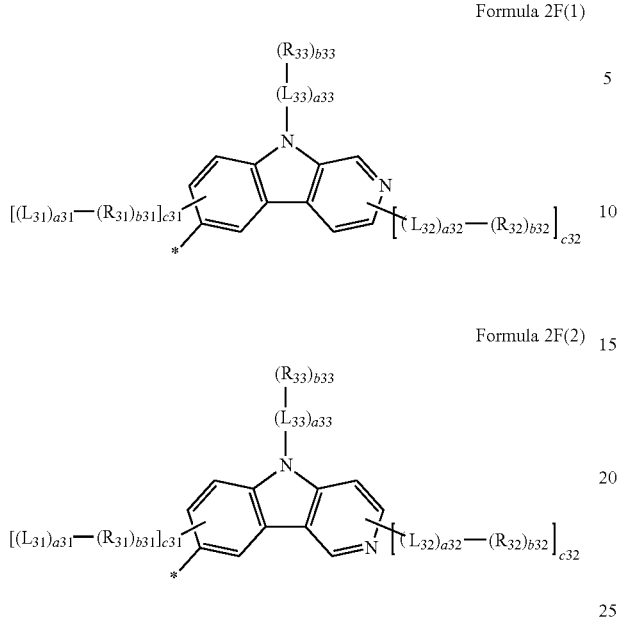

Formula 2F(2)

$L_{21}$ to $L_{24}$, a21 to a24, $R_{21}$ to $R_{23}$, b21 to b23, $L_{31}$ to $L_{33}$, a31 to a33, $R_{31}$ to $R_{33}$, b31 to b33, c21 to c23, c31, and c32 in Formulae 2A(1) to 2A(5), 2B(1), 2B(2), 2E(1) to 2E(5), 2F(1), and 2F(2) are as described above.

For example, a24 in Formulae 2A(1) to 2A(5), 2B(1), and 2B(2) is 0, 1, or 2, and $L_{24}$ is selected from Formulae 2-1 to 2-37, and c11, c12, and c13 may each be a hydrogen, but they are not limited thereto.

The condensed cyclic compound represented by Formula 1 may be represented by one of Formulae 1A(1) to 1A(8) below:

Formula 1A(1)

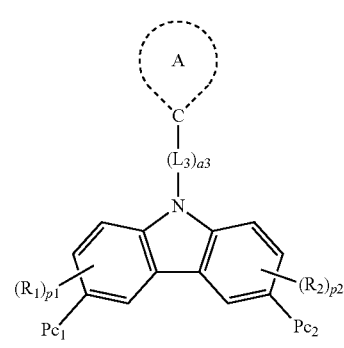

Formula 1A(2)

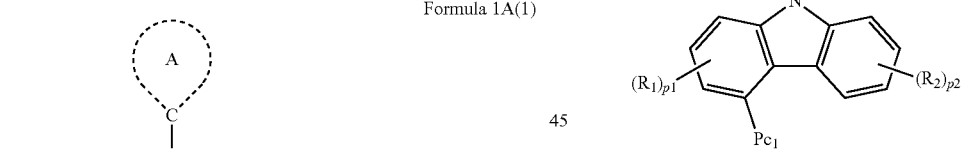

Formula 1A(3)

Formula 1A(4)

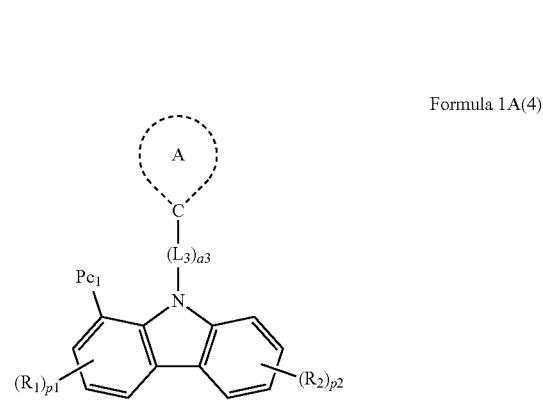

Formula 1A(5)

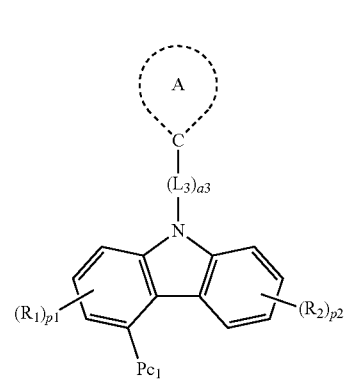

Formula 1A(6)

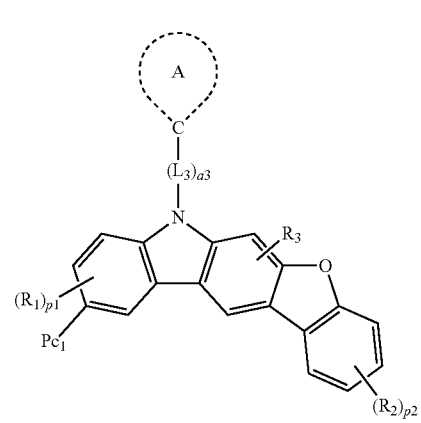

Formula 1A(7)

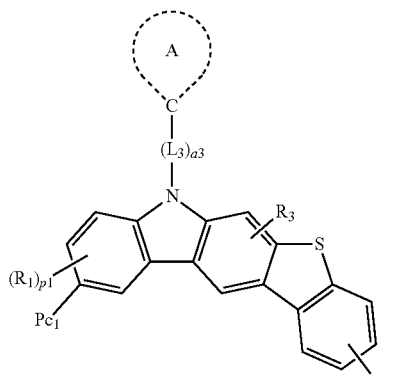

Formula 1A(8)

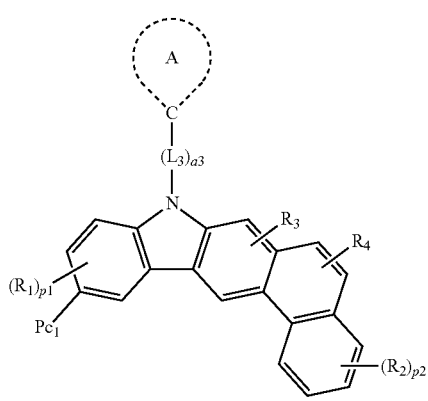

In Formulae 1A(1) and 1A(8),

Ring A is a substituted or unsubstituted $C_2$-$C_{10}$ heterocycloalkyl group, a substituted or unsubstituted $C_2$-$C_{10}$ heterocycloalkenyl group, a substituted or unsubstituted $C_2$-$C_{60}$ heteroaryl group, or a substituted or unsubstituted monovalent non-aromatic condensed hetero-polycyclic group, each including Moiety 1 as a ring-forming moiety, (for example, a group represented by one of Formulae 4-1 to 4-55), $Pc_2$, $Pc_2$, $L_3$, a3, $R_1$, $R_2$, p1, and p2 are as described above, and $R_3$ to $R_4$ are as described above.

In some embodiments, the condensed cyclic compound represented by Formula 1 may be represented by one of Formulae 1B(1) to 1B(10) below:

Formula 1B(1)

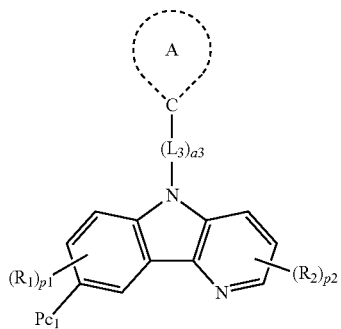

Formula 1B(2)

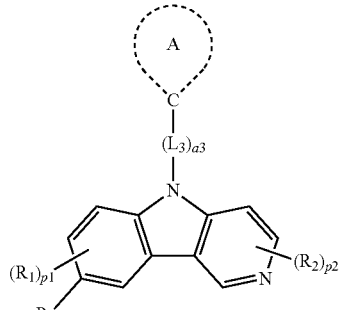

Formula 1B(3)

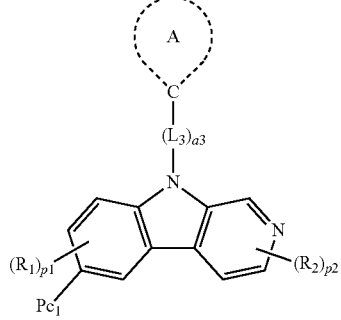

Formula 1B(4)

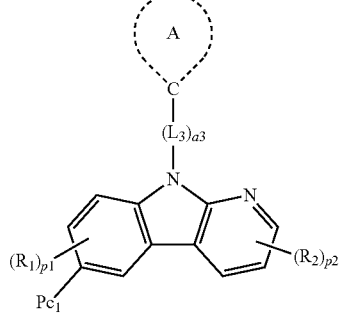

Formula 1B(5)

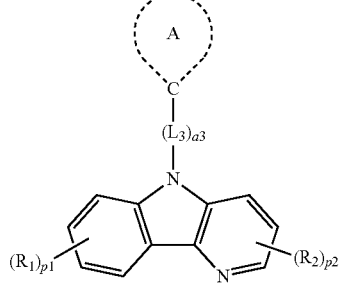

Formula 1B(6)

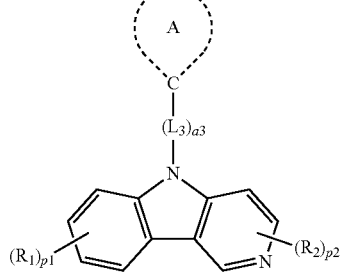

-continued

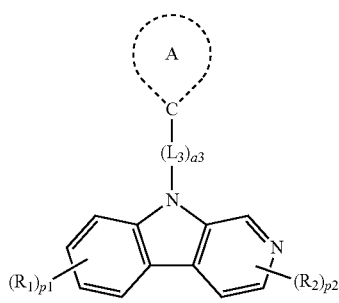
Formula 1B(7)

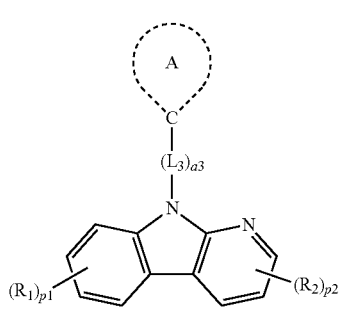
Formula 1B(8)

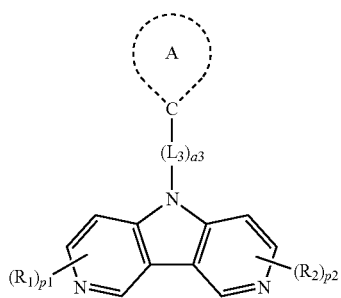
Formula 1B(9)

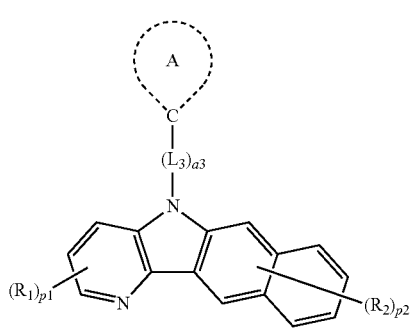
Formula 1B(10)

Ring A, Pc$_1$, Pct, L$_3$, a3, R$_1$, R$_2$, p1, and p2 in Formulae 1B(1) to 1B(10) are as described above.

In some embodiments, the condensed cyclic compound may be represented by Formulae 1C(1) or 1C(2) below:

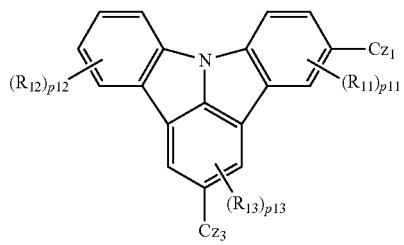
Formula 1C(1)

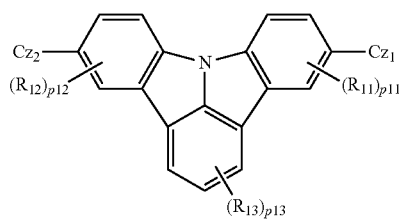
Formula 1C(2)

Cz$_1$, Cz$_2$, Cz$_3$, R$_{11}$, R$_{12}$, R$_{13}$, p11, p12, and p13 in Formulae 1C(1) and 1C(2) are as described above.

In some embodiments, the condensed cyclic compound may be represented by Formulae 1C(3) below:

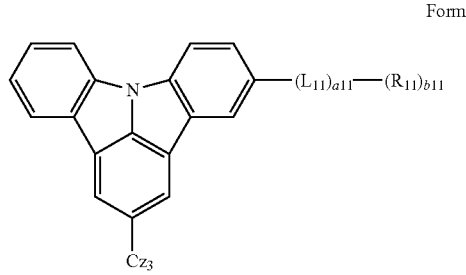
Formula 1C(3)

wherein in Formula 1C(3),

Cz$_3$, L$_{11}$, and a11 are as described above;

R$_{11}$ may be a substituted or unsubstituted C$_2$-C$_{10}$ heterocycloalkyl group, a substituted or unsubstituted C$_2$-C$_{10}$ heterocycloalkenyl group, a substituted or unsubstituted C$_2$-C$_{60}$ heteroaryl group, or a substituted or unsubstituted monovalent non-aromatic condensed hetero-polycyclic group, each including Moiety 1 as a ring-forming moiety, (for example, a group represented by one of Formulae 4-1 to 4-55); and b11 is 1 or 2.

In some embodiments, the condensed cyclic compound may be represented by Formulae 1C(4) or 1C(5) below:

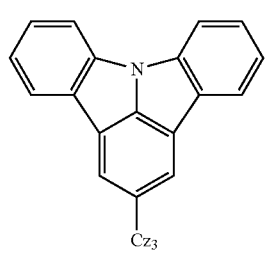
Formula 1C(4)

Formula 1C(5)
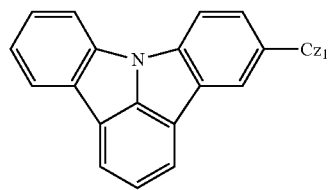
wherein in Formulae 1C (4) and 1C (5), $Cz_1$ and $Cz_3$ are each a group represented by Formula 2E or a group represented by Formula 2F.
The condensed cyclic compound may be one of Compounds 1 to 76 below, but is not limited thereto:
1
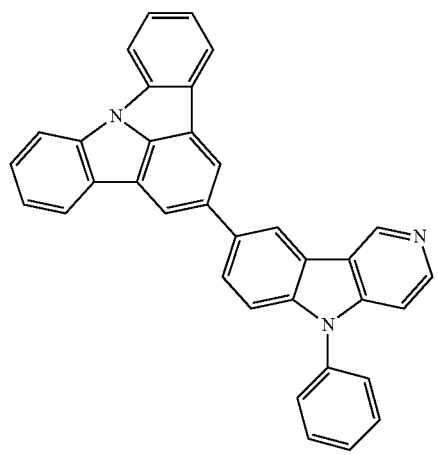
2
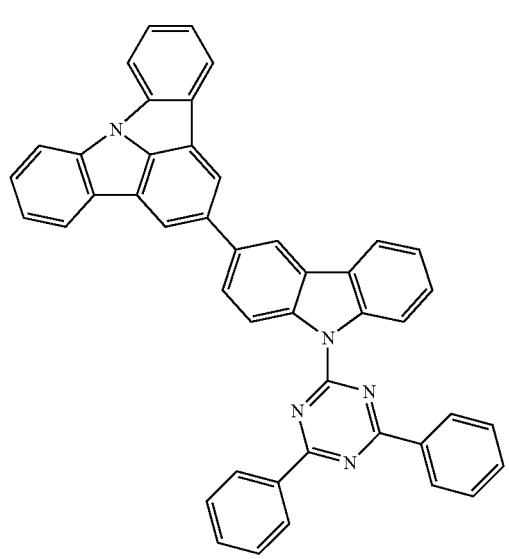
3
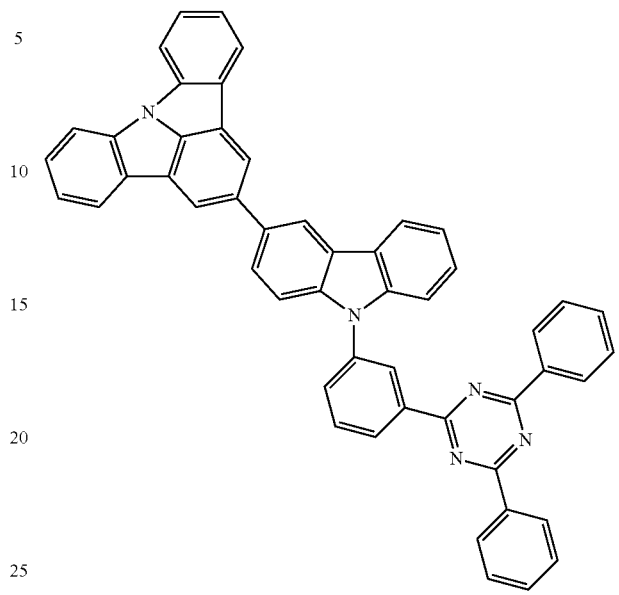
4
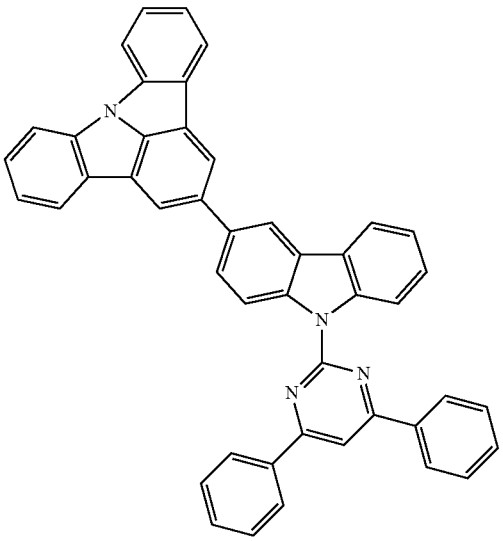

-continued
5
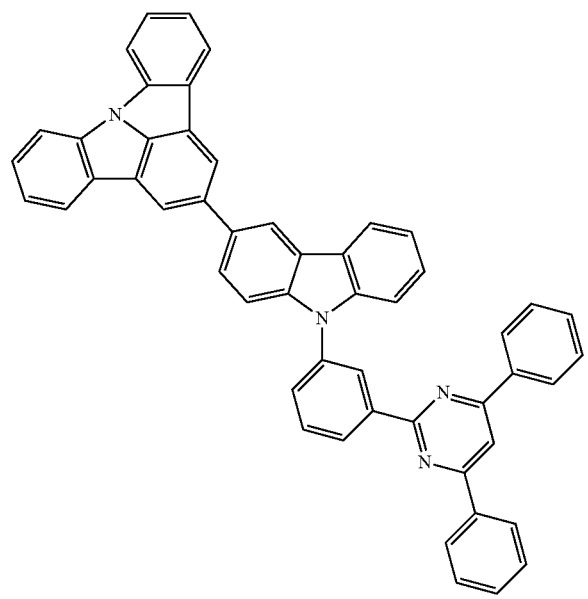
6
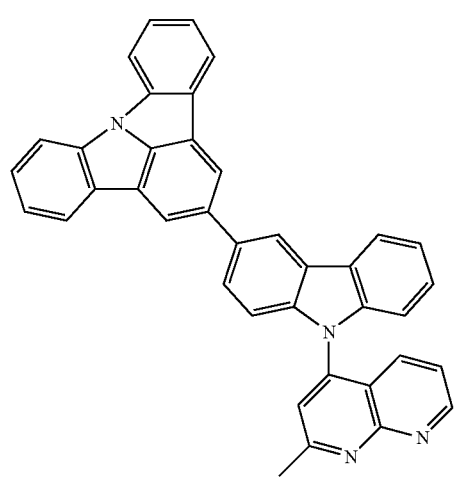
7
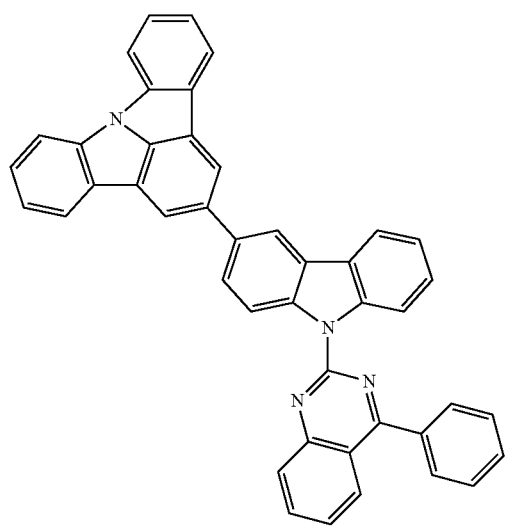
8
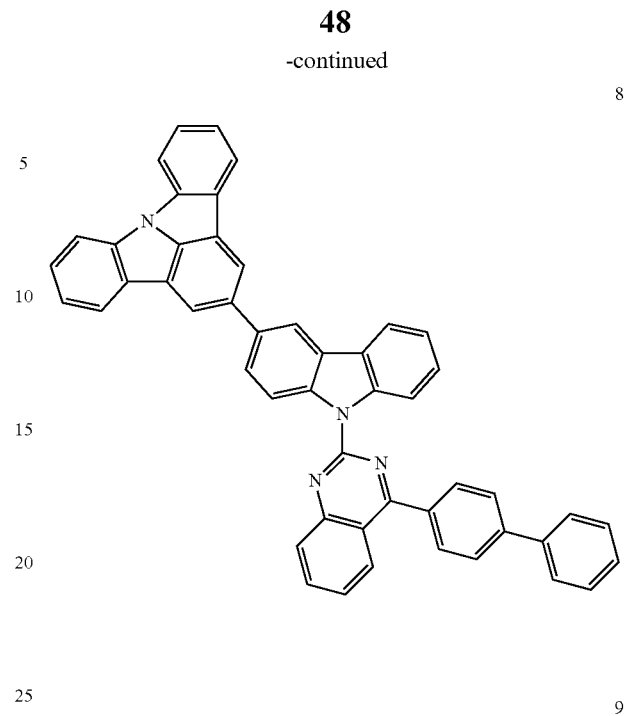
9
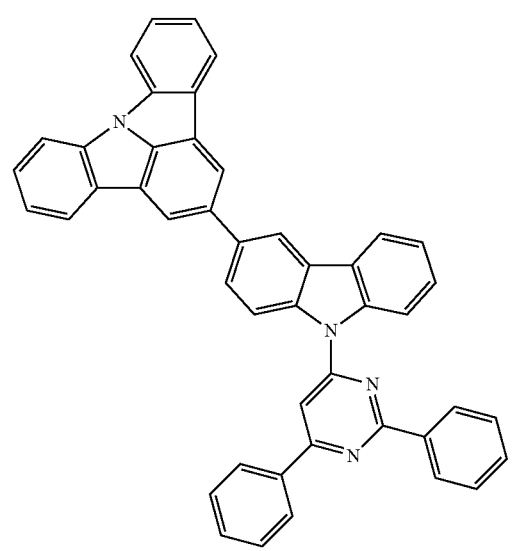
10
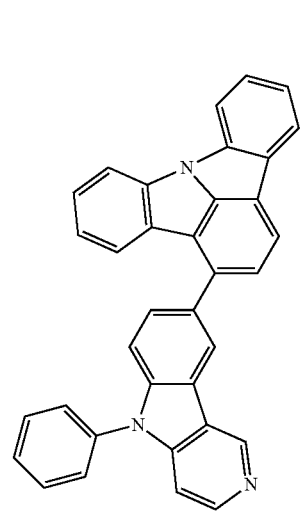

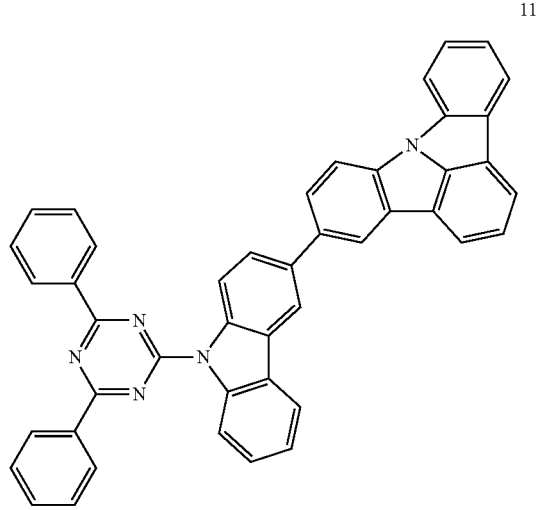
11
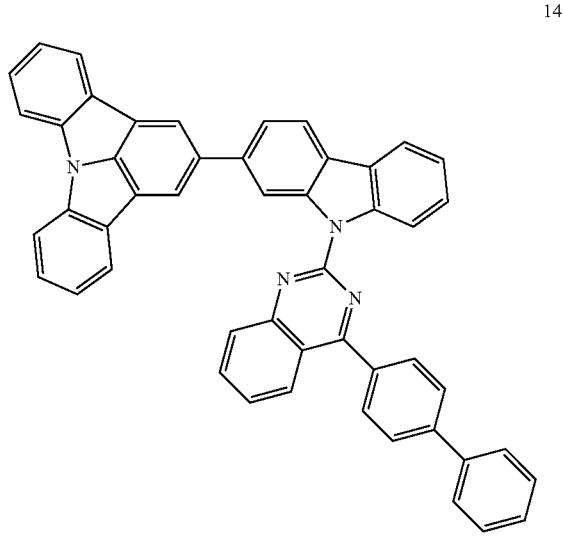
14
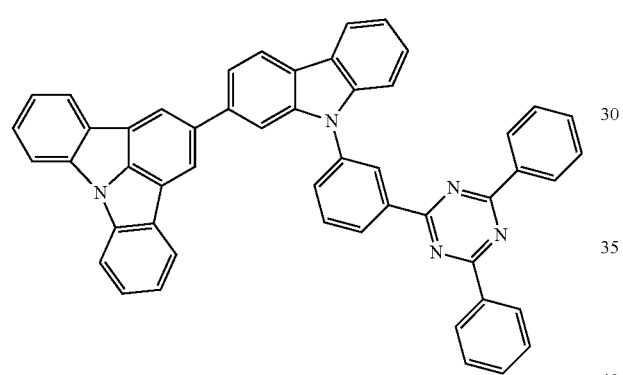
12
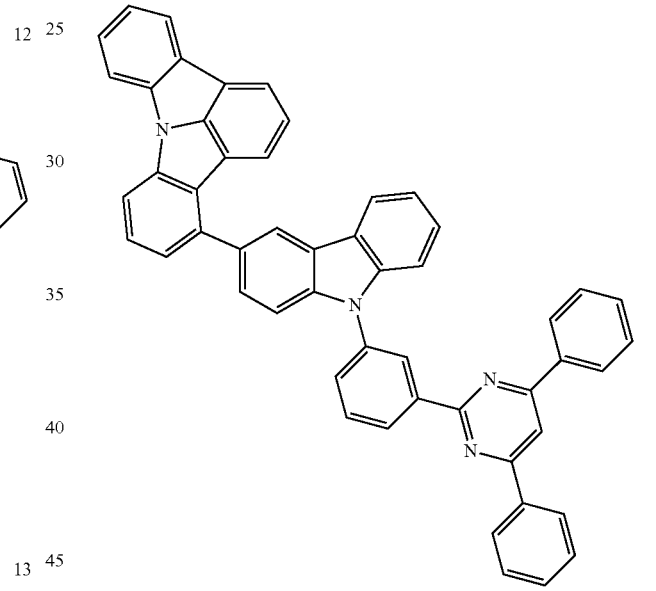
15
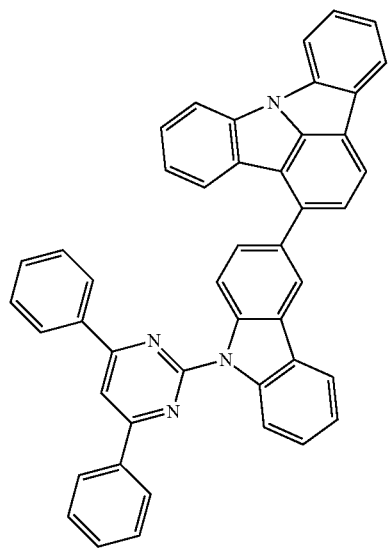
13
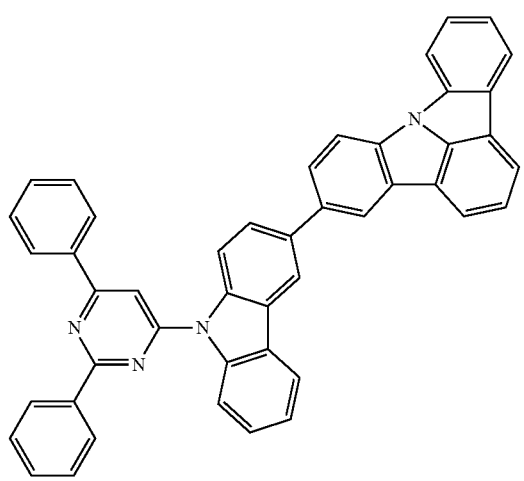
16

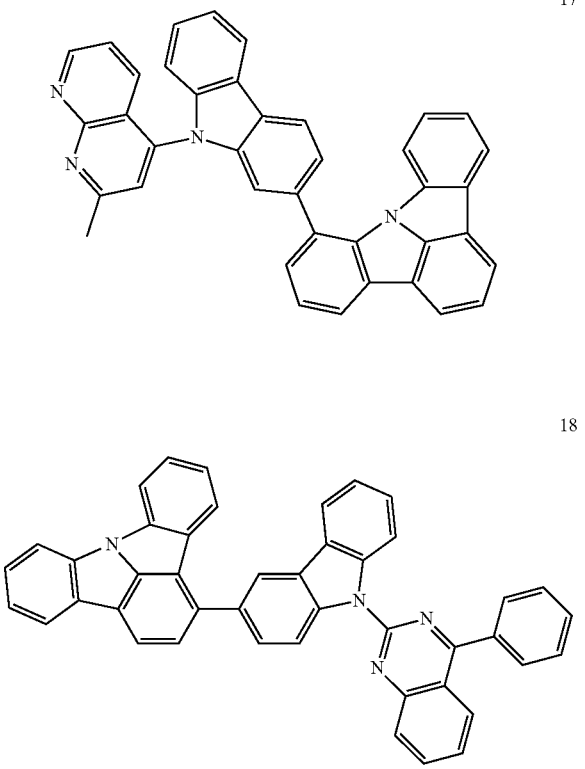
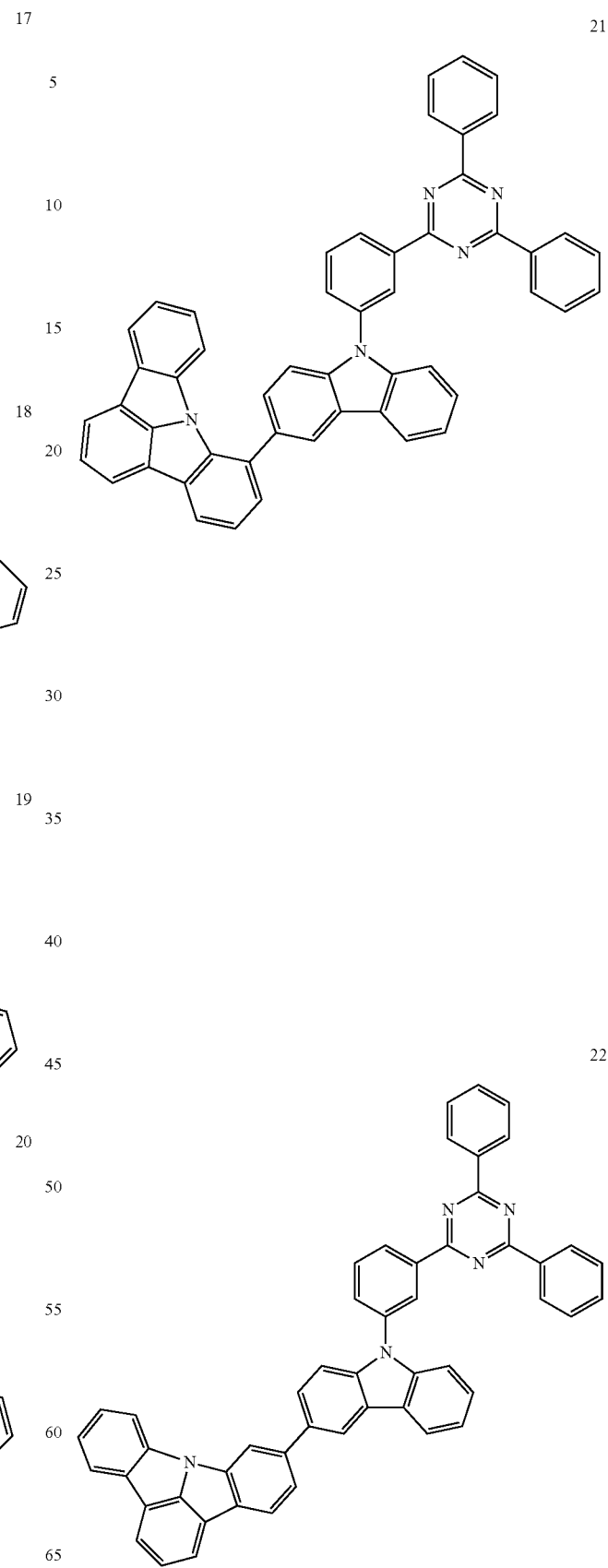

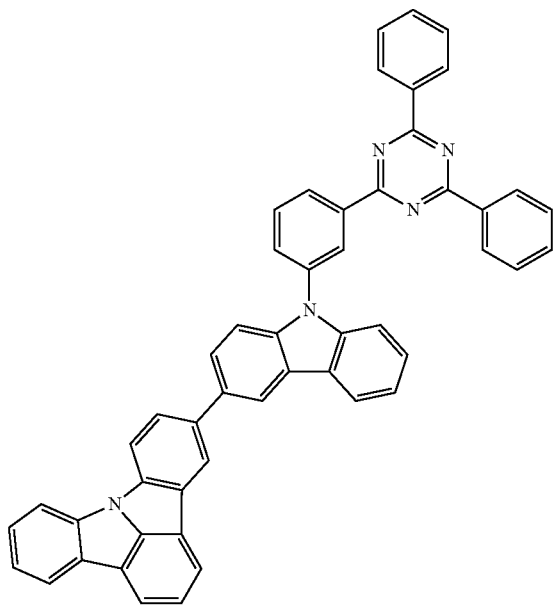
23
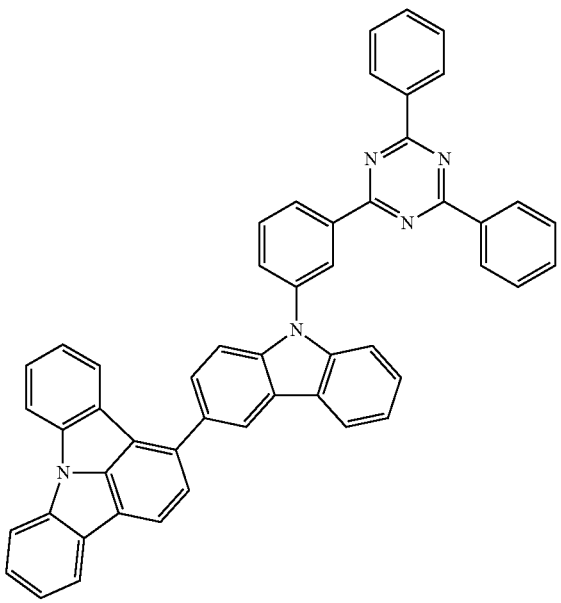
25
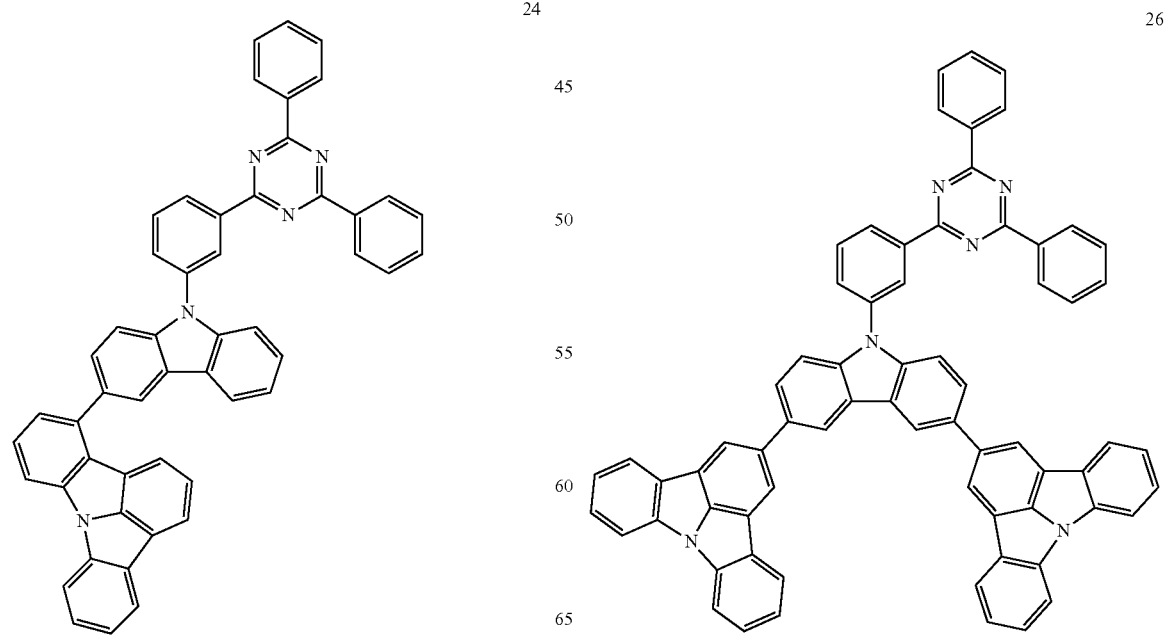
24
26

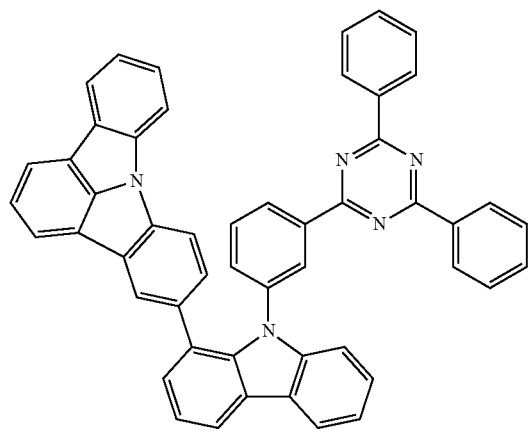
27
28
29
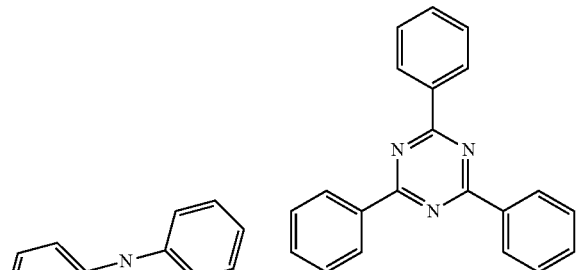
30
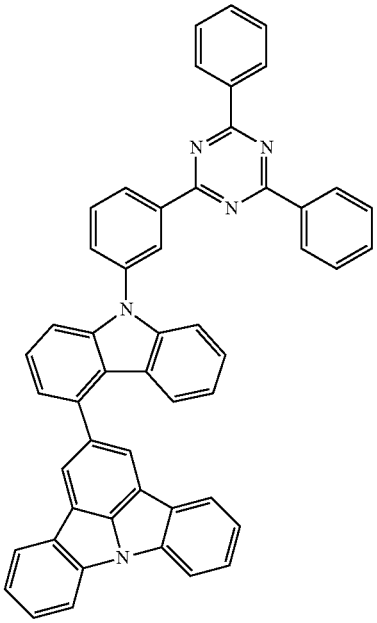
31
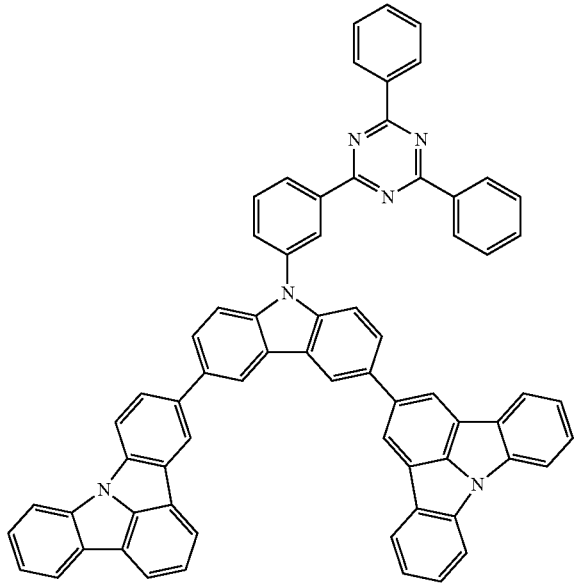
32

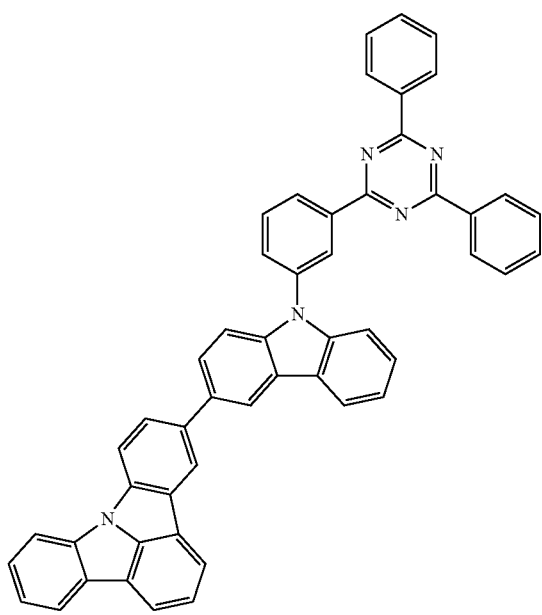
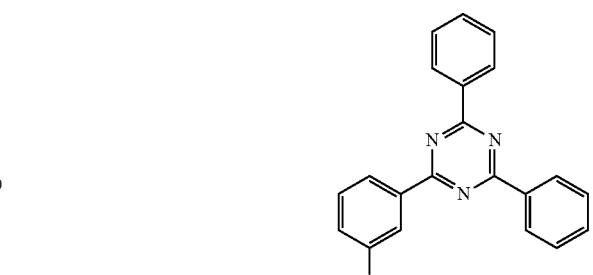
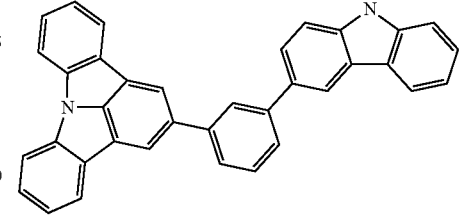
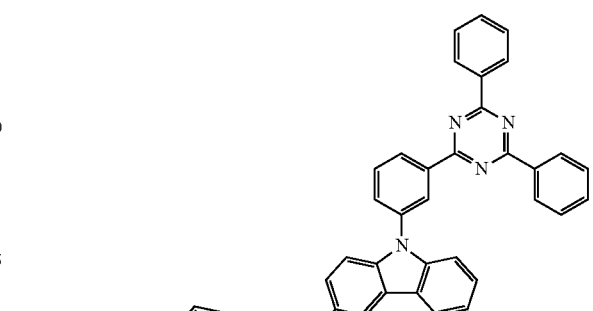
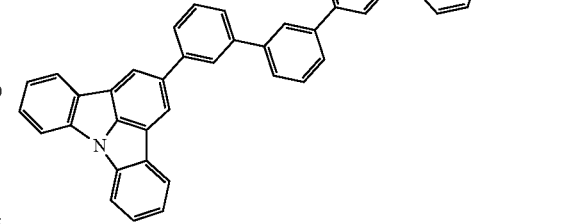
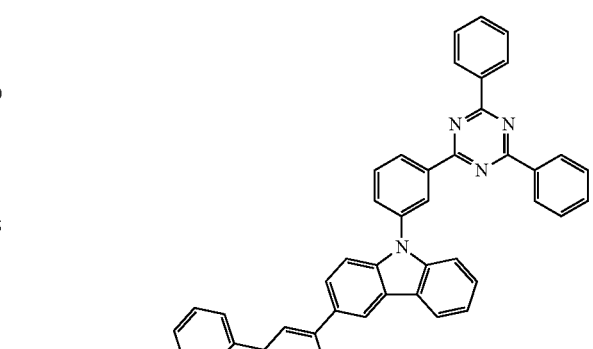
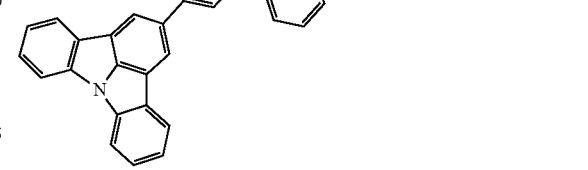

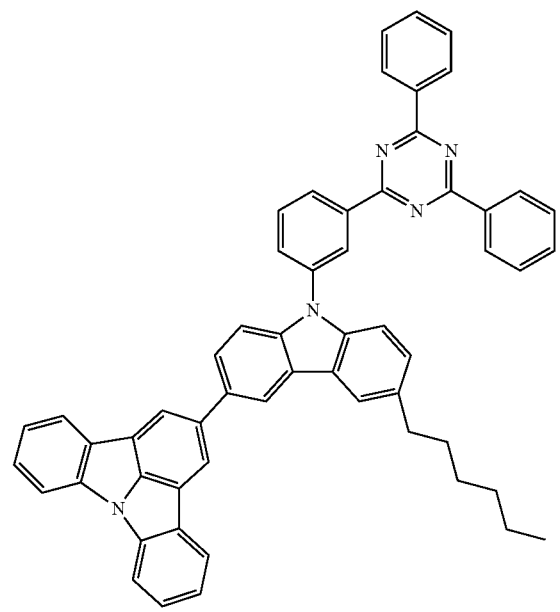
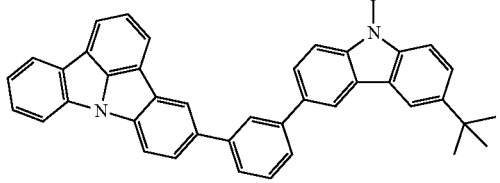
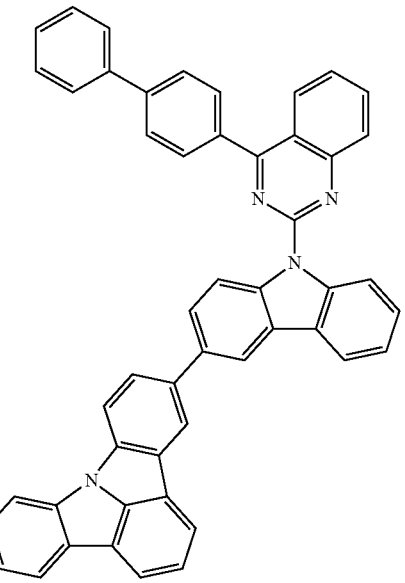
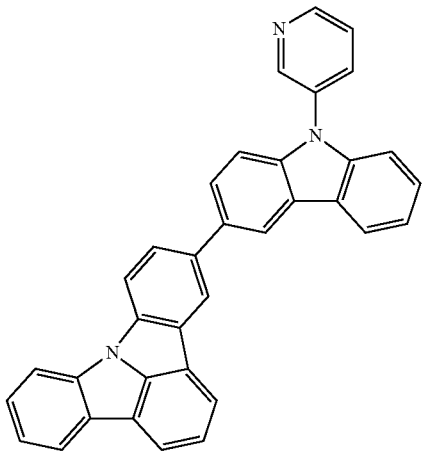
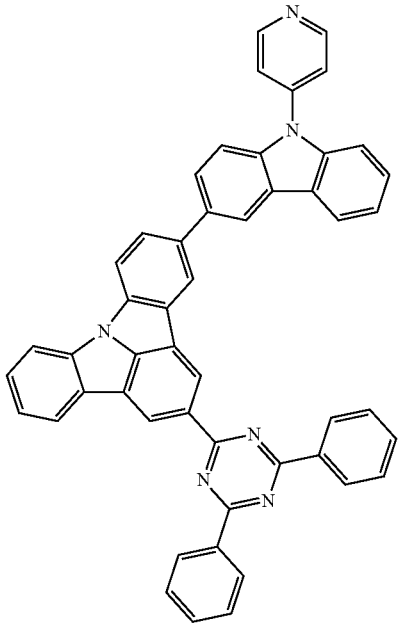

45
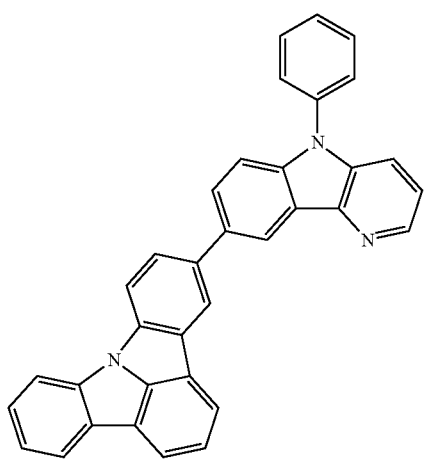
46
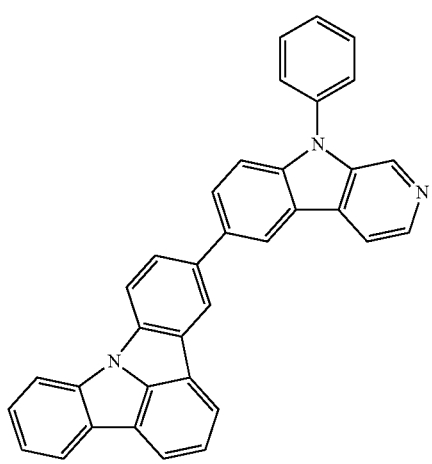
47
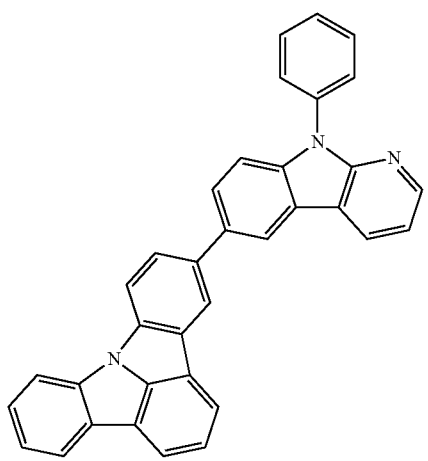
48
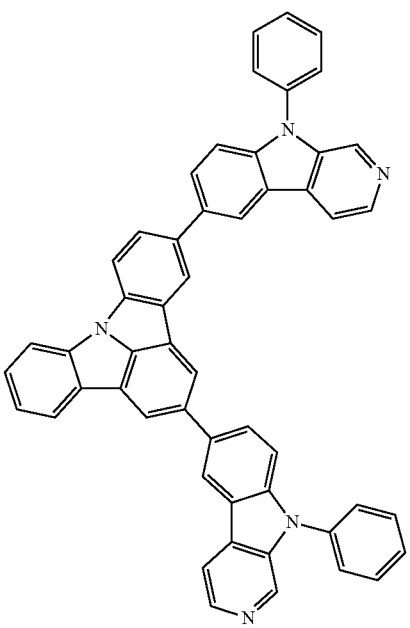
49
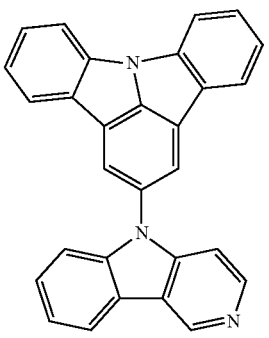
50
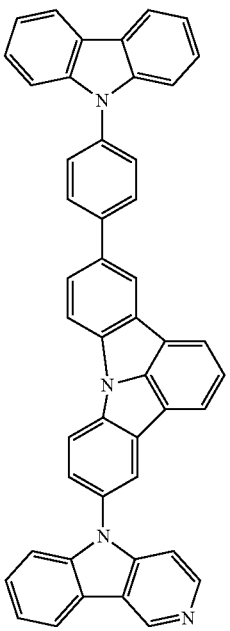

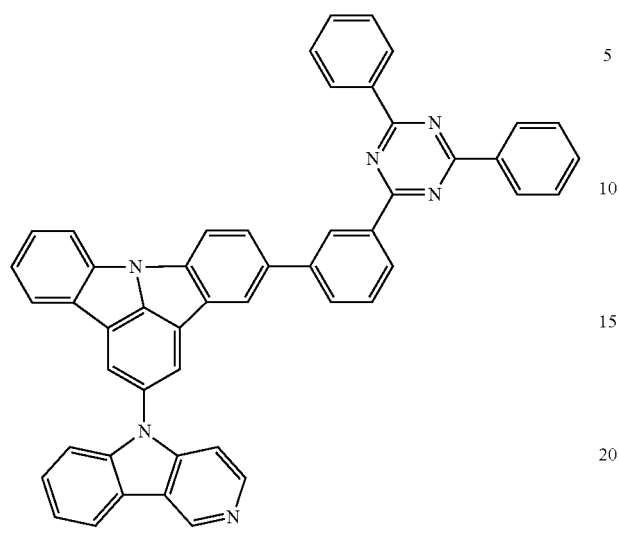
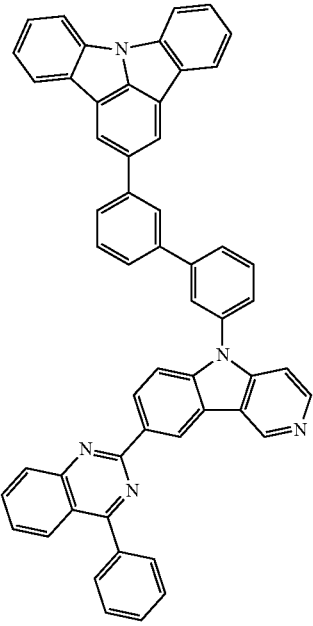
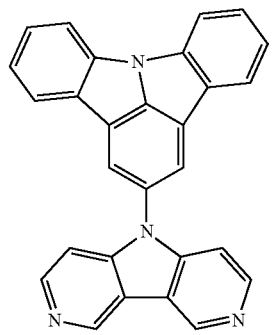
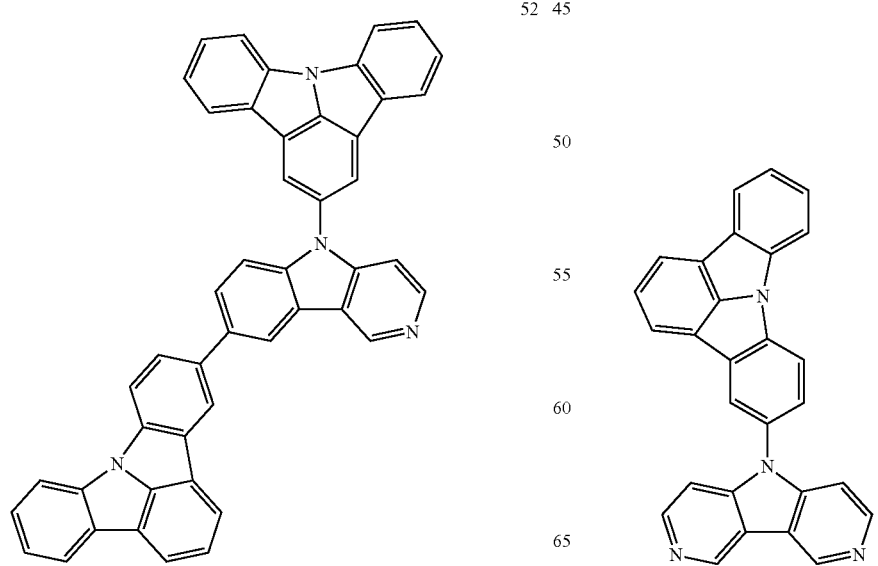

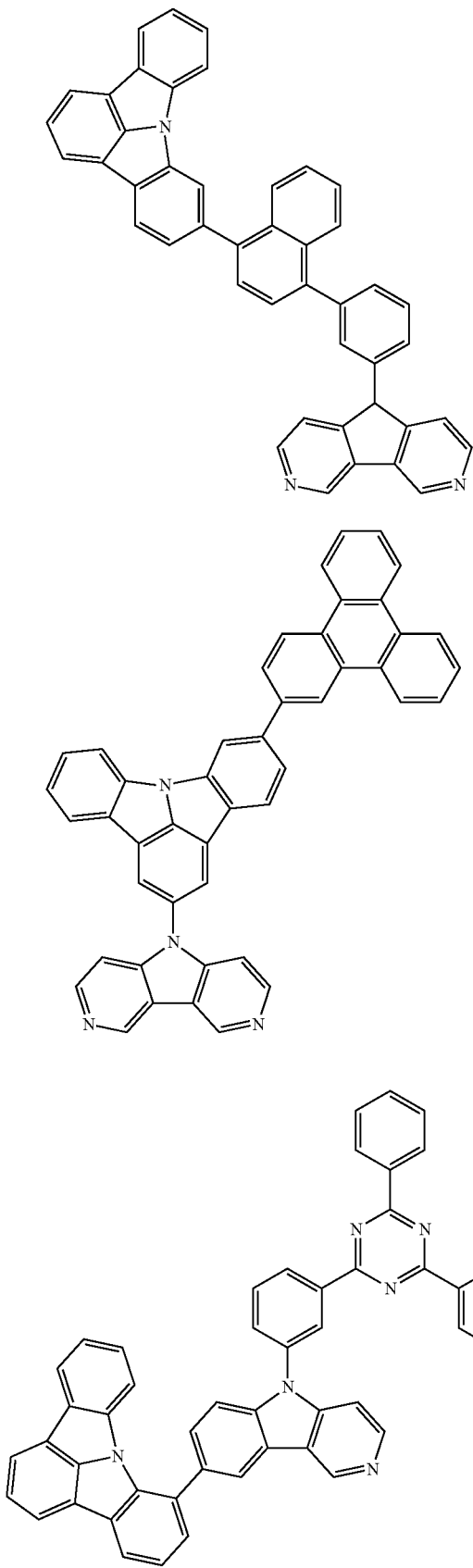
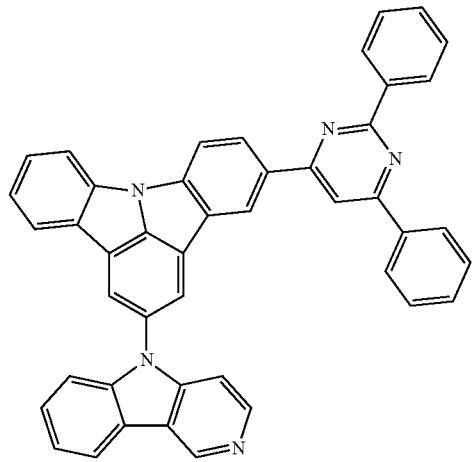
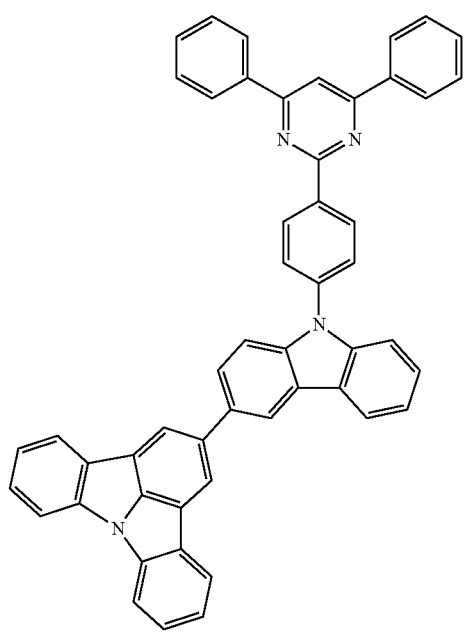

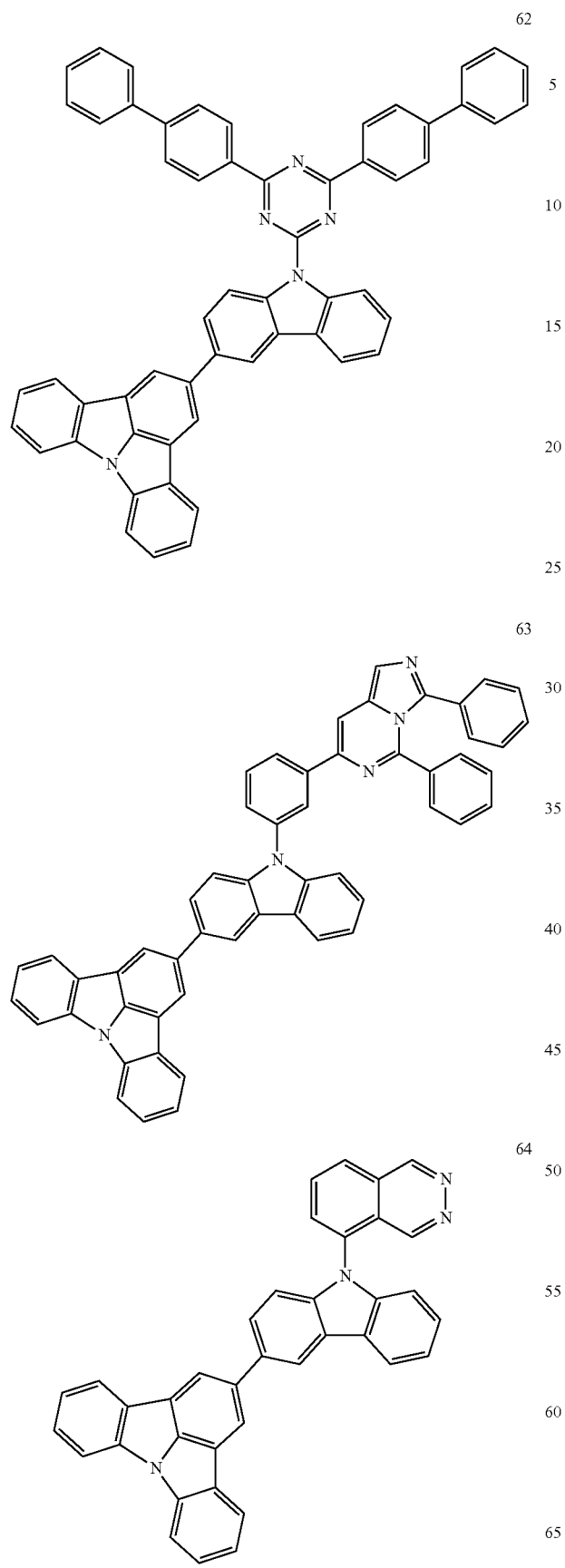
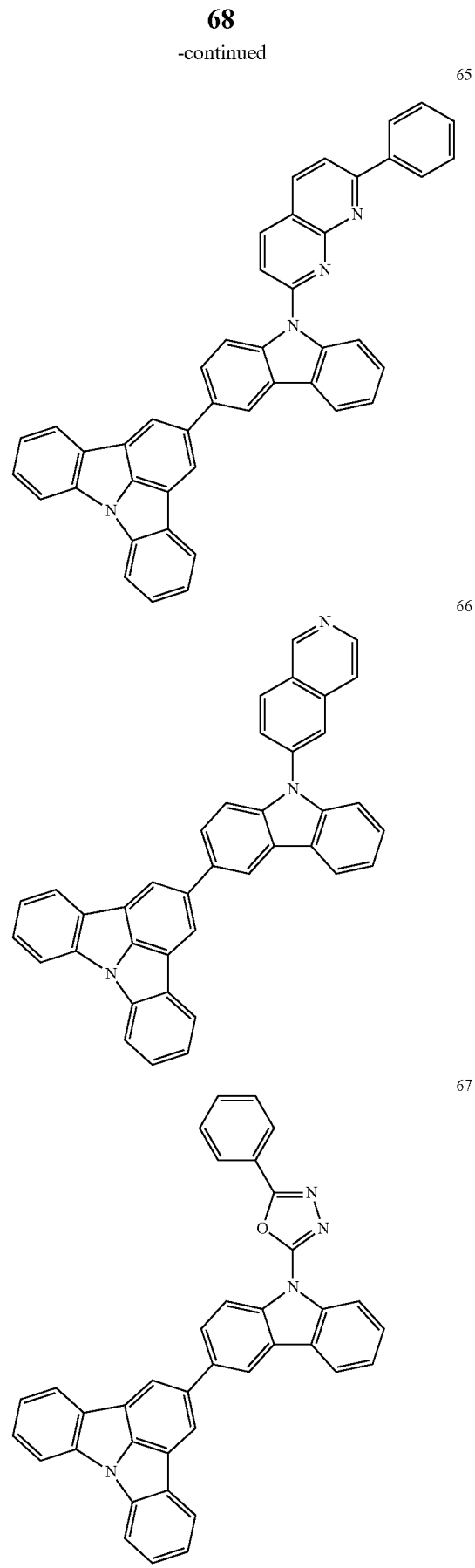

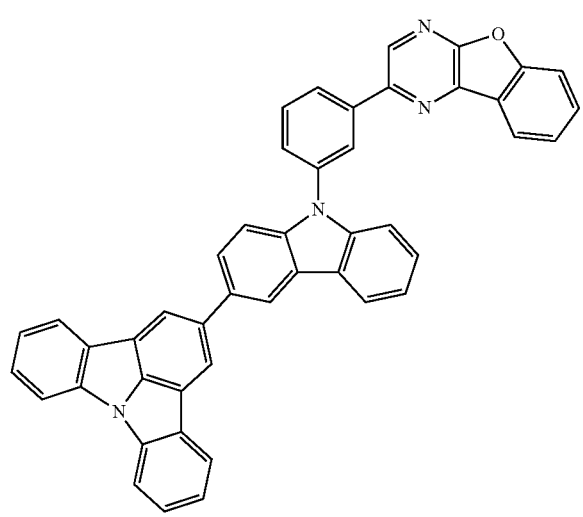
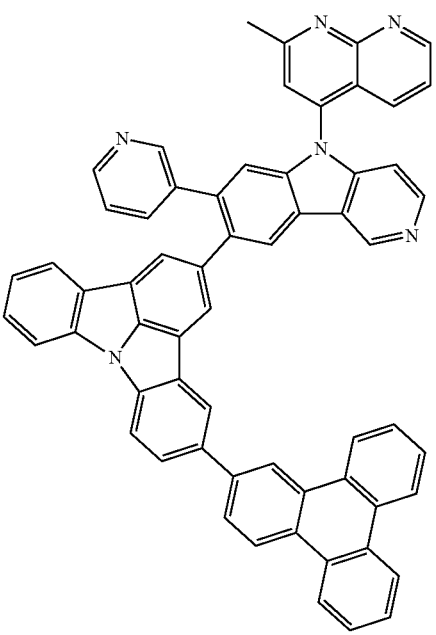
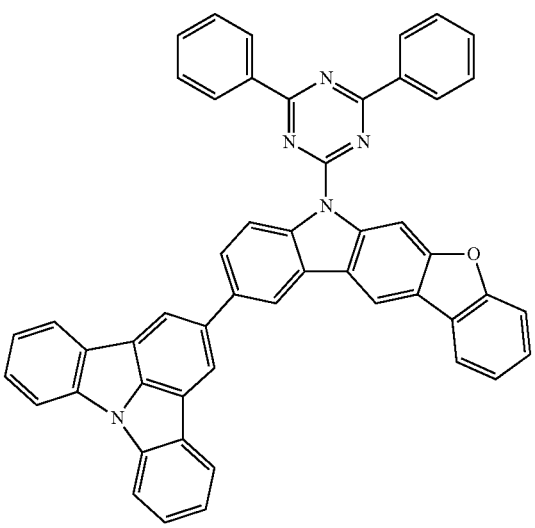
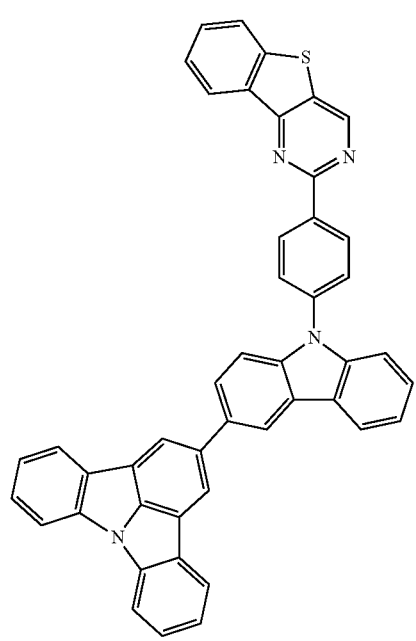

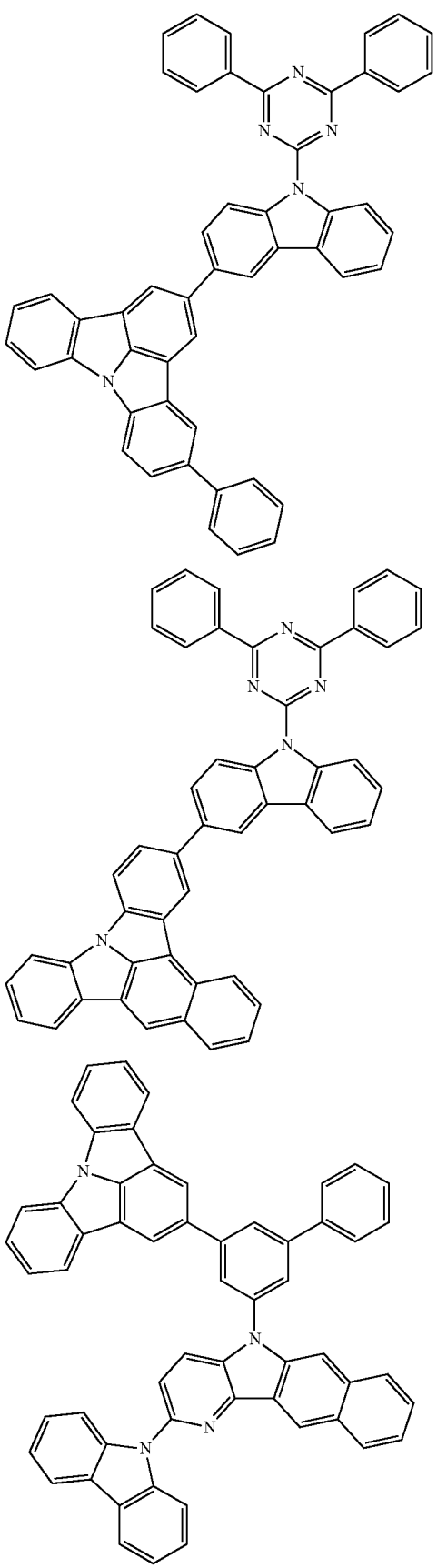

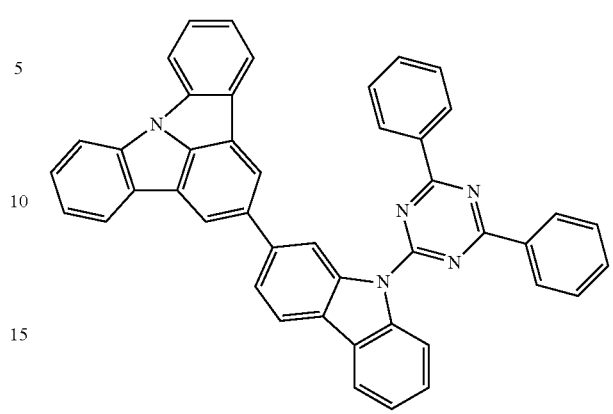

Formulae 1A and 1B necessarily include at least one group represented by one of Formulae 2A and 2B, and Formula 1C has a core that is substantially similar to Formulae 2A and 2B. Accordingly, excellent thermal stability may be obtained.

In some embodiments, Formula 1A necessarily includes the electron transport moiety (for example, see Formulae 4-1 to 4-55) used herein, at least one selected from Ring $B_1$ and Ring $B_2$ in Formula 1B necessarily includes at least one nitrogen as a ring-forming atom, and Formula 1C necessarily includes either the electron transport moiety used herein in its molecular structure or a group represented by at least one of Formulae 2E and 2F. Accordingly, the condensed cyclic compound represented by one of Formulae 1A to 1C may have excellent bipolar characteristics and high $T_1$ energy levels, and due to these characteristics, the condensed cyclic compound is appropriate for use as a material for forming an electric device, for example, an organic light-emitting device. For example, the condensed cyclic compound represented by one of Formulae 1A to 1C may be appropriate for use as a host for an organic light-emitting device.

For example, the highest occupied molecular orbital (HOMO), lowest unoccupied molecular orbital (LUMO), $T_1$ energy level, and $S_1$ energy level of Compounds 2 to 19 and 21 to 76 and Compounds A and B were simulated by using Gaussian, and simulation evaluation results are shown in Table 1 below:

TABLE 1

| | HOMO (eV) | LUMO (eV) | $T_1$ (eV) | $S_1$ (eV) |
|---|---|---|---|---|
| Compound A | −5.113 | −1.25 | 2.933 | 3.224 |
| Compound B | −5.118 | −1.589 | 2.856 | 3.039 |
| Compound 2 | −5.344 | −1.916 | 2.912 | 3.02 |
| Compound 3 | −5.133 | −1.991 | 2.627 | 2.731 |
| Compound 4 | −5.196 | −1.798 | 2.781 | 2.947 |
| Compound 5 | −5.083 | −1.792 | 2.862 | 2.928 |
| Compound 6 | −5.32 | −1.891 | 2.74 | 2.924 |
| Compound 7 | −5.167 | −1.973 | 2.424 | 2.767 |
| Compound 8 | −5.167 | −2.019 | 2.399 | 2.728 |
| Compound 9 | −5.282 | −1.664 | 2.924 | 3.04 |
| Compound 11 | −5.337 | −1.933 | 2.886 | 3.01 |
| Compound 12 | −5.273 | −1.953 | 2.773 | 2.919 |
| Compound 13 | −5.308 | −1.84 | 2.733 | 2.999 |

TABLE 1-continued

|  | HOMO (eV) | LUMO (eV) | $T_1$ (eV) | $S_1$ (eV) |
|---|---|---|---|---|
| Compound 14 | −5.259 | −1.992 | 2.47 | 2.835 |
| Compound 15 | −5.100 | −1.793 | 2.878 | 3.040 |
| Compound 16 | −5.279 | −1.691 | 2.901 | 3.085 |
| Compound 17 | −5.487 | −1.957 | 2.865 | 3.126 |
| Compound 18 | −5.291 | −2.015 | 2.455 | 2.845 |
| Compound 19 | −5.284 | −1.925 | 2.508 | 2.924 |
| Compound 76 | −5.343 | −1.927 | 2.802 | 3.023 |
| Compound 21 | −5.430 | −1.997 | 2.836 | 3.012 |
| Compound 22 | −5.246 | −2.021 | 2.688 | 2.804 |
| Compound 23 | −5.139 | −2.004 | 2.643 | 2.743 |
| Compound 24 | −5.269 | −2.015 | 2.727 | 2.843 |
| Compound 25 | −5.252 | −2.018 | 2.7 | 2.816 |
| Compound 26 | −5.045 | −1.996 | 2.554 | 2.649 |
| Compound 27 | −5.255 | −1.934 | 2.811 | 2.846 |
| Compound 28 | −5.266 | −2.011 | 2.737 | 2.87 |
| Compound 29 | −5.267 | −1.985 | 2.713 | 2.837 |
| Compound 30 | −5.419 | −1.992 | 2.697 | 2.965 |
| Compound 31 | −5.243 | −1.972 | 2.697 | 2.821 |
| Compound 32 | −5.06 | −2.01 | 2.564 | 2.656 |
| Compound 33 | −5.155 | −2.007 | 2.657 | 2.764 |
| Compound 34 | −5.224 | −2.004 | 2.523 | 2.843 |
| Compound 35 | −5.213 | −2.012 | 2.538 | 2.804 |
| Compound 36 | −5.256 | −1.997 | 2.693 | 2.819 |
| Compound 37 | −5.292 | −2.004 | 2.704 | 2.837 |
| Compound 38 | −5.282 | −2.001 | 2.559 | 2.833 |
| Compound 39 | −5.082 | −1.974 | 2.586 | 2.696 |
| Compound 40 | −5.201 | −1.986 | 2.64 | 2.769 |
| Compound 41 | −5.111 | −1.939 | 2.576 | 2.703 |
| Compound 42 | −5.17 | −2.035 | 2.403 | 2.726 |
| Compound 43 | −5.227 | −1.279 | 2.917 | 3.191 |
| Compound 44 | −5.384 | −1.78 | 2.849 | 3.121 |
| Compound 45 | −5.214 | −1.222 | 2.92 | 3.129 |
| Compound 46 | −5.295 | −1.327 | 2.918 | 3.108 |
| Compound 47 | −5.269 | −1.302 | 2.915 | 3.158 |
| Compound 48 | −5.236 | −1.387 | 2.894 | 3.057 |
| Compound 49 | −5.589 | −1.653 | 2.986 | 3.32 |
| Compound 50 | −5.361 | −1.704 | 2.892 | 3.24 |
| Compound 51 | −5.603 | −1.914 | 2.907 | 3.102 |
| Compound 52 | −5.252 | −1.675 | 2.927 | 3.062 |
| Compound 53 | −5.509 | −1.857 | 2.499 | 3.107 |
| Compound 54 | −5.895 | −1.767 | 2.992 | 3.297 |
| Compound 55 | −5.87 | −1.693 | 2.959 | 3.345 |
| Compound 56 | −5.709 | −1.642 | 2.532 | 3.188 |
| Compound 57 | −5.819 | −1.894 | 2.667 | 3.124 |
| Compound 58 | −5.436 | −2.124 | 2.924 | 3.016 |
| Compound 59 | −5.666 | −1.853 | 2.865 | 3.096 |
| Compound 60 | −5.501 | −1.492 | 2.713 | 3.119 |
| Compound 61 | −5.089 | −1.762 | 2.745 | 3.022 |
| Compound 62 | −5.331 | −2.008 | 2.827 | 2.925 |
| Compound 63 | −5.097 | −1.815 | 2.053 | 2.901 |
| Compound 64 | −5.314 | −2.015 | 2.587 | 2.804 |
| Compound 65 | −5.177 | −1.964 | 2.571 | 2.816 |
| Compound 66 | −5.248 | −1.655 | 2.662 | 3.094 |
| Compound 67 | −5.369 | −1.413 | 2.879 | 3.118 |
| Compound 68 | −5.153 | −1.984 | 2.785 | 2.839 |
| Compound 69 | −5.094 | −1.804 | 2.734 | 2.94 |
| Compound 70 | −5.426 | −2.123 | 2.73 | 2.977 |
| Compound 71 | −5.334 | −1.938 | 2.868 | 2.964 |
| Compound 72 | −5.254 | −1.915 | 2.441 | 2.887 |
| Compound 73 | −5.321 | −1.918 | 2.894 | 3.017 |
| Compound 74 | −5.276 | −1.926 | 2.305 | 2.971 |
| Compound 75 | −5.016 | −1.580 | 2.186 | 2.964 |

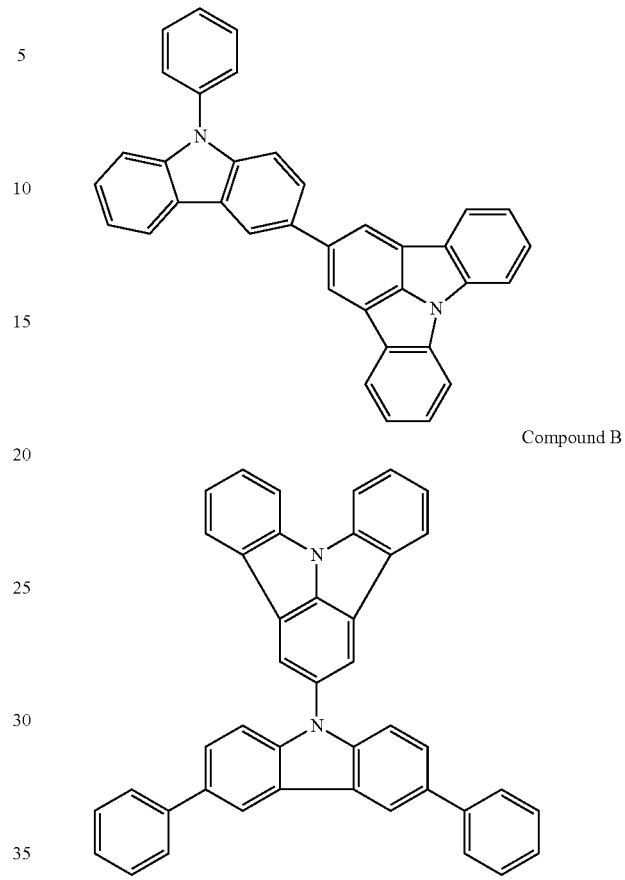

Compound A

Compound B

From Table 1, it is confirmed that Compounds 2 to 19 and 21 to 76 have lower LUMO levels (that is, larger LUMO absolute values) than Compounds A and B. Accordingly, it is confirmed that the condensed cyclic compound represented by one of Formulae 1A to 1C is appropriate for use as a material for an organic layer, for example, an auxiliary layer or an emission layer, of an organic light-emitting device.

A method of synthesizing the condensed cyclic compound represented by one of Formulae 1A to 1C may be apparent to one of ordinary skill in the art by referring to Synthesis Examples used herein.

Accordingly, since the condensed cyclic compound represented by one of Formulae 1A to 1C is appropriate for use in an organic layer of an organic light-emitting device, for example, for use as a host in an emission layer of the organic layer, another aspect provides an organic light-emitting device including:

a first electrode;

a second electrode; and an organic layer disposed between the first electrode and the second electrode, wherein the organic layer includes an emission layer and at least one condensed cyclic compound represented by one of Formulae 1A to 1C.

Due to the inclusion of the organic layer including the condensed cyclic compound represented by one of Formulae 1A to 1C, the organic light-emitting device may have low driving voltage, high efficiency, high brightness, and long lifespan.

The condensed cyclic compound represented by one of Formulae 1A to 1C may be used between a pair of electrodes of an organic light-emitting device. For example, the condensed cyclic compound may be included in at least one selected from an emission layer, a hole transport region (including, for example, at least one of a hole injection layer, a hole transport layer, a buffer layer, and an electron blocking layer) that is disposed between the first electrode and the emission layer, and an electron transport region (including, for example, at least one selected from a hole blocking layer, an electron transport layer, and an electron injection layer) that is disposed between the emission layer and the second electrode. For example, the condensed cyclic compound represented by one of Formulae 1A to 1C may be included in the emission layer. In this regard, the emission layer may further include a dopant, and the condensed cyclic compound included in the emission layer may act as a host. The emission layer may be a green emission layer emitting green light or a blue emission layer emitting blue light, and the dopant may be a phosphorescent dopant.

The expression "(an organic layer) includes at least one condensed cyclic compound" as used herein may include a case in which "(an organic layer) includes identical condensed cyclic compounds represented by Formulae 1A to 1C and a case in which (an organic layer) includes two or more different condensed cyclic compounds represented by Formulae 1A to 1C.

For example, the organic layer may include, as the condensed cyclic compound, only Compound 1. In this regard, Compound 1 may be situated in an emission layer of the organic light-emitting device. In another embodiment, the organic layer may include, as the condensed cyclic compound, Compound 1 and Compound 2. In this regard, Compound 1 and Compound 2 may be situated in either an identical layer (for example, Compound 1 and Compound 2 all may be situated in an emission layer), or different layers.

The first electrode may be an anode, which is a hole injection electrode, and the second electrode may be a cathode, which is an electron injection electrode, or the first electrode may be a cathode, which is an electron injection electrode, or the second electrode may be an anode, which is a hole injection electrode.

For example, the first electrode is an anode, and the second electrode is a cathode, and the organic layer includes:
  i) a hole transport region disposed between the first electrode and the emission layer, including at least one of a hole injection layer, a hole transport layer, and an electron blocking layer, and
  ii) an electron transport region disposed between the emission layer and the second electrode, including at least one selected from a hole blocking layer, an electron transport layer, and an electron injection layer.

The term "organic layer" as used herein refers to a single layer and/or a plurality of layers disposed between the first electrode and the second electrode of an organic light-emitting device. The "organic layer" may include, in addition to an organic compound, an organometallic complex including metal.

FIG. 1 is a schematic view of an organic light-emitting device 10 according to an embodiment. Hereinafter, the structure of an organic light-emitting device according to an embodiment and a method of manufacturing an organic light-emitting device according to an embodiment will be described in connection with FIG. 1. The organic light-emitting device 10 includes a first electrode 11, an organic layer 15, and a second electrode 19, which are sequentially stacked.

In FIG. 1, a substrate may be additionally disposed under the first electrode 11 or above the second electrode 19. For use as the substrate, any substrate that is used in general organic light-emitting devices may be used, and the substrate may be a glass substrate or transparent plastic substrate, each with excellent mechanical strength, thermal stability, transparency, surface smoothness, ease of handling, and water-proofness.

The first electrode 11 may be formed by depositing or sputtering a material for forming the first electrode on the substrate. The first electrode 11 may be an anode. The material for the first electrode 11 may be selected from materials with a high work function to allow holes be easily provided. The first electrode 11 may be a reflective electrode or a transmissive electrode. The material for the first electrode 11 may be an indium tin oxide (ITO), indium zinc oxide (IZO), tin oxide ($SnO_2$), or zinc oxide (ZnO). In some embodiments, the material for the first electrode 11 may be metal, such as magnesium (Mg), aluminum (Al), aluminum-lithium (Al—Li), calcium (Ca), magnesium-indium (Mg—In), or magnesium-silver (Mg—Ag).

The first electrode 11 may have a single-layer structure or a multi-layer structure including two or more layers. For example, the first electrode 11 may have a three-layered structure of ITO/Ag/ITO, but the structure of the first electrode 110 is not limited thereto.

An organic layer 15 is disposed on the first electrode 11.

The organic layer 15 may include a hole transport region, an emission layer, and an electron transport region.

The hole transport region may be disposed between the first electrode 11 and the emission layer.

The hole transport region may include at least one of a hole injection layer, a hole transport layer, an electron blocking layer, and a buffer layer.

The hole transport region may include only either a hole injection layer or a hole transport layer. According to another embodiment, the hole transport region may have a structure of hole injection layer/hole transport layer or hole injection layer/hole transport layer/electron blocking layer, which are sequentially stacked in this stated order in the direction from the first electrode 11.

When the hole transport region includes a hole injection layer (HIL), the hole injection layer may be formed on the first electrode 11 by using any one of various methods, for example, vacuum deposition, spin coating, casting, or Langmuir-Blodgett (LB) deposition.

When a hole injection layer is formed by vacuum deposition, the deposition conditions may vary according to a material that is used to form the hole injection layer, and the structure and thermal characteristics of the hole injection layer. For example, the deposition conditions may include a deposition temperature of about 100 to about 500° C., a vacuum pressure of about $10^{-8}$ to about $10^{-3}$ torr, and a deposition rate of about 0.01 to about 100 Å/sec. However, the deposition conditions are not limited thereto.

When the hole injection layer is formed using spin coating, coating conditions may vary according to the material used to form the hole injection layer, and the structure and thermal properties of the hole injection layer. For example, a coating speed may be from about 2,000 revolutions per minute (rpm) to about 5,000 rpm, and a temperature at which a heat treatment is performed to remove a solvent after coating may be from about 80° C. to about 200° C. However, the coating conditions are not limited thereto.

Conditions for a hole transport layer and an electron blocking layer may be understood by referring to conditions for forming the hole injection layer.

The hole transport region may include at least one selected from m-MTDATA, TDATA, 2-TNATA, NPB, β-NPB, TPD, Spiro-TPD, Spiro-NPB, methylated NPB, TAPC, HMTPD, 4,4',4"-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), (polyaniline)/poly(4-styrenesulfonate) (PANI/PSS), a compound represented by Formula 201 below, and a compound represented by Formula 202 below:

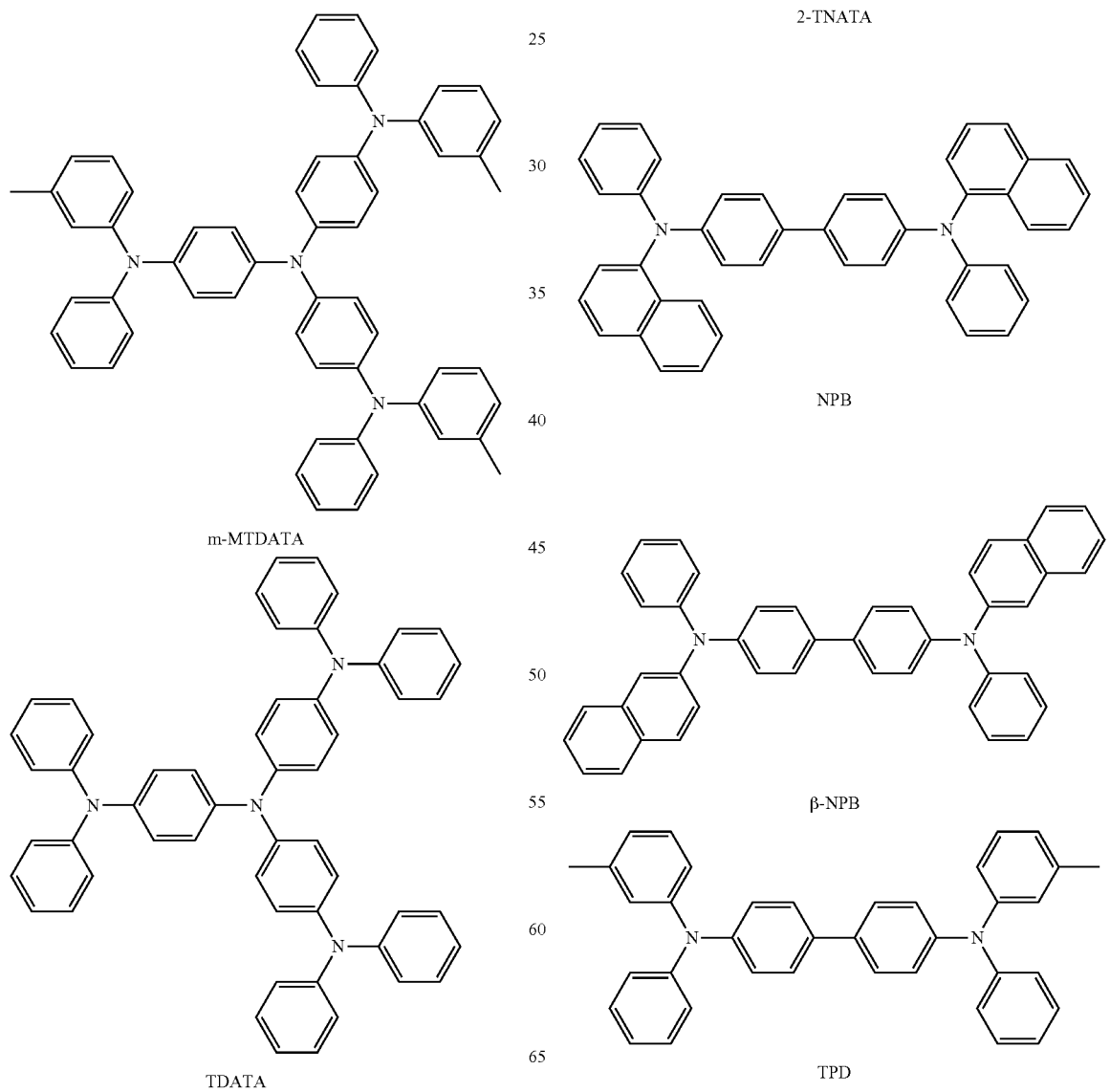

-continued

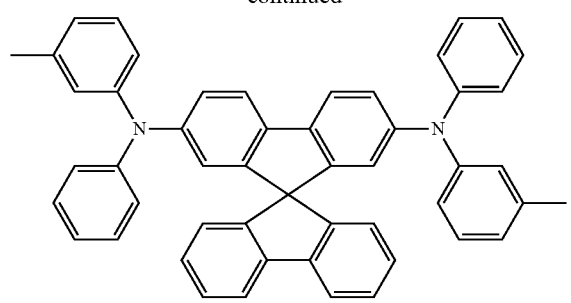
Spiro-TPD

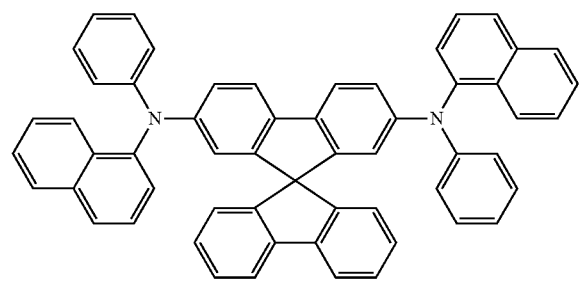
Spiro-NPB

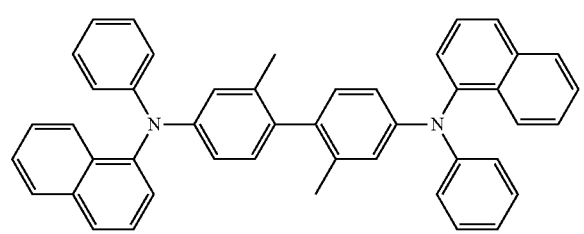
methylated NPB

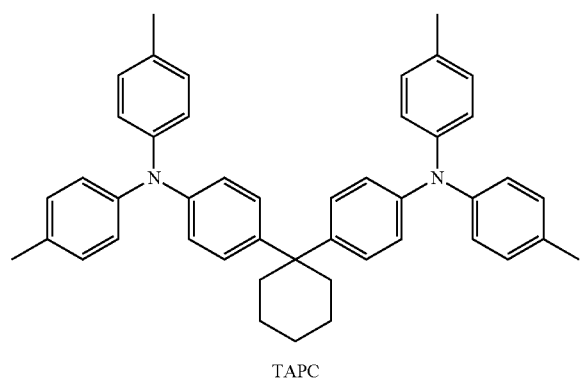
TAPC

-continued

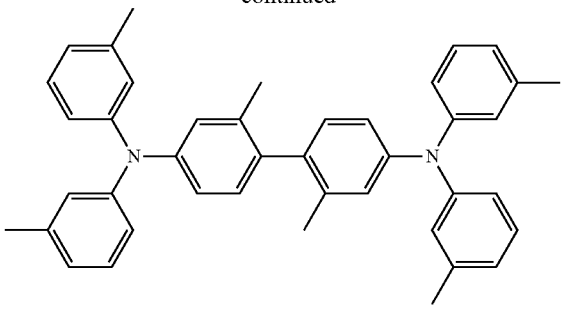
HMTPD

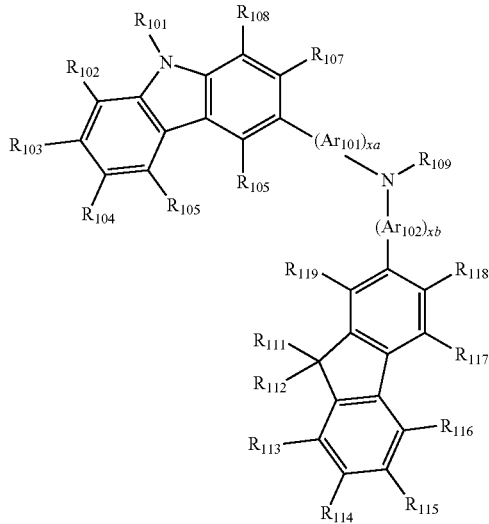
Formula 201

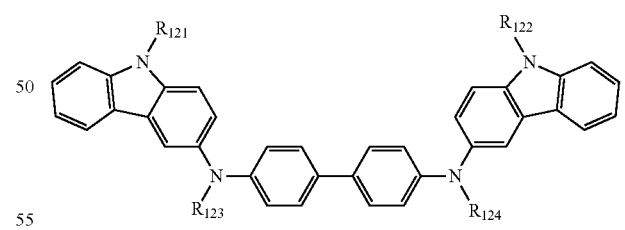
Formula 202

$Ar_{101}$ and $Ar_{102}$ in Formula 201 may be each independently selected from
a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_2$-$C_{10}$ heterocycloalkyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed hetero-polycyclic group.

xa and xb in Formula 201 may be each independently an integer of 0 to 5, or 0, 1 or 2. For example, xa may be 1 and xb may be 0, but xa and xb are not limited thereto.

$R_{101}$ to $R_{108}$, $R_{111}$ to $R_{119}$, and $R_{121}$ to $R_{124}$ in Formulae 201 and 202 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, a pentyl group, a hexyl group, and so on), and a $C_1$-$C_{10}$ alkoxy group (for example, a methoxy group, an ethoxy group, a propoxy group, a butoxy group, a pentoxy group, and so on);

a $C_1$-$C_{10}$ alkyl group and a $C_1$-$C_{10}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, and a phosphoric acid or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, or a $C_1$-$C_{10}$ alkoxy group, but they are not limited thereto.

$R_{109}$ in Formula 201 may be selected from a phenyl group, a naphthyl group, an anthracenyl group, and a pyridinyl group; or a phenyl group, a naphthyl group, an anthracenyl group, and a pyridinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group.

According to an embodiment, the compound represented by Formula 201 may be represented by Formula 201A below, but is not limited thereto:

Formula 201A

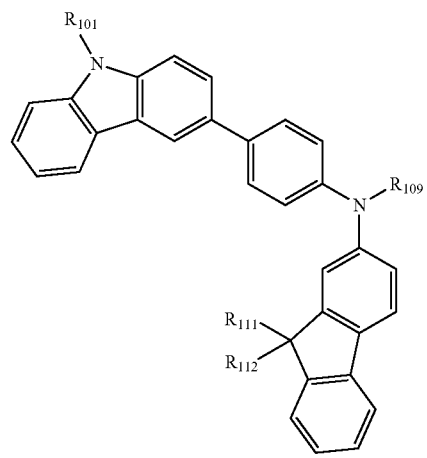

$R_{101}$, $R_{111}$, $R_{112}$, and $R_{109}$ in Formula 201A may be understood by referring to the description provided herein.

For example, the compound represented by Formula 201, and the compound represented by Formula 202 may include compounds HT1 to HT20 illustrated below, but are not limited thereto.

HT1

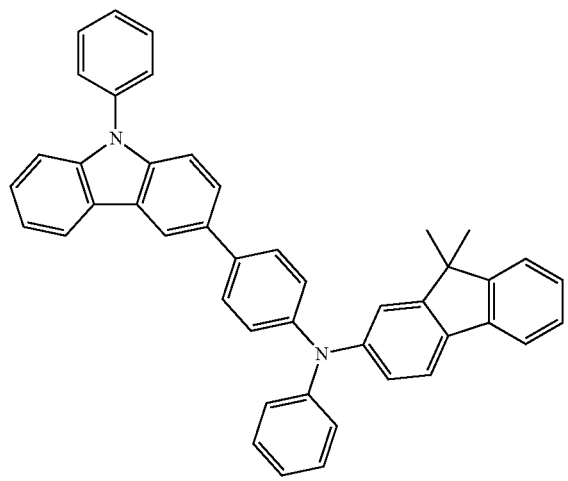

HT2
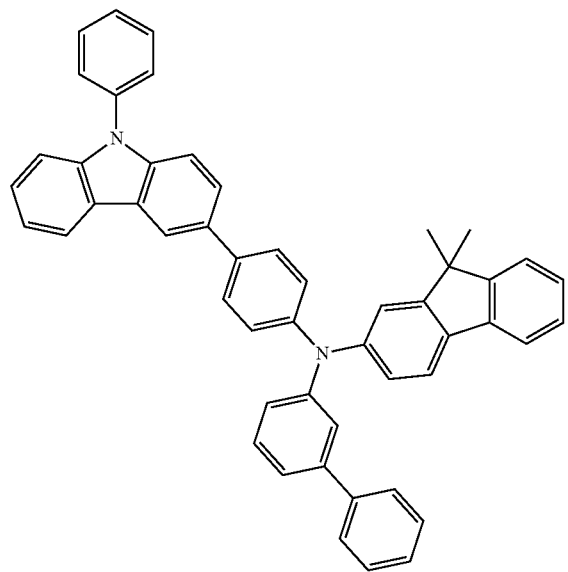
HT4
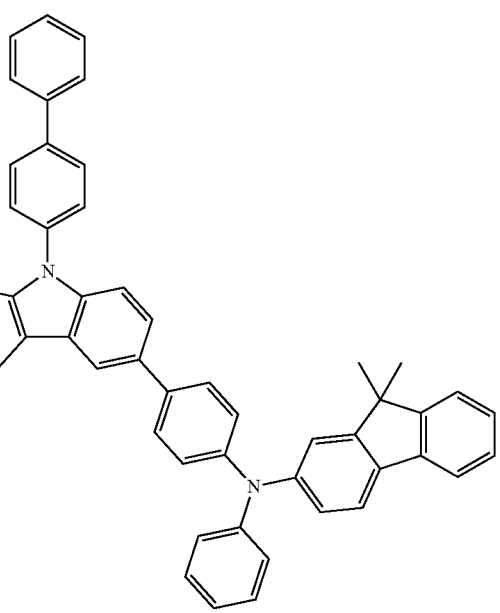
HT3
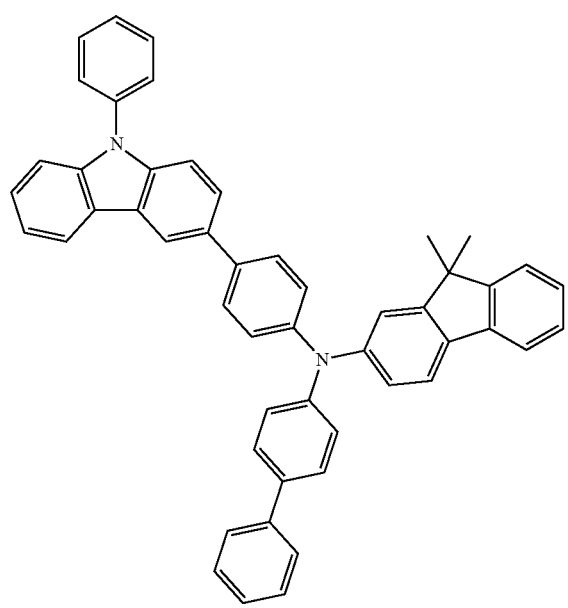
HT5
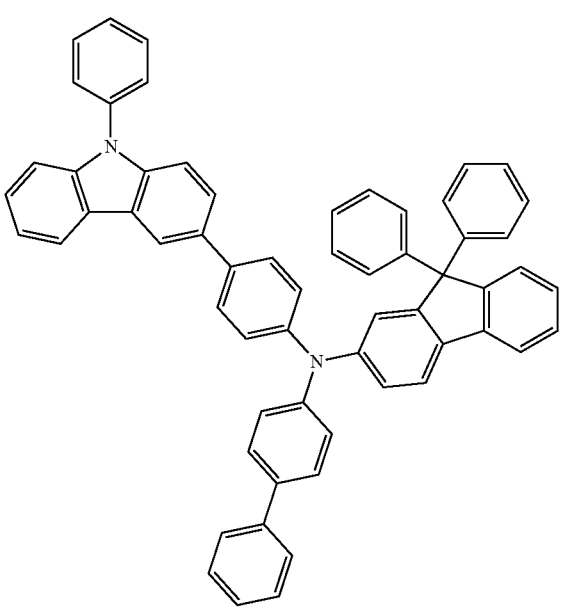

HT6
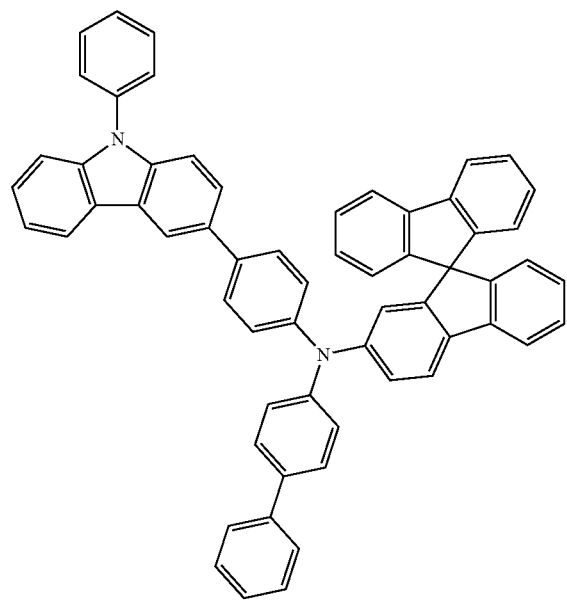
HT7
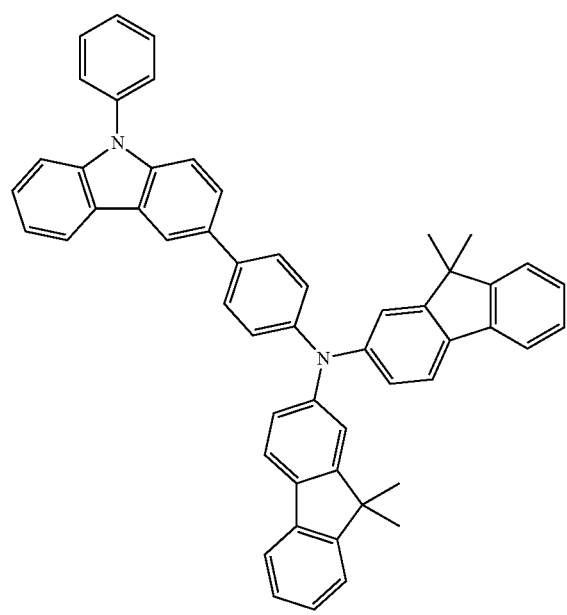
HT8
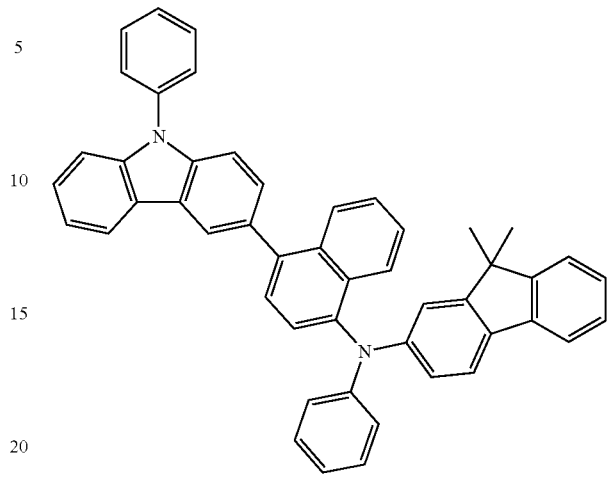
HT9
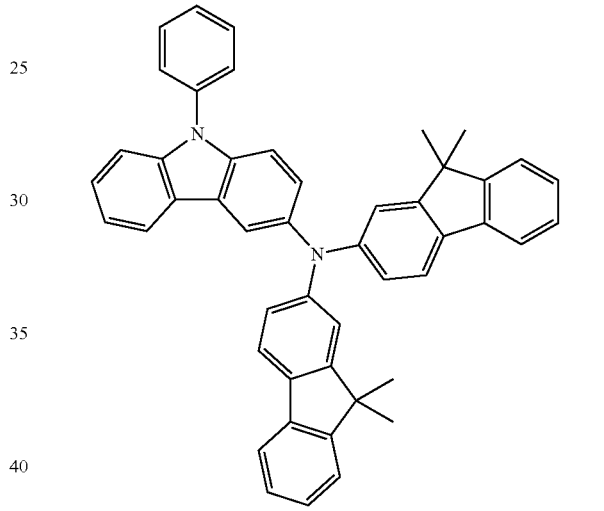
HT10
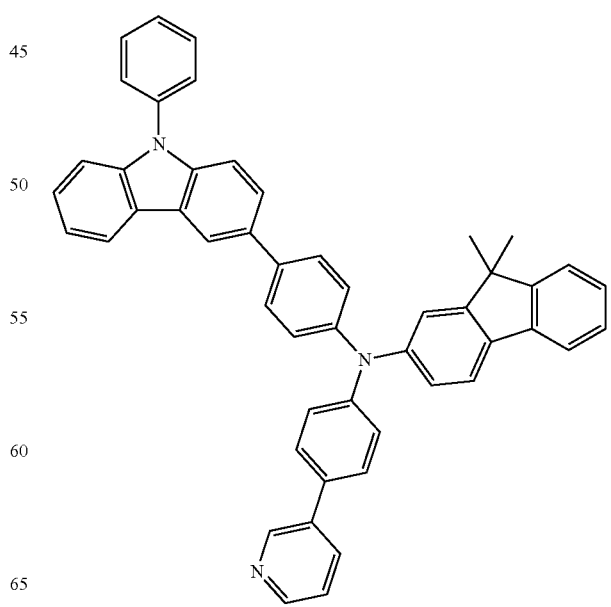

HT11
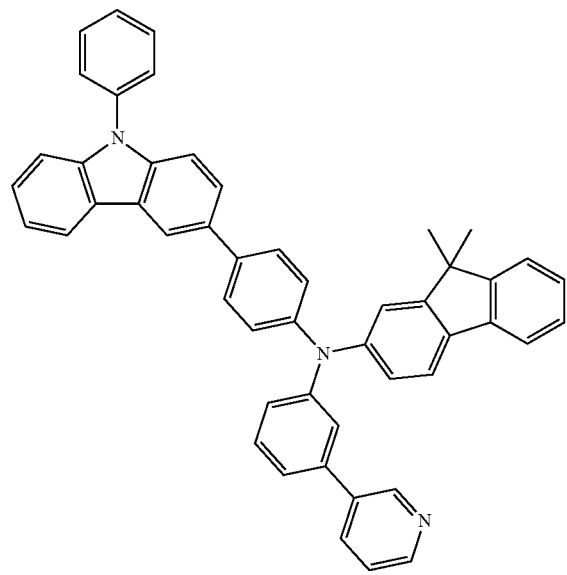
HT12
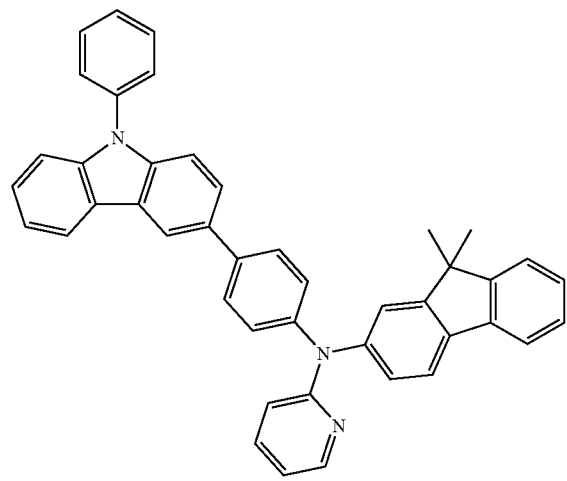
HT13
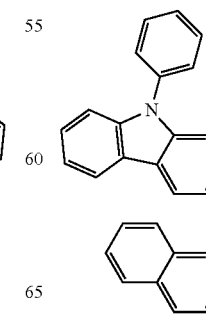
HT14
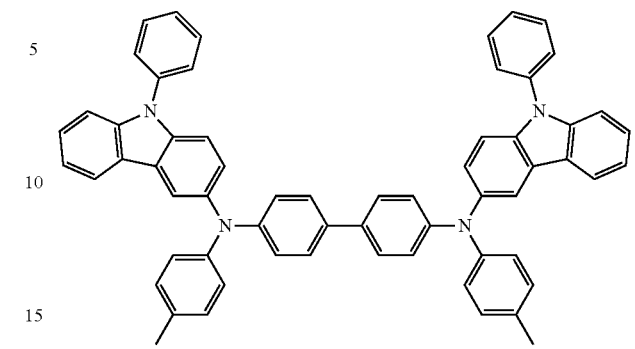
HT15
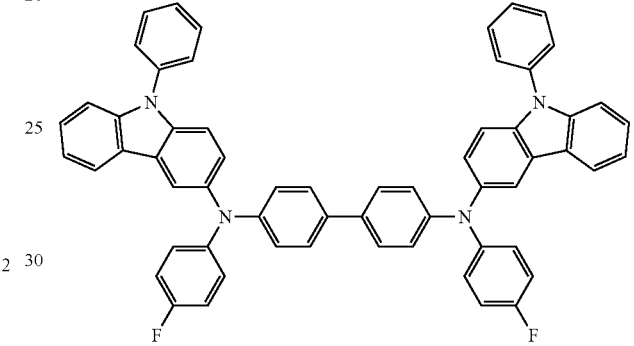
HT16
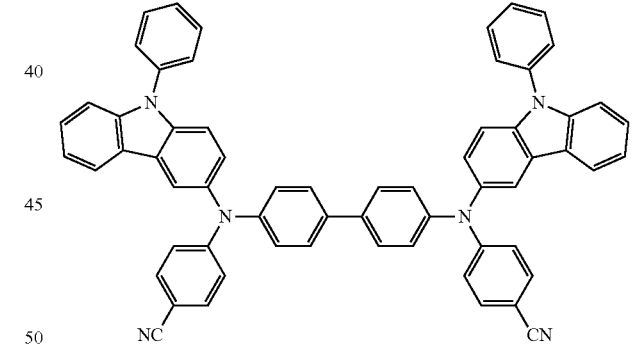
HT17
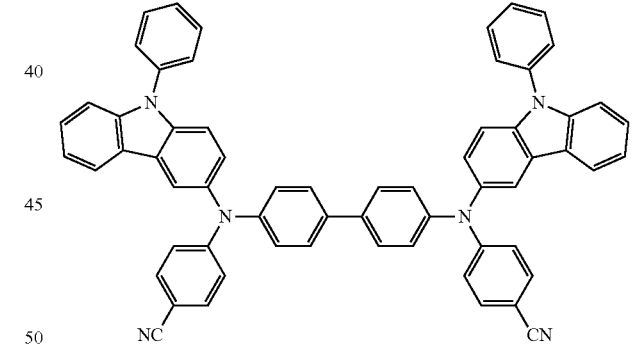

-continued

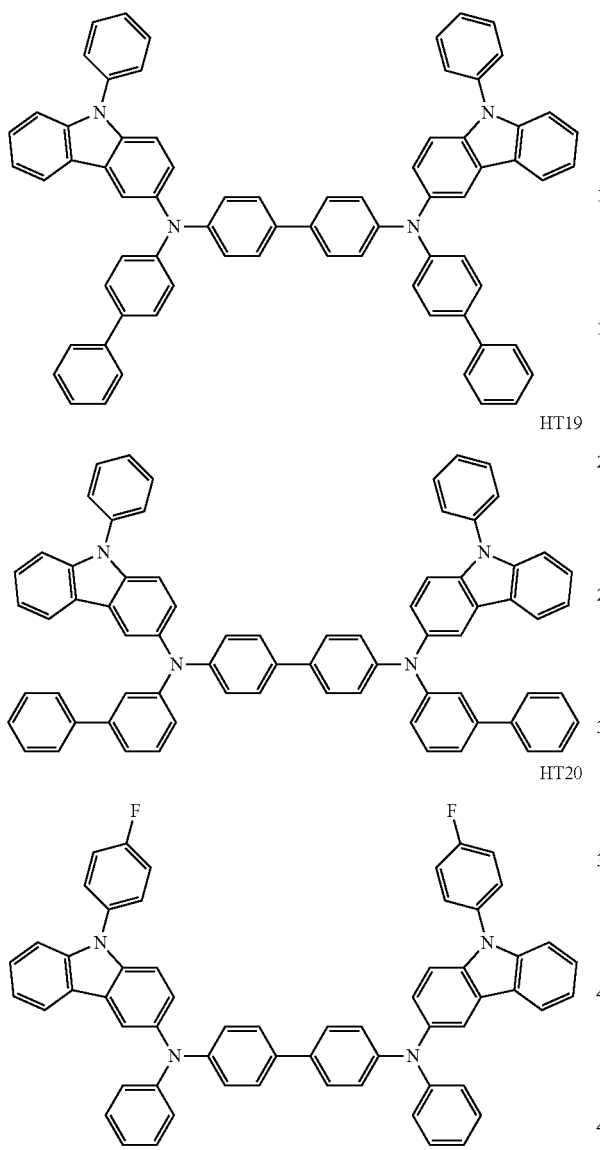

HT18

HT19

HT20

A thickness of the hole transport region may be in a range of about 100 Angstroms (Å) to about 10,000 Å, for example, about 100 Å to about 1,000 Å. When the hole transport region includes both a hole injection layer and a hole transport layer, a thickness of the hole injection layer may be in a range of about 100 Å to about 10,000 Å, for example, about 100 Å to about 1,000 Å, and a thickness of the hole transport layer may be in a range of about 50 Å to about 2,000 Å, for example about 100 Å to about 1,500 Å. When the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one of a quinone derivative, a metal oxide, and a cyano group-containing compound, but is not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenium oxide; and a cyano group-containing compound, such as Compound HT-D1 below, but are not limited thereto.

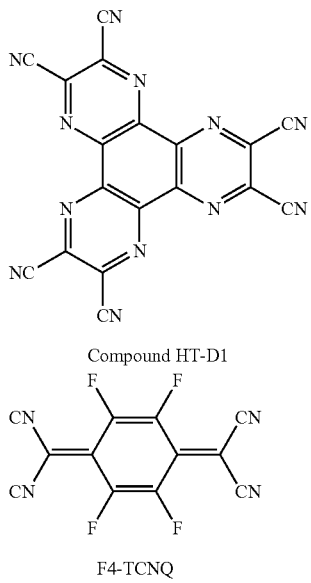

Compound HT-D1

F4-TCNQ

The hole transport region may include a buffer layer.

Also, the buffer layer may compensate for an optical resonance distance according to a wavelength of light emitted from the emission layer, and thus, efficiency of a formed organic light-emitting device may be improved.

Then, an emission layer (EML) may be formed on the hole transport region by vacuum deposition, spin coating, casting, LB deposition, or the like. When the emission layer is formed by vacuum deposition or spin coating, the deposition or coating conditions may be similar to those applied to form the hole injection layer although the deposition or coating conditions may vary according to the material that is used to form the emission layer.

When the organic light-emitting device is a full color organic light-emitting device, the emission layer may be patterned into a red emission layer, a green emission layer, and a blue emission layer. According to another embodiment, due to a stacking structure including a red emission layer, a green emission layer, and/or a blue emission layer, the emission layer may emit white light.

The emission layer may include at least one condensed cyclic compound represented by one of Formulae 1A to 1C. The emission layer may include a dopant. The dopant may be at least one selected from a phosphorescent dopant and a fluorescent dopant.

The emission layer includes a host and a dopant, and the host may include at least one condensed cyclic compound represented by one of Formulae 1A to 1C.

According to an embodiment, the emission layer includes a first host and a second host.

The condensed cyclic compound represented by one of Formulae 1A to 1C may be included in the emission layer.

The first host may include the condensed cyclic compound represented by one of Formulae 1A to 1C, and the second host may include at least one selected from a first compound represented by Formula 41 and a second compound represented by Formula 61:

Formula 41

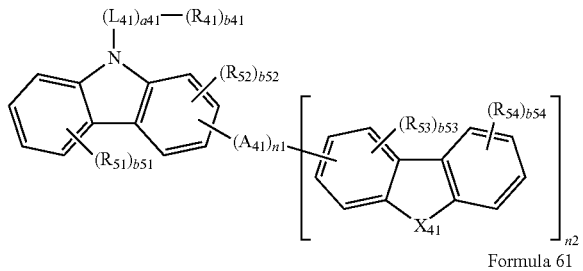

Formula 61

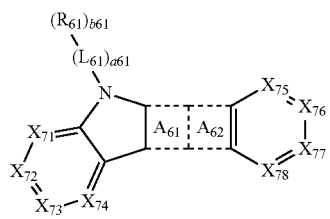

Formula 61A

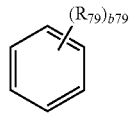

Formula 61B

X$_{61}$ wherein in the formulae above,

X$_{41}$ is N-[(L$_{42}$)$_{a42}$-(R$_{42}$)$_{b42}$], S, O, S(=O), S(=O)$_2$, C(=O), C(R$_{43}$)(R$_{44}$), Si(R$_{43}$)(R$_{44}$), P(R$_{43}$), P(=O)(R$_{43}$), or C=N(R$_{43}$);

Ring A$_{61}$ in Formula 61 is represented by Formula 61A;
Ring A$_{62}$ in Formula 61 is represented by Formula 61B;
X$_{61}$ is N-[(L$_{62}$)$_{a62}$-(R$_{62}$)$_{b62}$], S, O, S(=O), S(=O)$_2$, C(=O), C(R$_{63}$)(R$_{64}$), Si(R$_{63}$)(R$_{64}$), P(R$_{63}$), P(=O)(R$_{63}$), or C=N(R$_{63}$);

X$_{71}$ is C(R$_{71}$) or N;
X$_{72}$ is C(R$_{72}$) or N;
X$_{73}$ is C(R$_{73}$) or N;
X$_{74}$ is C(R$_{74}$) or N;
X$_{75}$ is C(R$_{75}$) or N;
X$_{76}$ is C(R$_{76}$) or N;
X$_{77}$ is C(R$_{77}$) or N;
X$_{78}$ is C(R$_{78}$) or N;

Ar$_{41}$, L$_{41}$, L$_{42}$, L$_{61}$, and L$_{62}$ are each independently selected from a substituted or unsubstituted C$_3$-C$_{10}$ cycloalkylene group, a substituted or unsubstituted C$_2$-C$_{10}$ heterocycloalkylene group, a substituted or unsubstituted C$_3$-C$_{10}$ cycloalkenylene group, a substituted or unsubstituted C$_2$-C$_{10}$ heterocycloalkenylene group, a substituted or unsubstituted C$_6$-C$_{60}$ arylene group, a substituted or unsubstituted C$_2$-C$_{60}$ heteroarylene group, a substituted or unsubstituted divalent non-aromatic condensed polycyclic group, and a substituted or unsubstituted divalent non-aromatic condensed hetero-polycyclic group;

n1 and n2 are each independently an integer selected from 0 to 3;

a41, a42, a61, and a62 are each independently an integer selected from 0 to 3;

R$_{41}$ to R$_{44}$, R$_{51}$ to R$_{54}$, R$_{61}$ to R$_{64}$, and R$_{71}$ to R$_{79}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_2$-C$_{10}$ heterocycloalkyl group, a substituted or unsubstituted C$_3$-C$_{10}$ cycloalkenyl group, a substituted or unsubstituted C$_2$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_2$-C$_{60}$ heteroaryl group, a substituted or unsubstituted monovalent non-aromatic condensed polycyclic group, a substituted or unsubstituted monovalent non-aromatic condensed hetero-polycyclic group, —N(Q$_1$)(Q$_2$), —Si(Q$_3$)(Q$_4$)(Q$_5$), and —B(Q$_6$)(Q$_7$);

b41, b42, b51 to b54, b61, b62, and b79 are each independently an integer selected from 1 to 3;

at least one of substituents of the substituted $C_1$-$C_{60}$ alkylene group, substituted $C_2$-$C_{60}$ alkenylene group, substituted $C_3$-$C_{10}$ cycloalkylene group, substituted $C_2$-$C_{10}$ heterocycloalkylene group, substituted $C_3$-$C_{10}$ cycloalkenylene group, substituted $C_2$-$C_{10}$ heterocycloalkenylene group, substituted $C_6$-$C_{60}$ arylene group, substituted $C_2$-$C_{60}$ heteroarylene group, substituted divalent non-aromatic condensed polycyclic group, substituted divalent non-aromatic condensed hetero-polycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_2$-$C_{60}$ heteroaryl group, a substituted monovalent non-aromatic condensed polycyclic group, and a substituted monovalent non-aromatic condensed hetero-polycyclic group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed hetero-polycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed hetero-polycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$);

wherein $Q_1$ to $Q_7$, $Q_{11}$ to $Q_{17}$, $Q_{21}$ to $Q_{27}$, and $Q_{31}$ to $Q_{37}$ may be each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent non-aromatic condensed polycyclic group, and a monovalent non-aromatic hetero-condensed polycyclic group.

According to an embodiment, $R_{41}$ to $R_{44}$, $R_{51}$ to $R_{54}$, $R_{61}$ to $R_{64}$, and $R_{71}$ to $R_{79}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, and a phosphoric acid or a salt thereof;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a furanyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl, an acridinyl, a phenanthrolinyl, a phenazinyl, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group, each substituted with at least one selected from a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a furanyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl, an acridinyl, a phenanthrolinyl, a phenazinyl, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, and a biphenyl group; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, and a biphenyl group; and —Si($Q_3$)($Q_4$)($Q_5$), a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, carboxylic acid or a salt thereof, sulfonic acid or a salt thereof, phosphoric acid or a salt thereof, a $C_1$-$C_{20}$ alkyl group, a $C_1$-$C_{20}$ alkoxy group, —Si($Q_{33}$)($Q_{34}$)($Q_{35}$), a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, and a biphenyl group; and —Si($Q_3$)($Q_4$)($Q_5$), wherein $Q_3$ to $Q_5$ and $Q_{33}$ to $Q_{35}$ are each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group, but are not limited thereto.

For example, the first compound may be represented by one of Formulae 41-1 to 41-12 below, and the second compound may be represented by one of Formulae 61-1 to 61-6:

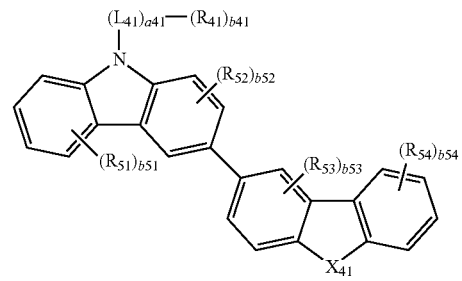

Formula 41-1

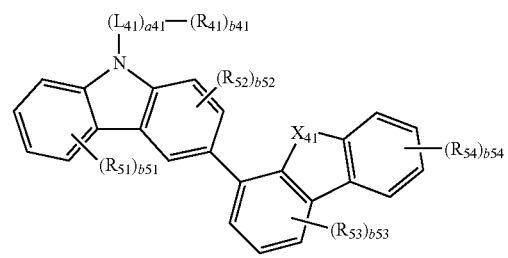

Formula 41-2

-continued
Formula 41-3
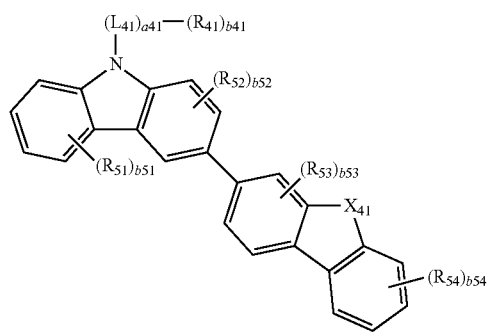
Formula 41-4
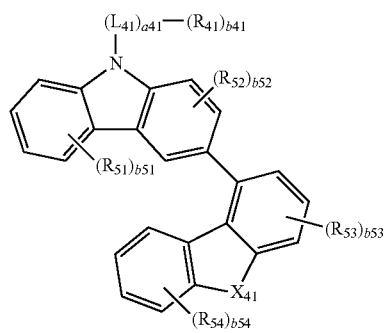
Formula 41-5
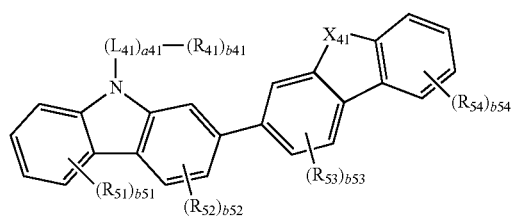
Formula 41-6
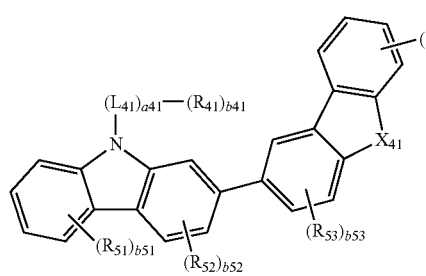
Formula 41-7
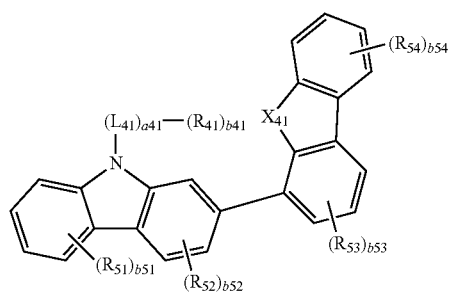
-continued
Formula 41-8
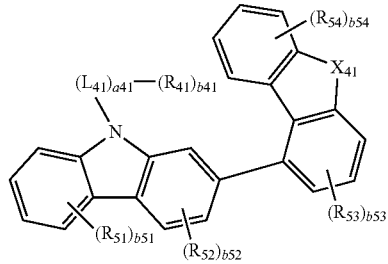
Formula 41-9
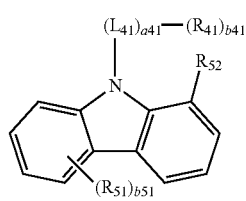
Formula 41-10
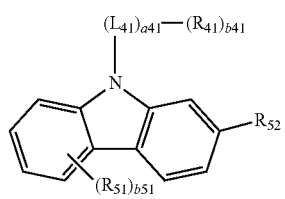
Formula 41-11
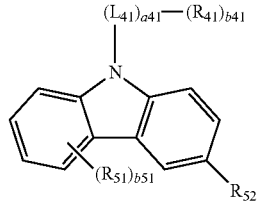
Formula 41-12
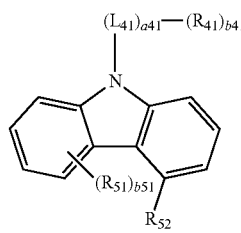
Formula 61-1
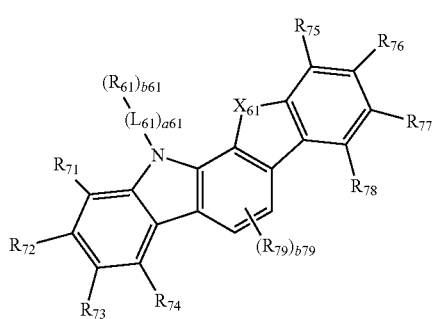

-continued

Formula 61-2

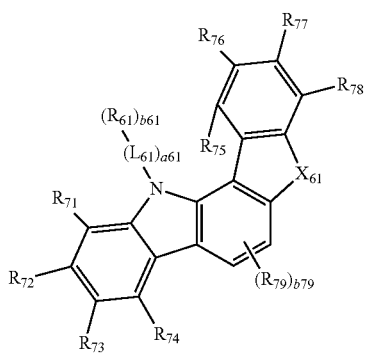

Formula 61-3

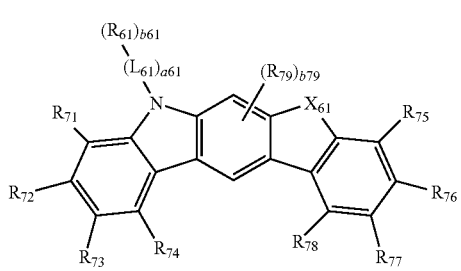

Formula 61-4

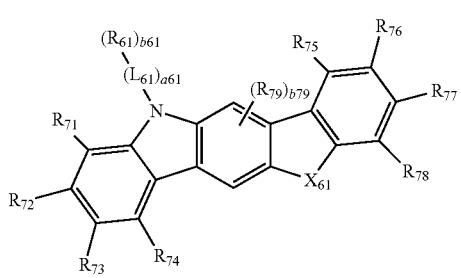

Formula 61-5

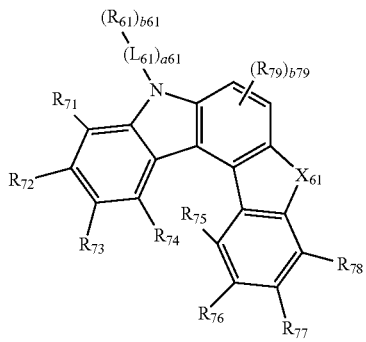

Formula 61-6

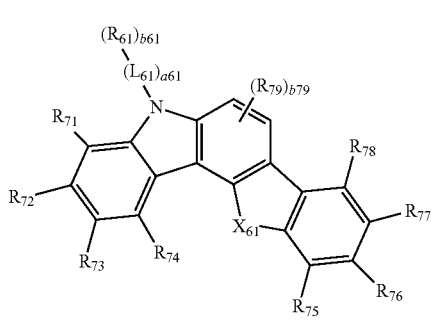

$X_{41}$, $X_{61}$, $L_{41}$, $L_{42}$, a41, a42, $L_{61}$, $L_{62}$, a61, a62, $R_{41}$ to $R_{44}$, b41, b42, $R_{61}$ to $R_{64}$, b61, b62, $R_{71}$ to, $R_{76}$ and b79 in Formulae 41-1 to 41-12 and 61-1 to 61-6 are as described above.

For example, when the second host includes the first compound represented by Formula 41, at least one selected from $R_{41}$, $R_{42}$, and $R_{52}$ of the first compound, and when the second host includes the second compound represented by Formula 61, at least one selected from $R_{61}$ and $R_{62}$ of the second compound may be each independently selected from a thiophenyl group, a furanyl group, a carbazolyl group, an acridinyl group, a dibenzofuranyl group, a dibenzothiophenyl group, a benzocarbazolyl group, a dibenzocarbazolyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, and an ovalenyl group; and a thiophenyl group, a furanyl group, a carbazolyl group, acridinyl, a dibenzofuranyl group, a dibenzothiophenyl group, a benzocarbazolyl group, a dibenzocarbazolyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group. and an ovalenyl group, each substituted with at least one selected from a deuterium, —F, —Cl, —Br, —I, a hydroxyl group, a cyano group, a nitro group, an amino group, an amidino group, a hydrazine group, a hydrazone group, carboxylic acid or a salt thereof, sulfonic acid or a salt thereof, phosphoric acid or a salt thereof, a $C_1$-$C_{20}$ alkyl group, a $C_1$-$C_{20}$ alkoxy group, a phenyl group, a phenyl group substituted with $C_1$-$C_{20}$ alkyl group, a naphthyl group, a phenalenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, a naphthyridinyl group, a quinoxalinyl group, a quinazolinyl group, a biphenyl group, and —Si$(Q_{33})(Q_{34})(Q_{35})$, wherein $Q_{33}$ to $Q_{35}$ may be each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group.

In some embodiments, when the second host includes the first compound represented by Formula 41, at least one selected from $R_{41}$, $R_{42}$, and $R_{52}$ of the first compound, and when the second host includes the second compound represented by Formula 61, at least one selected from $R_{61}$ and $R_{62}$ of the second compound may be represented by one of Formulae 5-1 to 5-6 and 6-1 to 6-5.

According to an embodiment, the first compound represented by Formula 41 may include one of Compounds A1 to A83 below, and the second compound represented by Formula 61 may include one of Compounds B1 to B20, but they are not limited thereto:

-continued
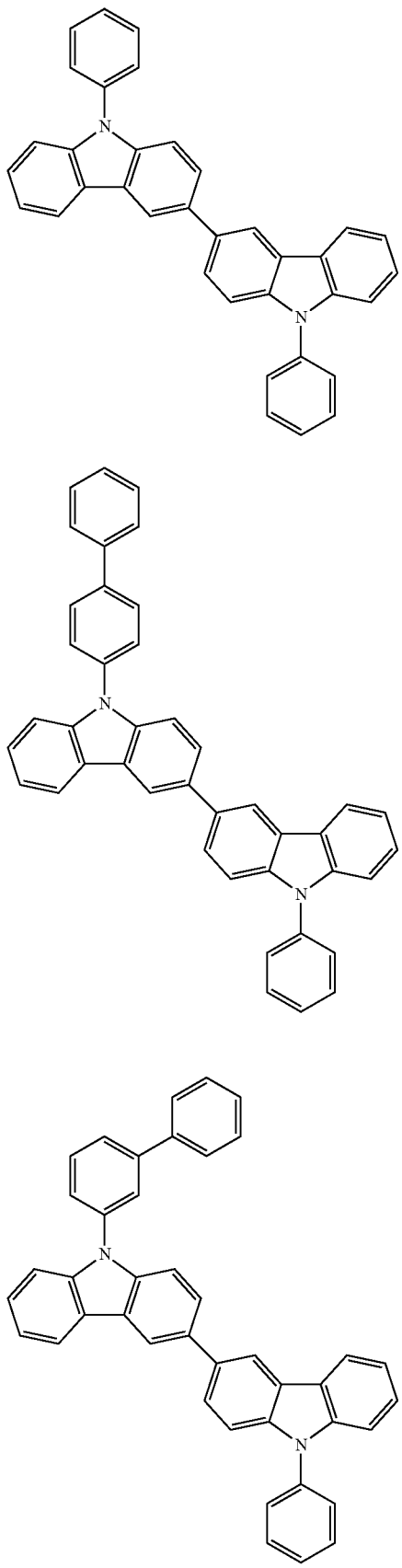
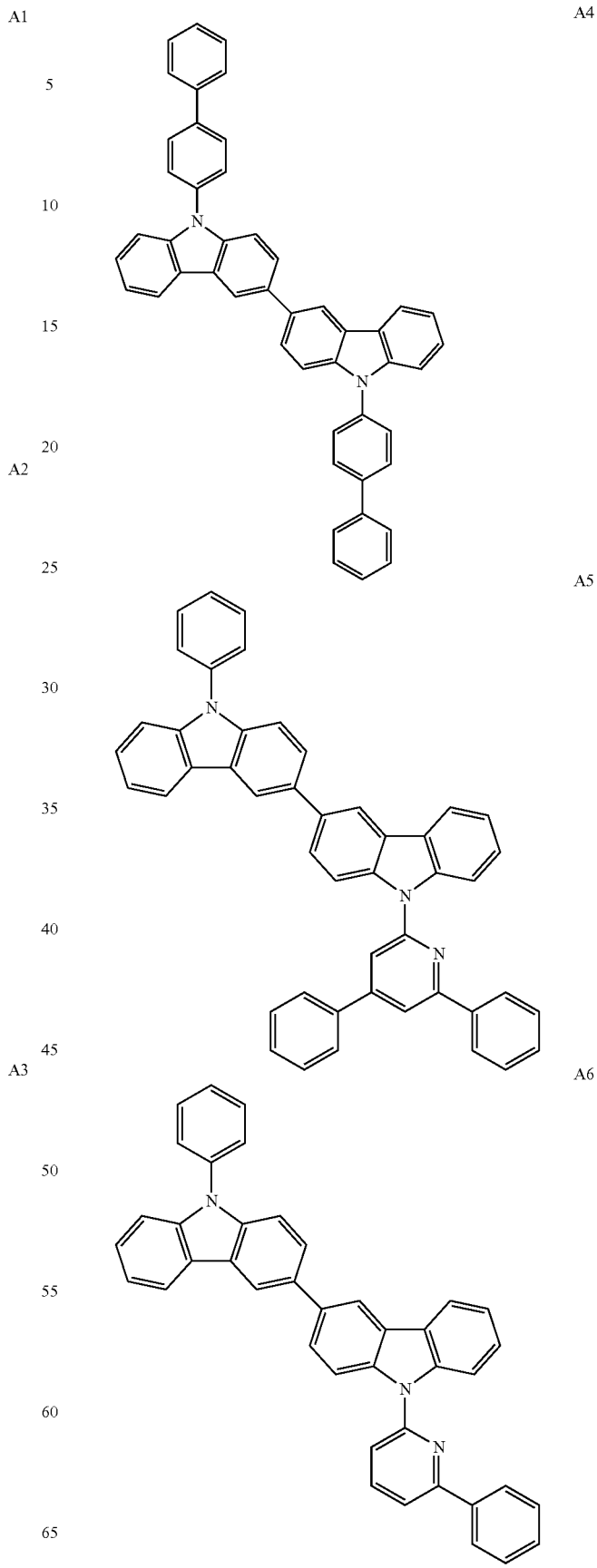

-continued
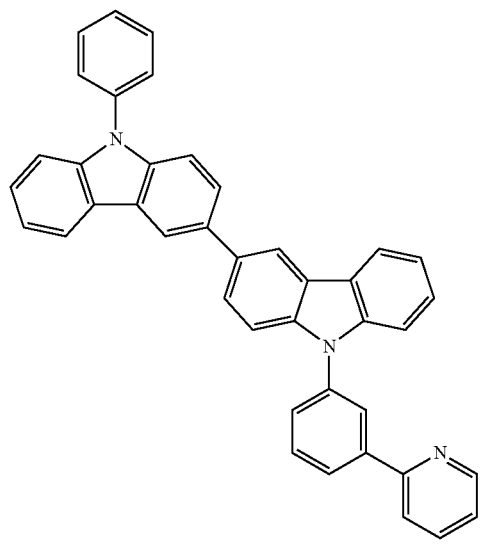
A7
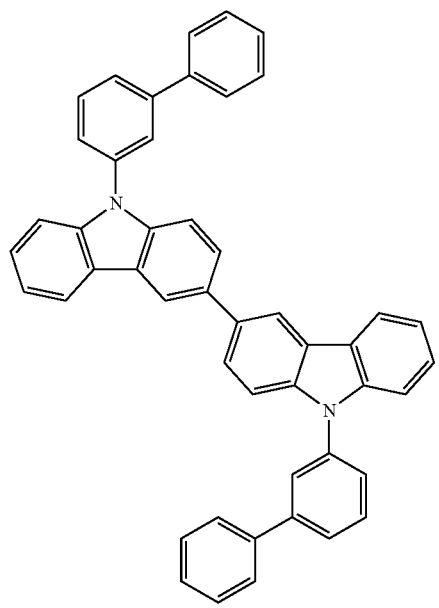
A8
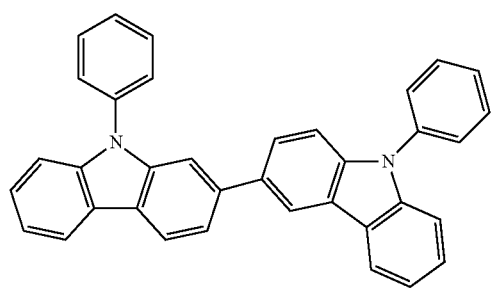
A9
-continued
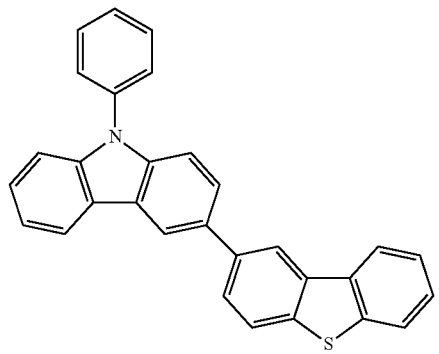
A10
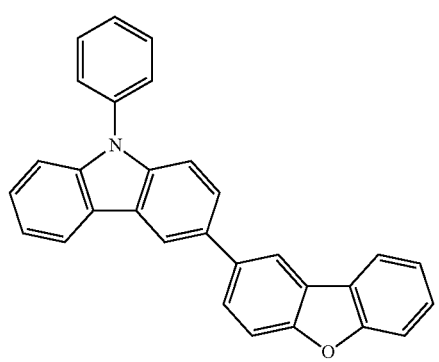
A11
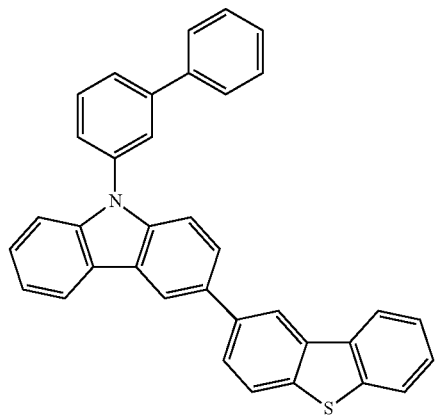
A12
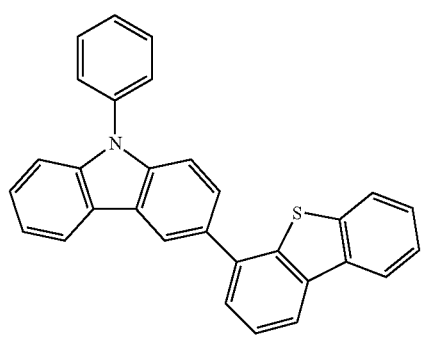
A13

A14
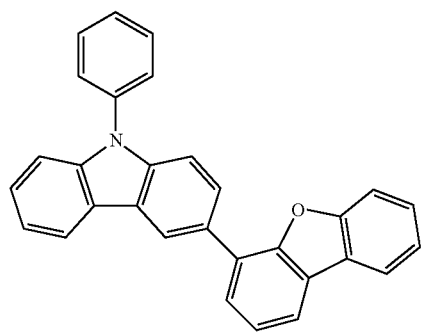
A15
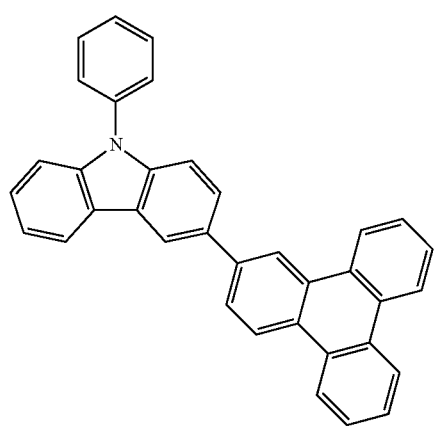
A16
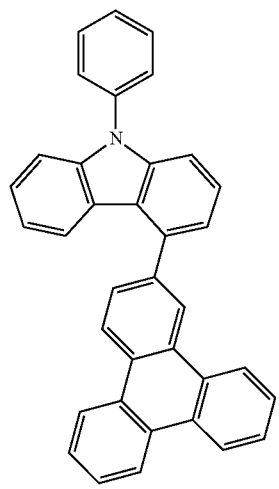
A17
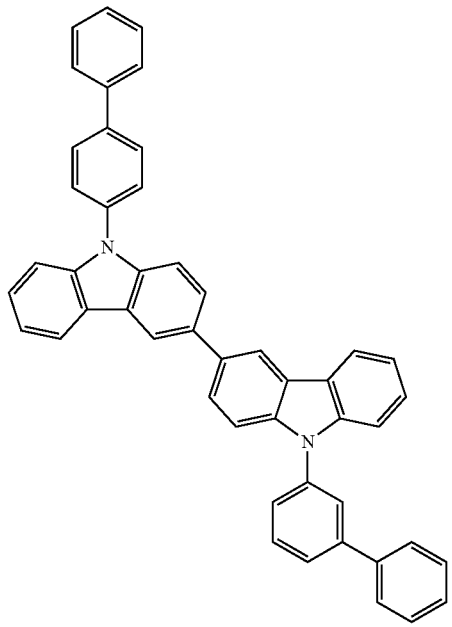
A18
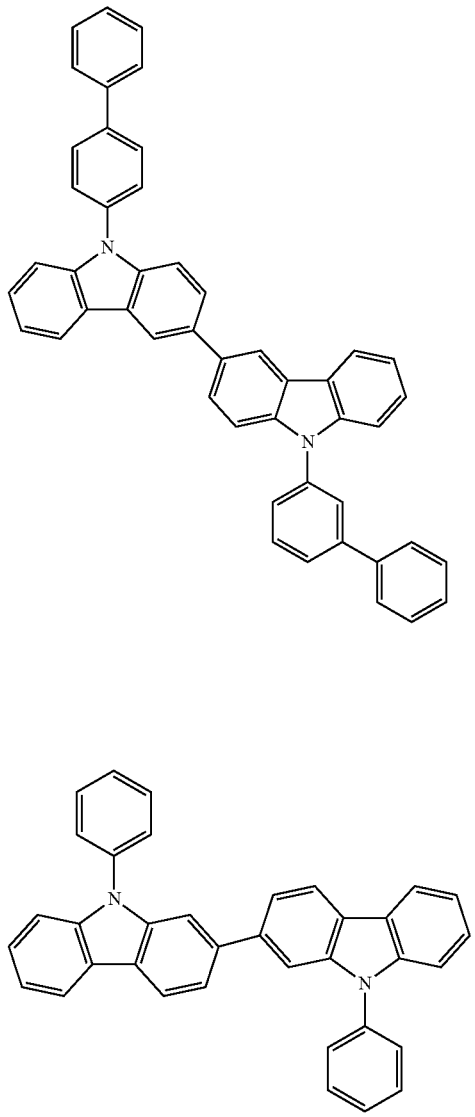
A19
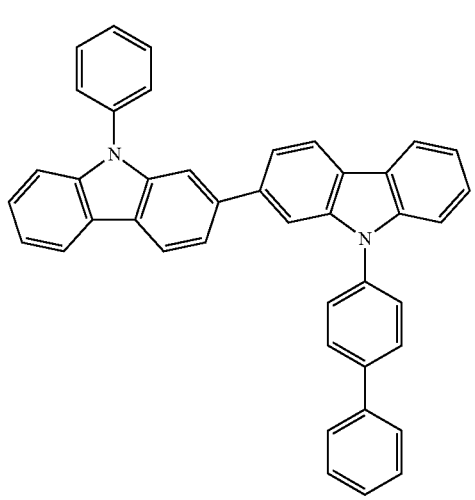

A20
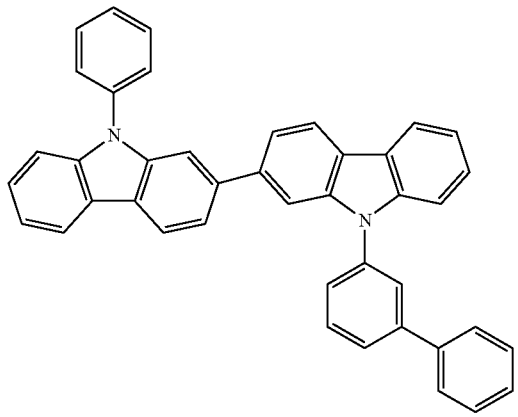
A21
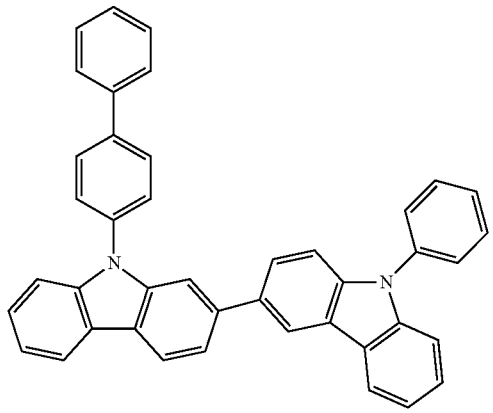
A22
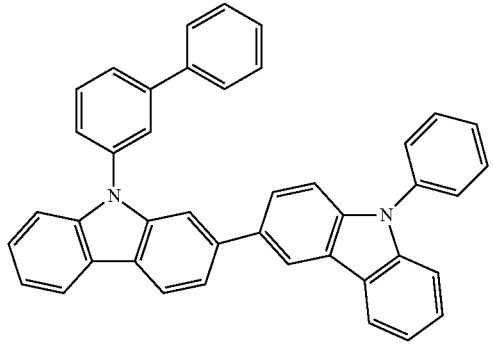
A23
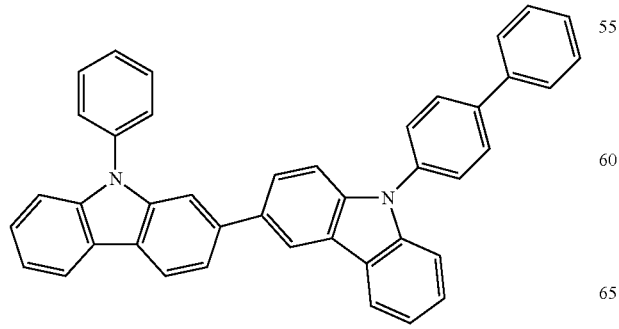
A24
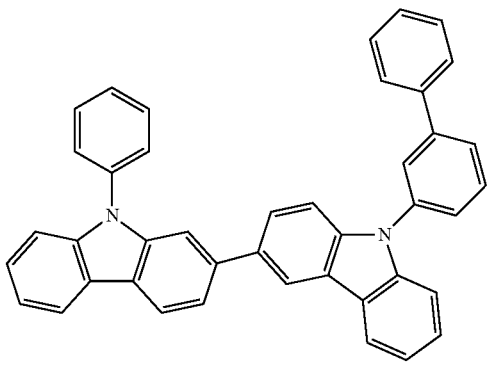
A25
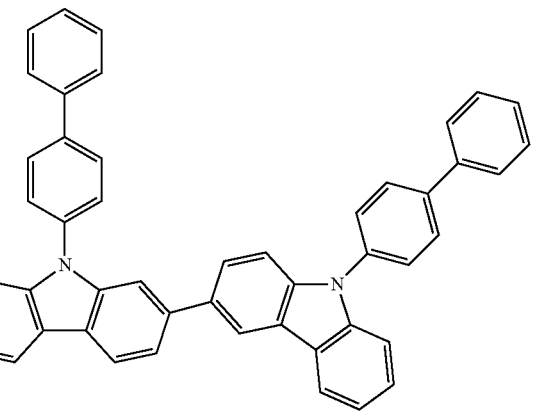
A26
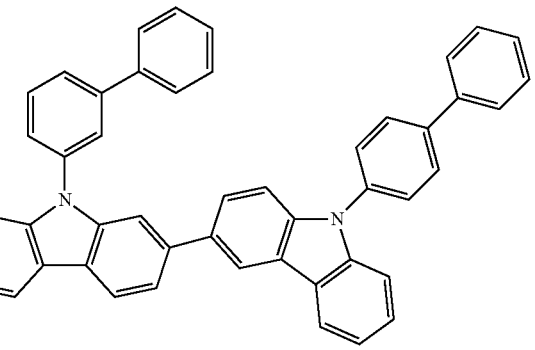
A27
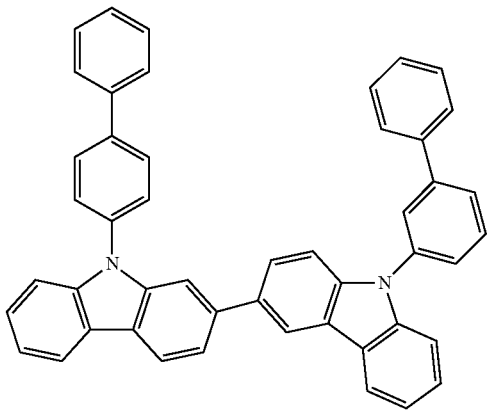

-continued
A28
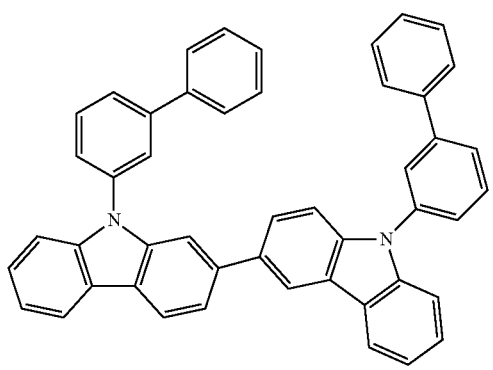
A29
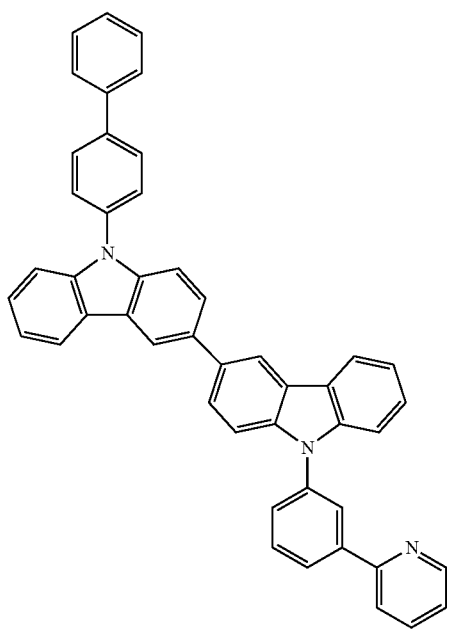
A30
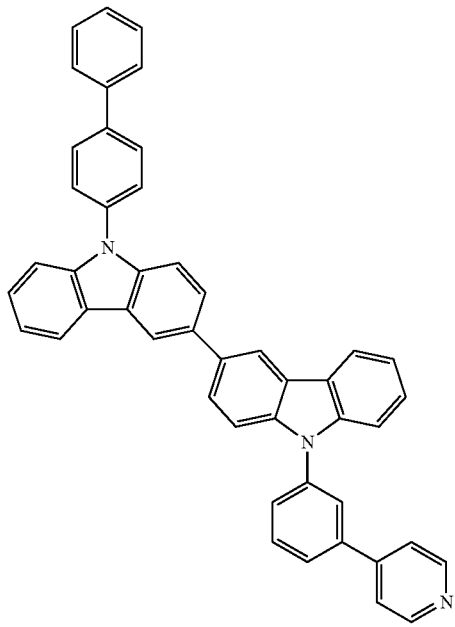
-continued
A31
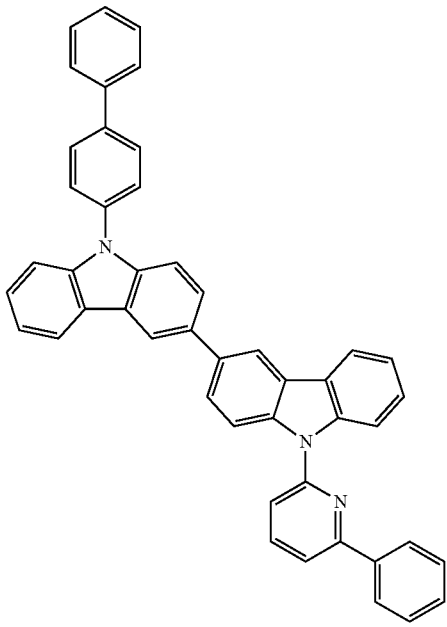
A32
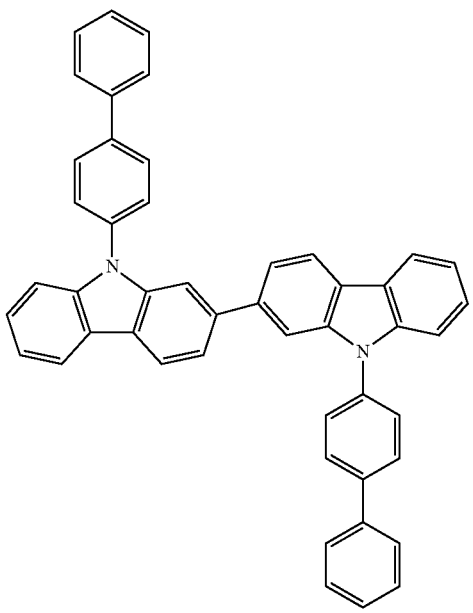

A33
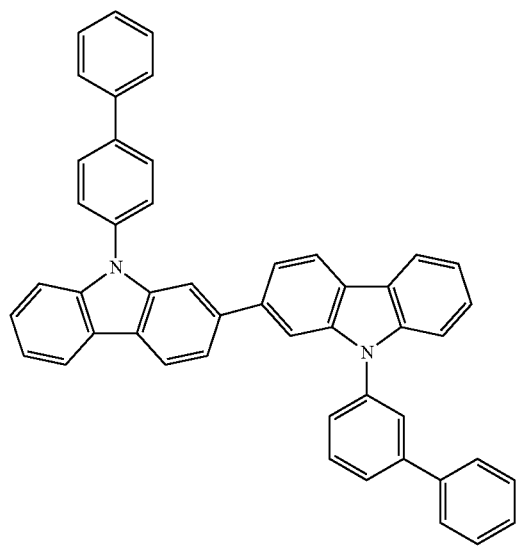
A34
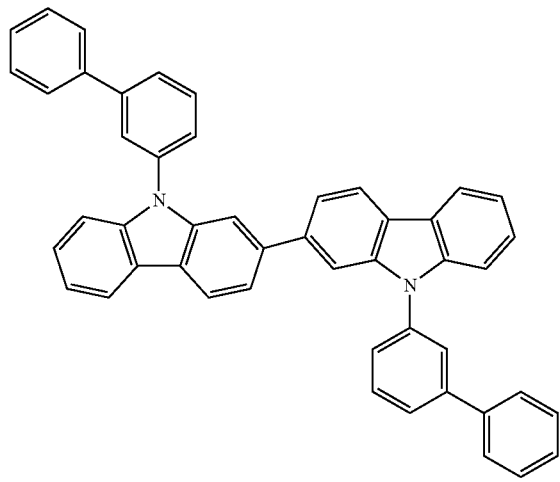
A35
A36
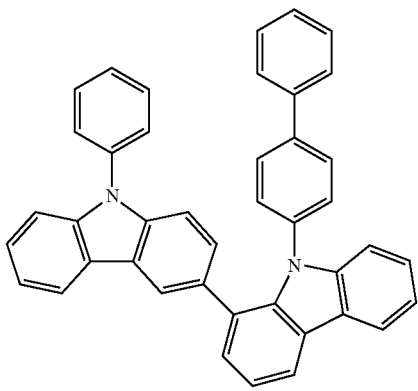
A37
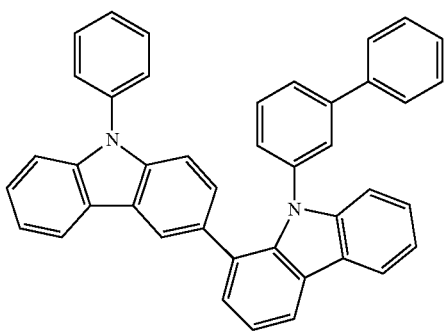
A38
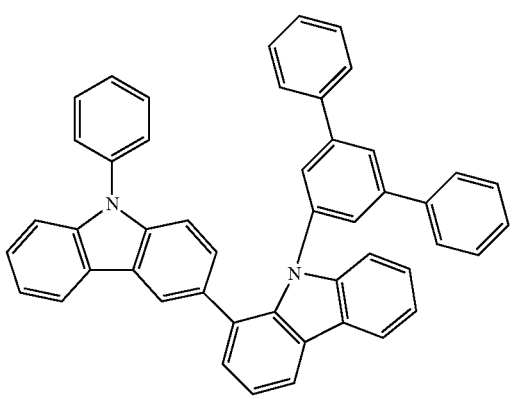
A39
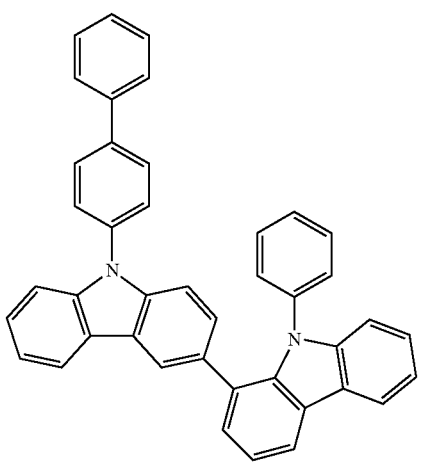

A40
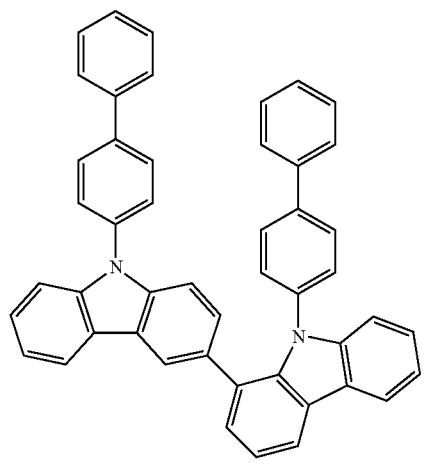
A41
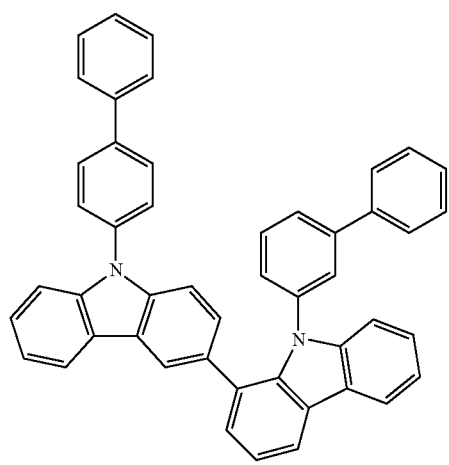
A42
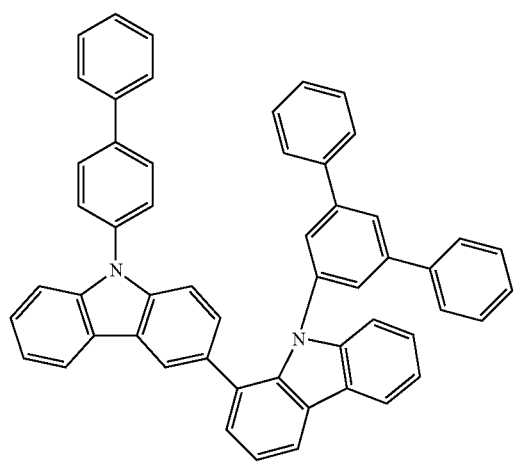
A43
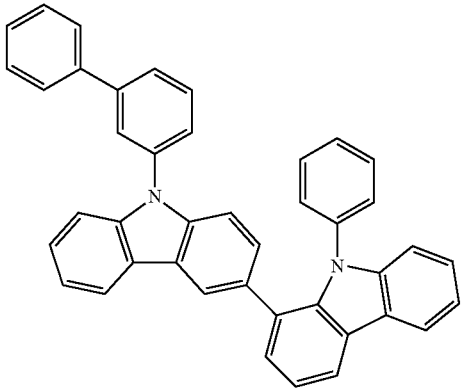
A44
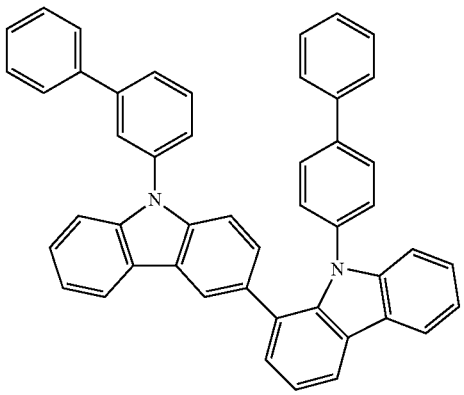
A45
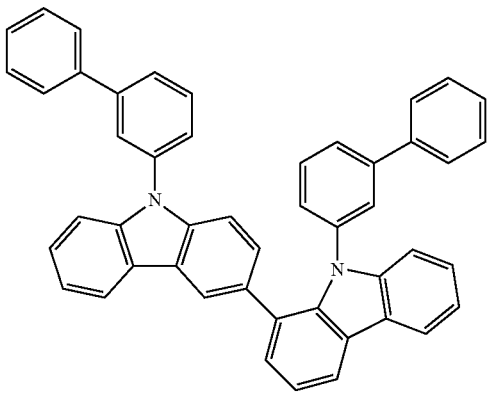
A46
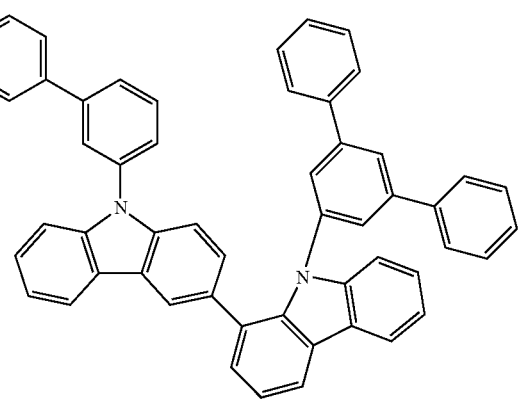

-continued
A47
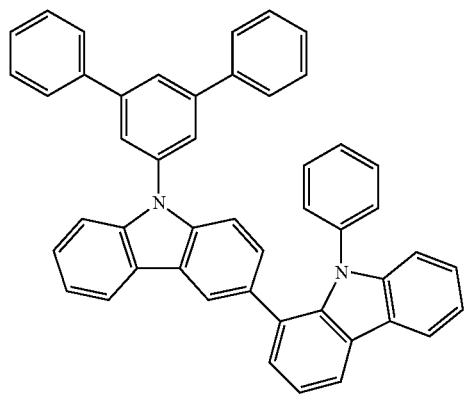
A48
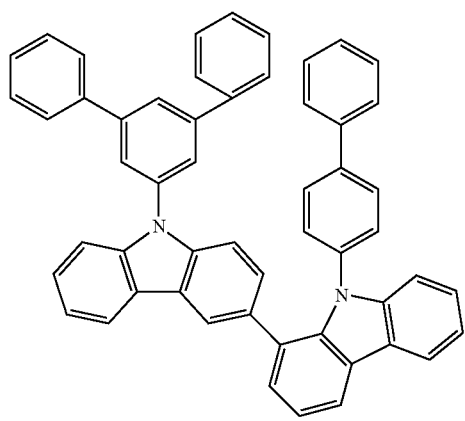
A49
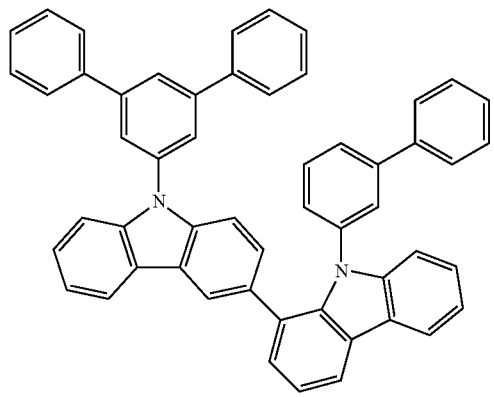
A50
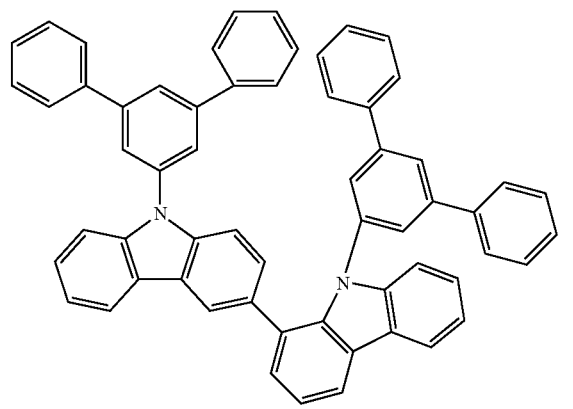
-continued
A51
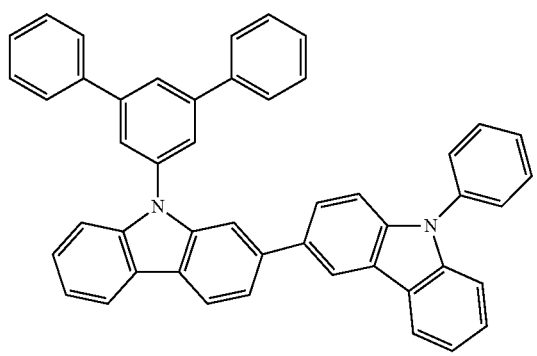
A52
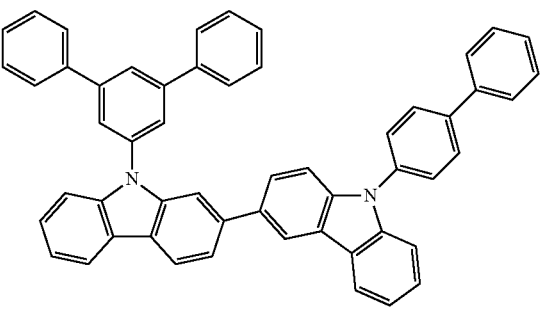
A53
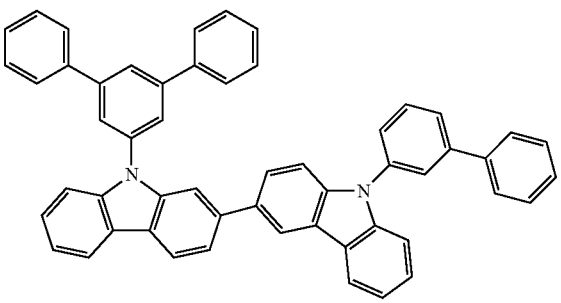
A54
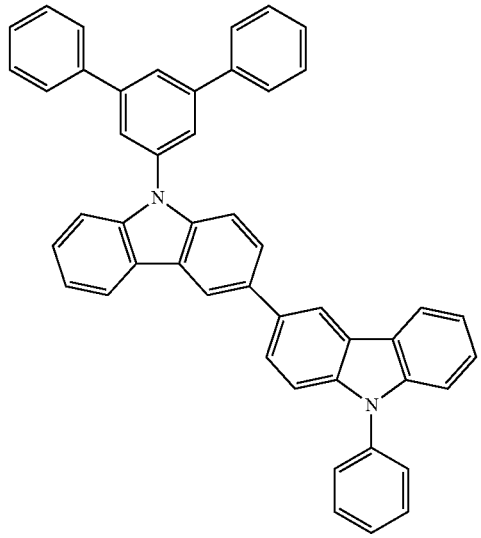

A55
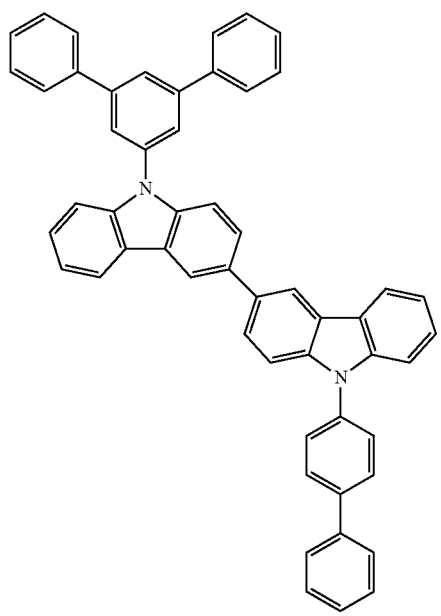
A56
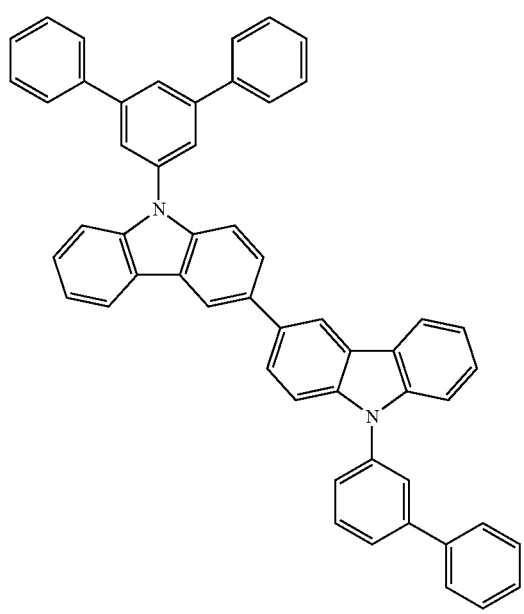
A57
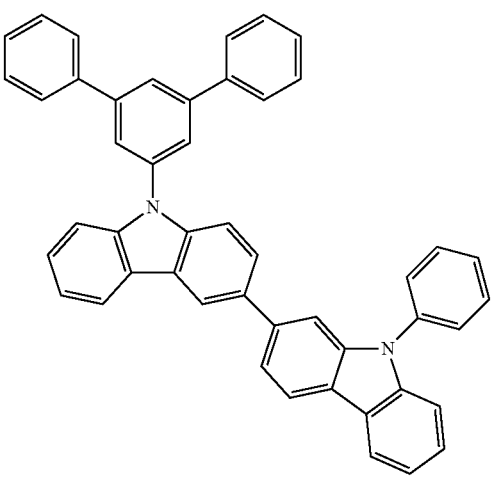
A58
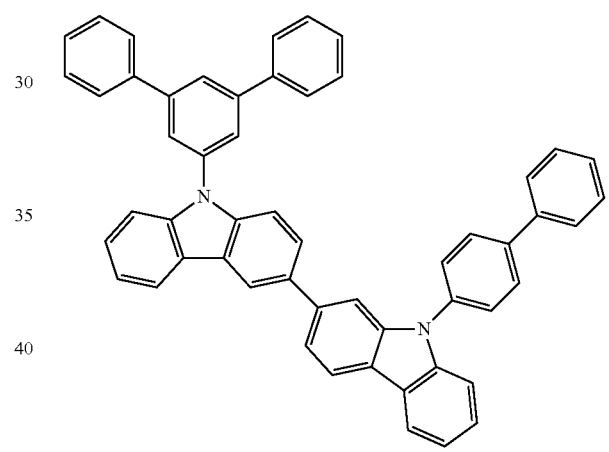
A59
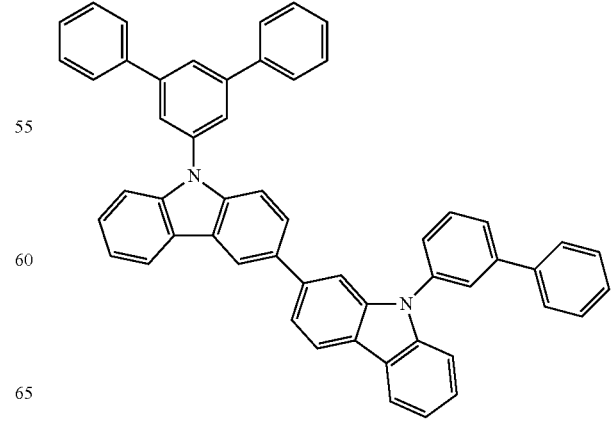

-continued
A60
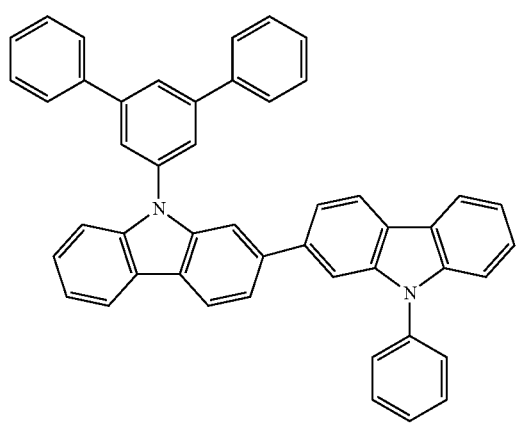
A61
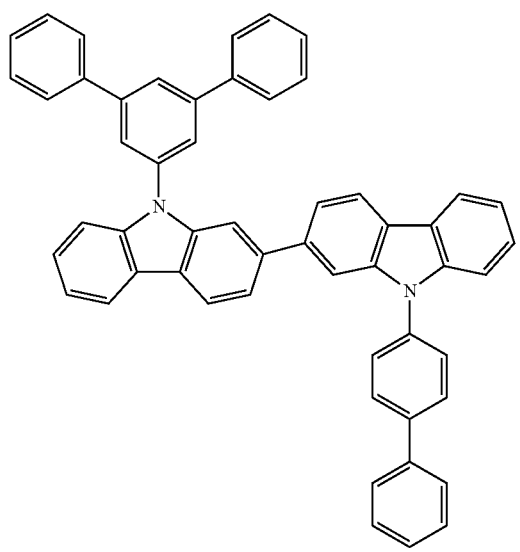
A62
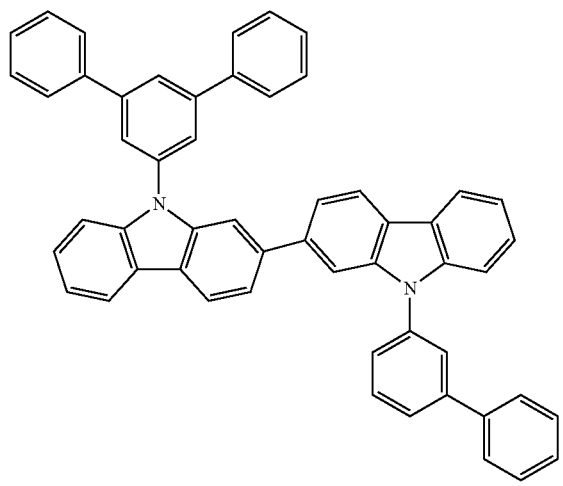
-continued
A63
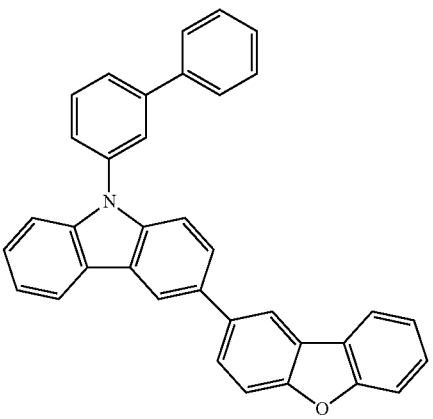
A64
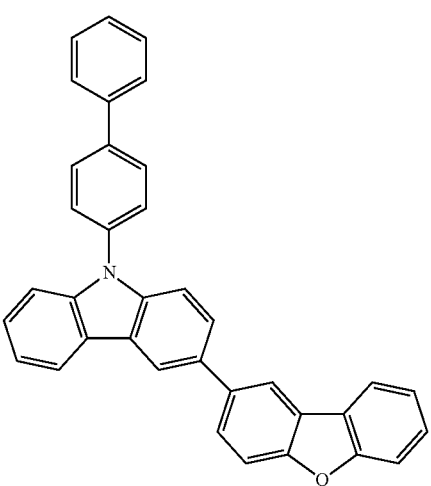
A65
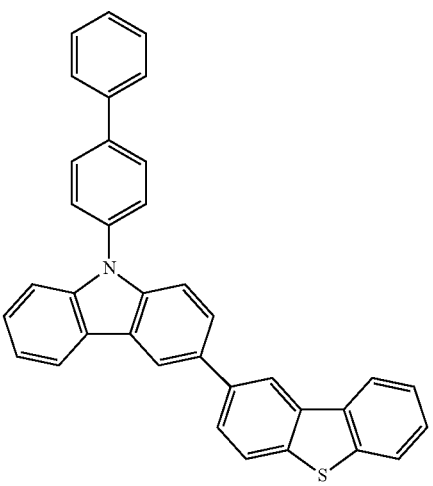

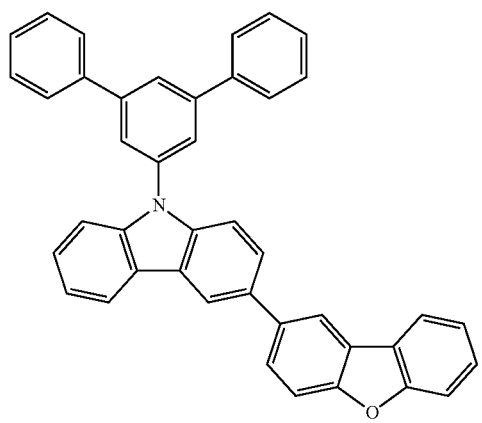
A66
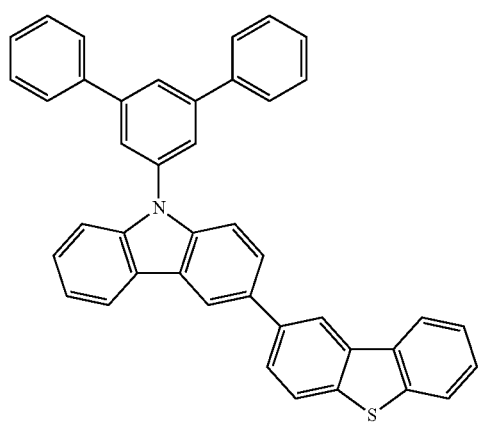
A67
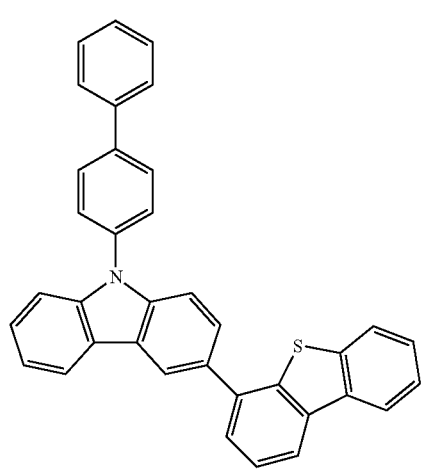
A68
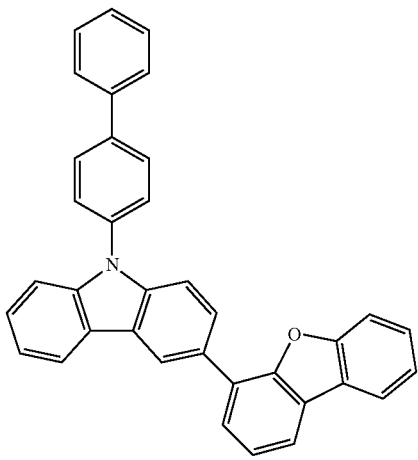
A69
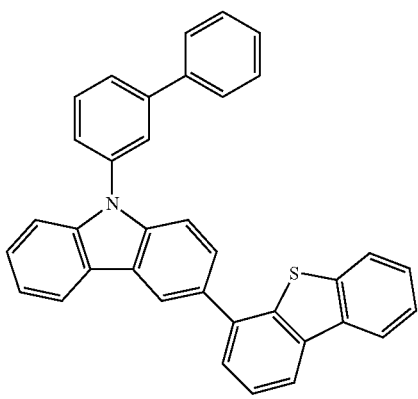
A70
A71
A72

-continued
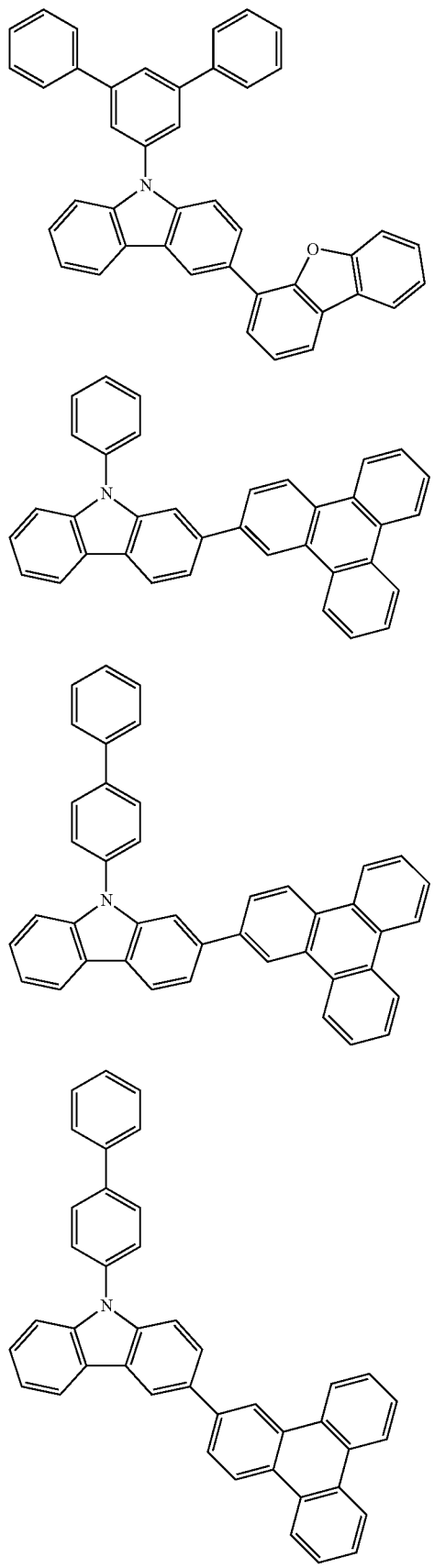
A73
A74
A75
A76
-continued
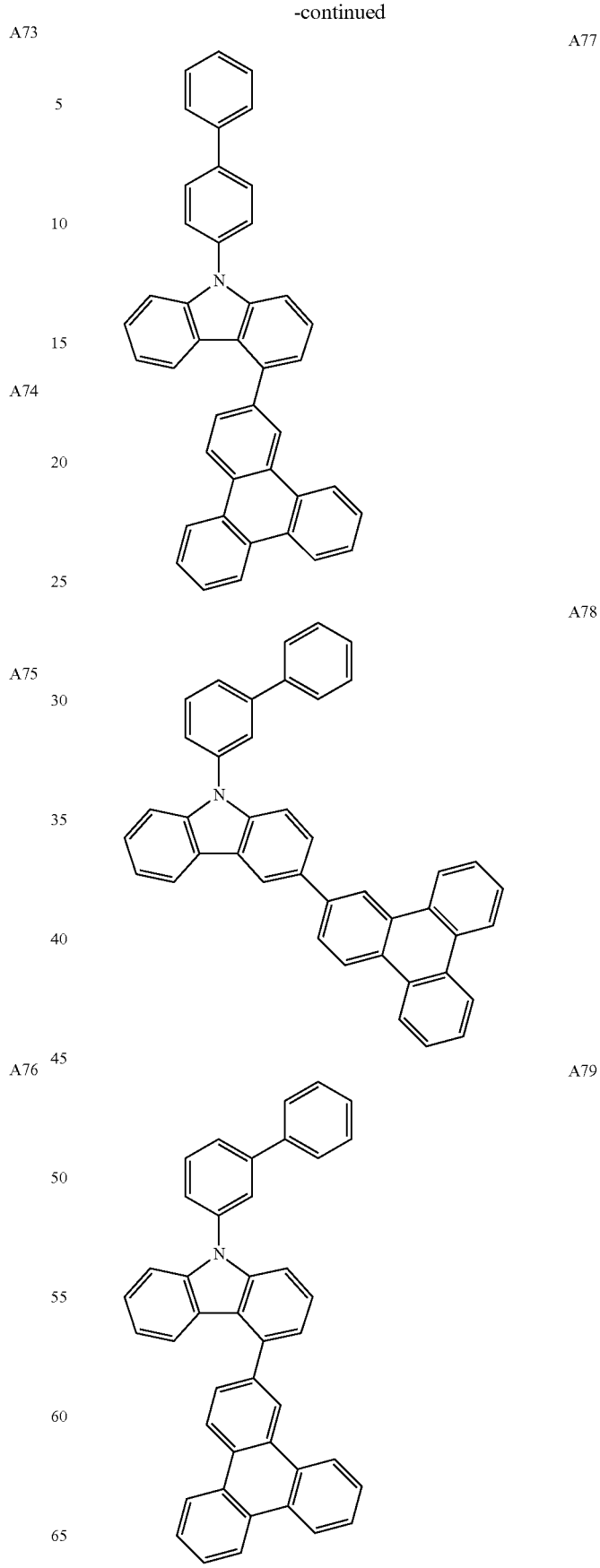
A77
A78
A79

A80
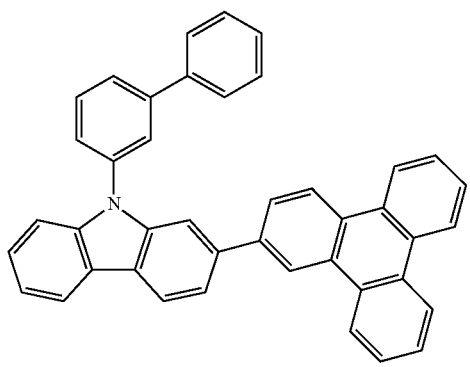
A81
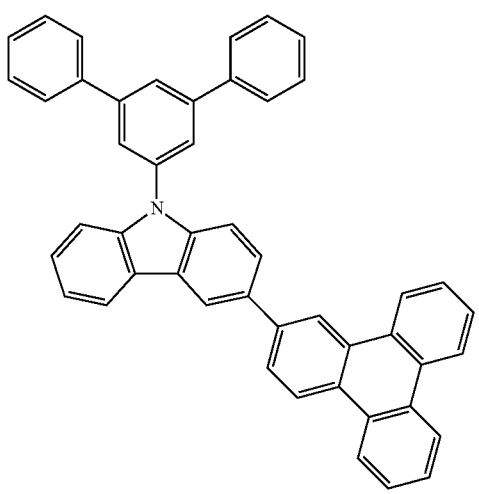
A82
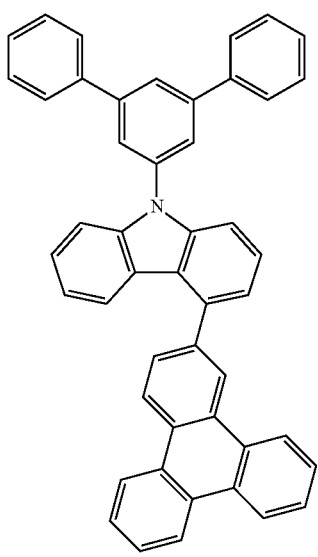
A83
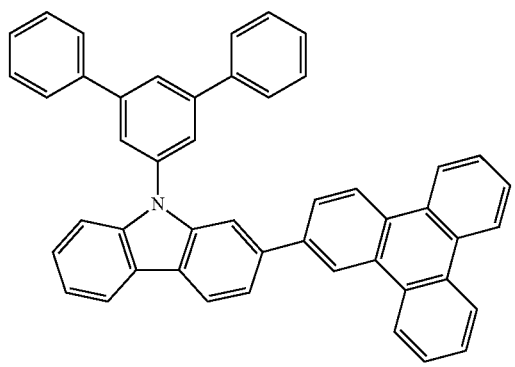
B1
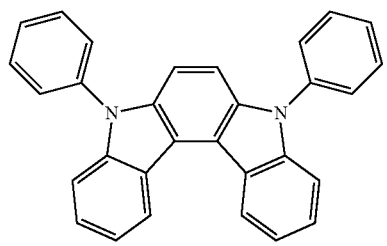
B2
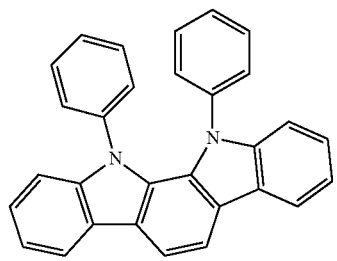
B3
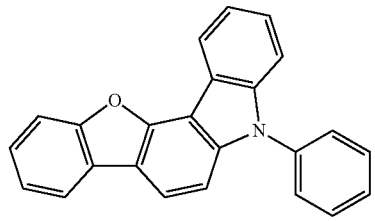
B4
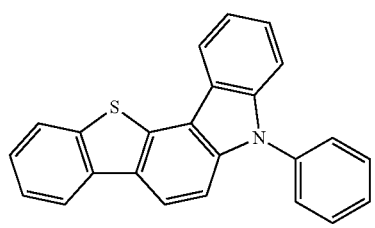
B5
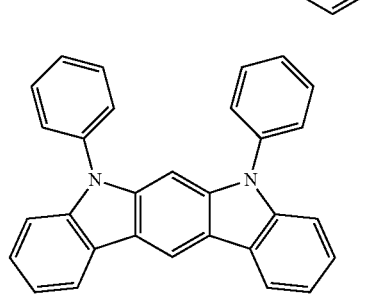

-continued
B6
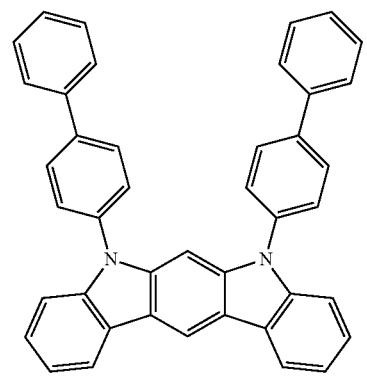
B7
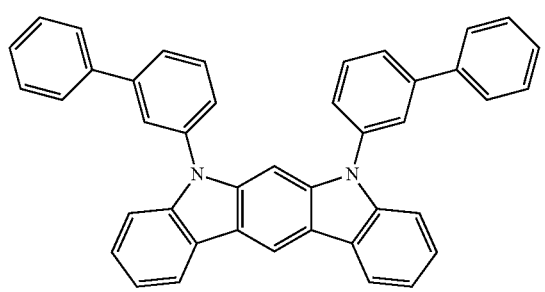
B8
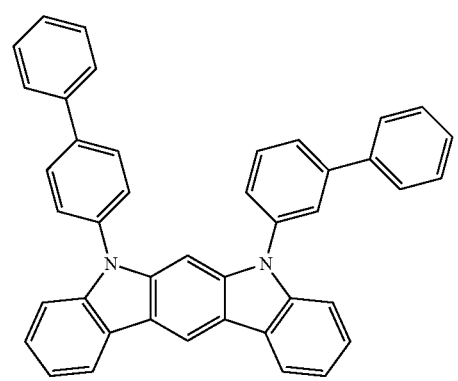
B9
B10
-continued
B11
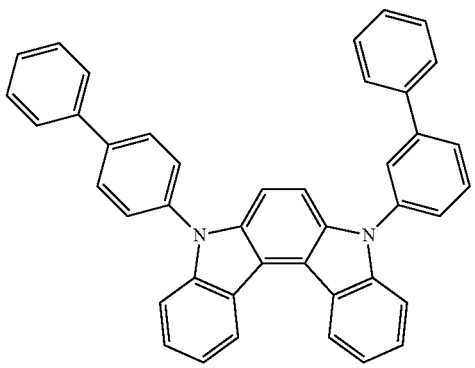
B12
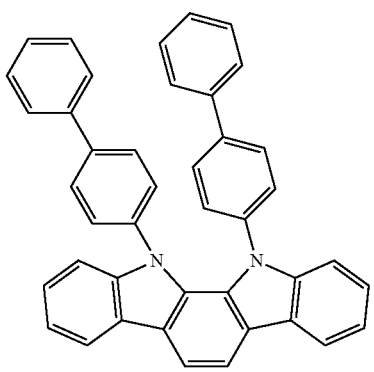
B13
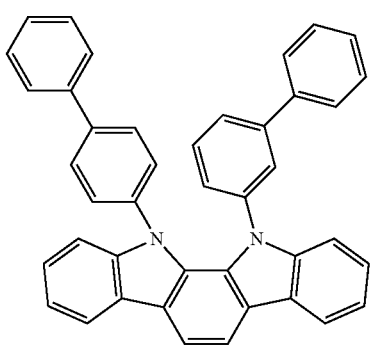
B14
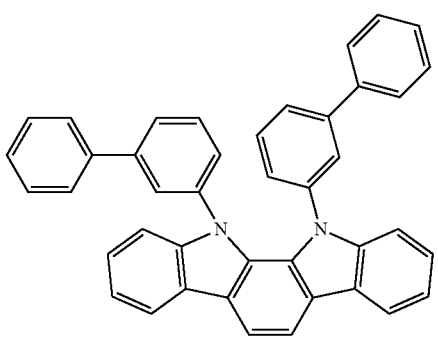

-continued

B15
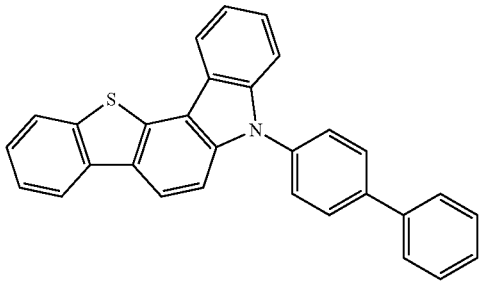

B16
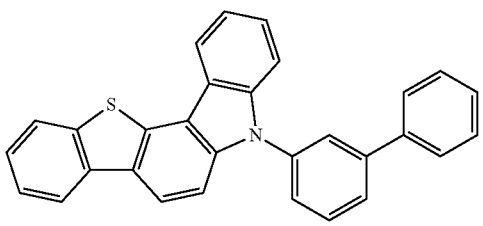

B17
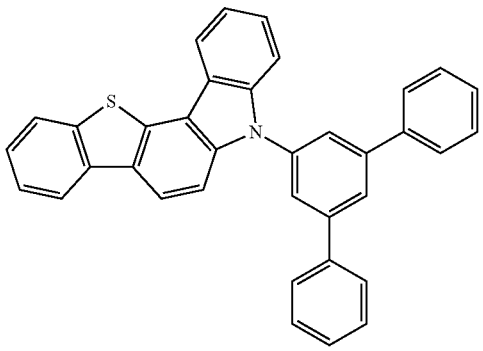

B18

B19
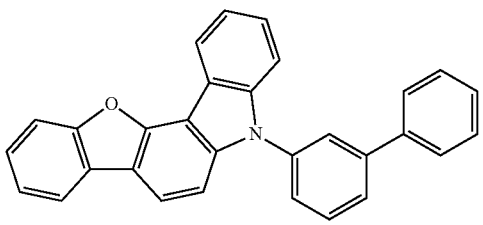

-continued

B20
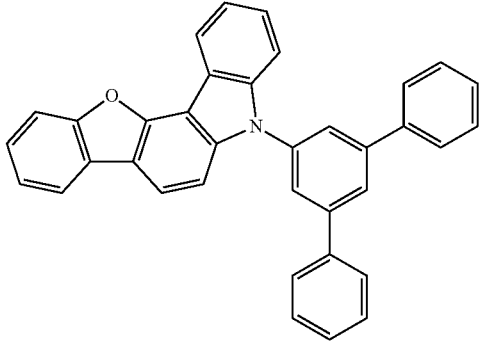

When the first host and the second host all are included in an emission layer, holes and electrons provided to the emission layer may be effectively controlled. Accordingly, an organic light-emitting device with high luminescent efficiency and long lifespan may be obtained.

A weight ratio of the first host to the second host in the emission layer may be each independently in a range of 1:99 to 99:1, for example, 10:90 to 90:10. When the weight ratio of the first host and the second host is within these ranges, holes and electrons provided to the emission layer may be effectively controlled.

A dopant in the emission layer may be a fluorescent dopant that emits light according to a fluorescent emission mechanism or a phosphorescent dopant that emits light according to a phosphorescent emission mechanism.

According to an embodiment, the dopant in the emission layer may be a phosphorescent dopant, and the phosphorescent dopant may include an organometallic compound represented by Formula 81 below:

Formula 81

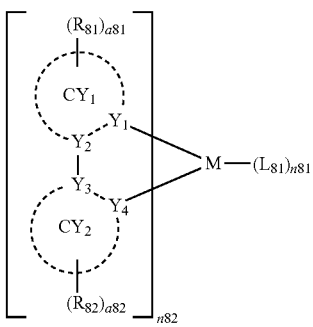

wherein in Formula 81,

M may be selected from iridium (Ir), platinum (Pt), osmium (Os), titanium (Ti), zirconium (Zr), hafnium (Hf), europium (Eu), terbium (Tb), and thulium (Tm);

$Y_1$ to $Y_4$ are each independently carbon (C) or nitrogen (N);

$Y_1$ and $Y_2$ are linked via a single bond or a double bond, and $Y_3$ and $Y_4$ are linked via a single bond or a double bond;

$CY_1$ and $CY_2$ are each independently selected from a benzene, a naphthalene, a fluorene, a spiro-fluorene, an indene, a pyrrole, a thiophene, a furan, an imidazole, a pyrazole, a thiazole, an isothiazole, an oxazole, an isooxazole, a pyridine, a pyrazine, a pyrimidine, a pyridazine, a quinoline, an isoquinoline, a benzoquinoline, a quinoxaline, a quinazoline, a carbazole, a benzoimidazole, a benzofuran, a benzothiophene, an isobenzothiophene, a benzooxazole, an isobenzooxazole, a triazole, a tetrazole, an oxadiazole, a triazine, a dibenzofuran, and a dibenzothiophene, and $CY_1$ and $CY_2$ are optionally linked to each other through a single bond or an organic linking group;

$R_{81}$ to $R_{82}$ may be each independently a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, —$SF_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —$N(Q_1)(Q_2)$, —$Si(Q_3)(Q_4)(Q_5)$, or —$B(Q_6)(Q_7)$;

a81 and a82 are each independently an integer of 1 to 5;

n81 is an integer of 0 to 4;

n82 is 1, 2, or 3; and $L_{81}$ is a monovalent organic ligand, a divalent organic ligand, or a trivalent organic ligand.

$R_{81}$ and $R_{82}$ may be understood by referring to the description provided herein in connection with $R_{41}$.

The phosphorescent dopant may include at least one of Compounds PD1 to PD78 below, but is not limited thereto:

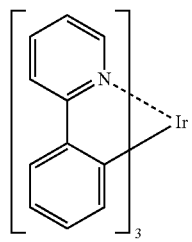
PD1

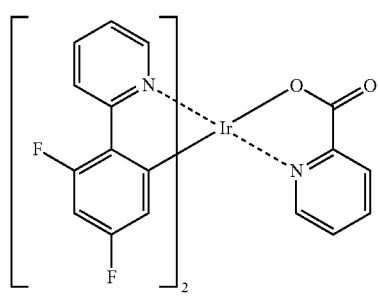
PD2

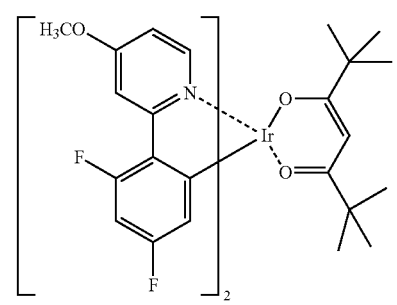
PD3

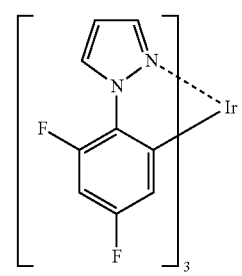
PD4

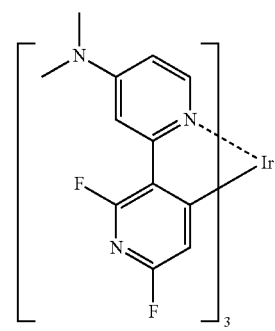
PD5

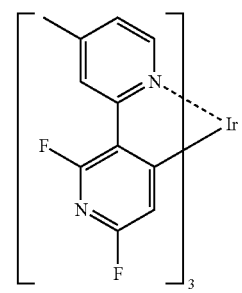
PD6

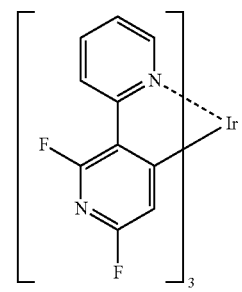
PD7

PD8
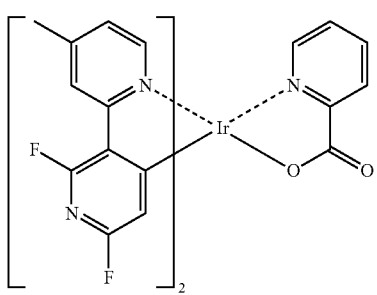
PD9
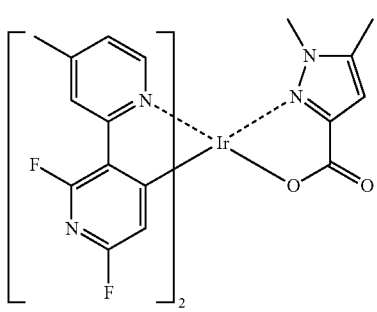
PD10
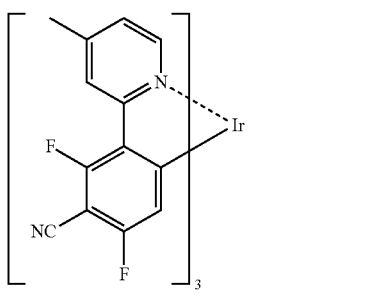
PD11
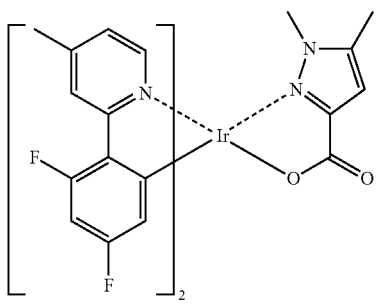
PD12
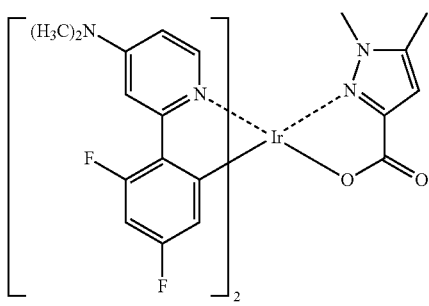
PD13
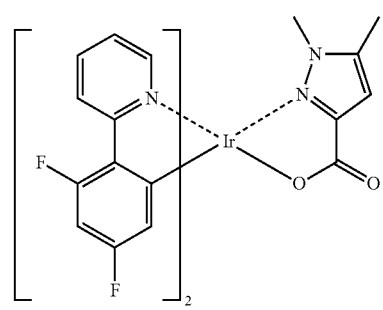
PD14
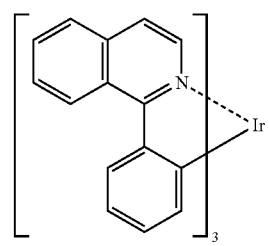
PD15
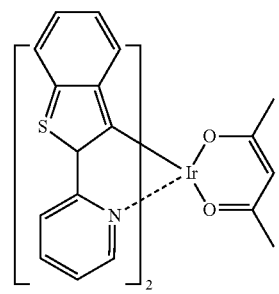
PD16
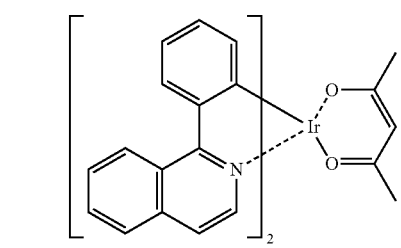
PD17
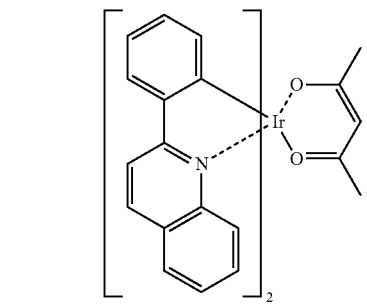

135
-continued
PD18
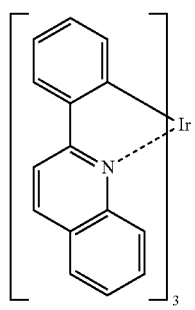
PD19
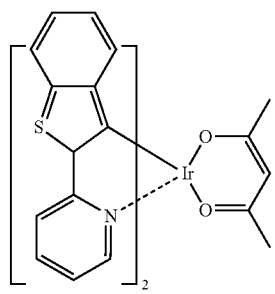
PD20
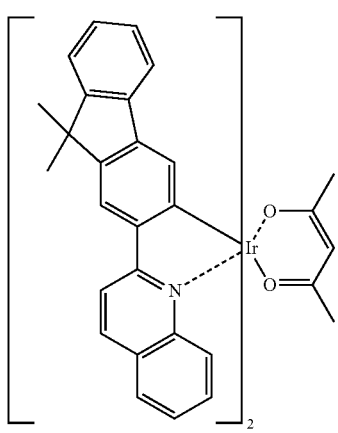
PD21
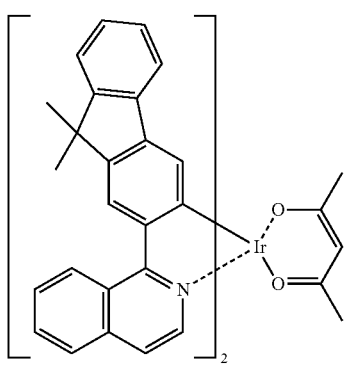
PD22
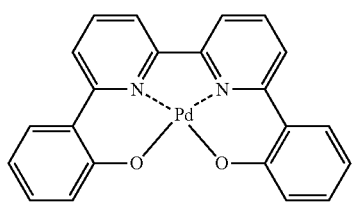
136
-continued
PD23
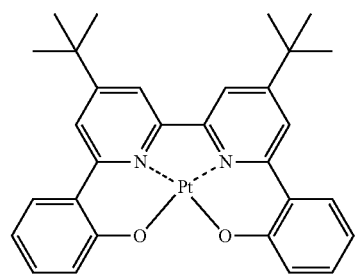
PD24
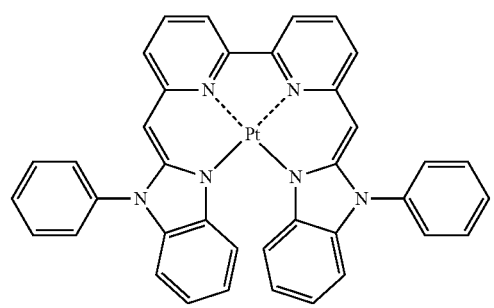
PD26
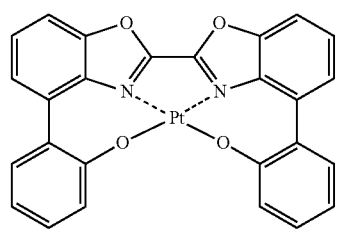
PD26
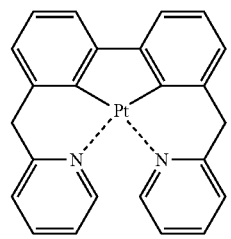
PD27
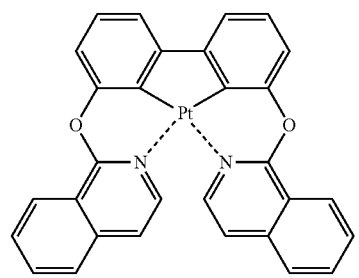
PD28
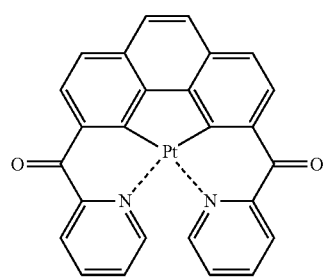

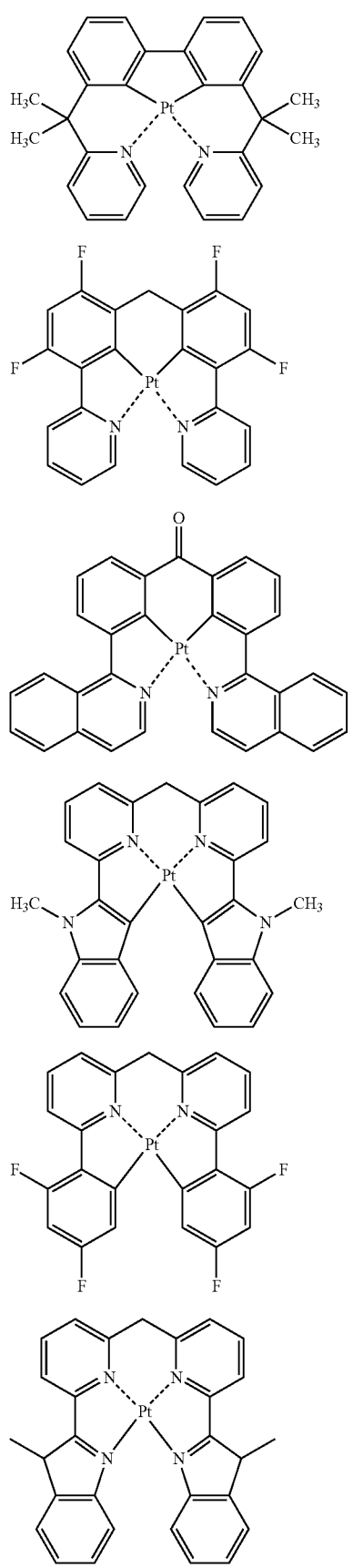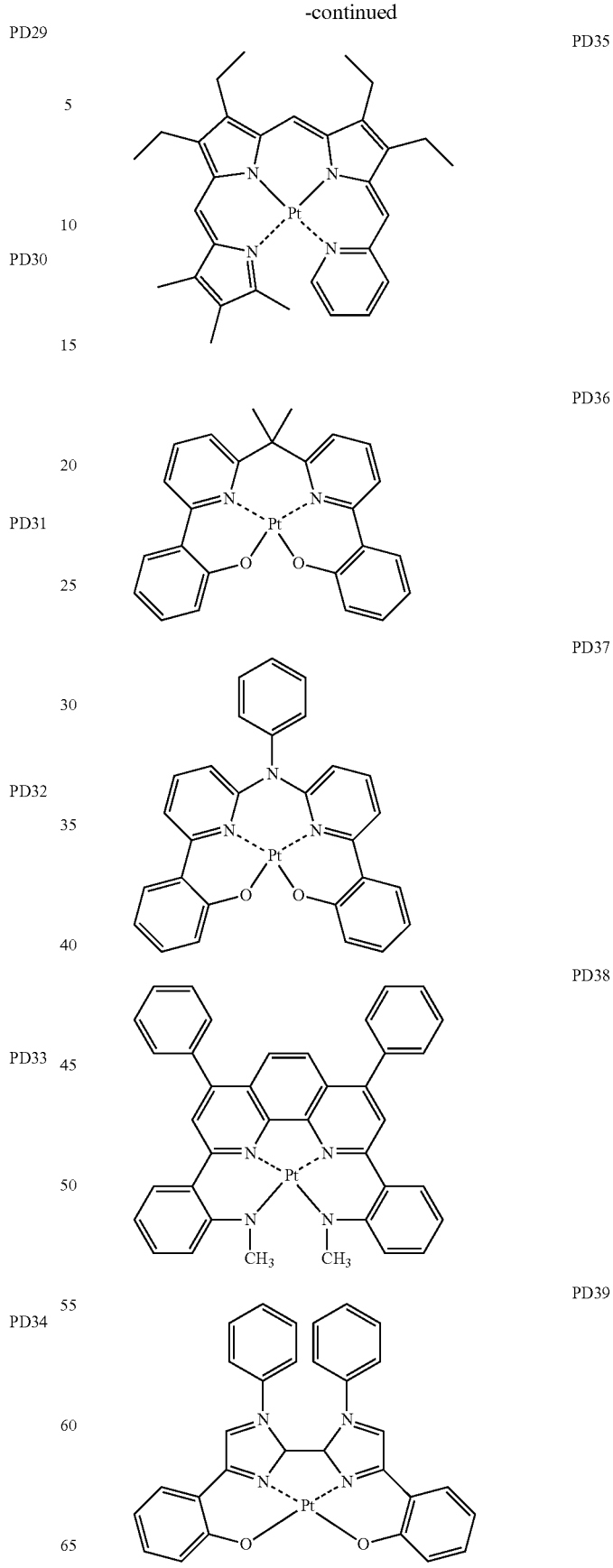

PD40 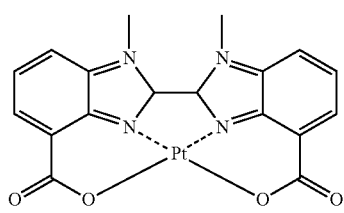
PD41 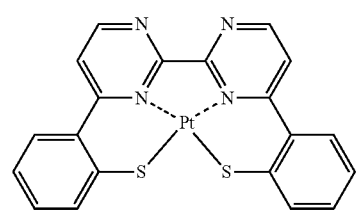
PD42 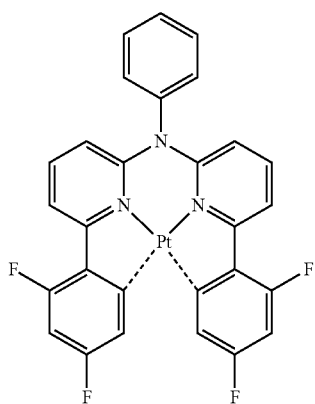
PD43 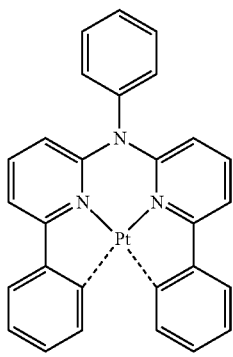
PD44 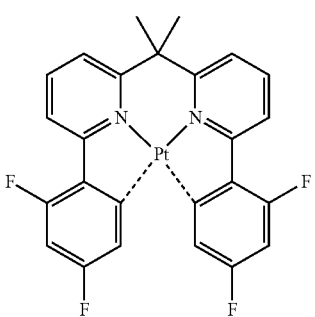
PD45 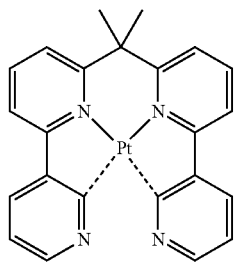
PD46 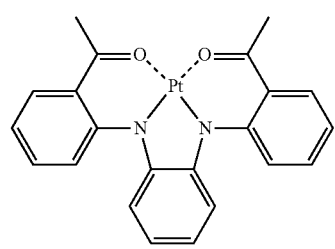
PD47 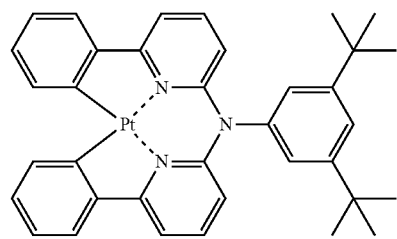
PD48 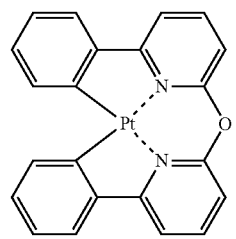
PD49 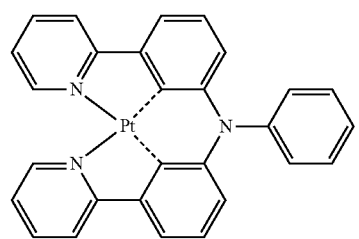
PD50 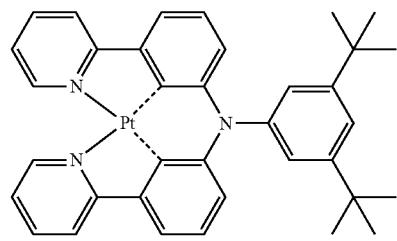

PD51 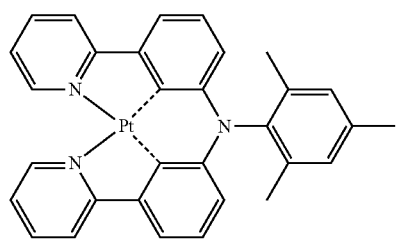
PD56 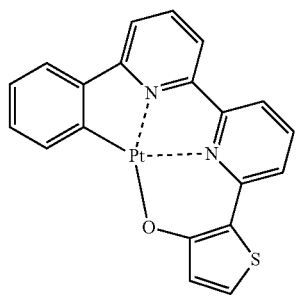
PD52 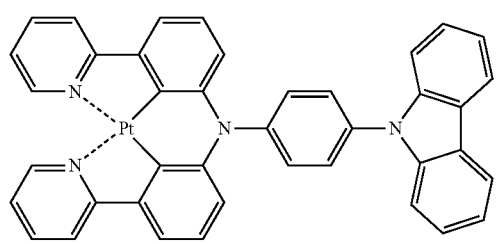
PD57 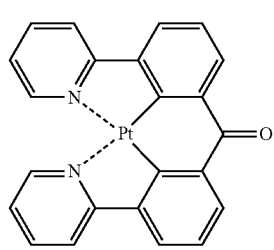
PD53 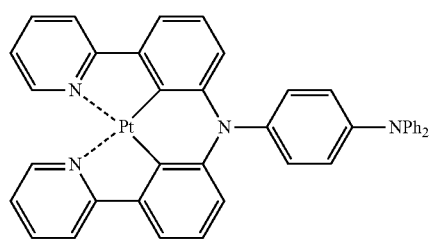
PD58 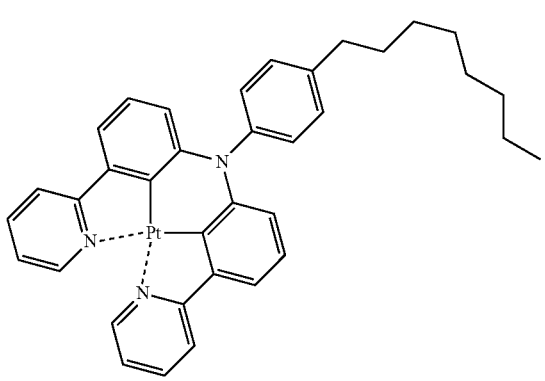
PD54 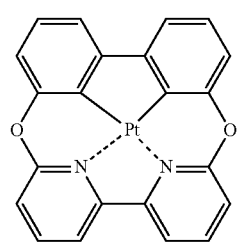
PD59 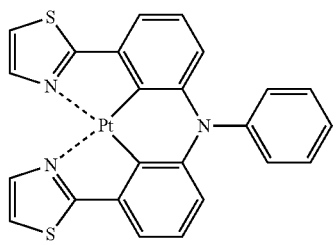
PD55 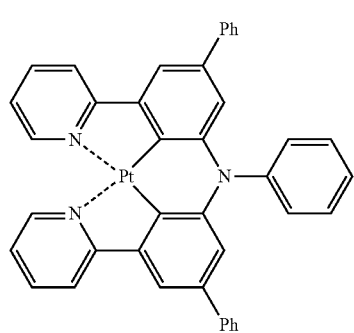
PD60 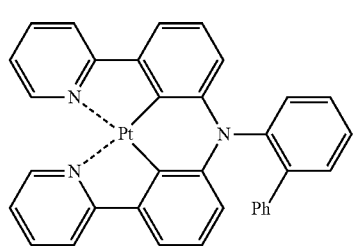

PD61 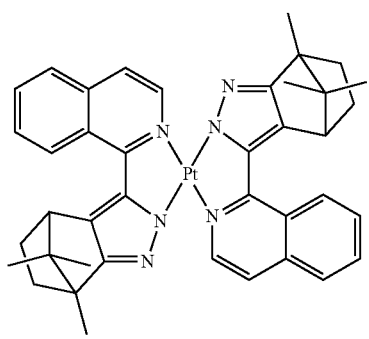
PD62 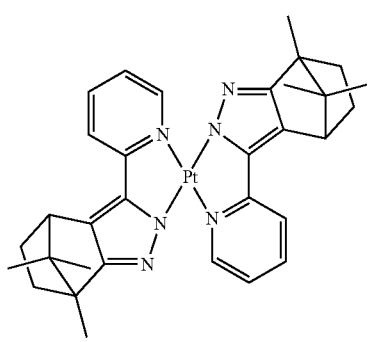
PD63 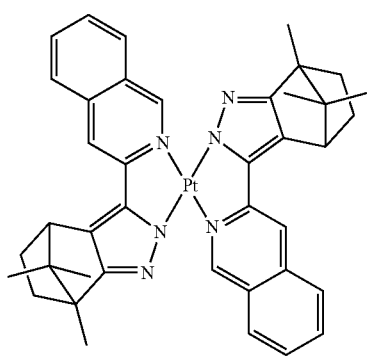
PD64 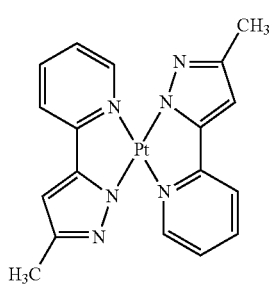
PD65 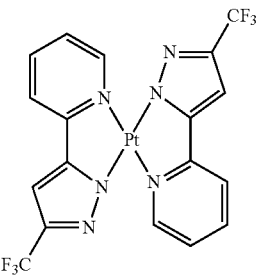
PD66 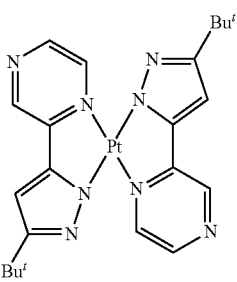
PD67 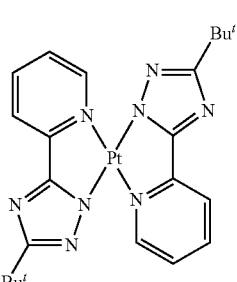
PD68 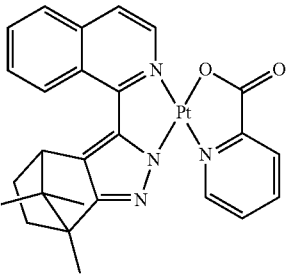
PD69 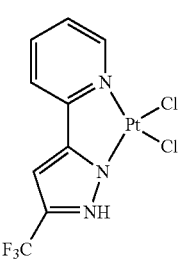

-continued
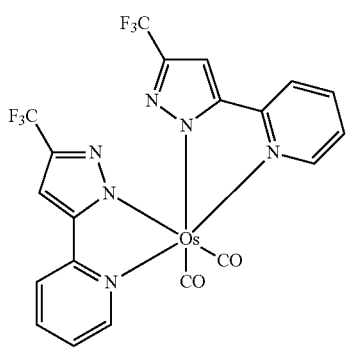
PD70
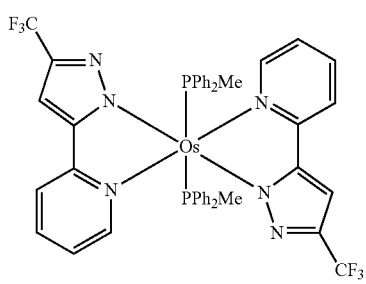
PD71
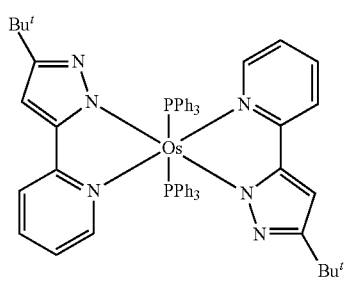
PD72
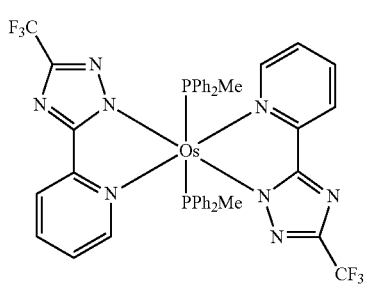
PD73
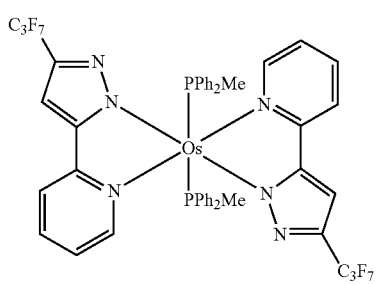
PD74
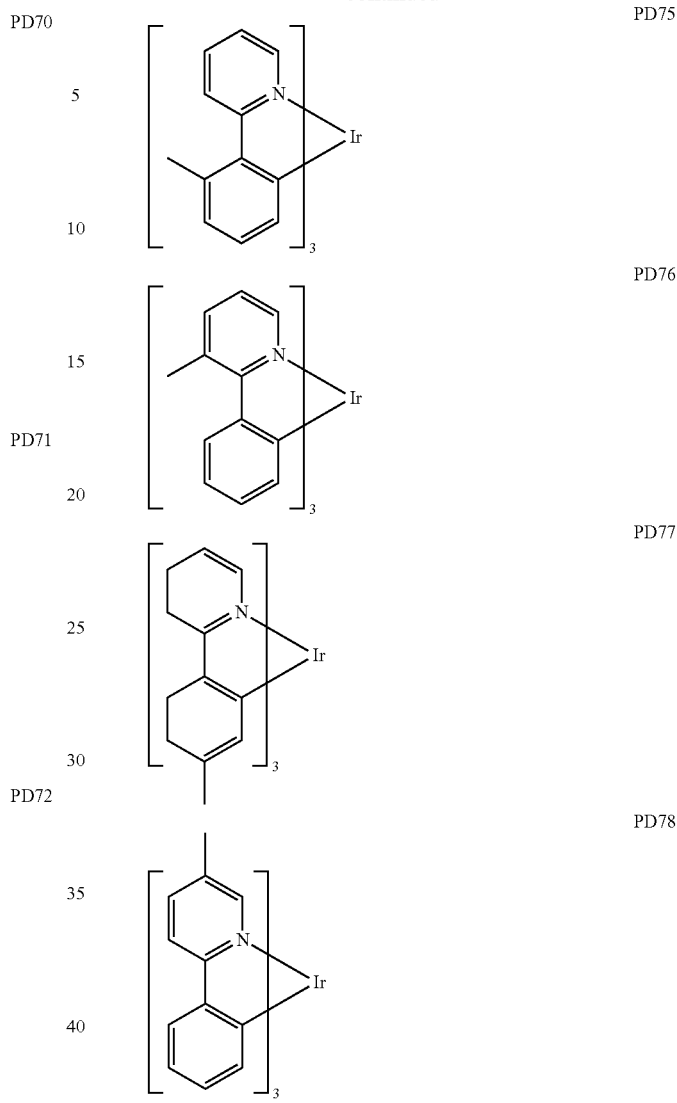
PD75
PD76
PD77
PD78
According to another embodiment, the phosphorescent dopant may include PtOEP illustrated below:
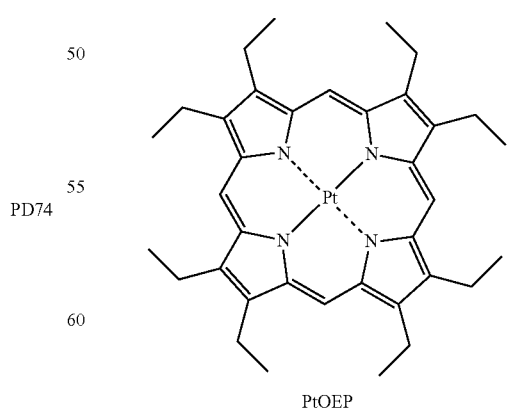
PtOEP
The fluorescent dopant may include at least one selected from DPAVBi, BDAVBi, TBPe, DCM, DCJTB, Coumarin 6, and C545T.

DPAVBi
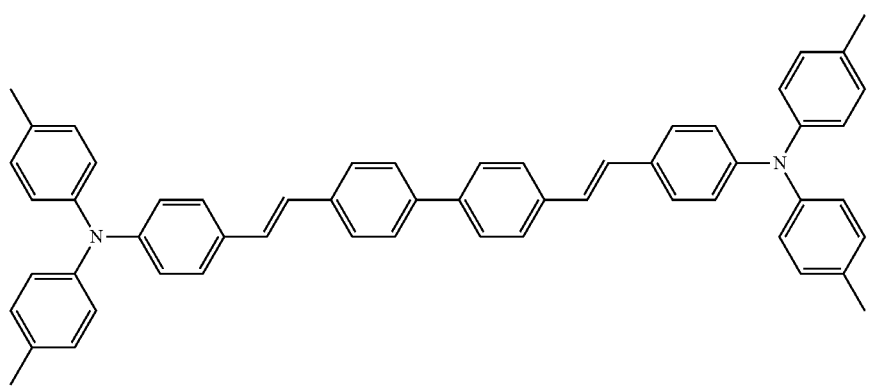
BDAVBi
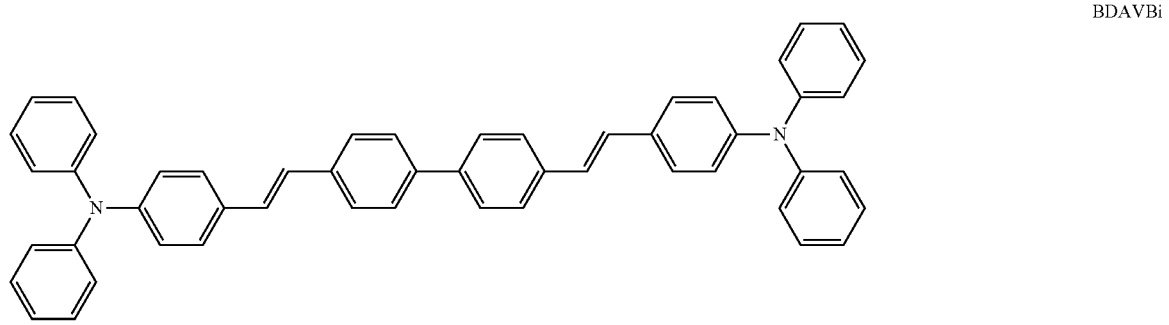
TBPe
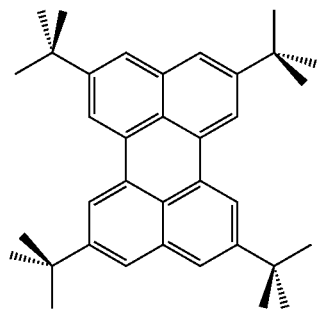
DCM
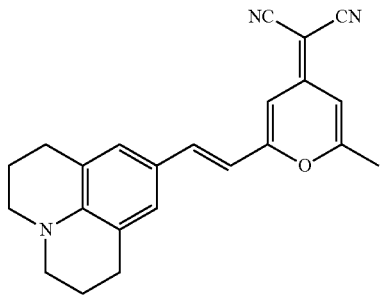
DCJTB
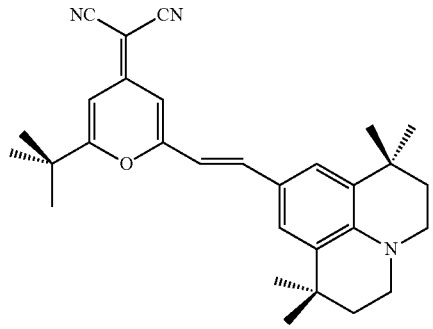
Coumarin 6
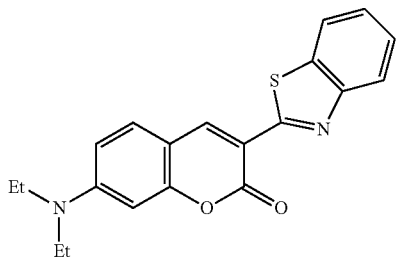
C545T
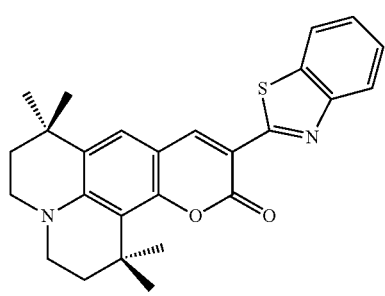

When the emission layer includes a host and a dopant, an amount of the dopant may be in a range of about 0.01 to about 20 parts by weight based on 100 parts by weight of the host, but is not limited thereto.

A thickness of the emission layer may be in a range of about 100 Å to about 1,000 Å, for example, about 200 Å to about 600 Å. When the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer, and an electron injection layer.

For example, the electron transport region may have a structure of hole blocking layer/electron transport layer/electron injection layer or a structure of electron transport layer/electron injection layer, but the structure of the electron transport region is not limited thereto. The electron transport layer may have a single-layered structure or a multi-layer structure including two or more different materials.

Conditions for forming the hole blocking layer, the electron transport layer, and the electron injection layer which constitute the electron transport region may be understood by referring to the conditions for forming the hole injection layer.

When the electron transport layer includes a hole blocking layer, the hole blocking layer may include, for example, at least one of BCP and Bphen, but may also include other materials.

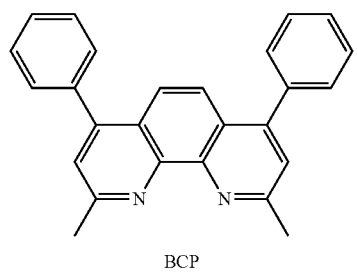

BCP

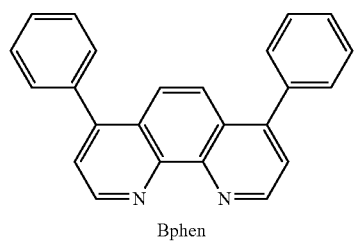

Bphen

A thickness of the hole blocking layer may be in a range of about 20 Å to about 1,000 Å, for example, about 30 Å to about 300 Å. When the thickness of the hole blocking layer is within these ranges, the hole blocking layer may have excellent hole blocking characteristics without a substantial increase in driving voltage.

The electron transport layer may further include, in addition to the organometallic compound represented by Formula 1, at least one selected from BCP, Bphen, $Alq_3$, Balq, TAZ, and NTAZ.

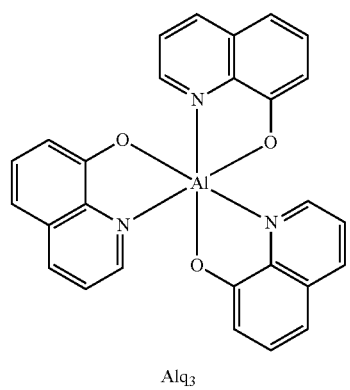

$Alq_3$

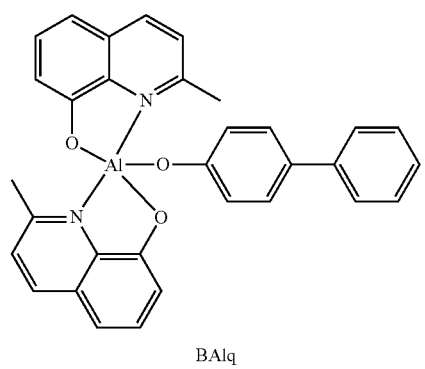

BAlq

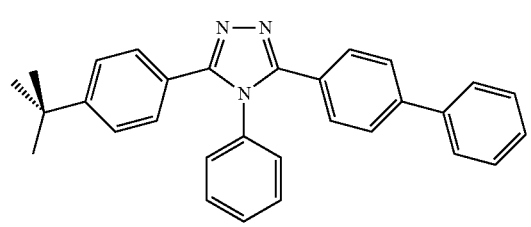

TAZ

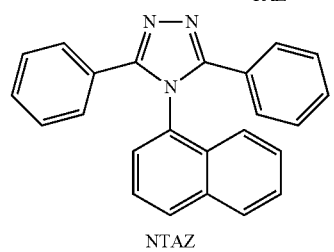

NTAZ

According to another embodiment, the electron transport layer may include at least one of ET1 and ET2, but are not limited thereto:

ET1

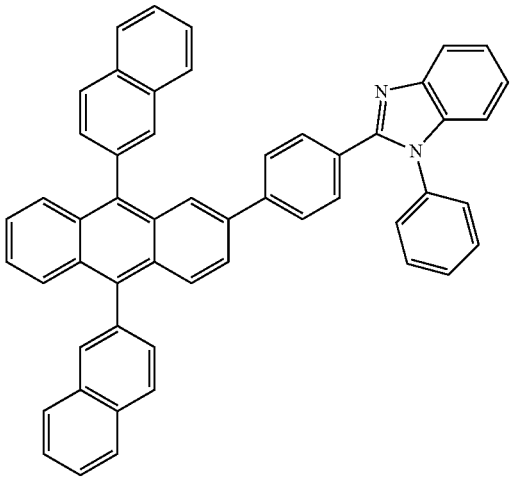

ET2

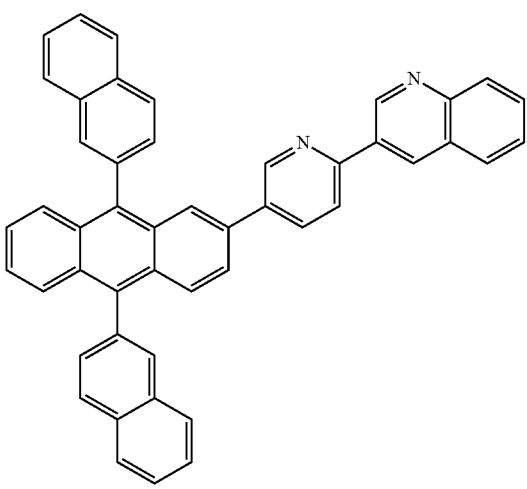

A thickness of the electron transport layer may be in a range of about 100 Å to about 1,000 Å, for example, about 150 Å to about 500 Å. When the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, for example, Compound ET-D1 (lithium quinolate, LiQ) or ET-D2.

ET-D1

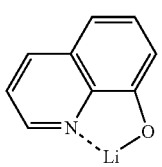

ET-D2

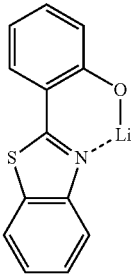

The electron transport region may include an electron injection layer (EIL) that allows electrons to be easily provided from a second electrode 19.

The electron injection layer may include at least one selected from, LiF, NaCl, CsF, $Li_2O$, BaO, and LiQ.

A thickness of the electron injection layer may be in a range of about 1 Å to about 100 Å, for example, about 3 Å to about 90 Å. When the thickness of the electron injection layer is within the range described above, the electron injection layer may have satisfactory electron injection characteristics without a substantial increase in driving voltage.

The second electrode 19 is disposed on the organic layer 15. The second electrode 19 may be a cathode. A material for forming the second electrode 19 may be metal, an alloy, an electrically conductive compound, and a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be used as the material for forming the second electrode 19. To manufacture a top emission type light-emitting device, a transmissive electrode formed using ITO or IZO may be used as the second electrode 19.

Hereinbefore, the organic light-emitting device has been described with reference to FIG. 1, but is not limited thereto.

A $C_1$-$C_{60}$ alkyl group used herein refers to a linear or branched aliphatic hydrocarbon monovalent group having 1 to 60 carbon atoms. Detailed examples thereof are a methyl group, an ethyl group, a propyl group, an isobutyl group, a sec-butyl group, a tert-butyl group, a pentyl group, an iso-amyl group, and a hexyl group. A $C_1$-$C_{60}$ alkylene group used herein refers to a divalent group having the same structure as the $C_1$-$C_{60}$ alkyl group.

A $C_1$-$C_{60}$ alkoxy group used herein refers to a monovalent group represented by —$OA_{101}$ (wherein $A_{101}$ is the $C_1$-$C_{60}$ alkyl group). Detailed examples thereof are a methoxy group, an ethoxy group, and an isopropyloxy group.

A $C_2$-$C_{60}$ alkenyl group used herein refers to a hydrocarbon group formed by substituting at least one carbon double bond in the middle or at the terminal of the $C_2$-$C_{60}$ alkyl group. Detailed examples thereof are an ethenyl group, a propenyl group, and a butenyl group. A $C_2$-$C_{60}$ alkenylene group used herein refers to a divalent group having the same structure as the $C_2$-$C_{60}$ alkenyl group.

A $C_2$-$C_{60}$ alkynyl group used herein refers to a hydrocarbon group formed by substituting at least one carbon triple bond in the middle or at the terminal of the $C_2$-$C_{60}$ alkyl group. Detailed examples thereof are an ethynyl group, and a propynyl group. A $C_2$-$C_{60}$ alkynylene group used herein refers to a divalent group having the same structure as the $C_2$-$C_{60}$ alkynyl group.

A $C_3$-$C_{10}$ cycloalkyl group used herein refers to a monovalent hydrocarbon monocyclic group having 3 to 10 carbon atoms. Detailed examples thereof are a cyclopropyl group, a cyclobutyl group, a cyclopentyl group, a cyclohexyl group, and a cycloheptyl group. A $C_3$-$C_{10}$ cycloalkylene group used herein refers to a divalent group having the same structure as the $C_3$-$C_{10}$ cycloalkyl group.

A $C_2$-$C_{10}$ heterocycloalkyl group used herein refers to a monovalent monocyclic group having at least one hetero atom selected from N, O, P, and S as a ring-forming atom and 2 to 10 carbon atoms. Detailed examples thereof are a tetrahydrofuranyl group, and a tetrahydrothiophenyl group. A $C_2$-$C_{10}$ heterocycloalkylene group used herein refers to a divalent group having the same structure as the $C_2$-$C_{10}$ heterocycloalkyl group.

A $C_3$-$C_{10}$ cycloalkenyl group used herein refers to a monovalent monocyclic group that has 3 to 10 carbon atoms and at least one double bond in the ring thereof and does not have aromaticity. Detailed examples thereof are a cyclopentenyl group, a cyclohexenyl group, and a cycloheptenyl group. A $C_3$-$C_{10}$ cycloalkenylene group used herein refers to a divalent group having the same structure as the $C_3$-$C_{10}$ cycloalkenyl group.

A $C_2$-$C_{10}$ heterocycloalkenyl group used herein refers to a monovalent monocyclic group that has at least one hetero atom selected from N, O, P, and S as a ring-forming atom, 2 to 10 carbon atoms, and at least one double bond in its ring. Detailed examples of the $C_2$-$C_{10}$ heterocycloalkenyl group are a 2,3-dihydrofuranyl group and a 2,3-dihydrothiophenyl group. A $C_2$-$C_{10}$ heterocycloalkenylene group used herein refers to a divalent group having the same structure as the $C_2$-$C_{10}$ heterocycloalkenyl group.

A $C_6$-$C_{60}$ aryl group used herein refers to a monovalent group having a carbocyclic aromatic system having 6 to 60 carbon atoms, and a $C_6$-$C_{60}$ arylene group used herein refers to a divalent group having a carbocyclic aromatic system having 6 to 60 carbon atoms. Detailed examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

A $C_2$-$C_{60}$ heteroaryl group used herein refers to a monovalent group having a carbocyclic aromatic system that has at least one hetero atom selected from N, O, P, and S as a ring-forming atom, and 2 to 60 carbon atoms. A $C_2$-$C_{60}$ heteroarylene group used herein refers to a divalent group having a carbocyclic aromatic system that has at least one hetero atom selected from N, O, P, and S as a ring-forming atom, and 2 to 60 carbon atoms. Examples of the $C_2$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_2$-$C_{60}$ heteroaryl group and the $C_2$-$C_{60}$ heteroarylene group each include two or more rings, the rings may be fused to each other.

A $C_6$-$C_{60}$ aryloxy group used herein indicates —$OA_{102}$ (wherein $A_{102}$ is the $C_6$-$C_{60}$ aryl group), and a $C_6$-$C_{60}$ arylthio group indicates —$SA_{103}$ (wherein $A_{103}$ is the $C_6$-$C_{60}$ aryl group).

A monovalent non-aromatic condensed polycyclic group used herein refers to a monovalent group that has two or more rings condensed to each other, only carbon atoms (for example, the number of carbon atoms may be in a range of 8 to 60) as ring forming atoms, wherein the molecular structure as a whole is non-aromatic in the entire molecular structure. An example of the monovalent non-aromatic condensed polycyclic group is a fluorenyl group. A divalent non-aromatic condensed polycyclic group used herein refers to a divalent group having the same structure as the monovalent non-aromatic condensed polycyclic group.

A monovalent non-aromatic condensed hetero-polycyclic group used herein refers to a monovalent group that has two or more rings condensed to each other, has a heteroatom selected from N, O P, and S, other than carbon atoms (for example, the number of carbon atoms may be in a range of 2 to 60), as ring-forming atoms, wherein the molecular structure as a whole is non-aromatic in the entire molecular structure. An example of the monovalent non-aromatic condensed hetero-polycyclic group is a carbazolyl group. A divalent non-aromatic condensed hetero-polycyclic group used herein refers to a divalent group having the same structure as the monovalent non-aromatic condensed hetero-polycyclic group.

In the present specification, at least one of substituents of substituents of the substituted $C_1$-$C_{60}$ alkylene group, substituted $C_2$-$C_{60}$ alkenylene group, substituted $C_2$-$C_{60}$ alkynylene group, substituted $C_3$-$C_{10}$ cycloalkylene group, substituted $C_2$-$C_{10}$ heterocycloalkylene group, substituted $C_3$-$C_{10}$ cycloalkenylene group, substituted $C_2$-$C_{10}$ heterocycloalkenylene group, substituted $C_6$-$C_{60}$ arylene group, substituted $C_2$-$C_{60}$ heteroarylene group, substituted divalent non-aromatic condensed polycyclic group, substituted divalent non-aromatic condensed hetero-polycyclic group, substituted $C_1$-$C_{60}$ alkyl group, substituted $C_2$-$C_{60}$ alkenyl group, substituted $C_2$-$C_{60}$ alkynyl group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_2$-$C_{60}$ heteroaryl group, substituted monovalent non-aromatic condensed polycyclic group, and substituted monovalent non-aromatic condensed hetero-polycyclic group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed hetero-polycyclic group, —$N(Q_{11})(Q_{12})$, —$Si(Q_{13})(Q_{14})(Q_{15})$, and —$B(Q_{16})(Q_{17})$;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed hetero-polycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed hetero-polycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed hetero-polycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), wherein $Q_1$ to $Q_7$, $Q_{11}$ to $Q_{17}$, and $Q_{31}$ to $Q_{37}$ used herein may be each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent non-aromatic condensed polycyclic group, and a monovalent non-aromatic condensed hetero-polycyclic group.

In the present specification, at least one of substituents of the substituted $C_1$-$C_{60}$ alkylene group, substituted $C_2$-$C_{60}$ alkenylene group, substituted $C_2$-$C_{60}$ alkynylene group, substituted $C_3$-$C_{10}$ cycloalkylene group, substituted $C_2$-$C_{10}$ heterocycloalkylene group, substituted $C_3$-$C_{10}$ cycloalkenylene group, substituted $C_2$-$C_{10}$ heterocycloalkenylene group, substituted $C_6$-$C_{60}$ arylene group, substituted $C_2$-$C_{60}$ heteroarylene group, substituted divalent non-aromatic condensed polycyclic group, substituted divalent non-aromatic condensed hetero-polycyclic group, substituted $C_1$-$C_{60}$ alkyl group, substituted $C_2$-$C_{60}$ alkenyl group, substituted $C_2$-$C_{60}$ alkynyl group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_2$-$C_{60}$ heteroaryl group, substituted monovalent non-aromatic condensed polycyclic group, and substituted monovalent non-aromatic condensed hetero-polycyclic group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed hetero-polycyclic group, —N($Q_{11}$)($Q_{12}$), —Si($Q_{13}$)($Q_{14}$)($Q_{16}$), and —B($Q_{16}$)($Q_{17}$);

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthrenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isooxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, and an imidazopyridinyl group, each substituted with at least one selected from a cyclopentyl group, a cyclohexyl group, a cycloheptyl group, cyclooctyl group, a cyclopentenyl group, a cyclohexenyl group, a cycloheptenyl group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthrenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a furanyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isooxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, and an imidazopyridinyl group, each substituted with at least one selected from a cyclopentyl group, a cyclohexyl group, a cycloheptyl group, a cyclooctyl group, a cyclopentenyl group, a cyclohexenyl group, a cycloheptenyl group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group, each substituted with at least one selected from a deuterium, —F, —Cl, —Br, —I, a hydroxyl group, a cyano group, a nitro group, an amino group, an amidino group, a hydrazine group, a hydrazone group, carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, monovalent non-aromatic hetero-condensed polycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), wherein $Q_1$ to $Q_7$, $Q_{11}$ to $Q_{17}$, and $Q_{31}$ to $Q_{37}$ may be each independently a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthrenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a furanyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isooxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, and an imidazopyridinyl group, each substituted with at least one selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclooctyl group, a cyclopentenyl group, a cyclohexenyl group, a cycloheptenyl group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, or a quinazolinyl group, but they are not limited thereto.

The term "biphenyl group" as used therein refers to "a phenyl group substituted with a phenyl group."

Hereinafter, a compound and an organic light-emitting device according to embodiments are described in detail with reference to Synthesis Example and Examples. However, the organic light-emitting device is not limited thereto. The wording "B was used instead of A" used in describing Synthesis Examples means that a molar equivalent of A was identical to a molar equivalent of B.

EXAMPLES

Synthesis Example 1: Synthesis of Compound 3

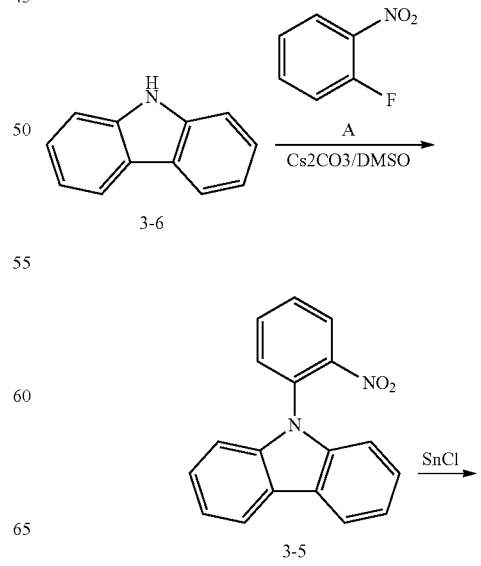

-continued

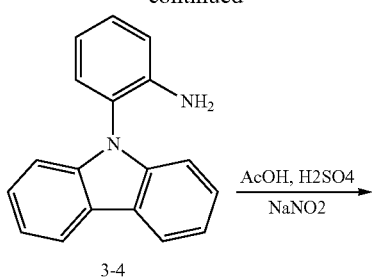

3-4

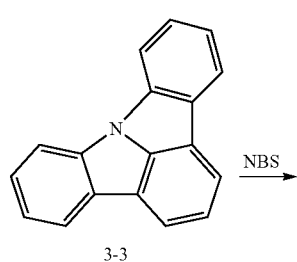

3-3

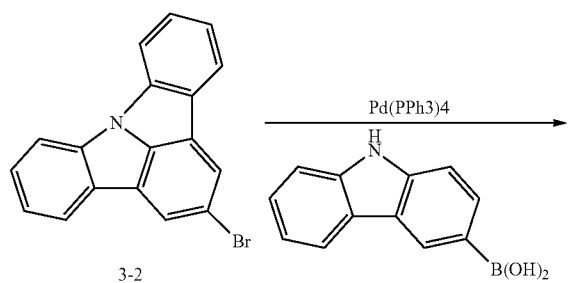

3-2

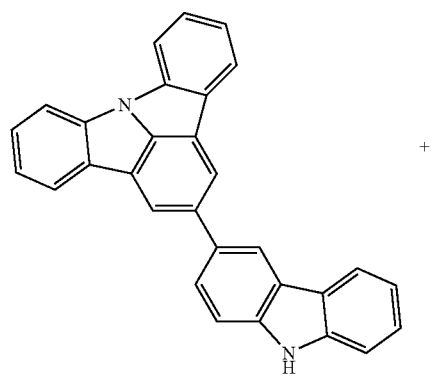

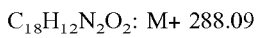

-continued

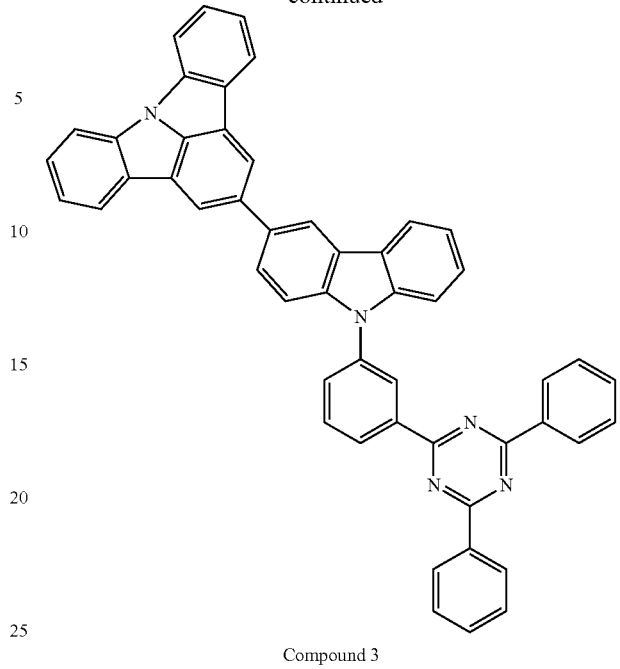

Compound 3

Synthesis of Intermediate 3-5

Intermediate 3-6 (10 g, 59.8 mmol) and Intermediate A (8.44 g, 59.8 mmol) were dissolved in 200 mL of DMSO, and then, $Cs_2CO_3$ (23.4 g, 71.8 mmol) was added to the resultant and stirred for 15 hours. 500 mL of water was added to the reaction product, and the resultant was filtered and a solid was collected. The solid was dissolved in 300 mL of methylene chloride, and 300 mL of water was added thereto, and then the resultant was extracted. An organic layer obtained therefrom was dried by using $MgSO_4$, and the residual obtained by evaporating the solvent was separation-purified by silica gel column chromatography to obtain Intermediate 3-5 (12.93 g, yield of 75%). The obtained compound was identified by LC-MS.

$C_{18}H_{12}N_2O_2$: M+ 288.09

Synthesis of Intermediate 3-4

Intermediate 3-5 (10 g, 34.7 mmol) and $SnCl_2 \cdot 2H_2O$ (25.16 g, 111 mmol) was added to EtOH and then, the mixture was heated to 70° C. for 8 hours or more. When the reaction stopped, the reaction product was cooled to room temperature, and then, concentrated, and an organic layer obtained by adding 300 mL of methylene chloride and 300 mL of $NaHCO_3$ (aq) thereto was dried by using $MgSO_4$, and the residual obtained by evaporating the solvent was separation-purified by silica gel column chromatography to obtain Intermediate 3-4 (6.27 g, yield of 70%). The obtained compound was identified by LC-MS.

$C_{18}H_{14}N_2$: M+ 258.12

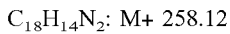

Synthesis of Intermediate 3-3

Intermediate 3-4 (6 g, 23.23 mmol), 60 mL of acetic acid, 5 mL of conc. $H_2SO_4$ in a reaction container were deposited to an ice bath to decrease the temperature to 10° C. Then, $NaNO_2$ (1.6 g, 1 eq) was dissolved in 150 mL of water, and the resultant was added dropwise thereto for 20 minutes, and stirred for 10 minutes, and then, the temperature of the mixture was raised to 130° C., and then stirred for 20 minutes. When the reaction stopped, the temperature was decreased to room temperature, and then, 300 mL of water was added thereto, and filtered to isolate a precipitated solid. The residual was separation-purified by silica gel column chromatography to obtain Intermediate 3-3 (4.03 g, 72%). The obtained compound was identified by LC-MS.

$C_{18}H_{11}N$: M+ 241.09

Synthesis of Intermediate 3-2

Intermediate 3-3 (3 g, 12.43 mmol) and NBS (2.21 g, 12.43 mmol) were dissolved in 100 mL of methylene chloride, and then, the mixture was stirred at room temperature for 15 hours. When the reaction stopped, the reaction product was cooled to room temperature, and 200 mL of methylene chloride was added thereto, and then 200 mL of water was added dropwise thereto, and an obtained organic layer was dried by using $MgSO_4$, and the residual obtained by evaporating the solvent was separation-purified by silica gel column chromatography to obtain Intermediate 3-2 (2.03 g, 51%). The obtained compound was identified by LC-MS.

$C_{18}H_{10}BrN$: M+ 319.00

Synthesis of Intermediate 3-1

Intermediate 3-2 (1.5 g, 4.68 mmol), Intermediate B (1.19 g, 5.62 mmol), $Pd(PPh_3)_4$ (0.27 g, 0.234 mmol), and $K_2CO_3$ (3.24 g, 23.4 mmol) were mixed with 100 mL of THF and 30 mL of distilled water. The mixture was heated to a temperature of 120° C. and stirred for 24 hours while refluxing, and then, cooled to room temperature, and extracted using 200 mL of water and 200 mL of methylene chloride. An organic layer obtained therefrom was dried by using $MgSO_4$, and the residual obtained by evaporating the solvent was separation-purified by silica gel column chromatography to obtain Intermediate 3-1 (1.5 g, 79%). The obtained compound was identified by LC-MS.

$C_{30}H_{18}N_2$: M+ 406.15

Synthesis of Compound 3

Intermediate 3-1 (1 g, 2.46 mmol) was dissolved in 30 mL of DMF, and then, sodium hydride was added thereto, and the result was stirred for 1 hour. Intermediate C (0.8 g, 2.95 mmol) dissolved in 10 mL of DMF was added thereto, and then, stirred for 12 hours at room temperature. Resulting precipitate was washed with methylene chloride, and then added to dichlorobenzene, and the result was heated, and then, while cooling to room temperature, recrystallized and separated to obtain Compound 3 (1.14 g, 65%). The obtained compound was identified by LC-MS and NMR.

$C_{51}H_{31}N_5$: M+ 713.26

1H NMR ($CDCl_3$, 300 MHz) δ (ppm) 8.36-8.19 (m, 11H), 7.89 (s, 1H), 7.68-7.50 (m, 16H), 7.20 (m, 3H)

Synthesis Example 2: Synthesis of Compound 2

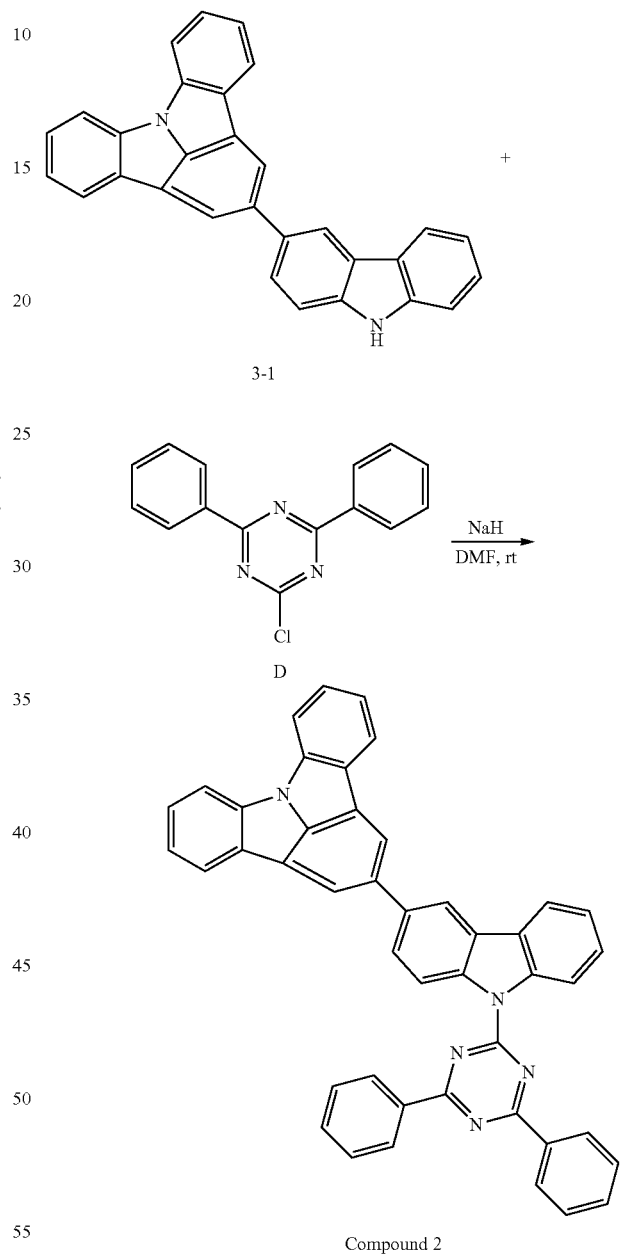

Compound 2 (68%) was synthesized in the same manner as in Synthesis Example 1, except that in synthesizing Compound 3, Intermediate D was used instead of Intermediate C. The obtained compound was identified by LC-MS and NMR.

$C_{45}H_{27}N_5$: M+ 637.75

1H NMR ($CDCl_3$, 300 MHz) δ (ppm) 7.36-8.30 (m, 5H), 8.19-8.13 (m, 4H), 7.89 (s, 1H), 7.65-7.50 (m, 14H), 7.20 (m, 3H)

Synthesis Example 3: Synthesis of Compound 4

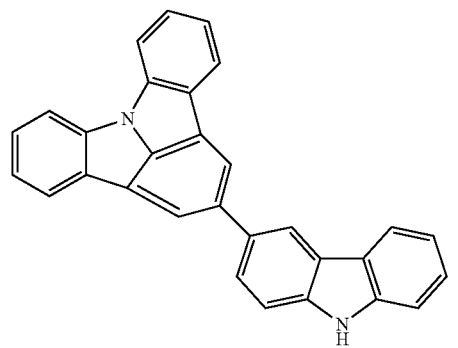

Intermediate 3-1

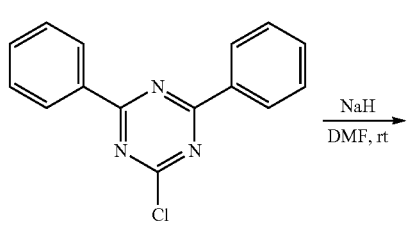

Intermediate E

Synthesis Example 4: Synthesis of Compound 7

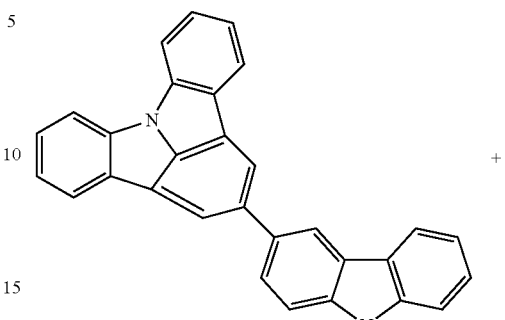

Intermediate 3-1

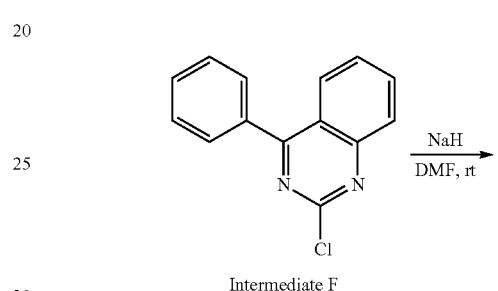

Intermediate F

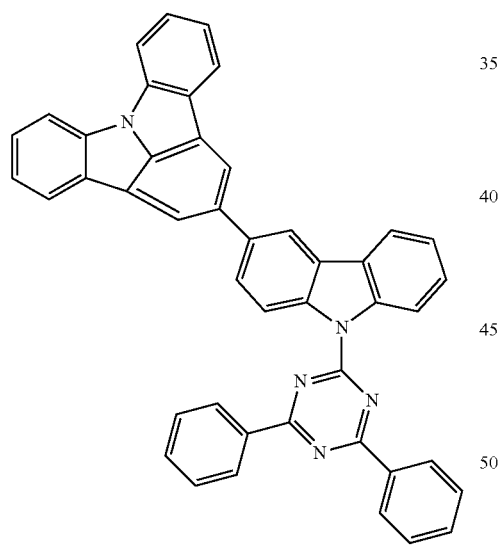

Compound 4

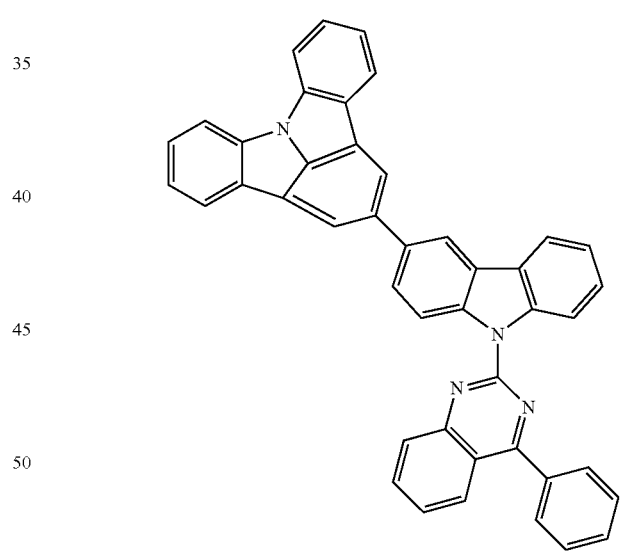

Compound 7

Compound 4 (70%) was synthesized in the same manner as in Synthesis Example 1, except that in synthesizing Compound 3, Intermediate E was used instead of Intermediate C. The obtained compound was identified by LC-MS and NMR.

$C_{46}H_{28}N_4$: M+ 636.23

1H NMR (CDCl$_3$, 300 MHz) δ (ppm) 8.9 (s, 1H), 8.30-8.13 (m, 5H), 7.94-7.89 (m, 5H), 7.65-7.50 (m, 14H), 7.20 (m, 3H)

Compound 7 (62%) was synthesized in the same manner as in Synthesis Example 1, except that in synthesizing Compound 3, Intermediate F was used instead of Intermediate C. The obtained compound was identified by LC-MS and NMR.

$C_{44}H_{26}N_4$: M+ 610.22

1H NMR (CDCl$_3$, 300 MHz) δ (ppm) 8.30-8.13 (m, 6H), 7.89-7.80 (m, 5H), 7.65-7.50 (m, 12H), 7.20 (m, 3H)

Synthesis Example 5: Synthesis of Compound 8

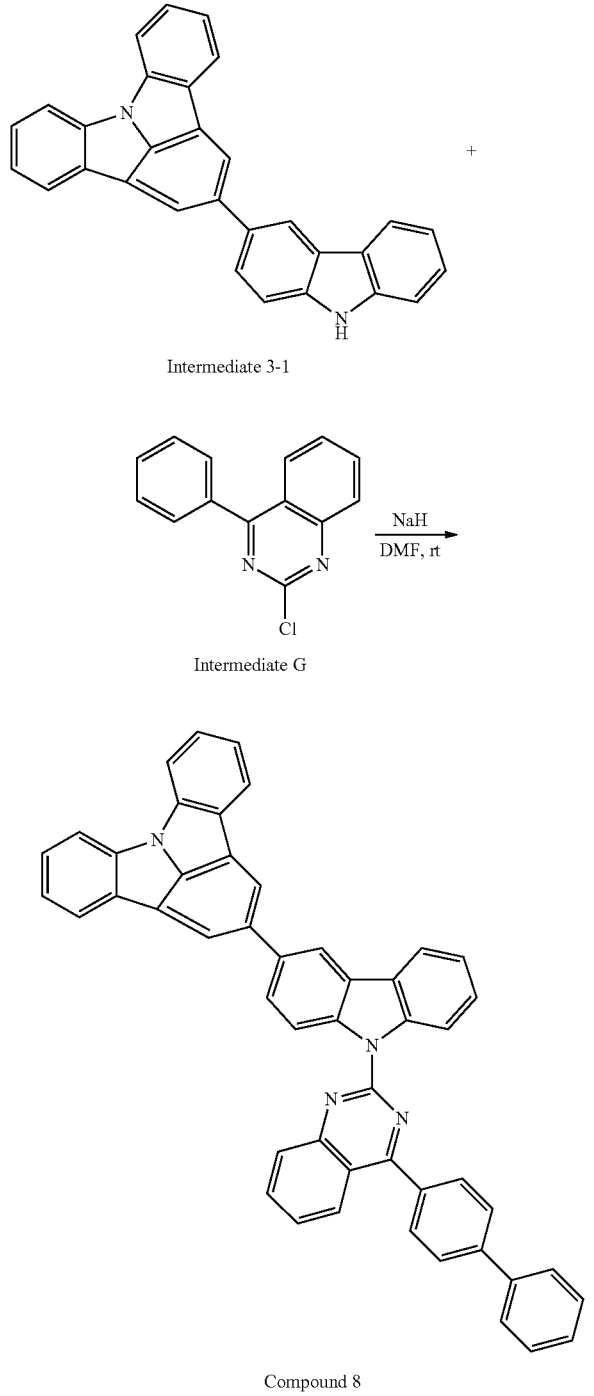

Compound 8

Compound 8 (62%) was synthesized in the same manner as in Synthesis Example 1, except that in synthesizing Compound 3, Intermediate G was used instead of Intermediate C. The obtained compound was identified by LC-MS and NMR.

$C_{50}H_{30}N_4$: M+ 686.25

1H NMR (CDCl$_3$, 300 MHz) δ (ppm) 8.30-8.13 (m, 8H), 7.89-7.75 (m, 7H), 7.65-7.41 (m, 12H), 7.20 (m, 3H)

Synthesis Example 6: Synthesis of Compound 76

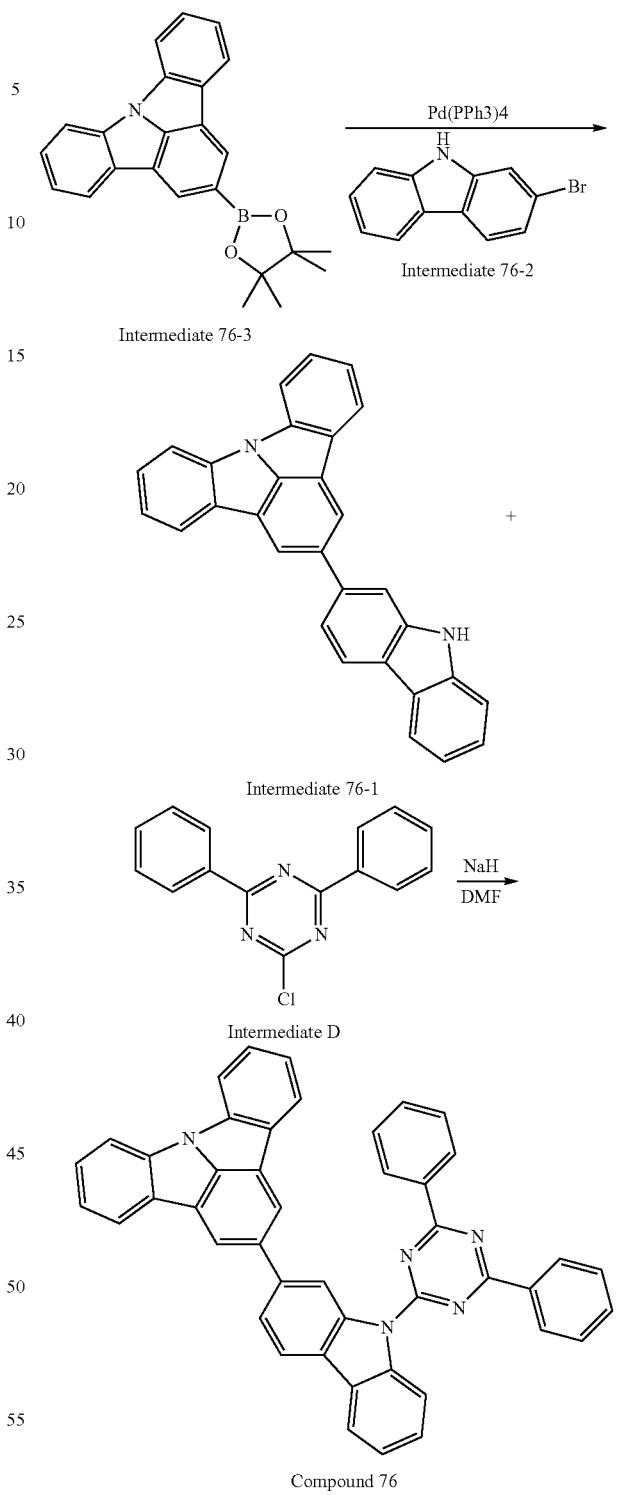

Compound 76

Synthesis of Intermediate 76-1

Intermediate 76-1 was prepared in the same manner as used in synthesizing Intermediate 3-1 of Synthesis Example 1, except that Intermediate 76-2 and Intermediate 76-3 were respectively used instead of Intermediate 3-2 and Intermediate B.

Synthesis of Compound 76

Compound 76 (yield of 74%) was prepared in the same manner as used in synthesizing Intermediate 3 of Synthesis Example 1, except that in synthesizing Compound 3, Intermediate 76-1 and Intermediate D were respectively used instead of Intermediate 3-1 and Intermediate C. The obtained compound was identified by LC-MS and NMR.

$C_{45}H_{27}N_5$: M+ 686.25

1H NMR (CDCl$_3$, 300 MHz) δ (ppm) 8.62 (d, 1H), 8.36 (m, 4H), 8.22-8.19 (m, 4H), 7.74 (s, 1H), 7.65-7.50 (m, 14H), 7.20 (m, 3H)

Synthesis Example 7: Synthesis of Compound 60

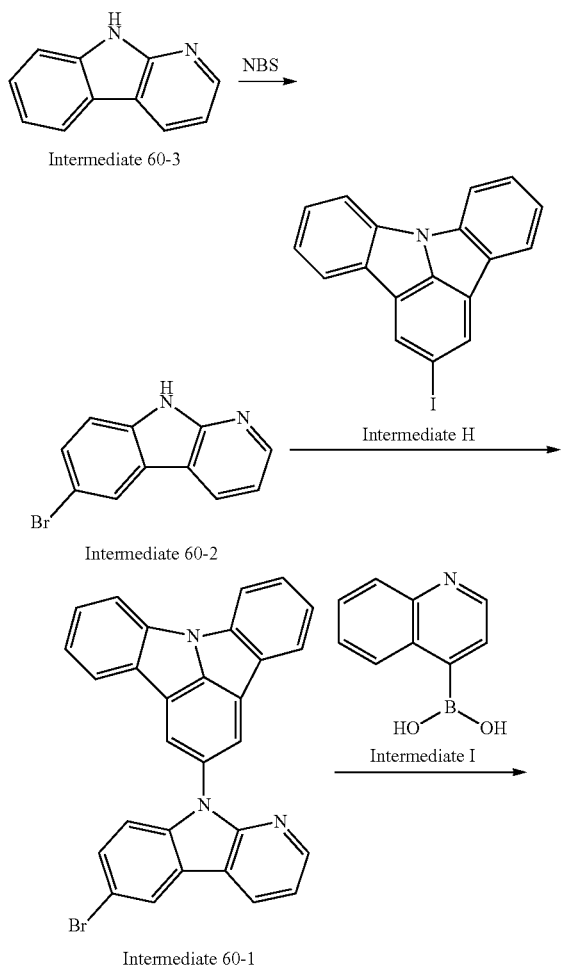

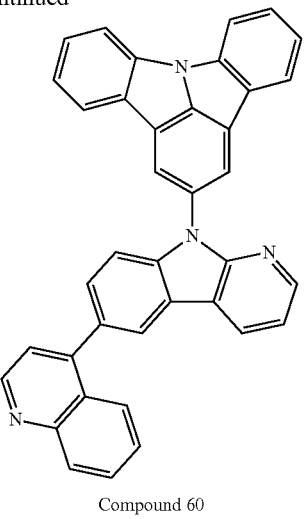

Compound 60

Synthesis of Intermediate 60-2

Intermediate 60-2 was synthesized in the same manner as in synthesizing Intermediate 3-2 of Synthesis Example 1, except that Intermediate 60-3 was used instead of Intermediate 3-3.

Synthesis of Intermediate 60-1

Intermediate 60-1 was prepared in the same manner as used in synthesizing Intermediate 3-1 of Synthesis Example 1, except that Intermediate 60-2 and Intermediate H were respectively used instead of Intermediate 3-2 and Intermediate B.

Synthesis of Compound 60

Compound 60 (yield of 51%) was prepared in the same manner as used in synthesizing Intermediate 3 of Synthesis Example 1, except that Intermediate 60-1 and Intermediate I were respectively used instead of Intermediate 3-1 and Intermediate C.

$C_{38}H_{22}N_4$: M+ 534.18

1H NMR (CDCl$_3$, 300 MHz) δ (ppm) 8.87 (d, 1H), 8.51-8.01 (m, 8H), 7.89 (s, 1H), 7.70-7.43 (m, 8H), 7.20-7.15 (m, 4H)

Evaluation Example 1: Evaluation on HOMO, LUMO, and Triplets (T1) Energy Levels HOMO, LUMO and T1 energy levels of Compounds 2, 3, and 7 were evaluated according to the method indicated in Table 2, and results thereof are shown in Table 3.

TABLE 2

| | |
|---|---|
| HOMO energy level evaluation method | A potential (V)-current (A) graph of each compound was obtained by using cyclic voltammetry (CV) (electrolyte: 0.1M Bu$_4$NClO$_4$/solvent: CH$_2$Cl$_2$/electrode: 3 electrode system (working electrode: GC, reference electrode: Ag/AgCl, auxiliary electrode: Pt)), and then, from reduction onset of the graph, a HOMO energy level of the compound was calculated. |
| LUMO energy level evaluation method | Each compound was diluted at a concentration of 1 × 10$^{-5}$ M in CHCl$_3$, and an UV absorption spectrum thereof was measured at room temperature by using a Shimadzu UV-350 spectrometer, and a LUMO energy level thereof was calculated by using an optical band gap (Eg) from an edge of the absorption spectrum. |

TABLE 2-continued

| | |
|---|---|
| T1 energy level evaluation method | A mixture (each compound was dissolved in an amount of 1 mg in 3 cc of toluene) of toluene and each compound was loaded into a quartz cell, and then, the resultant quartz cell was loaded into liquid nitrogen (77 K) and a photoluminescence spectrum thereof was measured by using a device for measuring photoluminescence, and the obtained spectrum was compared with a photoluminescence spectrum measured at room temperature, and peaks observed only at low temperature were analyzed to calculate T1 energy levels. |

TABLE 3

| Compound No. | HOMO (eV) (calc.) | LUMO (eV) (calc.) | T1 energy level (eV) |
|---|---|---|---|
| 2 | −5.515 | −2.376 | 2.63 |
| 3 | −5.303 | −2.298 | 2.66 |
| 7 | −5.587 | −2.385 | 2.47 |

From Table 3, it is confirmed that the compounds above have electric characteristics that are suitable for use as a material for forming an organic light-emitting device.

Evaluation Example 2: Thermal Characteristics Evaluation

Thermal analysis ($N_2$ atmosphere, temperature range: from room temperature to 800° C. (10° C./min)-TGA, from room temperature to 400° C.-DSC, Pan Type: Pt Pan in disposable Al Pan (TGA), and disposable Al pan (DSC)) was performed on Compounds 7 and 8 and Compounds C and D by using thermo gravimetric analysis (TGA) and differential scanning calorimetry (DSC), and results thereof are shown in Table 4. As shown in Table 4, it was confirmed that the synthesized compounds had excellent thermal stability.

TABLE 4

| Compound No. | Tg (° C.) | Td (1%, ° C.) | Td (5%, ° C.) |
|---|---|---|---|
| Compound 7 | 149.45 | 447.8 | 486.4 |
| Compound 8 | 167.33 | 482.5 | 521.5 |
| Compound C | 128.8 | 427.3 | 473.9 |
| Compound D | 144.2 | 462.5 | 502.1 |

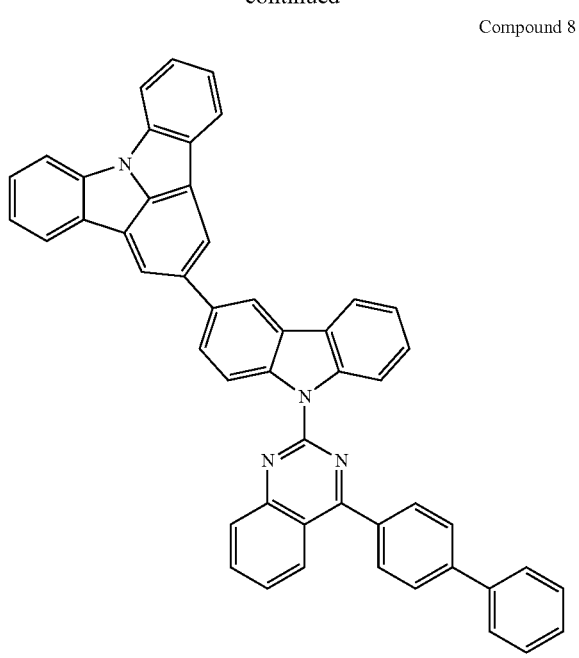

Compound 8

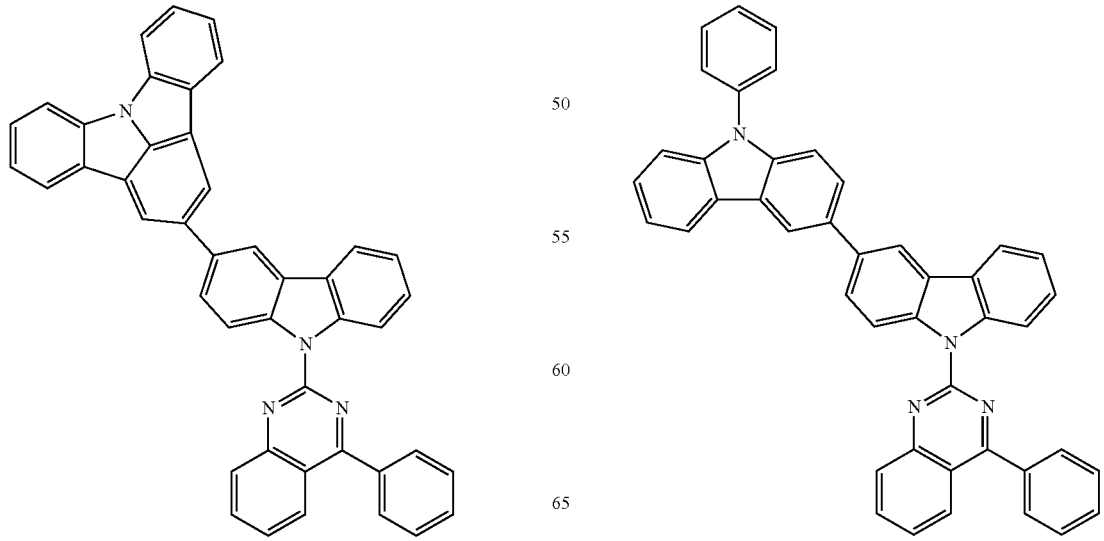

Compound 7

Compound C

Compound D

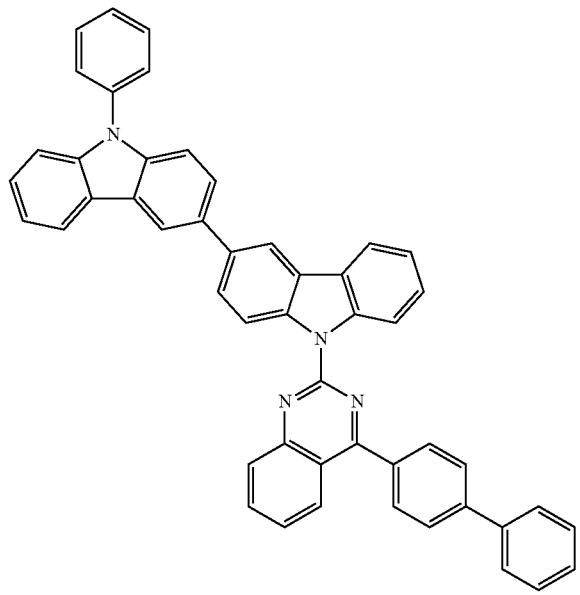

Example 1

A glass substrate with ITO/Ag/ITO (70/1,000/70 Å) anode thereon was cut to a size of 50 mm×50 mm×0.5 mm, and then, ultrasonically cleaned with isopropyl alcohol, acetone, and pure water for 5 minutes each, and then exposed to ultraviolet (UV) light for 30 minutes and then ozone. Then, the glass substrate was loaded into a vacuum deposition apparatus.

2-TNATA was deposited on the anode on the glass substrate to form a hole injection layer having a thickness of 600 Å, and then NPB was deposited on the hole injection layer to form a hole transport layer having a thickness of 1,000 Å to form a hole transport region.

Subsequently, Compound 3 (host) and Ir(ppy)$_3$ (dopant, referred to as Compound PD1 in this application) were co-deposited on the hole transport layer were co-deposited at a weight ratio of 91:9 to form an emission layer having a thickness of 250 Å.

BCP was deposited on the emission layer to form a hole blocking layer having a thickness of 50 Å, and Alq$_3$ was deposited on the hole blocking layer to form an electron transport layer having a thickness of 350 Å, and LiF was deposited on the electron transport layer to form an electron injection layer having a thickness of 10 Å to form an electron transport region.

Mg and Ag were deposited on the electron injection layer at a weight ratio of 90:10 to form a cathode having a thickness of 120 Å, thereby completing the manufacture of an organic light-emitting device.

Example 2

An organic light-emitting device was manufactured in the same manner as in Example 1, except that in forming an emission layer, as a host, Compound 2 was used instead of Compound 3.

Example 3

An organic light-emitting device was manufactured in the same manner as in Example 1, except that in forming an emission layer, as a host, Compound 4 was used instead of Compound 3.

Example 4

An organic light-emitting device was manufactured in the same manner as in Example 1, except that in forming an emission layer, as a host, Compound 76 was used instead of Compound 3.

Example 5

An organic light-emitting device was manufactured in the same manner as in Example 1, except that a thickness of the hole transport layer was 1,350 Å, and in forming an emission layer, Compound 7 was used as the host, PtOEP was used as the dopant, and a thickness of the emission layer was 400 Å.

Example 6

An organic light-emitting device was manufactured in the same manner as in Example 4, except that in forming an emission layer, as a host, Compound 8 was used instead of Compound 7.

Comparative Example 1

An organic light-emitting device was manufactured in the same manner as in Example 1, except that in forming an emission layer, as a host, Compound A was used instead of Compound 3.

Compound A

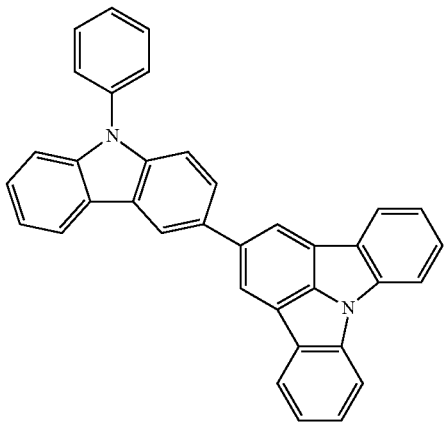

Comparative Example 2

An organic light-emitting device was manufactured in the same manner as in Example 1, except that in forming an emission layer, as a host, Compound B was used instead of Compound 3.

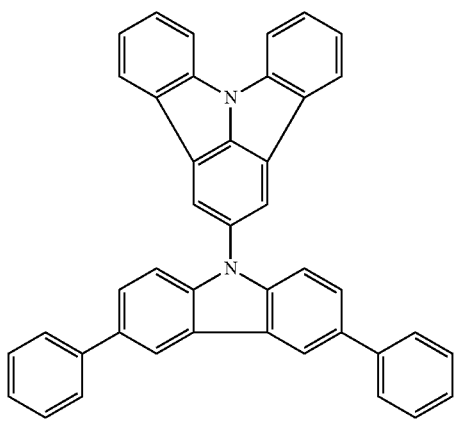

Compound B

Comparative Example 3

An organic light-emitting device was manufactured in the same manner as in Example 5, except that in forming an emission layer, as a host, Compound A was used instead of Compound 7.

Comparative Example 3

An organic light-emitting device was manufactured in the same manner as in Example 5, except that in forming an emission layer, as a host, Compound B was used instead of Compound 7.

Evaluation Example 4: Evaluation on Characteristics of an Organic Light-Emitting Device Driving voltage, current density, brightness, luminescence color, efficiency, and $LT_{97}$ (@10 milliamperes per square centimeter, mA/cm$^2$) of the organic light-emitting devices of Examples 1 to 6 and Comparative Examples 1 to 4 were evaluated by using PR650 Spectroscan Source Measurement Unit. (a product of PhotoResearch Company). Results thereof are shown in Table 6 below.

From Table 6, it was confirmed that the organic light-emitting devices of Examples 1 to 4 had lower driving voltage, higher efficiency, and longer lifespan of the organic light-emitting devices of Comparative Examples 1 and 2, and the organic light-emitting devices of Examples 5 and 6 had lower driving voltage, higher efficiency, and longer lifespan than the organic light-emitting devices of Comparative Examples 3 and 4.

The condensed cyclic compounds according to embodiments have excellent electric characteristics and thermal stability. Accordingly, organic light-emitting devices including the condensed cyclic compounds may have a low driving voltage, high efficiency, high brightness, and a long lifespan.

It should be understood that the exemplary embodiments described herein should be considered in a descriptive sense only and not for purposes of limitation. Descriptions of features or aspects within each embodiment should typically be considered as available for other similar features or aspects in other embodiments.

What is claimed is:

1. A condensed cyclic compound represented by one of Formulae 1A to 1C:

Formula 1A

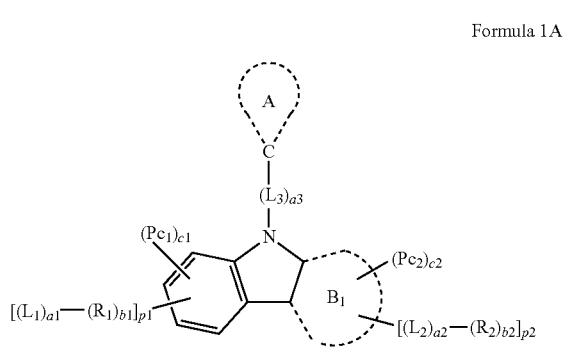

TABLE 6

| | EML | | Driving Voltage | Current Density | Brightness | Efficiency | Emission | |
|---|---|---|---|---|---|---|---|---|
| | Host | Dopant | (V) | (mA/cm$^2$) | (cd/m$^2$) | (cd/A) | color | $LT_{97}$ (hr) |
| Example 1 | Compound 3 | Ir(ppy)$_3$ | 5.4 | 10 | 6,829 | 68.3 | Green | 75 |
| Example 2 | Compound 2 | Ir(ppy)$_3$ | 5.3 | 10 | 6,724 | 67.2 | Green | 79 |
| Example 3 | Compound 4 | Ir(ppy)$_3$ | 5.9 | 10 | 6,709 | 67.1 | Green | 76 |
| Example 4 | Compound 76 | Ir(ppy)$_3$ | 5.6 | 10 | 6,171 | 61.7 | Green | 70 |
| Example 5 | Compound 7 | PtOEP | 5.8 | 10 | 3,422 | 34.2 | Red | 110 |
| Example 6 | Compound 8 | PtOEP | 6.0 | 10 | 3,117 | 31.2 | Red | 114 |
| Comparative Example 1 | Compound A | Ir(ppy)$_3$ | 8.2 | 10 | 4,564 | 45.6 | Green | 32 |
| Comparative Example 2 | Compound B | Ir(ppy)$_3$ | 7.3 | 10 | 4,276 | 42.8 | Green | 35 |
| Comparative Example 3 | Compound A | PtOEP | 7.9 | 10 | 1,810 | 18.1 | Red | 52 |
| Comparative Example 4 | Compound B | PtOEP | 7.7 | 10 | 1,921 | 19.2 | Red | 50 |

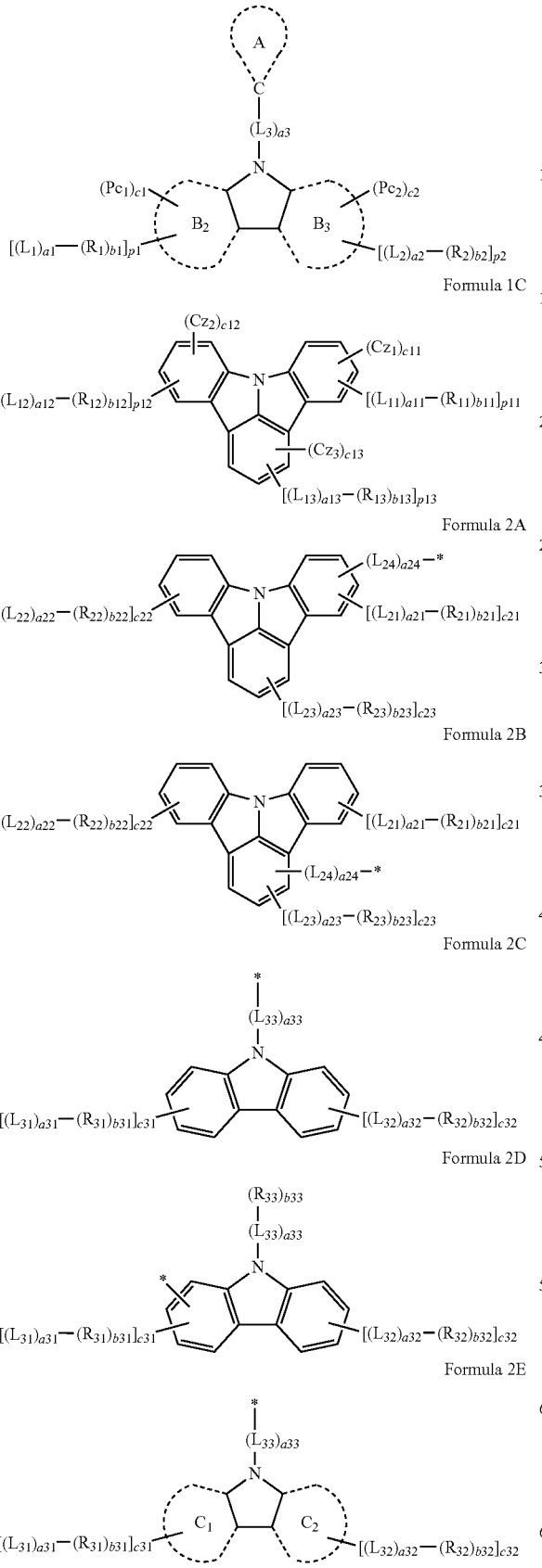
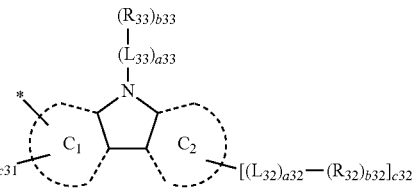

wherein in the Formulae 1A to 1C and 2A to 2F,

Ring A is selected from a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, a group represented by Formula 2A, and a group represented by Formula 2B;

Ring $B_1$ is a $C_5$-$C_{20}$ carbocyclic group or a $C_2$-$C_{20}$ heterocyclic group that does not comprise a nitrogen atom as a ring-forming atom;

Ring $B_2$, Ring $B_3$, Ring $C_1$, and Ring $C_2$ are each independently a $C_5$-$C_{20}$ carbocyclic group, or a $C_2$-$C_{20}$ heterocyclic group, provided that at least one selected from Ring $B_2$ and Ring $B_3$ is a $C_2$-$C_{20}$ heterocyclic group comprising a nitrogen atom as a ring-forming atom, and at least one selected from Ring $C_1$ and Ring $C_2$ is a $C_2$-$C_{20}$ heterocyclic group comprising a nitrogen atom as a ring-forming atom;

$Pc_1$ and $Pc_2$ in Formula 1A and 1B are each independently a group represented by Formulae 2A or a group represented by Formula 2B;

$Cz_1$, $Cz_2$, and $Cz_3$ in Formula 1C are each independently selected from a group represented by Formula 2C, a group represented by Formula 2D, a group represented by Formula 2E, and a group represented by Formula 2F;

c1, c2, c11, c12, c13, p1, p2, p11, p12, and p13 are each independently an integer selected from 0 to 3;

when c1 and c2 in Formula 1A and 1B both are 0, Ring A is a group represented by Formula 2A or a group represented by Formula 2B;

when Ring A in Formula 1A and 1B is neither a group represented by Formula 2A nor a group represented by Formula 2B, c1+c2≠0;

at least one selected from Ring A in Formula 1A, all $R_1$ in Formula 1A, and all $R_2$ in Formula 1A is a substituted or unsubstituted $C_2$-$C_{10}$ heterocycloalkyl group, a substituted or unsubstituted $C_2$-$C_{10}$ heterocycloalkenyl group, a substituted or unsubstituted $C_2$-$C_{60}$ heteroaryl group, or a substituted or unsubstituted monovalent non-aromatic condensed hetero-polycyclic group, each comprising at least one Moiety 1 as a ring-forming moiety;

the sum of c11, c12, and c13 in Formula 1C is not 0;

when each of $Cz_1$, $Cz_2$, and $Cz_3$ in Formula 1C is independently a group represented by Formula 2C or a group represented by Formula 2D, p11+p12+p13≠0 and at least one selected from all $R_{11}$ in Formula 1C, all $R_{12}$ in Formula 1C, and all $R_{13}$ in Formula 1C is a substituted or unsubstituted $C_2$-$C_{10}$ heterocycloalkyl group, a substituted or unsubstituted $C_2$-$C_{10}$ heterocycloalkenyl group, a substituted or unsubstituted $C_2$-$C_{60}$ heteroaryl group, or a substituted or unsubstituted monovalent non-aromatic condensed hetero-polycyclic group, each comprising at least one Moiety 1 as a ring-forming moiety;

$L_1$ to $L_3$, $L_{11}$ to $L_{13}$, $L_{21}$ to $L_{24}$, and $L_{31}$ to $L_{33}$ are each independently selected from a substituted or unsubstituted $C_1$-$C_{60}$ alkylene group, a substituted or unsubstituted $C_2$-$C_{60}$ alkenylene group, a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, and a substituted or unsubstituted divalent non-aromatic condensed hetero-polycyclic group;

a1 to a3, a11 to a13, a21 to a24, and a31 to a33 are each independently an integer selected from 0 to 6;

$R_1$, $R_2$, $R_{11}$ to $R_{13}$, $R_{21}$ to $R_{23}$, and $R_{31}$ to $R_{33}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed hetero-polycyclic group, —N($Q_1$)($Q_2$), —Si($Q_3$)($Q_4$)($Q_5$), and —B($Q_6$)($Q_7$);

b1, b2, b11 to b13, b21 to b23, and b31 to b33 are each independently an integer selected from 1 to 4;

at least one of substituents of the substituted $C_1$-$C_{60}$ alkylene group, substituted $C_2$-$C_{60}$ alkenylene group, substituted $C_3$-$C_{10}$ cycloalkylene group, substituted $C_2$-$C_{10}$ heterocycloalkylene group, substituted $C_3$-$C_{10}$ cycloalkenylene group, substituted $C_2$-$C_{10}$ heterocycloalkenylene group, substituted $C_6$-$C_{60}$ arylene group, substituted $C_2$-$C_{60}$ heteroarylene group, substituted divalent non-aromatic condensed polycyclic group, substituted divalent non-aromatic condensed hetero-polycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_2$-$C_{60}$ heteroaryl group, a substituted monovalent non-aromatic condensed polycyclic group, and a substituted monovalent non-aromatic condensed hetero-polycyclic group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed hetero-polycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed hetero-polycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$);

wherein $Q_1$ to $Q_7$, $Q_{11}$ to $Q_{17}$, $Q_{21}$ to $Q_{27}$, and $Q_{31}$ to $Q_{37}$ are each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent non-aromatic condensed polycyclic group, and a monovalent non-aromatic hetero-condensed polycyclic group:

=N—*  Moiety 1 wherein in Moiety 1,  and * each indicates a binding site to a ring-forming atom included in a ring comprising Moiety 1.

2. The condensed cyclic compound of claim 1, wherein Ring A in Formula 1A is selected from a phenyl group, a naphthyl group, a phenalenyl group, a phenanthrenyl group, an anthracenyl group, a triphenylenyl group, a pyrenyl group, a chrysenyl group, a pyrrolyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, phenanthridinyl, phenanthrolinyl, phenazinyl, a benzoimidazolyl group, an isobenzothiazolyl group, a benzooxazolyl group, an isobenzoxazolyl group, a triazolyl group, a tetrazolyl group, an oxadiazolyl group, a triazinyl group, an imidazopyridinyl group, an imidazopyrimidinyl group, a benzofuropyrazinyl group, a benzofuropyrimidinyl group, a benzofuropyridinyl group, a benzothienopyrazinyl group, a benzothienopyrimidinyl group, a benzothienopyridinyl group, a group represented by Formula 2A, and a group represented by Formula 2B; and a phenyl group, a naphthyl group, a phenalenyl group, a phenanthrenyl group, an anthracenyl group, a triphenylenyl group, a pyrenyl group, a chrysenyl group, a pyrrolyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, phenanthridinyl, phenanthrolinyl, phenazinyl, a benzoimidazolyl group, an isobenzothiazolyl group, a benzooxazolyl group, an isobenzoxazolyl group, a triazolyl group, a tetrazolyl group, an oxadiazolyl group, a triazinyl group, an imidazopyridinyl group, an imidazopyrimidinyl group, a benzofuropyrazinyl group, a benzofuropyrimidinyl group, a benzofuropyridinyl group, a benzothienopyrazinyl group, a benzothienopyrimidinyl group, and a benzothienopyridinyl group, each substituted with one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a phenyl group substituted with a $C_1$-$C_{20}$ alkyl group, a naphthyl group, a phenalenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, a naphthyridinyl group, a quinoxalinyl group, a quinazolinyl group, a biphenyl group, and —Si($Q_{33}$)($Q_{34}$)($Q_{35}$), wherein $Q_{33}$ to $Q_{35}$ are each independently selected from a hydrogen, a $C_1$-$C_{20}$ alkyl group, a $C_1$-$C_{20}$ alkoxy group, a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group.

3. The condensed cyclic compound of claim 1, wherein Ring A in Formula 1A is represented by one selected from Formulae 4-1 to 4-51, Formulae 6-1 to 6-5, a group represented Formula 2A, and a group represented by Formula 2B:

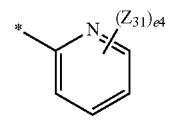

Formula 4-1

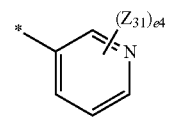

Formula 4-2

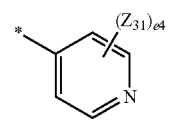

Formula 4-3

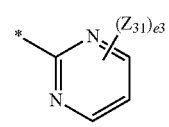

Formula 4-4

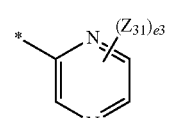

Formula 4-5

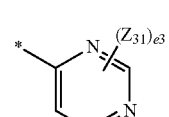

Formula 4-6

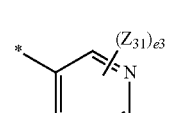

Formula 4-7

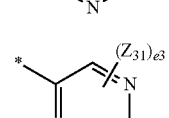

Formula 4-8

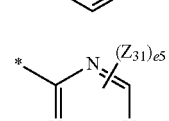

Formula 4-9

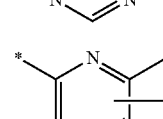

Formula 4-10

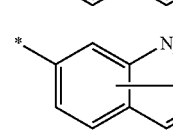

Formula 4-11

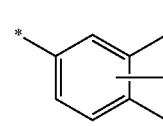

Formula 4-12

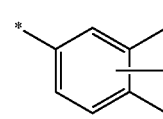

Formula 4-13

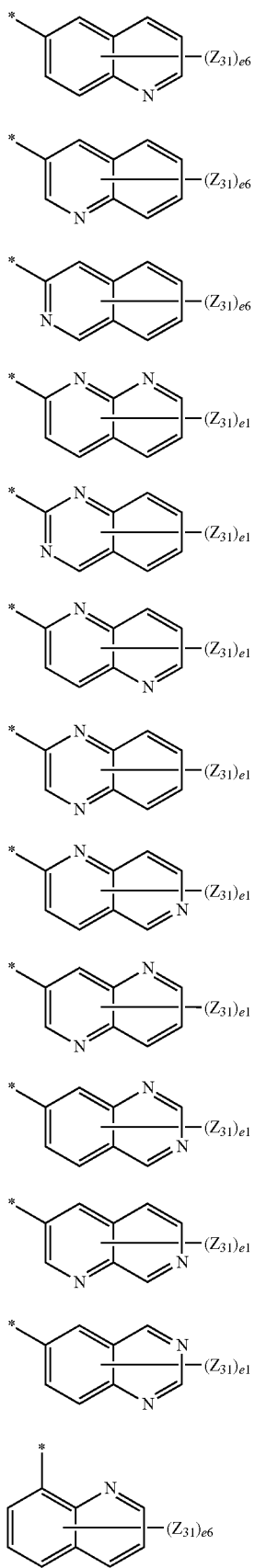
Formula 4-14
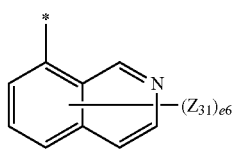
Formula 4-27
Formula 4-15
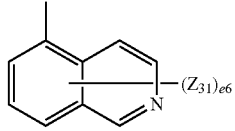
Formula 4-28
Formula 4-16
Formula 4-29
Formula 4-17
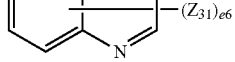
Formula 4-30
Formula 4-18
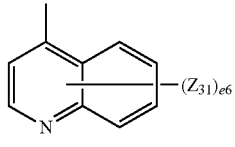
Formula 4-31
Formula 4-19
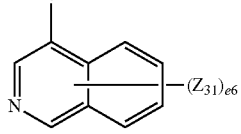
Formula 4-32
Formula 4-20
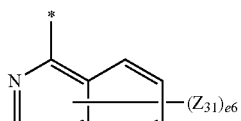
Formula 4-33
Formula 4-21
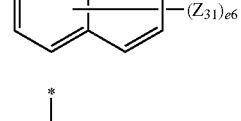
Formula 4-34
Formula 4-22
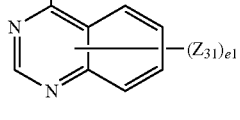
Formula 4-35
Formula 4-23
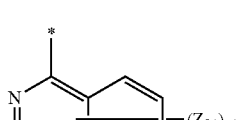
Formula 4-36
Formula 4-24
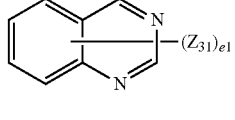
Formula 4-25
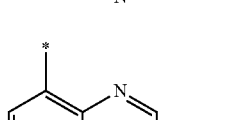
Formula 4-26
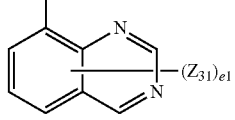

183
-continued

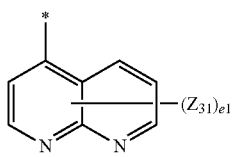
Formula 4-37

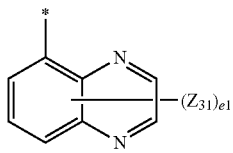
Formula 4-38

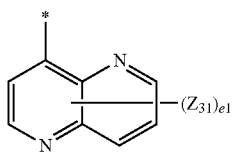
Formula 4-39

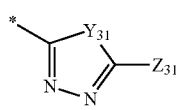
Formula 4-40

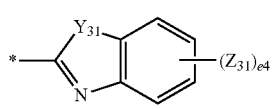
Formula 4-41

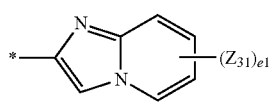
Formula 4-42

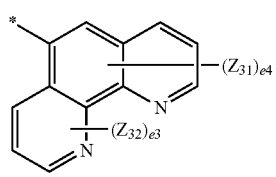
Formula 4-43

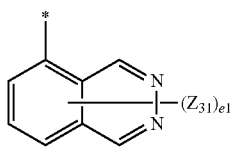
Formula 4-44

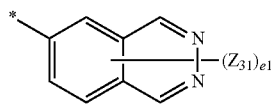
Formula 4-45

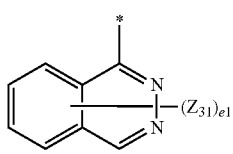
Formula 4-46

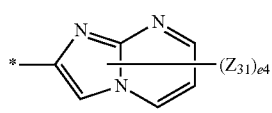
Formula 4-47

184
-continued

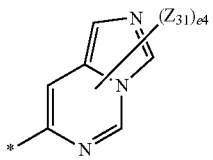
Formula 4-48

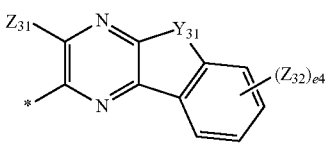
Formula 4-49

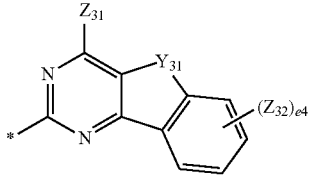
Formula 4-50

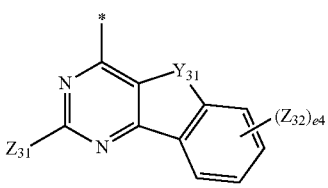
Formula 4-51

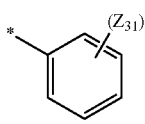
Formula 6-1

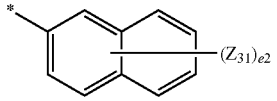
Formula 6-2

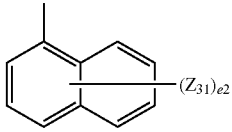
Formula 6-3

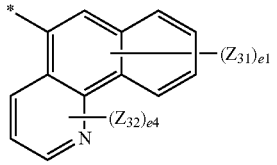
Formula 6-4

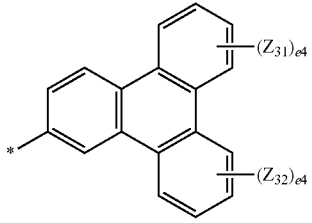
Formula 6-5 wherein in Formulae 4-1 to 4-51 and 6-1 to 6-5:
$Y_{31}$ is O, S, $C(Z_{33})(Z_{34})$, $N(Z_{35})$, or $Si(Z_{36})(Z_{37})$;
$Z_{31}$ to $Z_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group substituted with a $C_1$-$C_{20}$ alkyl group, a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, a quinoxalinyl group, a biphenyl group, and —Si($Q_{33}$)($Q_{34}$)($Q_{35}$), wherein $Q_{33}$ to $Q_{35}$ are each independently selected from a hydrogen, a $C_1$-$C_{20}$ alkyl group, a $C_1$-$C_{20}$ alkoxy group, a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group;

e1 is an integer of 1 to 5;
e2 is an integer of 1 to 7;
e3 is an integer of 1 to 3;
e4 is an integer of 1 to 4;
e5 is an integer of 1 or 2;
e6 is an integer of 1 to 6; and
* indicates a binding site to a neighboring atom.

4. The condensed cyclic compound of claim 1, wherein Ring $B_1$ is a benzene, a naphthalene, an anthracene, a phenanthrene, a benzofuran, or a benzothiophene.

5. The condensed cyclic compound of claim 1, wherein Ring $B_2$, Ring $B_3$, Ring $C_1$, and Ring $C_2$ are each independently a benzene, a naphthalene, an anthracene, a phenanthrene, a benzofuran, a benzothiophene, a pyridine, a pyrimidine, a pyrazine, a benzofuropyrazine, a benzofuropyrimidine, benzofuropyridine, a benzothienopyrazine, a benzothienopyrimidine, or a benzothienopyridine;

at least one selected from Ring $B_2$ and Ring $B_3$ is a pyridine, a pyrimidine, a pyrazine, a benzofuropyrazine, a benzofuropyrimidine, a benzofuropyridine, a benzothienopyrazine, a benzothienopyrimidine, or a benzothienopyridine; and at least one selected from Ring $C_1$ and Ring $C_2$ is a pyridine, a pyrimidine, a pyrazine, a benzofuropyrazine, a benzofuropyrimidine, a benzofuropyridine, a benzothienopyrazine, a benzothienopyrimidine, or a benzothienopyridine.

6. The condensed cyclic compound of claim 1, wherein
c1=0, c2=0, and Ring A is a group represented by Formula 2A or a group represented by Formula 2B;
c1=1 and c2=0;
c1=1, and c2=1;
c11=1, c12=0, and c13=0;
c11=0, c12=0, and c13=1;
c11=1, c12=1, and c13=0; or
c11=1, c12=0, and c13=1.

7. The condensed cyclic compound of claim 1, wherein $L_1$ to $L_3$, $L_{11}$ to $L_{13}$, $L_{21}$ to $L_{24}$, and $L_{31}$ to $L_{33}$ are each independently selected from a phenylene group, a pentalenylene group, an indenylene group, a naphthylene group, an azulenylene group, a heptalenylene group, an indacenylene group, an acenaphthylene group, a fluorenylene group, a spiro-fluorenylene group, a phenalenylene group, a phenanthrenylene group, an anthracenylene group, a fluoranthrenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoxazolylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, an imidazopyrimidinylene group, and an imidazopyridinylene group; and a phenylene group, a pentalenylene group, an indenylene group, naphthylene group, an azulenylene group, a heptalenylene group, an indacenylene group, an acenaphthylene group, a fluorenylene group, a spiro-fluorenylene group, a phenalenylene group, a phenanthrenylene group, an anthracenylene group, a fluoranthrenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzooxazolylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group an imidazopyrimidinylene group, or an imidazopyridinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a $C_6$-$C_{20}$ aryl group, a $C_2$-$C_{20}$ heteroaryl group, a monovalent non-aromatic condensed polycyclic group, a monovalent non-aromatic condensed heteropolycyclic group, and —Si($Q_{33}$)($Q_{34}$)($Q_{35}$),
wherein $Q_{33}$ to $Q_{35}$ are each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group a phthalazinyl group, a quinoxalinyl group, a cinnolinyl group, and a quinazolinyl group.

8. The condensed cyclic compound of claim 1, wherein $L_1$ to $L_3$, $L_{11}$ to $L_{13}$, $L_{21}$ to $L_{24}$, and $L_{31}$ to $L_{33}$ are each independently represented by one of Formulae 2-1 to 2-37:

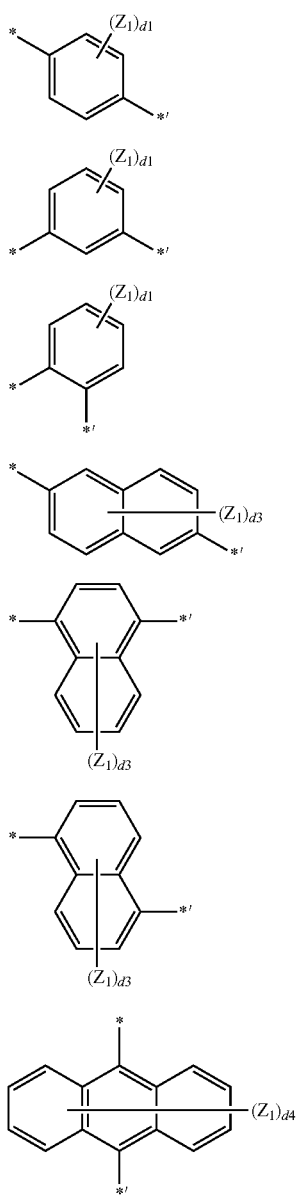

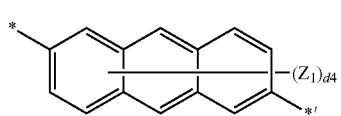

Formula 2-8

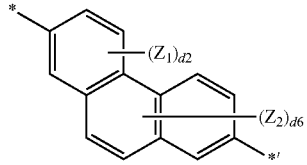

Formula 2-9

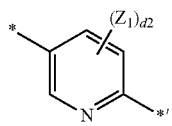

Formula 2-10

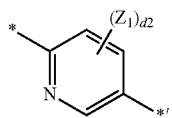

Formula 2-11

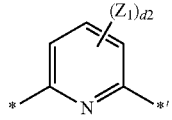

Formula 2-12

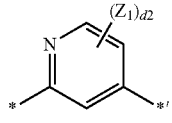

Formula 2-13

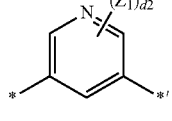

Formula 2-14

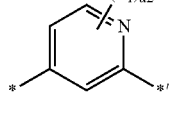

Formula 2-15

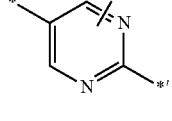

Formula 2-16

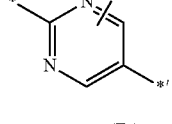

Formula 2-17

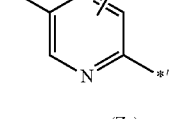

Formula 2-18

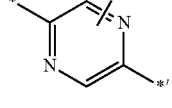

Formula 2-19

Formula 2-20
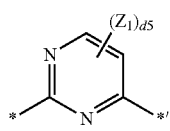
Formula 2-21
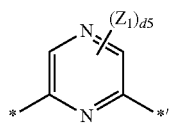
Formula 2-22
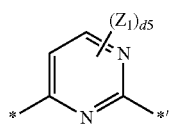
Formula 2-23
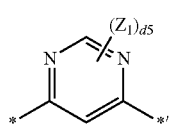
Formula 2-24
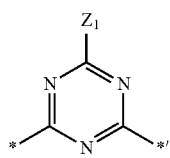
Formula 2-25
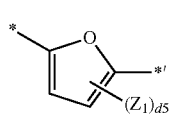
Formula 2-26
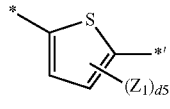
Formula 2-27
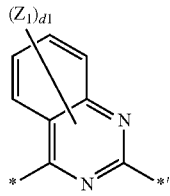
Formula 2-28
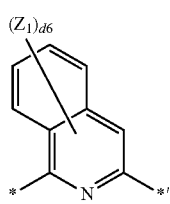
Formula 2-29
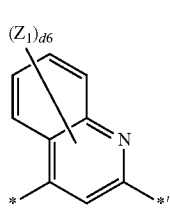
Formula 2-30
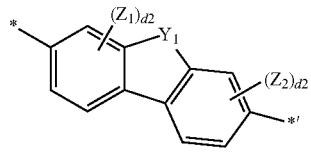
Formula 2-31
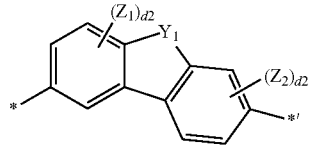
Formula 2-32
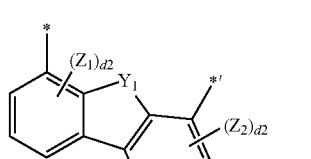
Formula 2-33
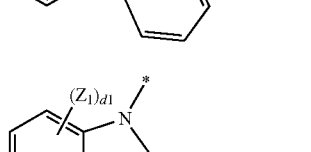
Formula 2-34
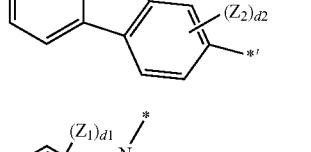
Formula 2-35
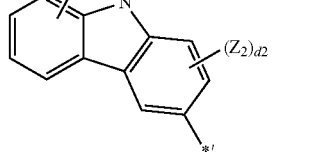
Formula 2-36
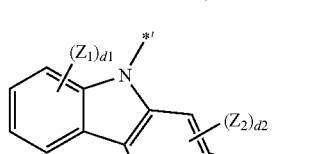
Formula 2-37
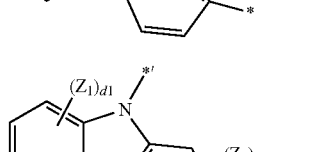
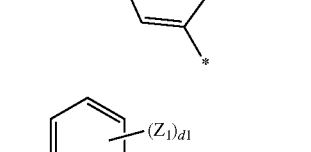
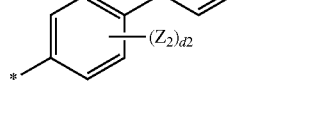
wherein in Formulae 2-1 to 2-37,
$Y_1$ may be O, S, S(=O), S(=O)$_2$, C($Z_3$)($Z_4$), N($Z_5$), or Si($Z_6$)($Z_7$);

$Z_1$ to $Z_7$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, a quinoxalinyl group, a biphenyl group, and —Si($Q_{33}$)($Q_{34}$)($Q_{35}$), wherein $Q_{33}$ to $Q_{35}$ are each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group a phthalazinyl group, a quinoxalinyl group, a cinnolinyl group, and a quinazolinyl group;

d1 is an integer of 1 to 4;
d2 is an integer of 1 to 3;
d3 is an integer of 1 to 6;
d4 is an integer of 1 to 8;
d5 is an integer of 1 or 2;
d6 is an integer of 1 to 5; and
* indicates a binding site to a neighboring atom.

9. The condensed cyclic compound of claim 1, wherein $L_1$ to $L_3$, $L_{11}$ to $L_{13}$, $L_{21}$ to $L_{24}$, and $L_{31}$ to $L_{33}$ are each independently selected from
a phenylene group, a naphthylene group, a phenanthrenylene group, an anthracenylene group, a triphenylenylene group, and a carbazolylene group; and
a phenylene group, naphthylene group, a phenanthrenylene group, an anthracenylene group, a triphenylenylene group, and a carbazolylene group each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, a triphenylenyl group, a phenanthrenyl group, and a biphenyl group.

10. The condensed cyclic compound of claim 1, wherein $L_1$ to $L_3$, $L_{11}$ to $L_{13}$, $L_{21}$ to $L_{24}$, and $L_{31}$ to $L_{33}$ are each independently represented by one of Formulae 3-1 to 3-33:

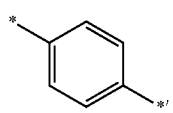

Formula 3-1

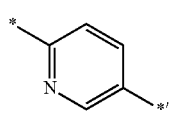

Formula 3-2

-continued

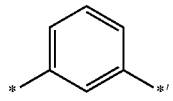

Formula 3-3

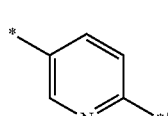

Formula 3-4

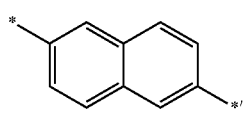

Formula 3-5

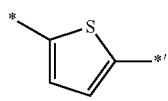

Formula 3-6

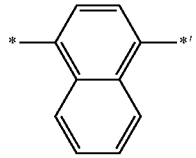

Formula 3-7

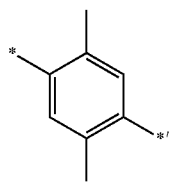

Formula 3-8

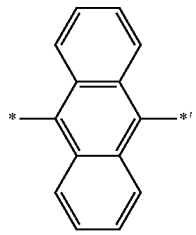

Formula 3-9

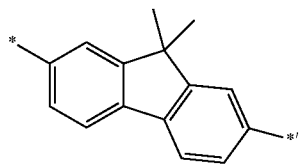

Formula 3-10

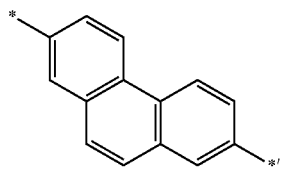

Formula 3-11

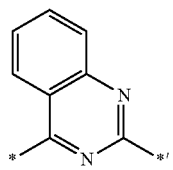

Formula 3-12

-continued
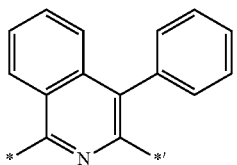
Formula 3-13
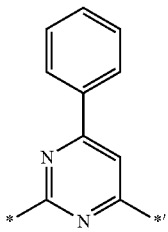
Formula 3-14
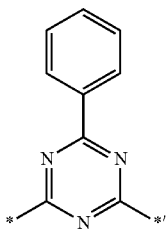
Formula 3-15
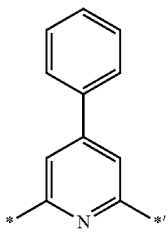
Formula 3-16
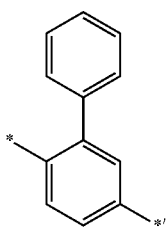
Formula 3-17
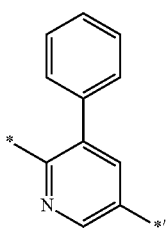
Formula 3-18
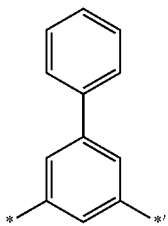
Formula 3-19
-continued
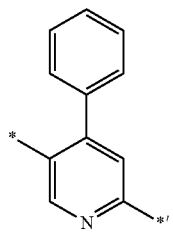
Formula 3-20
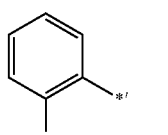
Formula 3-21
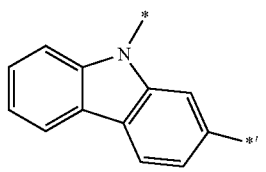
Formula 3-22
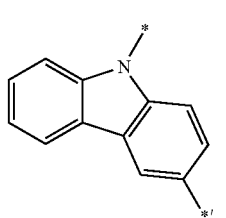
Formula 3-23
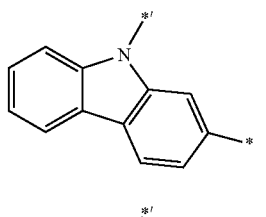
Formula 3-24
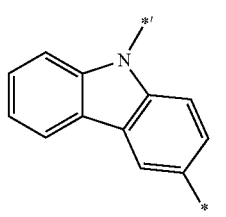
Formula 3-25
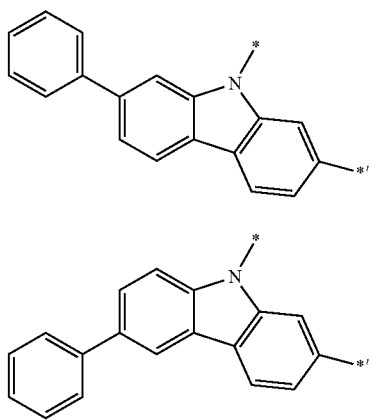
Formula 3-26
Formula 3-27

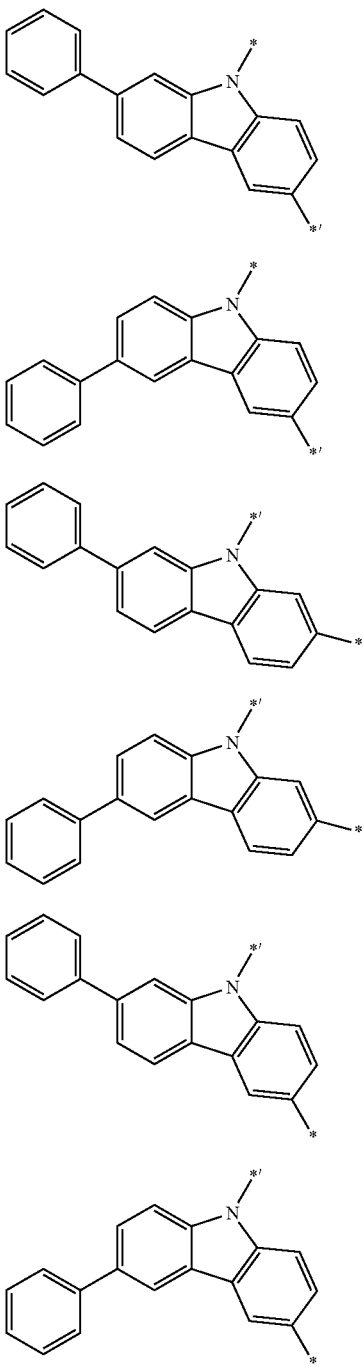

Formula 3-28
Formula 3-29
Formula 3-30
Formula 3-31
Formula 3-32
Formula 3-33 wherein * and *' in Formulae 3-1 to 3-33 each independently indicates a binding site to a neighboring atom.

11. The condensed cyclic compound of claim 1, wherein a1 to a3, a11 to a13, a21 to a24, and a31 to a33 are each independently 0, 1, or 2.

12. The condensed cyclic compound of claim 1, wherein $R_1$, $R_2$, $R_{11}$ to $R_{13}$, $R_{21}$ to $R_{23}$, and $R_{31}$ to $R_{33}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, and a phosphoric acid or a salt thereof;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, phenanthridinyl, acridinyl, phenanthrolinyl, phenazinyl, a benzoimidazolyl group, a benzofuranyl group, a benzothiophenyl group, an isobenzothiazolyl group, a benzooxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a phenyl group substituted with a $C_1$-$C_{20}$ alkyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, a biphenyl group, and —Si($Q_{33}$)($Q_{34}$)($Q_{35}$); and —Si($Q_3$)($Q_4$)($Q_5$), wherein $Q_3$ to $Q_5$ and $Q_{33}$ to $Q_{35}$ are each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group.

13. The condensed cyclic compound of claim 1, wherein $R_1$, $R_2$, $R_{11}$ to $R_{13}$, $R_{21}$ to $R_{23}$, and $R_{31}$ to $R_{33}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, and a phosphoric acid or a salt thereof;

one of Formulae 4-1 to 4-51, 5-1 to 5-6, and 6-1 to 6-5; and

—Si($Q_3$)($Q_4$)($Q_5$), wherein $Q_3$ to $Q_5$ are each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group:

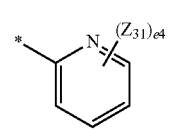

Formula 4-1

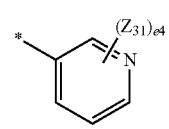

Formula 4-2

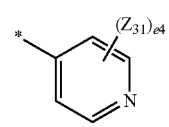

Formula 4-3

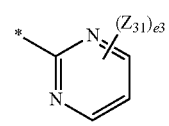

Formula 4-4

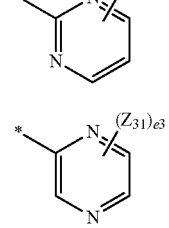

Formula 4-5

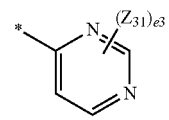

Formula 4-6

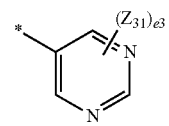

Formula 4-7

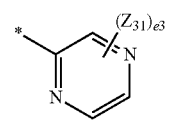

Formula 4-8

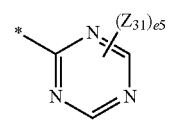

Formula 4-9

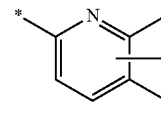

Formula 4-10

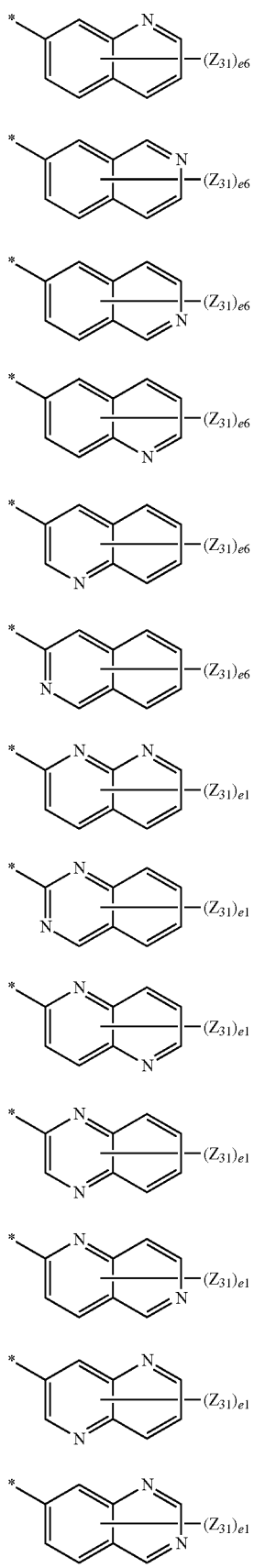
Formula 4-11
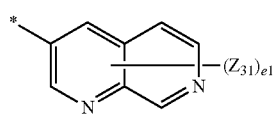
Formula 4-12
Formula 4-13
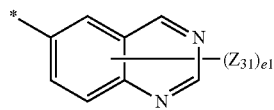
Formula 4-14
Formula 4-15
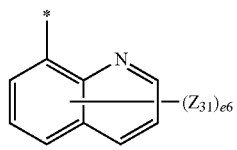
Formula 4-16
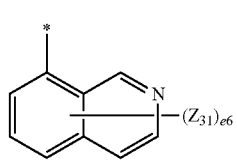
Formula 4-17
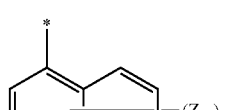
Formula 4-18
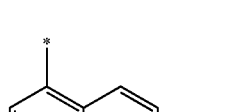
Formula 4-19
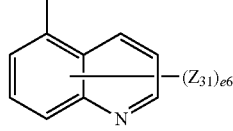
Formula 4-20
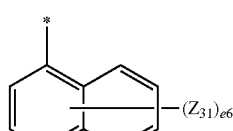
Formula 4-21
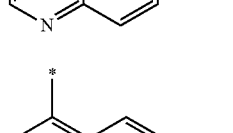
Formula 4-22
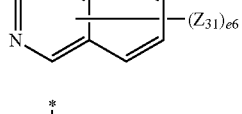
Formula 4-23
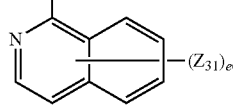
Formula 4-24
Formula 4-25
Formula 4-26
Formula 4-27
Formula 4-28
Formula 4-29
Formula 4-30
Formula 4-31
Formula 4-32
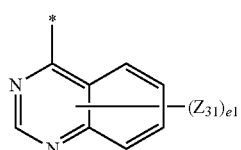
Formula 4-33

-continued
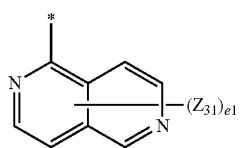
Formula 4-34
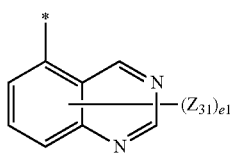
Formula 4-35
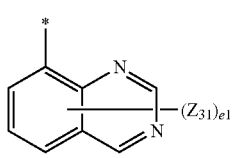
Formula 4-36
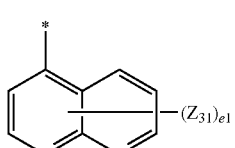
Formula 4-37
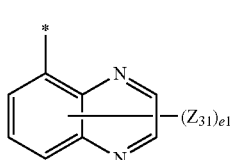
Formula 4-38
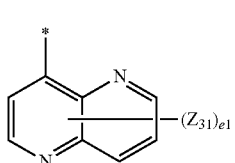
Formula 4-39
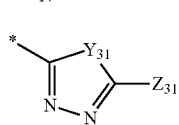
Formula 4-40
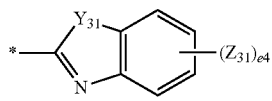
Formula 4-41
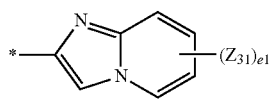
Formula 4-42
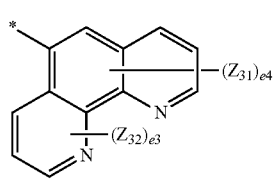
Formula 4-43
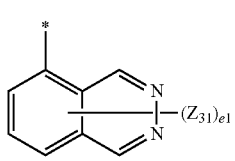
Formula 4-44
-continued
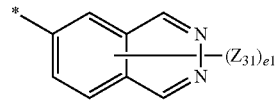
Formula 4-45
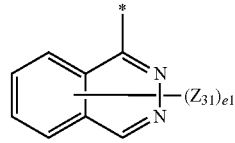
Formula 4-46
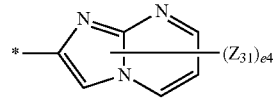
Formula 4-47
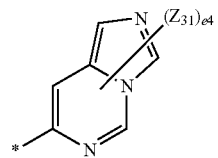
Formula 4-48
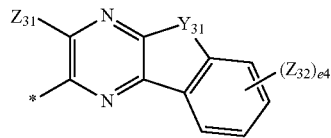
Formula 4-49
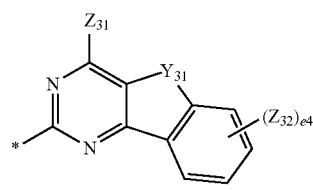
Formula 4-50
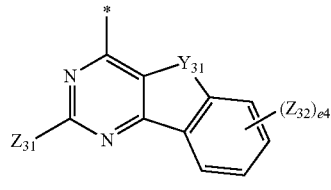
Formula 4-51
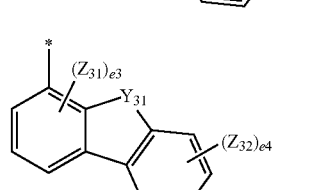
Formula 5-1
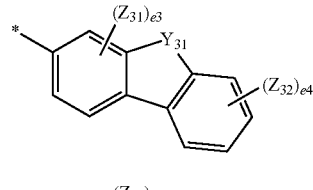
Formula 5-2
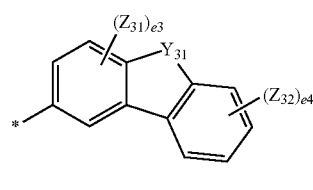
Formula 5-3

-continued

Formula 5-4
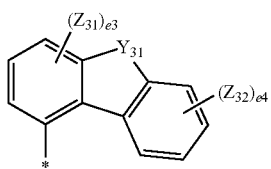

Formula 5-5
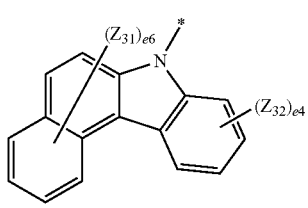

Formula 5-6
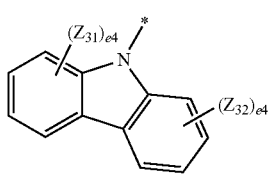

Formula 6-1
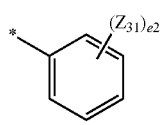

Formula 6-2
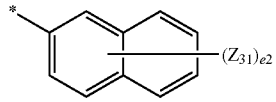

Formula 6-3
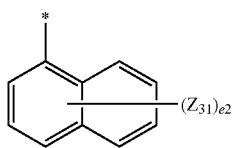

Formula 6-4
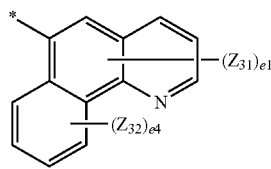

Formula 6-5
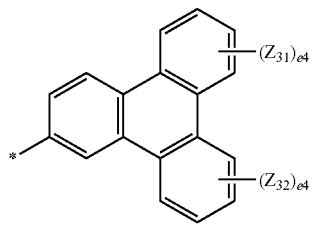

wherein in Formulae 4-1 to 4-51, 5-1 to 5-6, and 6-1 to 6-5, $Y_{31}$ is O, S, $C(Z_{33})(Z_{34})$, $N(Z_{35})$, or $Si(Z_{36})(Z_{37})$;

$Z_{31}$ to $Z_{37}$ are each independently selected from a hydrogen, a deuterium, —F, —Cl, —Br, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group substituted with a $C_1$-$C_{20}$ alkyl group, a phenyl group, a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, a quinoxalinyl group, a biphenyl group, and —$Si(Q_{33})(Q_{34})(Q_{35})$, wherein $Q_{33}$ to $Q_{35}$ are each independently selected from a hydrogen, a $C_1$-$C_{20}$ alkyl group, a $C_1$-$C_{20}$ alkoxy group, a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group;

e1 is an integer of 1 to 5;

e2 is an integer of 1 to 7;

e3 is an integer of 1 to 3;

e4 is an integer of 1 to 4;

e5 is an integer of 1 or 2;

e6 is an integer of 1 to 6; and

* indicates a binding site to a neighboring atom.

14. The condensed cyclic compound of claim 1, wherein Formula 2A is represented by one of Formulae 2A(1) to 2A(5), Formula 2B is represented by one of Formulae 2B(1) and 2B(2), Formula 2D is represented by one of Formulae 2D(1) to 2D(5), and Formula 2F is represented by one of Formulae 2F(1) and 2F(2):

Formula 2A(1)
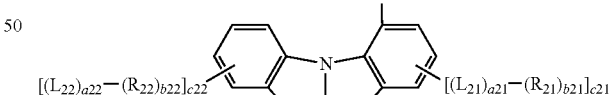

Formula 2A(2)
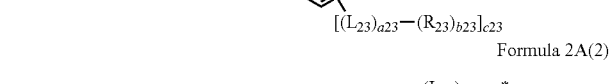
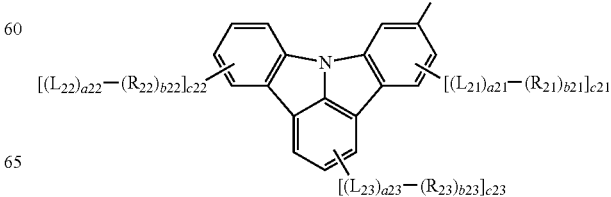

Formula 2A(3)
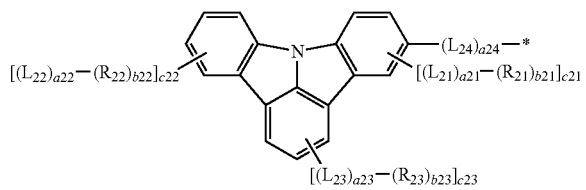

Formula 2A(4)
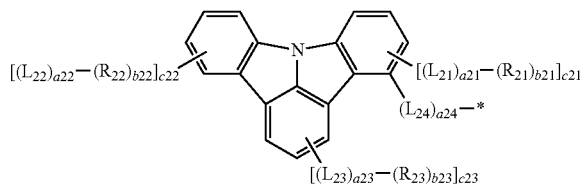

Formula 2A(5)
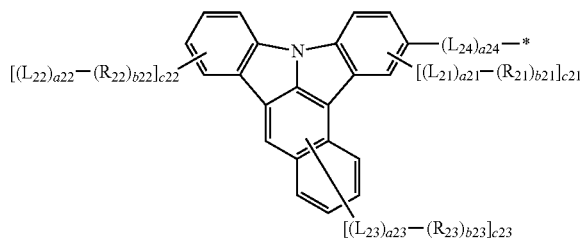

Formula 2B(1)
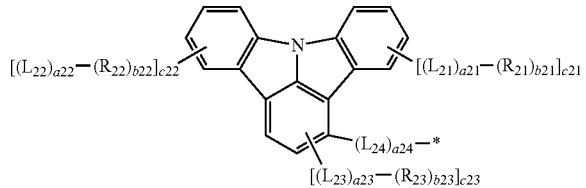

Formula 2B(2)
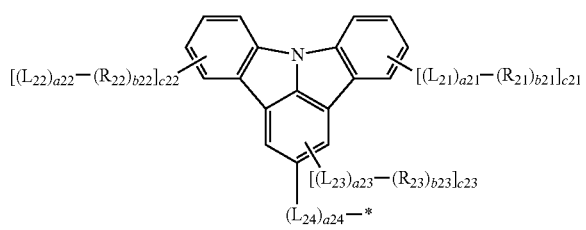

Formula 2E(1)
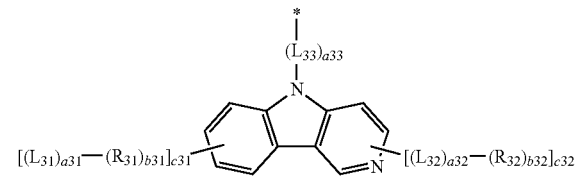

Formula 2E(2)
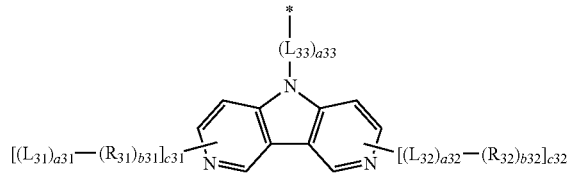

Formula 2E(3)

Formula 2E(4)

Formula 2E(5)
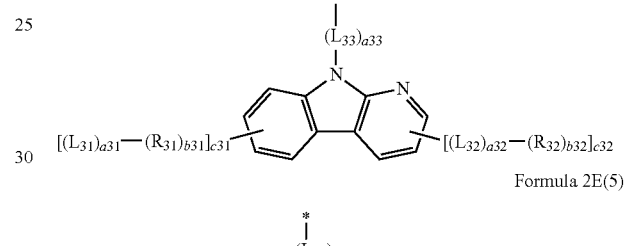

Formula 2F(1)
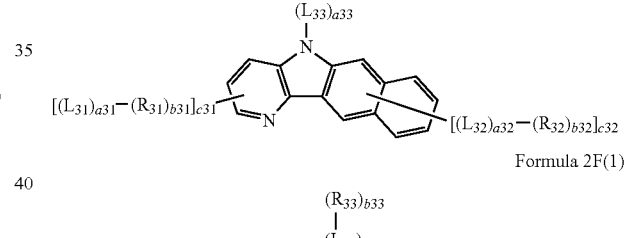
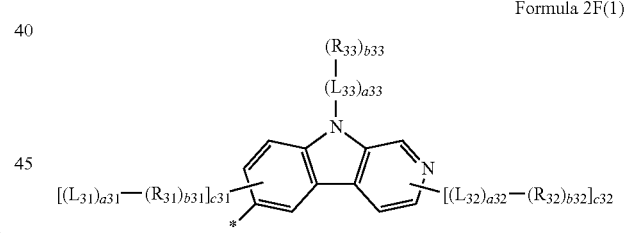

Formula 2F(2)
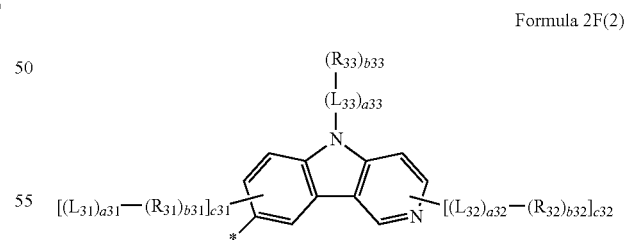

wherein $L_{21}$ to $L_{24}$, a21 to a24, $R_{21}$ to $R_{23}$, b21 to b23, $L_{31}$ to $L_{33}$, a31 to a33, $R_{31}$ to $R_{33}$, b31 to b33, c21 to c23, c31, and c32 in Formulae 2A (1) to 2A (5), 2B(1), 2B(2), 2E(1) to 2E(5), 2F(1), and 2F(2) are the same as recited in claim 1.

15. The condensed cyclic compound of claim 1, wherein the condensed cyclic compound is represented by one of Formulae 1A(1) to 1A(8):

-continued
Formula 1A(1)
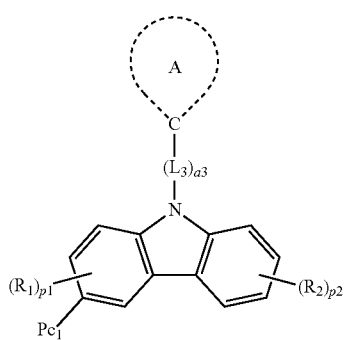
Formula 1A(5)
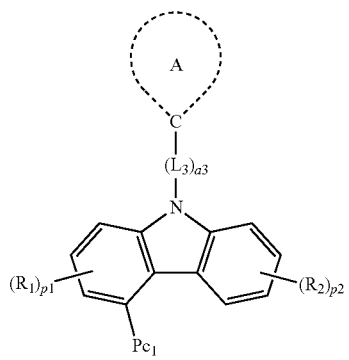
Formula 1A(2)
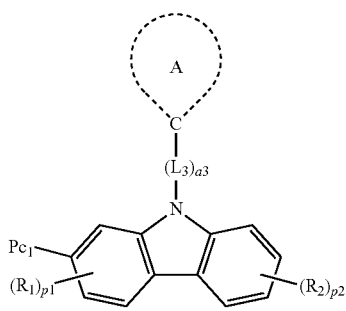
Formula 1A(6)
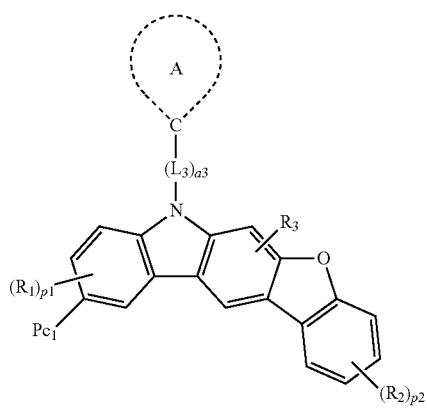
Formula 1A(3)
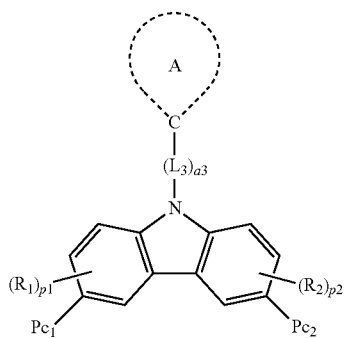
Formula 1A(7)
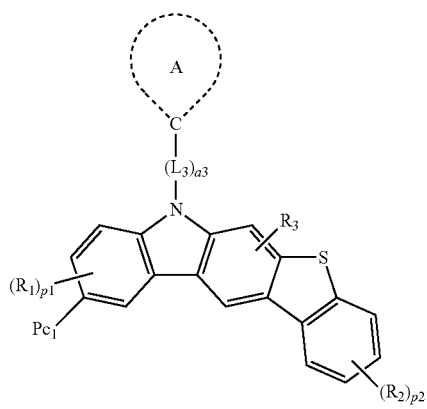
Formula 1A(4)
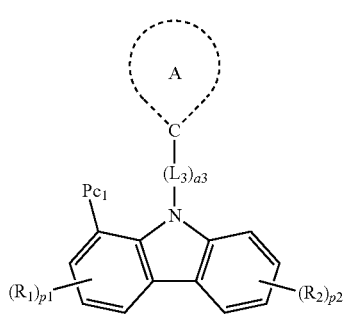
Formula 1A(8)
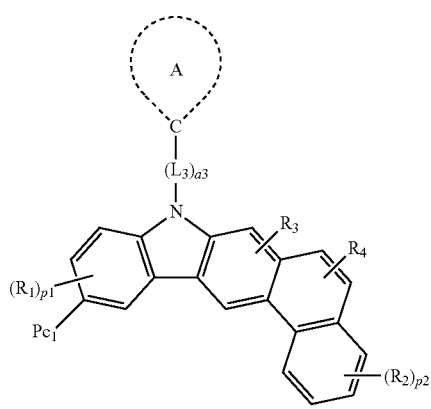

wherein, in Formulae 1A(1) and 1A(8),

Ring A is a substituted or unsubstituted $C_2$-$C_{10}$ heterocycloalkyl group, a substituted or unsubstituted $C_2$-$C_{10}$ heterocycloalkenyl group, a substituted or unsubstituted $C_2$-$C_{60}$ heteroaryl group, or a substituted or unsubstituted monovalent non-aromatic condensed hetero-polycyclic group, each comprising Moiety 1 as a ring-forming moiety;

$Pc_1$, $Pc_2$, $L_3$, a3, $R_1$, $R_2$, p1, and p2 are the same as recited in claim 1; and $R_3$ and $R_4$ are the same as recited in claim 1.

16. The condensed cyclic compound of claim 1, wherein the condensed cyclic compound is represented by one selected from Formulae 1B(1) to 1B(10):

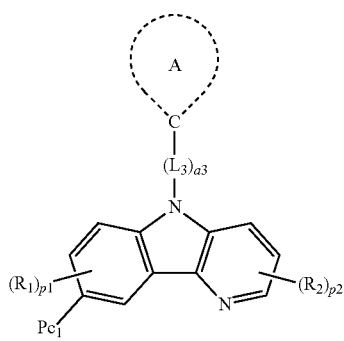

Formula 1B(1)

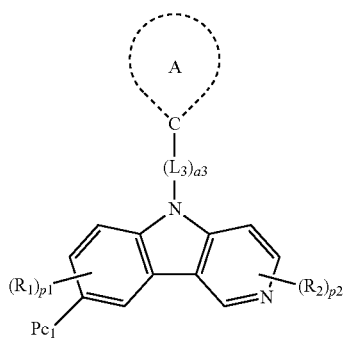

Formula 1B(2)

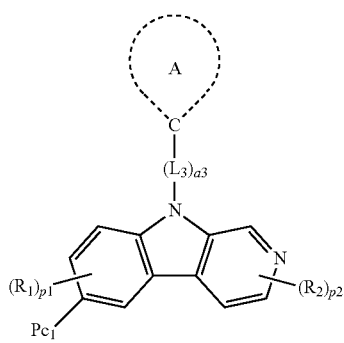

Formula 1B(3)

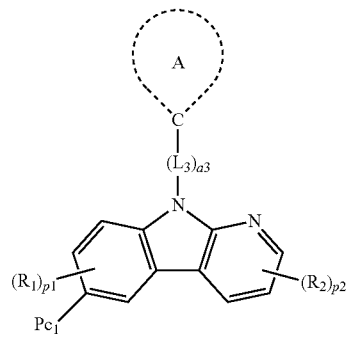

Formula 1B(4)

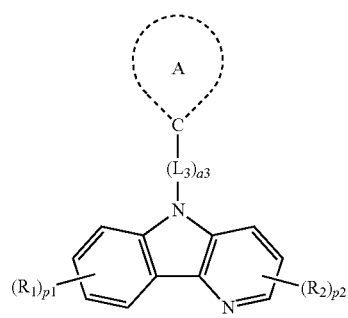

Formula 1B(5)

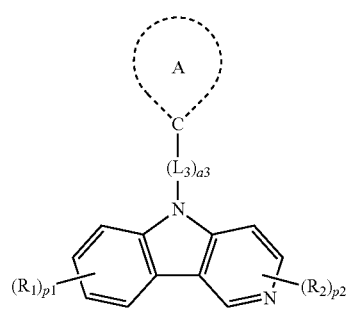

Formula 1B(6)

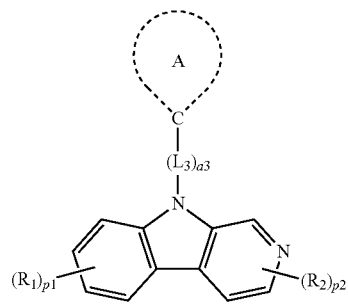

Formula 1B(7)

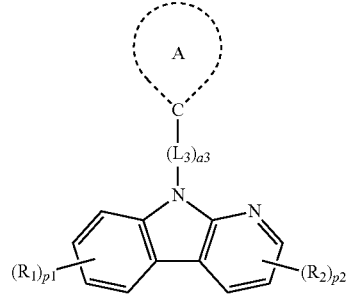

Formula 1B(8)

Formula 1B(9)

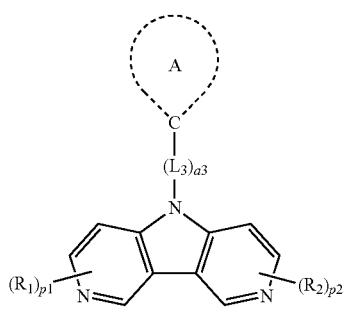

Formula 1B(10)

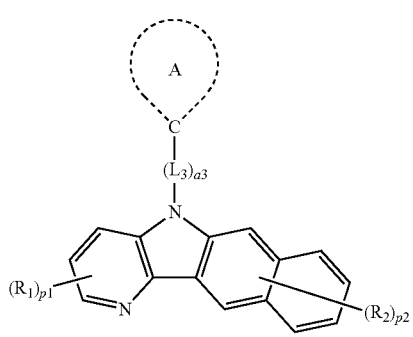

wherein Ring A, Pc$_1$, Pc$_2$, L$_3$, a3, R$_1$, R$_2$, p1, and p2 in Formulae 1B(1) to 1B(10) are the same as recited in claim 1.

17. The condensed cyclic compound of claim 1, wherein the condensed cyclic compound is represented by Formulae 1C(1) or 1C(2):

Formula 1C(1)

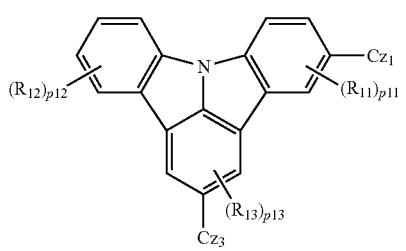

Formula 1C(2)

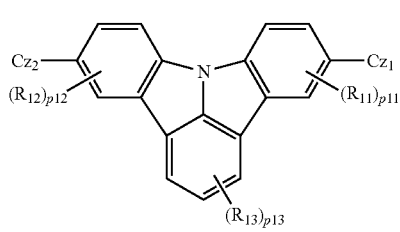

wherein Cz$_1$, Cz$_2$, Cz$_3$, R$_{11}$, R$_{12}$, R$_{13}$, p11, p12, and p13 in Formulae 1C(1) and 1C(2) are the same as recited in claim 1.

18. The condensed cyclic compound of claim 1, wherein the condensed cyclic compound is represented by Formula 1C(3):

Formula 1C(3)

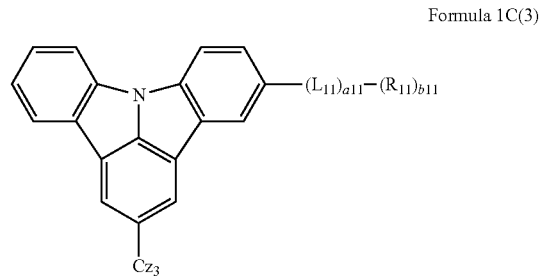

wherein in Formula 1C(3),

Cz$_3$, L$_{11}$, and all are the same as recited in claim 1;

R$_{11}$ is a substituted or unsubstituted C$_2$-C$_{10}$ heterocycloalkyl group, a substituted or unsubstituted C$_2$-C$_{10}$ heterocycloalkenyl group, a substituted or unsubstituted C$_2$-C$_{60}$ heteroaryl group, or a substituted or unsubstituted monovalent non-aromatic condensed hetero-polycyclic group, each comprising Moiety 1 as a ring-forming moiety; and b11 is 1 or 2.

19. The condensed cyclic compound of claim 1, wherein the condensed cyclic compound represented by Formulae 1C(4) or 1C(5):

Formula 1C(4)

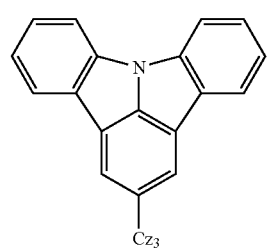

Formula 1C(5)

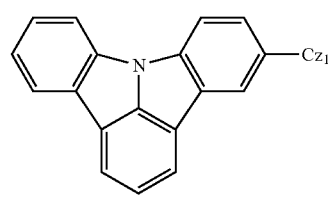

wherein in Formulae 1C (4) and 1C (5), Cz$_1$ and Cz$_3$ are each a group represented by Formula 2E or a group represented by Formula 2F.

20. The condensed cyclic compound of claim 1, wherein the condensed cyclic compound is one of Compounds 1 to 76:

213 214
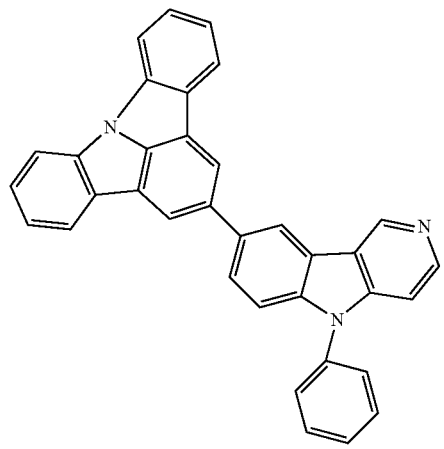
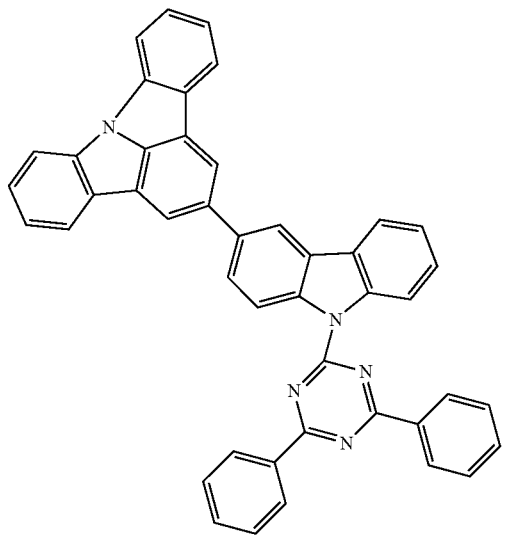
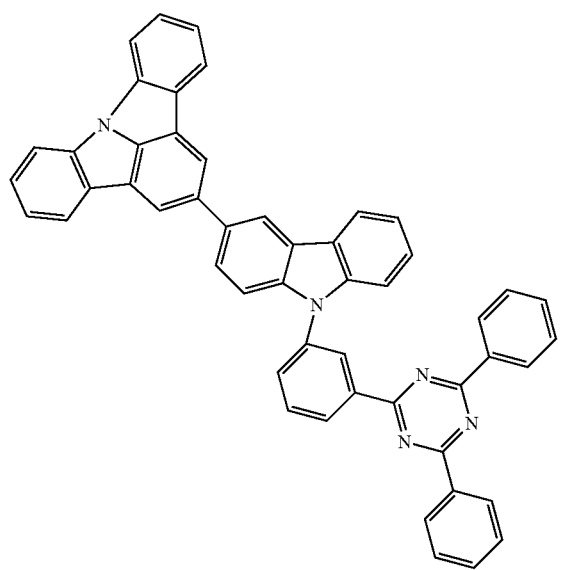
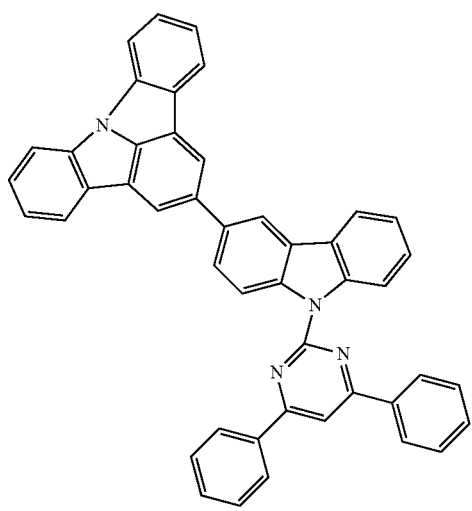
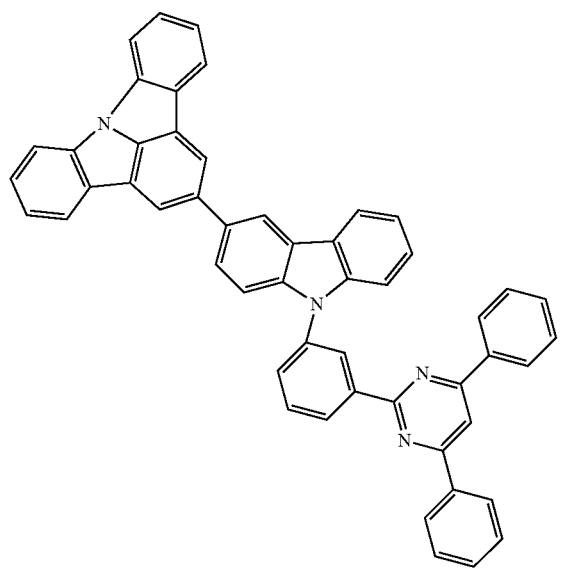
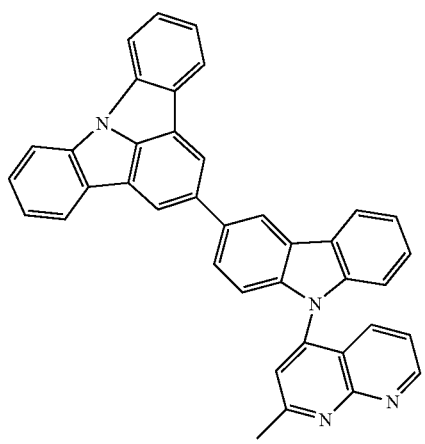

215
216
-continued
7
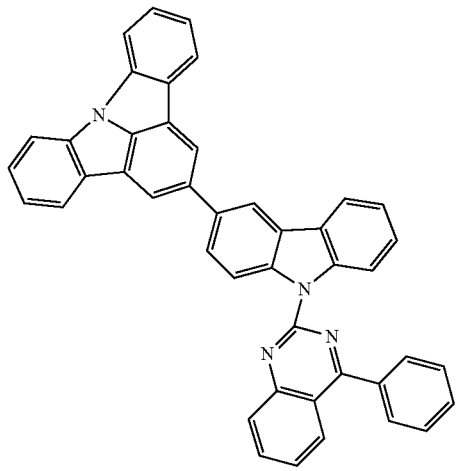
8
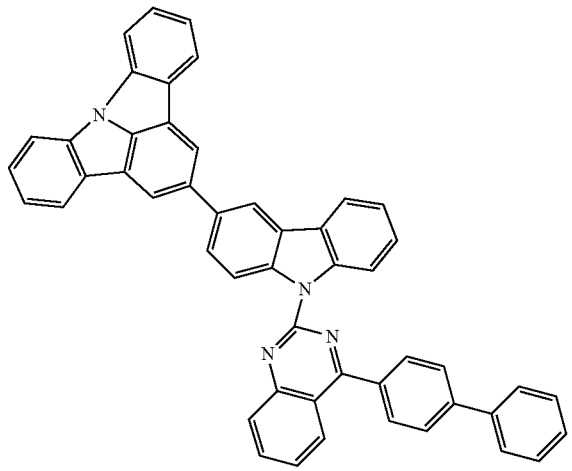
9
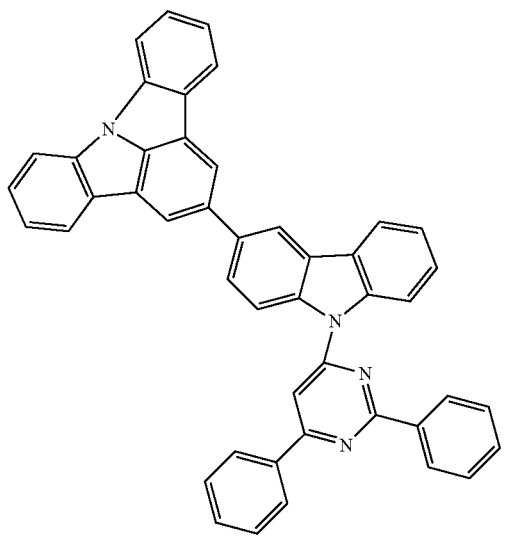
10
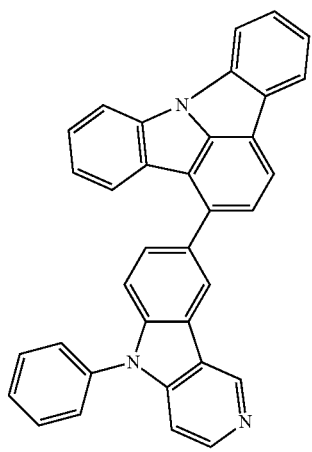
11
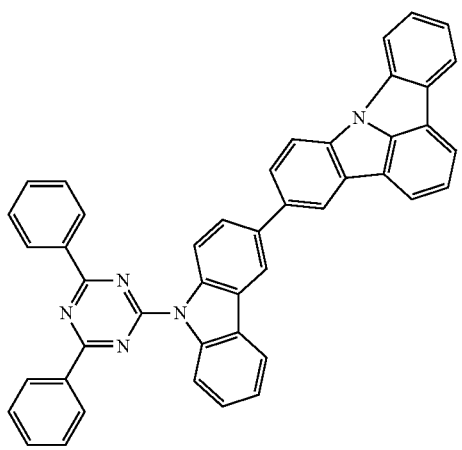
12
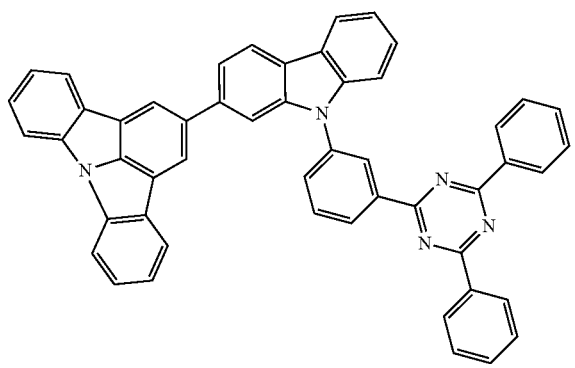

13
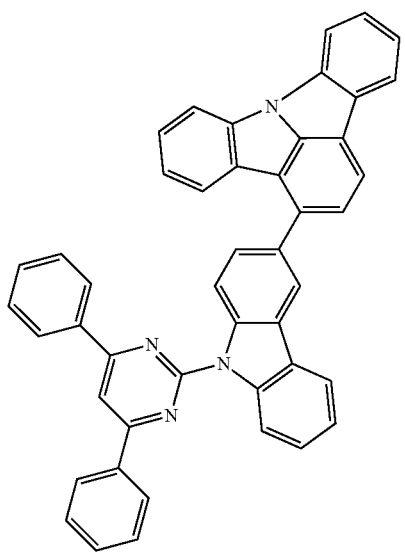
14
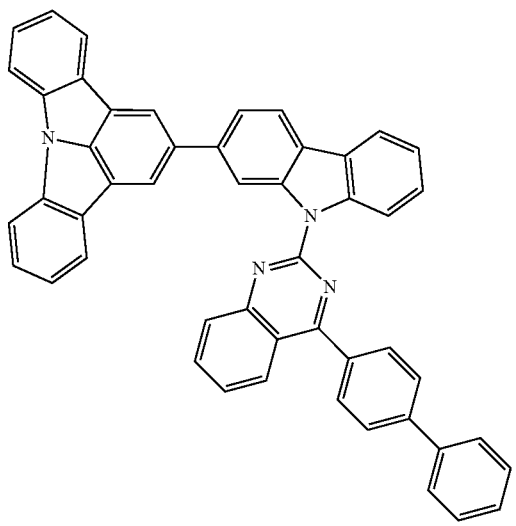
15
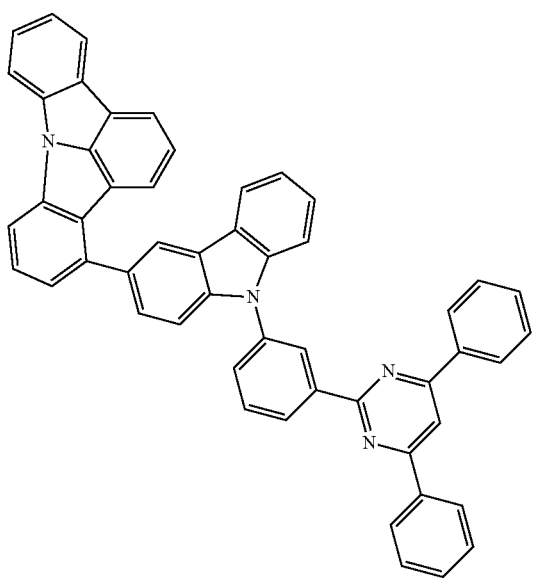
16
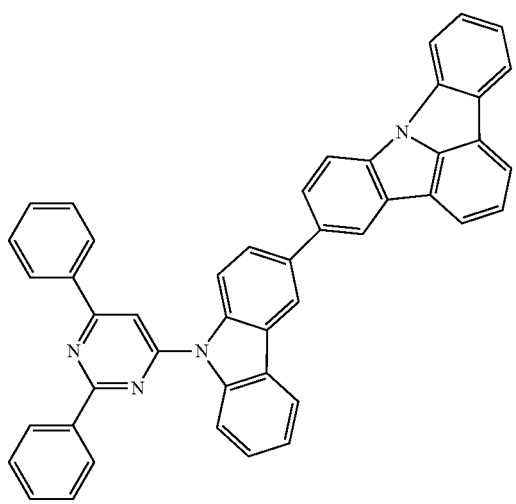
17
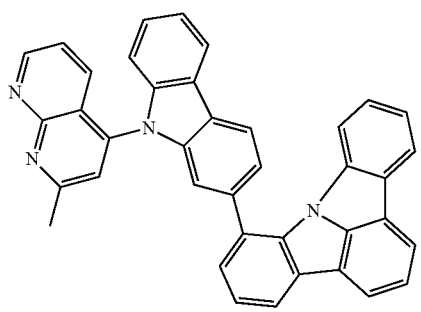
18
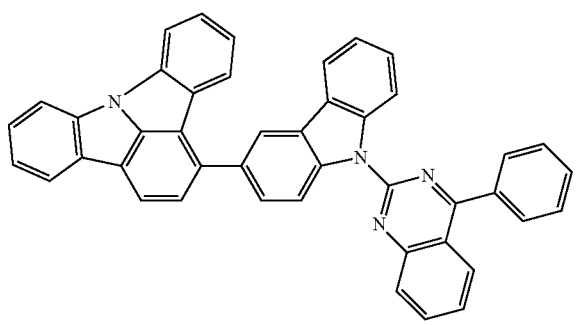

19
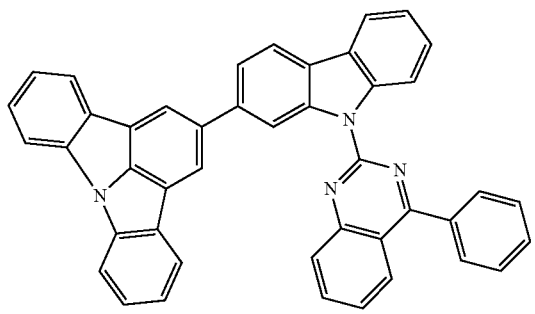
20
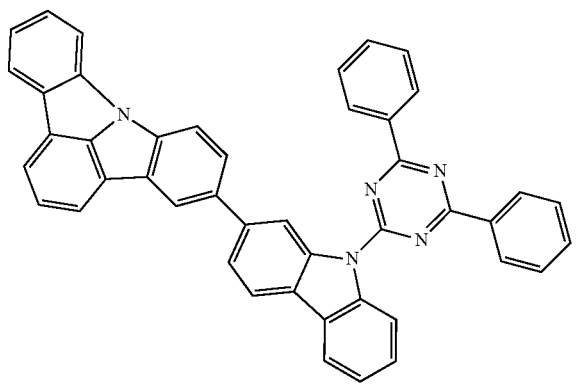
21
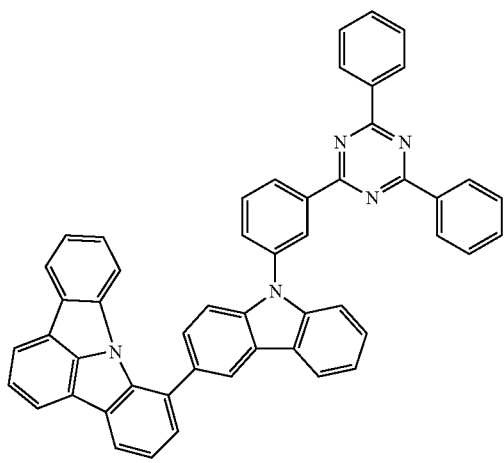
22
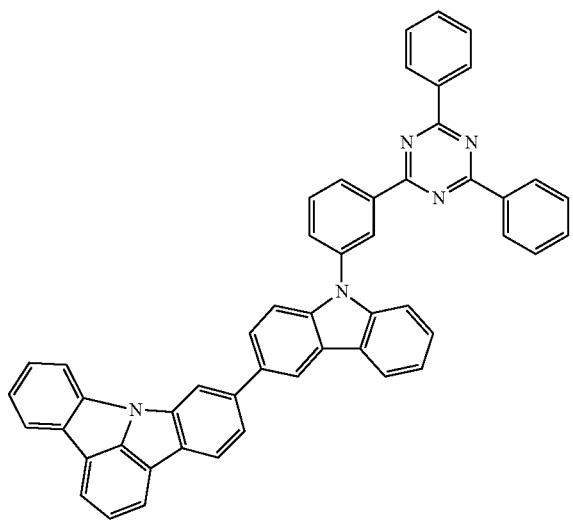
23
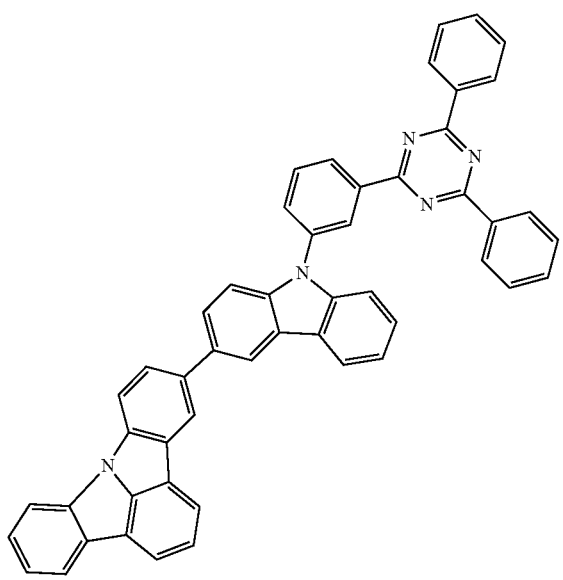
24
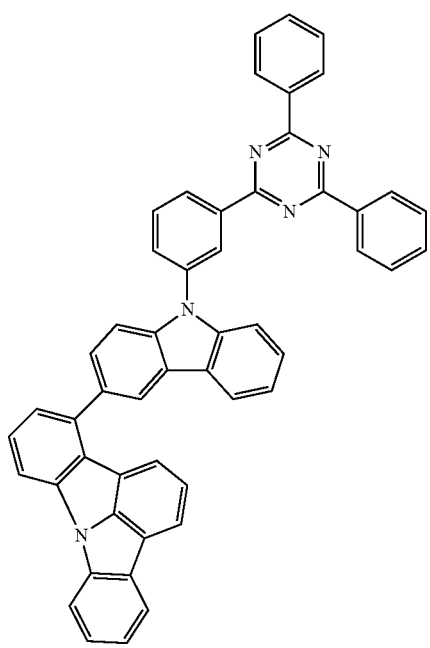

25
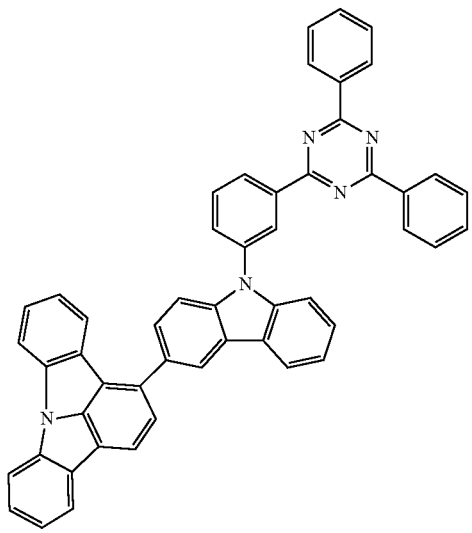
26
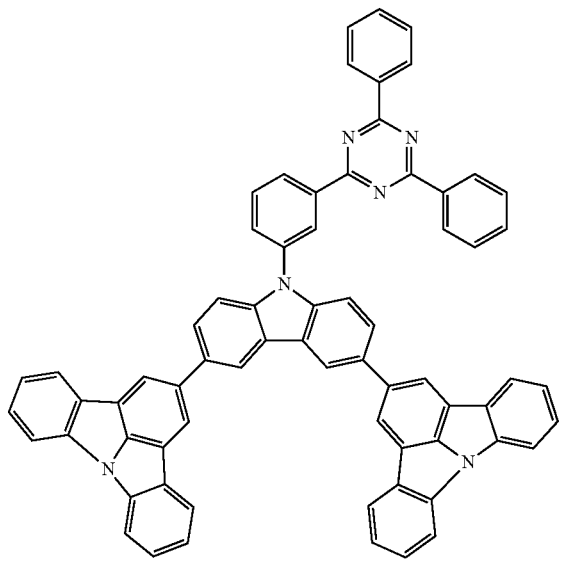
27
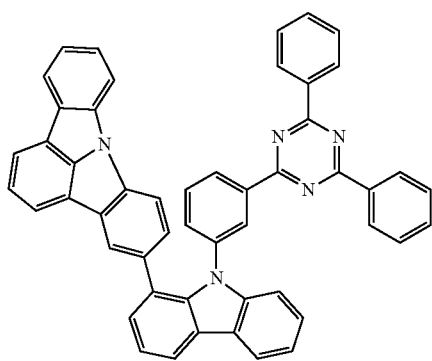
28
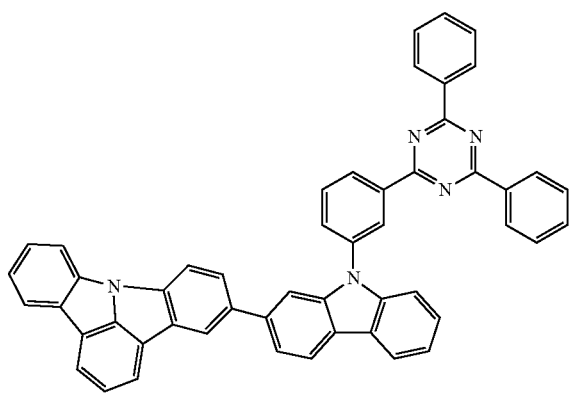
29
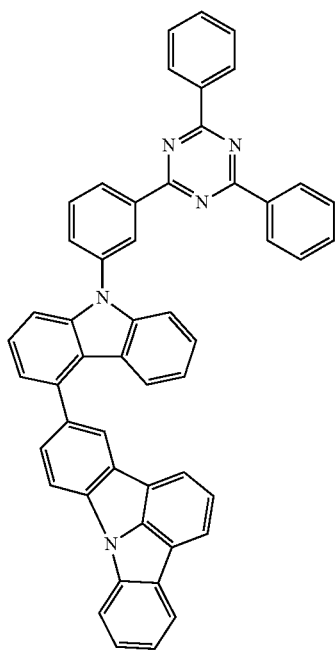
30
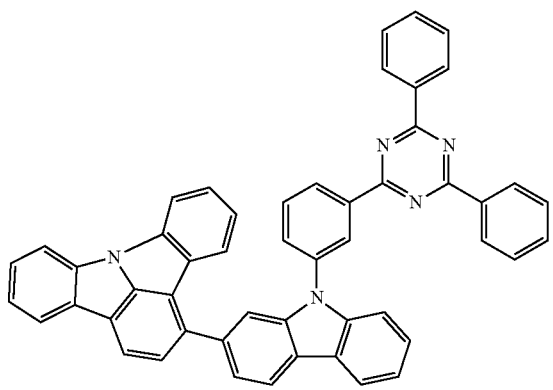

-continued
31
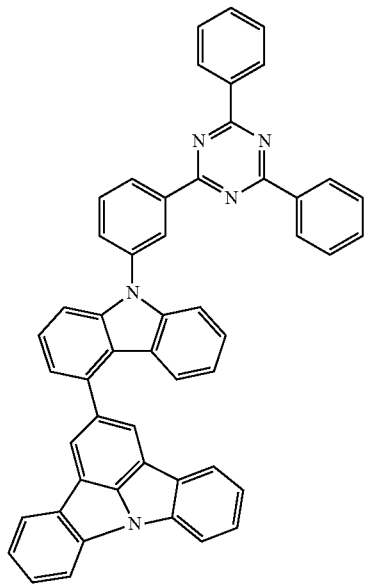
32
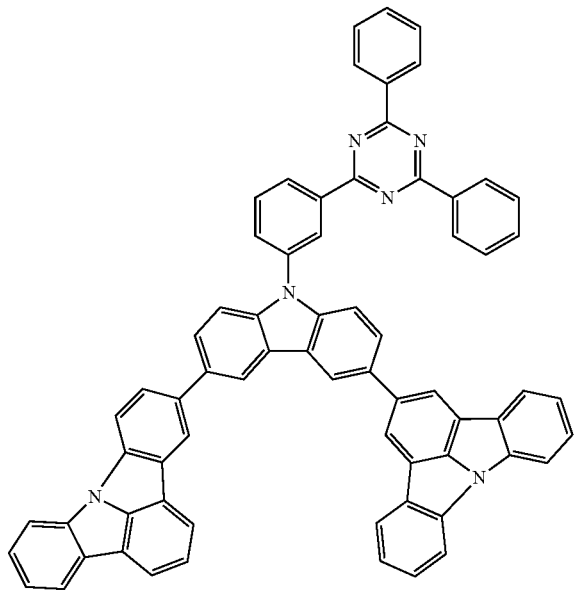
33
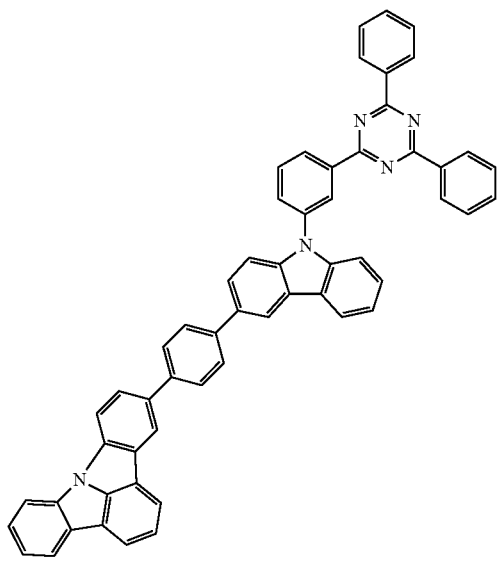
34
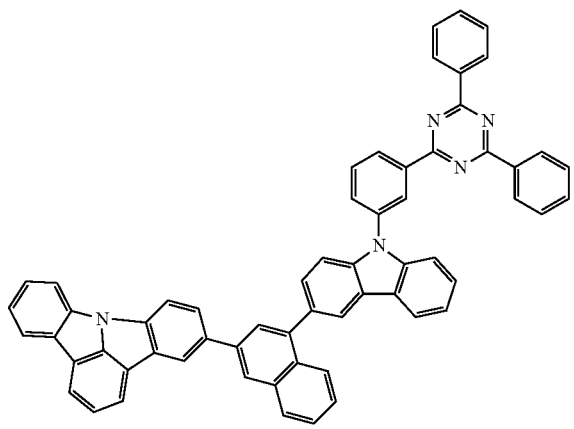

35
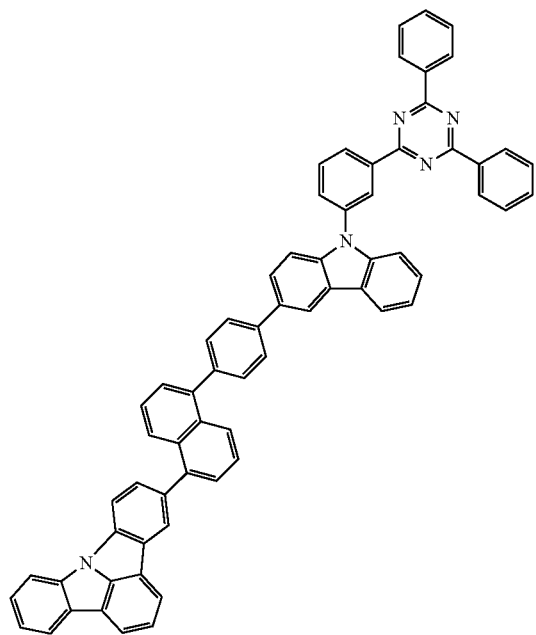
36
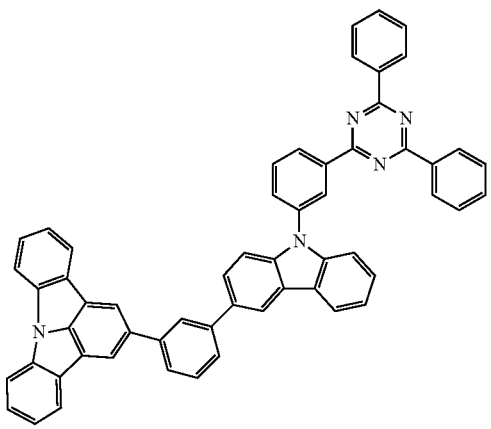
37
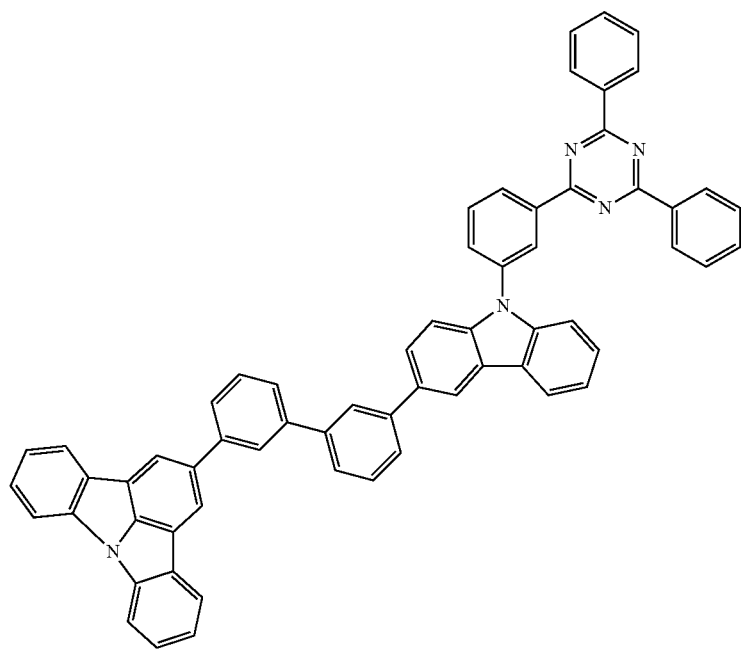

38
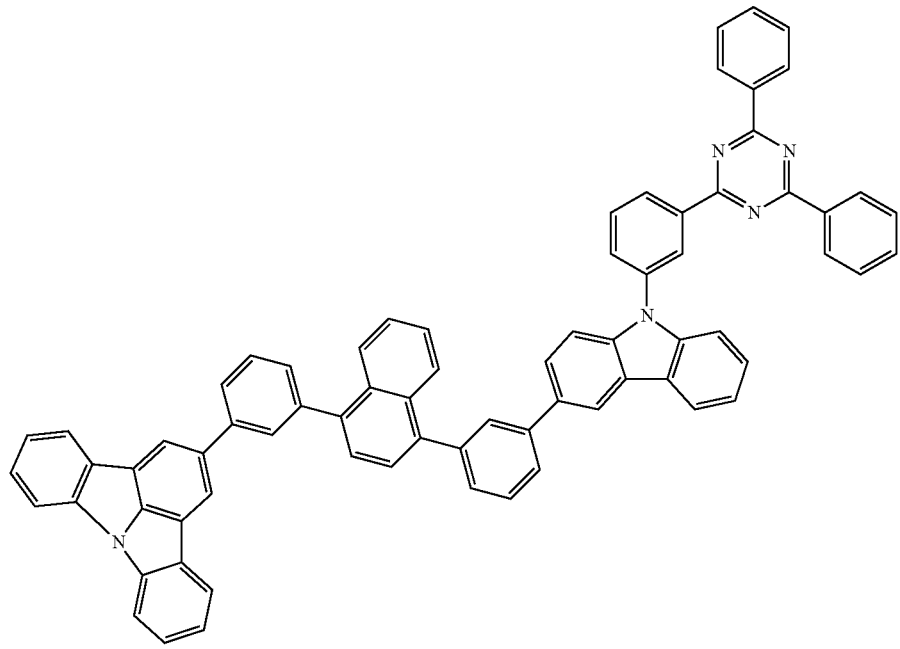
39
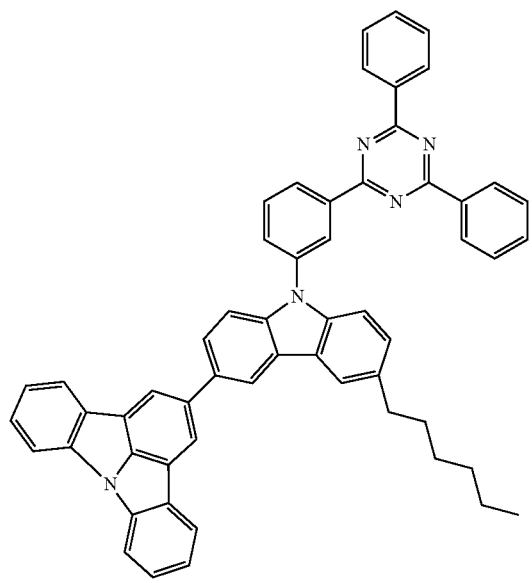

40
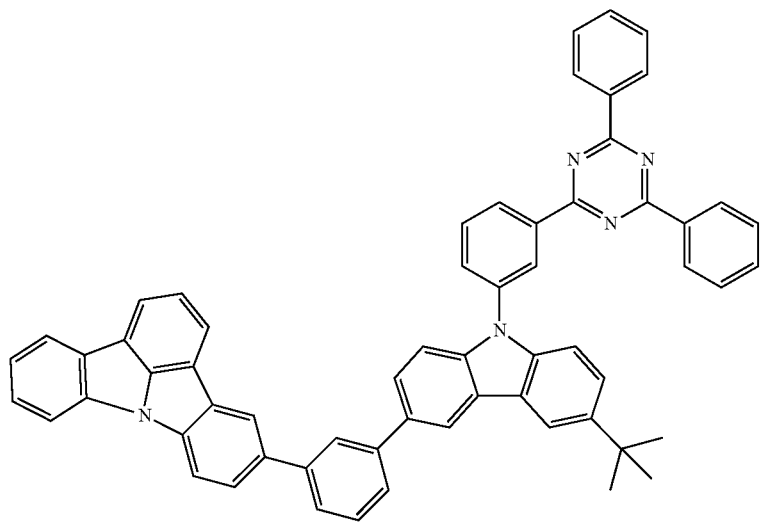
41
42
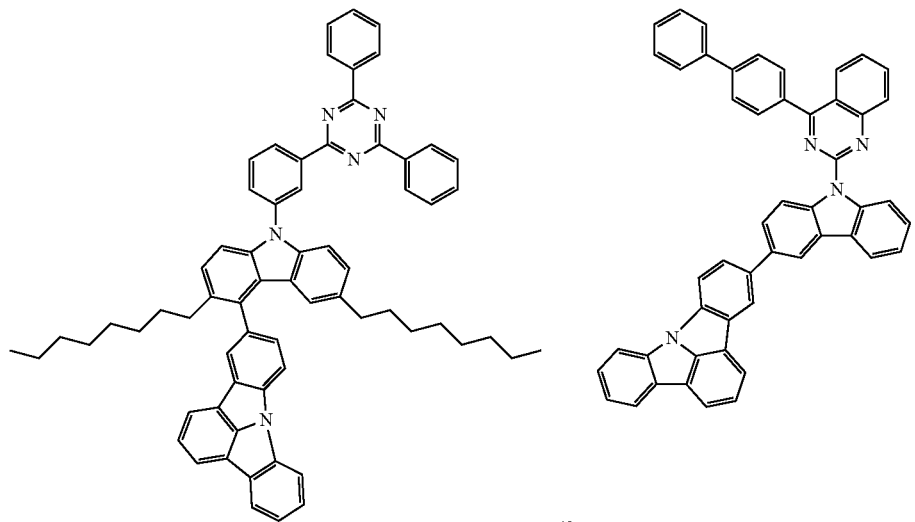
43
44
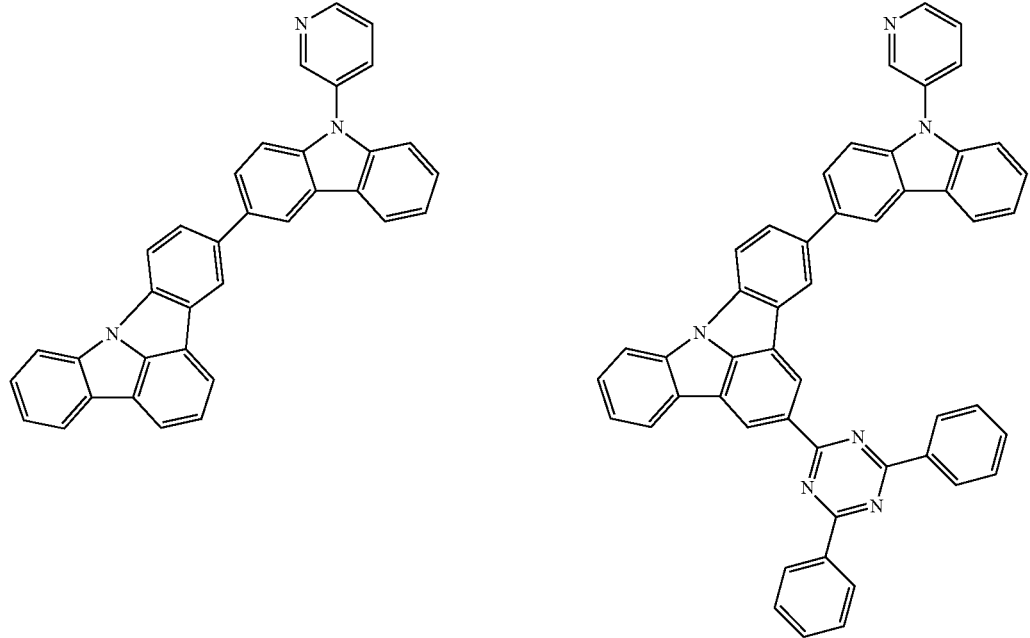

45
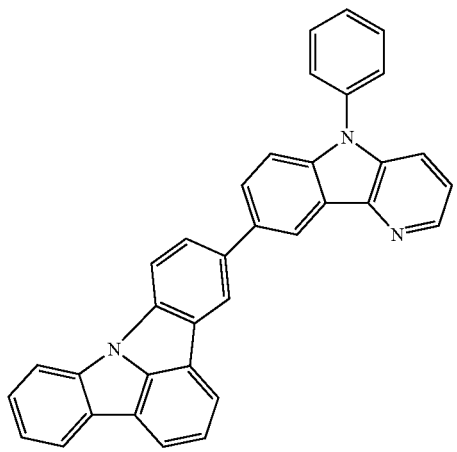
46
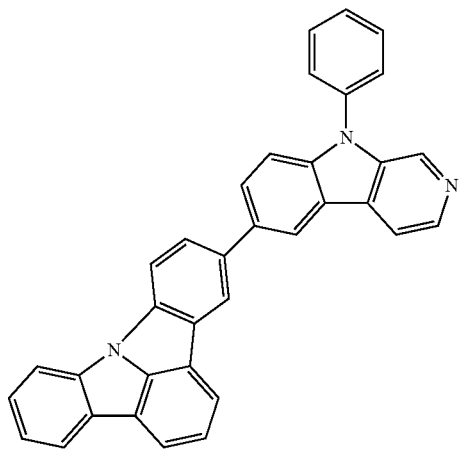
47
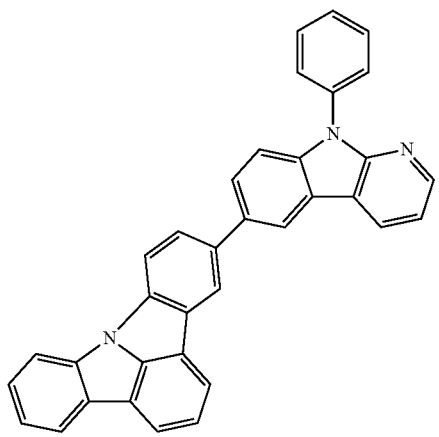
48
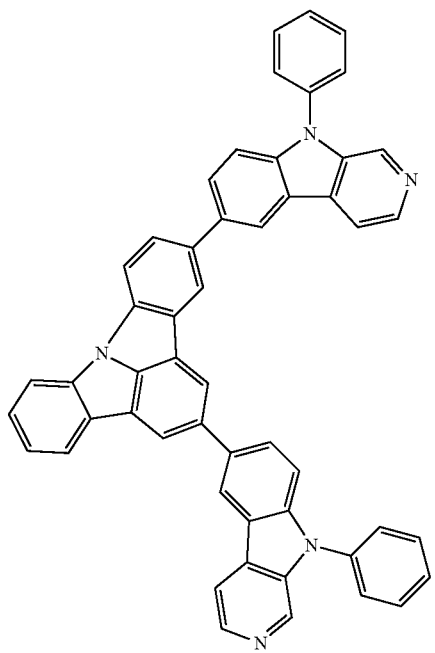

-continued
49
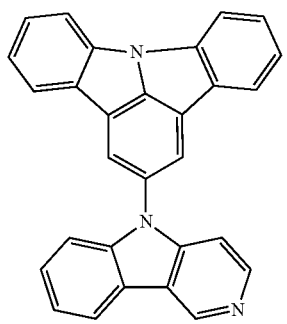
50
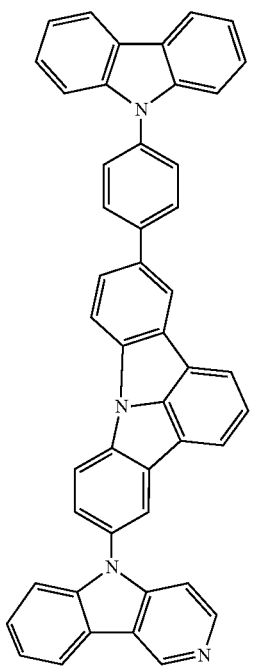
51
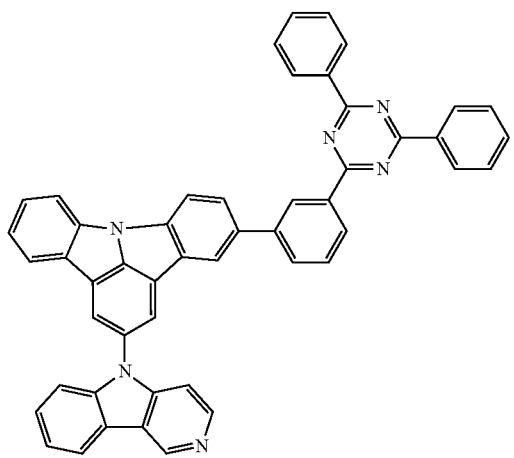
52
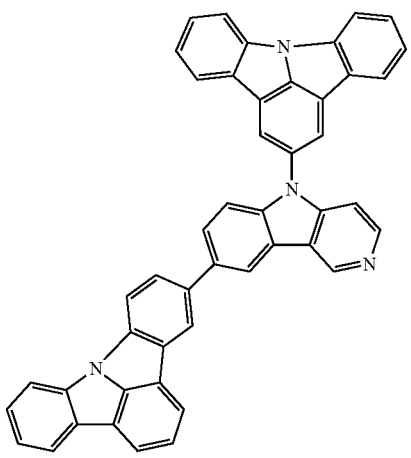

-continued
53
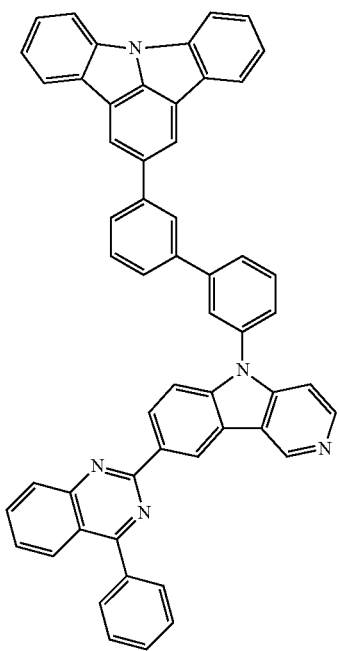
54
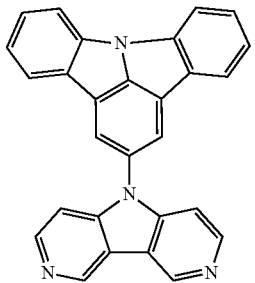
55
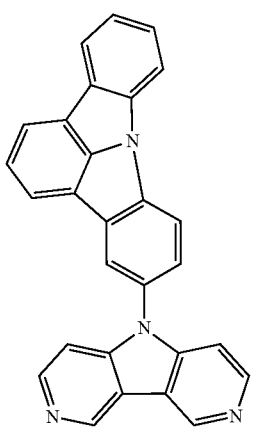
56
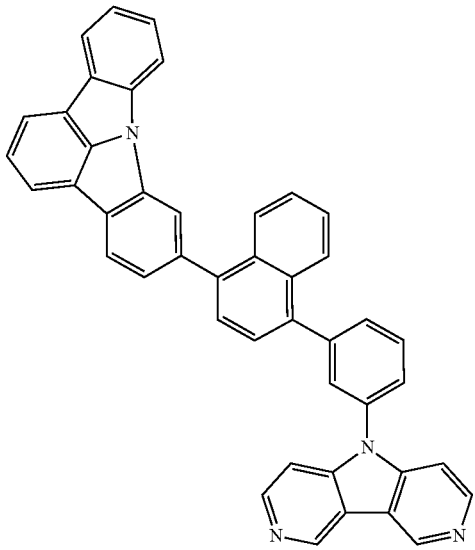

57
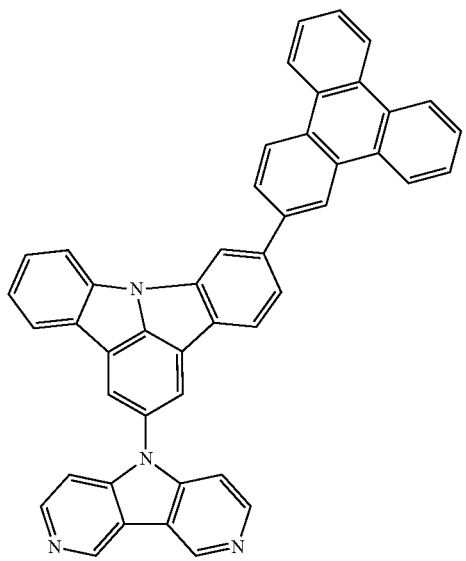
58
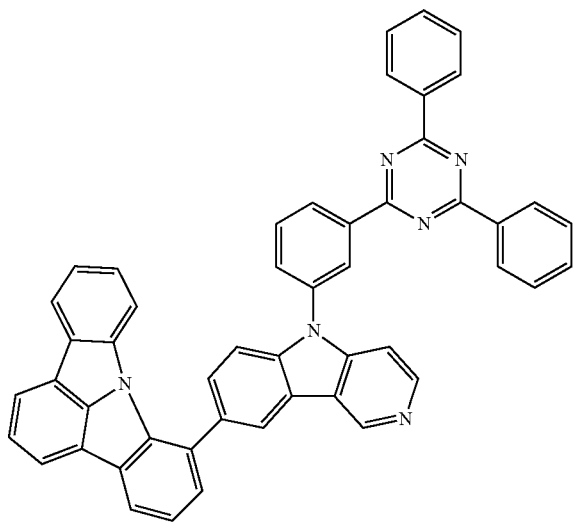
59
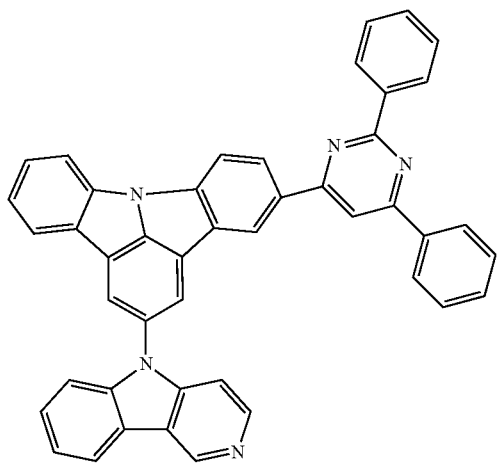
60
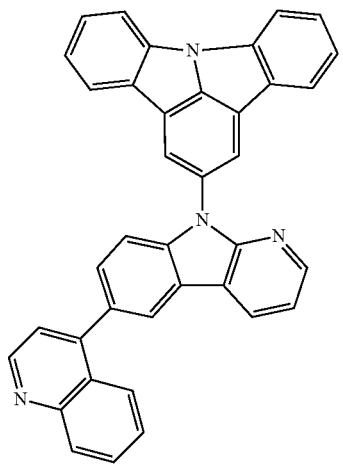
61
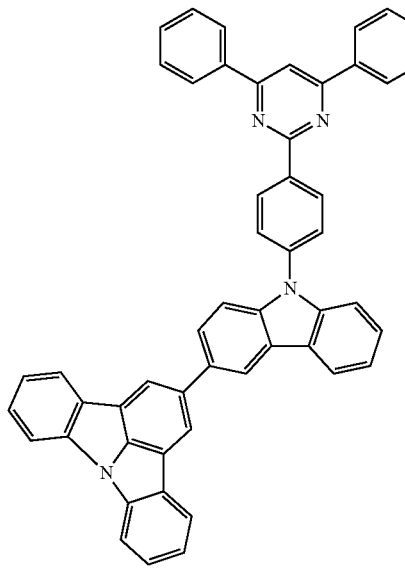
62
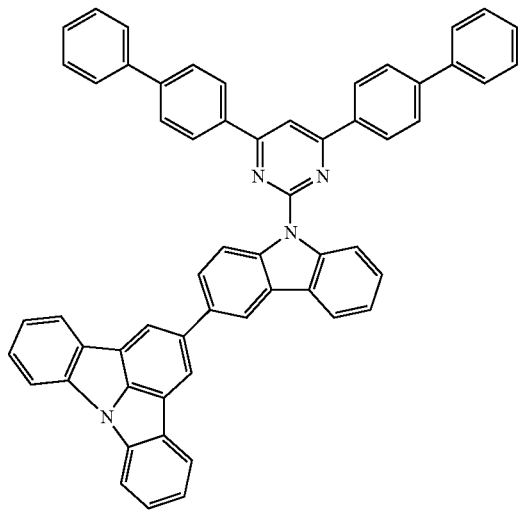

-continued
63
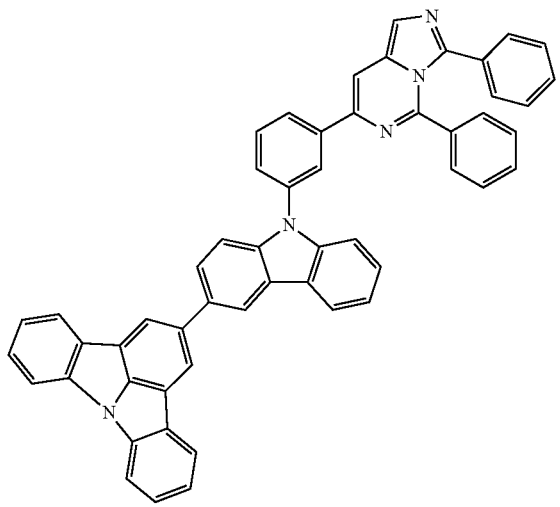
64
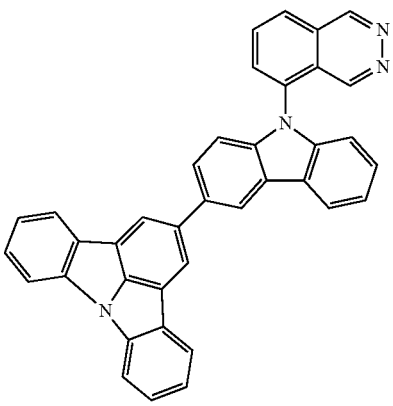
65
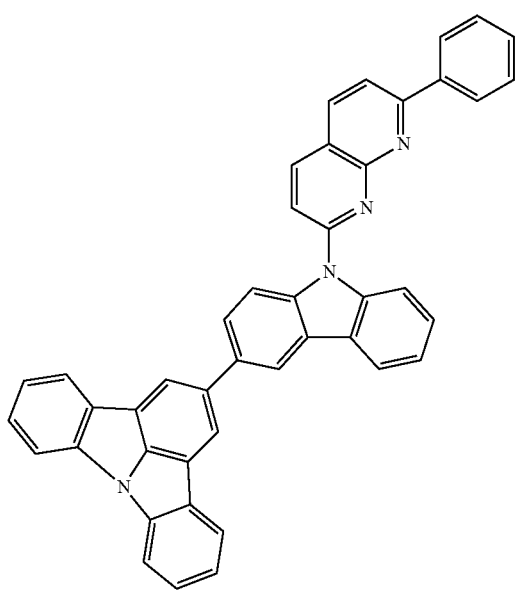
66
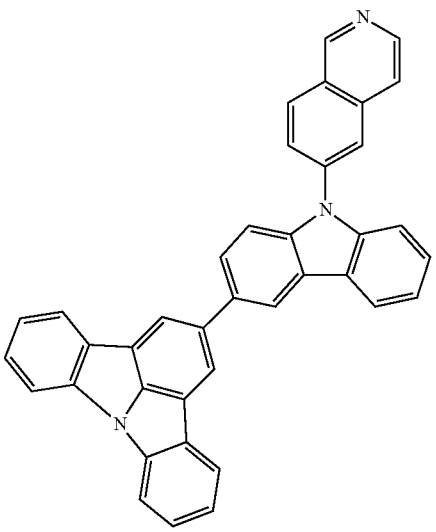
67
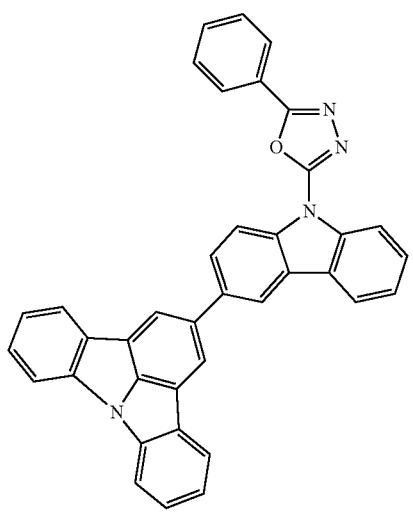
68
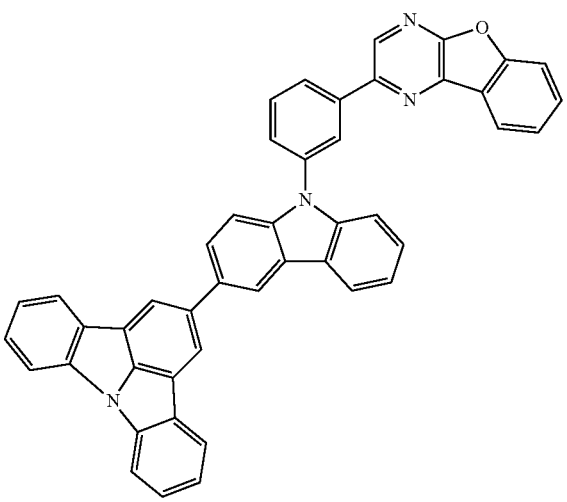

-continued
69
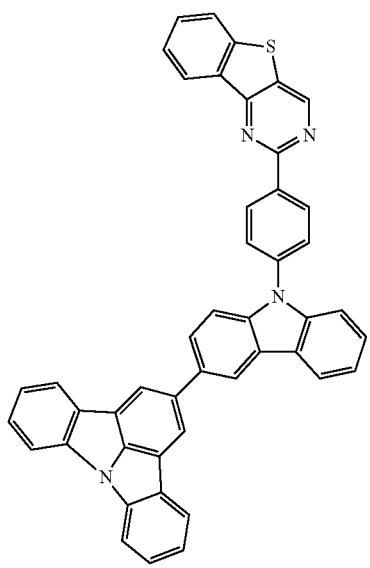
70
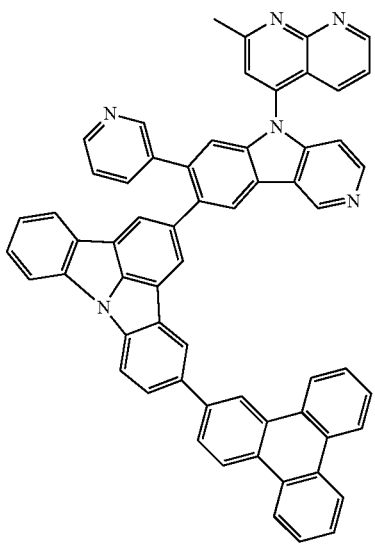
71
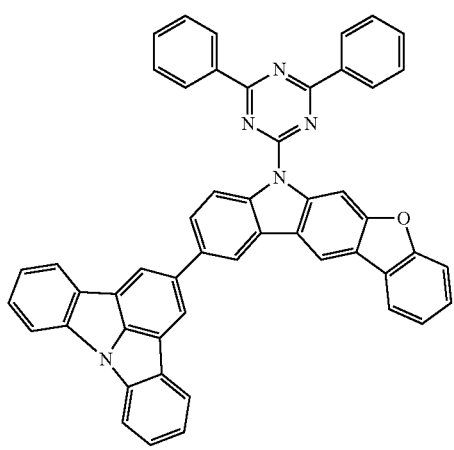
72
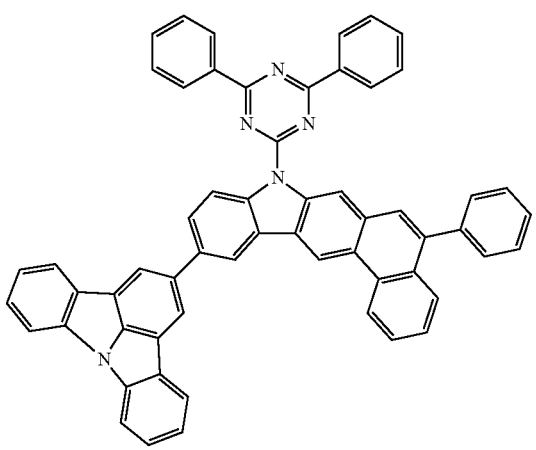
73
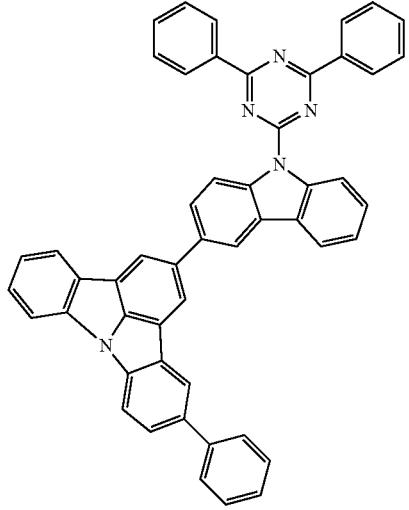
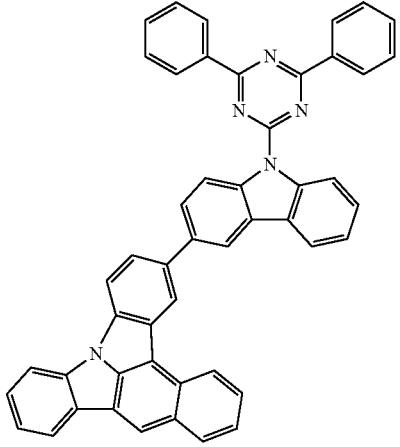

-continued

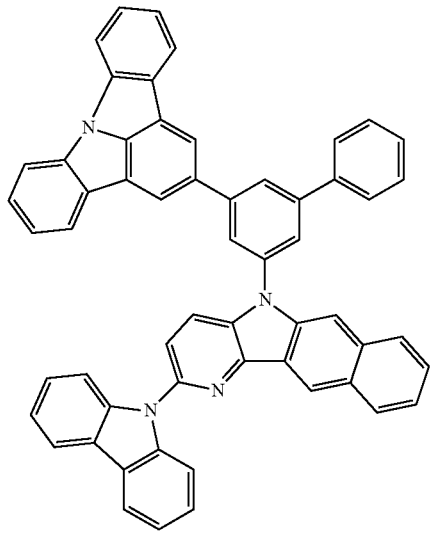
75

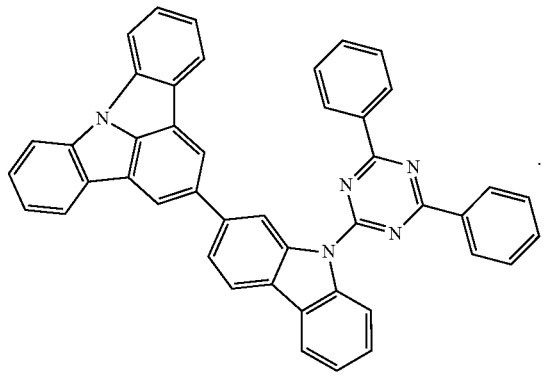
76

21. An organic light-emitting device comprising:
a first electrode;
a second electrode; and
an organic layer disposed between the first electrode and the second electrode,
wherein the organic layer comprises an emission layer and at least one condensed cyclic compound represented by Formula 1 of claim 1.

22. The organic light-emitting device of claim 21, wherein the emission layer comprises the condensed cyclic compound represented by Formula 1 of claim 1.

23. The organic light-emitting device of claim 21, wherein
the emission layer comprises a first host and a second host,
the condensed cyclic compound represented by one of Formulae 1A to 1C exists in the emission layer,
the first host comprises the condensed cyclic compound represented by one of Formulae 1A to 1C, and
the second host comprises at least one selected from a first compound represented by Formula 41 and a second compound represented by Formula 61:

Formula 41

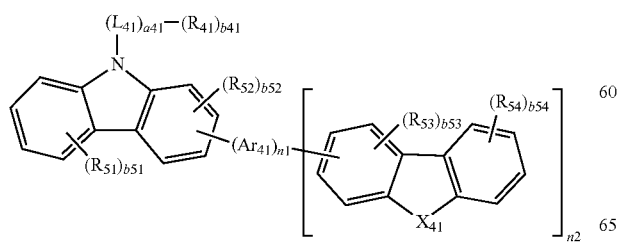

-continued

Formula 61

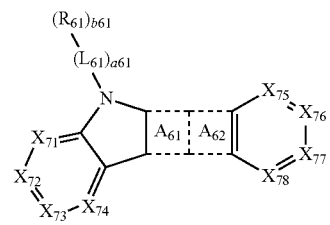

Formula 61A

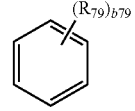

Formula 61B $X_{61}$ wherein in the formulae 41, 61, 61A, and 61B,
$X_{41}$ is $N-[(L_{42})_{a42}-(R_{42})_{b42}]$, S, O, S(=O), S(=O)$_2$, C(=O), C(R$_{43}$)(R$_{44}$), Si(R$_{43}$)(R$_{44}$), P(R$_{43}$), P(=O)(R$_{43}$), or C=N(R$_{43}$);
Ring $A_{61}$ in Formula 61 is represented by Formula 61A;
Ring $A_{62}$ in Formula 61 is represented by Formula 61B;
$X_{61}$ is $N-[(L_{62})_{a62}-(R_{62})_{b62}]$, S, O, S(=O), S(=O)$_2$, C(=O), C(R$_{63}$)(R$_{64}$), Si(R$_{63}$)(R$_{64}$), P(R$_{63}$), P(=O)(R$_{63}$), or C=N(R$_{63}$);
$X_{71}$ is C(R$_{71}$) or N;
$X_{72}$ is C(R$_{72}$) or N;
$X_{73}$ is C(R$_{73}$) or N;
$X_{74}$ is C(R$_{74}$) or N;
$X_{75}$ is C(R$_{75}$) or N;
$X_{76}$ is C(R$_{76}$) or N;
$X_{77}$ is C(R$_{77}$) or N;
$X_{78}$ is C(R$_{78}$) or N;
$Ar_{41}$, $L_{41}$, $L_{42}$, $L_{61}$, and $L_{62}$ are each independently selected from a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, or a substituted and unsubstituted divalent non-aromatic condensed hetero-polycyclic group;

n1 and n2 are each independently an integer selected from 0 to 3;

a41, a42, a61, and a62 are each independently an integer selected from 0 to 3;

$R_{41}$ to $R_{43}$, $R_{51}$ to $R_{54}$, $R_{61}$ to $R_{64}$, and $R_{71}$ to $R_{79}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed hetero-polycyclic group, —N($Q_1$)($Q_2$), —Si($Q_3$)($Q_4$)($Q_5$), and —B($Q_6$)($Q_7$);

b41, b42, b51 to b54, b61, b62, and b79 are each independently an integer selected from 1 to 3;

at least one of substituents of the substituted $C_1$-$C_{60}$ alkylene group, substituted $C_2$-$C_{60}$ alkenylene group, substituted $C_3$-$C_{10}$ cycloalkylene group, substituted $C_2$-$C_{10}$ heterocycloalkylene group, substituted $C_3$-$C_{10}$ cycloalkenylene group, substituted $C_2$-$C_{10}$ heterocycloalkenylene group, substituted $C_6$-$C_{60}$ arylene group, substituted $C_2$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_2$-$C_{60}$ heteroaryl group, a substituted monovalent non-aromatic condensed polycyclic group, and a substituted monovalent non-aromatic condensed hetero-polycyclic group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed hetero-polycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed hetero-polycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$);

wherein $Q_1$ to $Q_7$, $Q_{11}$ to $Q_{17}$, $Q_{21}$ to $Q_{27}$, and $Q_{31}$ to $Q_{37}$ are each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent non-aromatic condensed polycyclic group, and a monovalent non-aromatic heterocondensed polycyclic group.

24. The organic light-emitting device of claim 21, wherein the emission layer further comprises a phosphorescent dopant.

25. The organic light-emitting device of claim 21, wherein the electron transport region comprises at least one of the condensed cyclic compounds represented by Formula 1.

* * * * *